(12) United States Patent
Alphandery

(10) Patent No.: US 11,732,277 B2
(45) Date of Patent: Aug. 22, 2023

(54) CELLULAR PRODUCTION OF PURE IRON OXIDE NANOPARTICLES

(71) Applicant: NANOBACTERIE, Paris (FR)

(72) Inventor: Edouard Alphandery, Paris (FR)

(73) Assignee: NANOBACTERTE, Paris (FR)

( * ) Notice: Subject to any disclaimer, the term of this patent is extended or adjusted under 35 U.S.C. 154(b) by 265 days.

(21) Appl. No.: 16/589,227

(22) Filed: Oct. 1, 2019

(65) Prior Publication Data

US 2020/0102581 A1 Apr. 2, 2020

(30) Foreign Application Priority Data

Oct. 2, 2018 (FR) ...................................... 1801033
Oct. 2, 2018 (FR) ...................................... 1801034

(51) Int. Cl.

| | |
|---|---|
| *C12P 3/00* | (2006.01) |
| *C12N 1/38* | (2006.01) |
| *C12N 1/20* | (2006.01) |
| *C01G 49/08* | (2006.01) |
| *B82Y 35/00* | (2011.01) |
| *B82Y 40/00* | (2011.01) |

(52) U.S. Cl.
CPC ................ *C12P 3/00* (2013.01); *C01G 49/08* (2013.01); *C12N 1/20* (2013.01); *C12N 1/38* (2013.01); *B82Y 35/00* (2013.01); *B82Y 40/00* (2013.01); *C01P 2004/64* (2013.01)

(58) Field of Classification Search
CPC ..... C01P 2004/64; B82Y 40/00; B82Y 35/00; C12N 1/38; C12N 1/20; C01G 49/08; C12P 3/00
See application file for complete search history.

(56) References Cited

FOREIGN PATENT DOCUMENTS

| | | |
|---|---|---|
| CN | 101372364 A | 2/2009 |
| EP | 2666456 A1 | 11/2013 |
| FR | 2974815 A1 | 11/2012 |

OTHER PUBLICATIONS

ATCC medium 1653, ATCC, [retrieved on Nov. 9, 2021] retrieved from the internet <URL: https://www.atcc.org/products/700264>.*
LB broth, Thermo Fisher Scientific [retrieved on Dec. 8, 2021] retrieved from the internet <URL: https://www.thermofisher.com/order/catalog/product/10855021>.*
Bharde AA, Parikh RY, Baidakova M, Jouen S, Hannoyer B, Enoki T, Prasad BL, Shouche YS, Ogale S, Sastry M. Bacteria-mediated precursor-dependent biosynthesis of superparamagnetic iron oxide and iron sulfide nanoparticles. Langmuir. Jun. 3, 2008;24(11):5787-94. doi: 10.1021/la704019p. (Year: 2008).*
LB broth, Thermo Fisher Scientific [retrieved on Dec. 8, 2021] retrieved from the internet <URL: https://www.thermofisher.com/order/catalog/product/10855021> (Year: 2021).*
Bharde, A., Wani, A., Shouche, Y., Joy, P. A., Prasad, B. L., & Sastry, M. (2005). Bacterial aerobic synthesis of nanocrystalline magnetite. Journal of the American Chemical Society, 127(26), 9326-9327. (Year: 2005).*
González, L. M., Ruder, W. C., Messner, W. C., & LeDuc, P. R. (2012, June). Sensing of Local, Highly Concentrated Magnetic Field Gradients in Magnetotactic Bacteria Induces Motility Reversal. In Summer Bioengineering Conference (vol. 44809, pp. 1297-1298). American Society of Mechanical Engineers. (Year: 2012).*
Fernández-Castané, Alfred, et al. "Development of a simple intensified fermentation strategy for growth of Magnetospirillum gryphiswaldense MSR-1: physiological responses to changing environmental conditions." New biotechnology 46 (2018): 22-30 (Year: 2018).*
ATCC medium 1653, ATCC, [retrieved on Nov. 9, 2021] retrieved from the internet <URL: https://www.atcc.org/products/700264> (Year: 2021).*
Oestreicher, Z., Mumper, E., Gassman, C., Bazylinski, D., Lower, S., & Lower, B. (2016). Spatial localization of Mms6 during biomineralization of Fe3O4 nanocrystals in Magnetospirillum magneticum AMB-1. Journal of Materials Research, 31(5), 527-535. doi:10.1557/jmr.2016.41 (Year: 2016).*
Ali Talha Khalil, Muhammad Ovais, Ikram Ullah, Muhammad Ali, Zabta Khan Shinwari & Malik Maaza (2017) Biosynthesis of iron oxide (Fe2O3) nanoparticles via aqueous extracts of *Sageretia thea* (Osbeck.) and their pharmacognostic properties, Green Chemistry Letters and Review (Year: 2017).*
Search Report dated Feb. 24, 2020 in corresponding European Application No. 19020544.3; 13 pages.
Search Report dated Mar. 2, 2020 in corresponding European Application No. 19020545.0; 20 pages.
Araujo et al., "Magnetotactic Bacteria as Potential Sources of Bioproducts", Marine Drugs, vol. 13, No. 1, Jan. 16, 2015, pp. 389-430.
Ali et al., "Yield cultivation of magnetotactic bacteria and magnetosomes: A review", Journal of Basic Microbiology, vol. 57, No. 8, May 2, 2017, pp. 643-652.
Bazylinski et al., "*Magnetovibrio blakemorei* gen. nov., sp nov., a magnetotactic bacterium (Alphaproteobacteria: Rhodospirillaceae) isolated from a salt marsh", International Journal of Systematic and Evolutionary Microbiology, vol. 63, No. Pt 5, Sep. 14, 2012, pp. 1824-1833.

(Continued)

*Primary Examiner* — Louise W Humphrey
*Assistant Examiner* — Trevor L Kane
(74) *Attorney, Agent, or Firm* — Maier & Maier, PLLC

(57) ABSTRACT

A method for producing high purity iron oxide nanoparticles using nanoparticle-producing cells, including: a) a pre-growth step that includes amplifying the nanoparticle-producing cell(s) in a pre-growth and/or fed-batch medium/media, and b) a growth step that includes amplifying the nanoparticle-producing cell(s) originating from the pre-growth step in a growth and/or fed-batch medium/media, wherein the pre-growth and/or growth and/or fed-batch medium/media comprise(s), per kilogram or liter of pre-growth and/or growth and/or fed-batch medium/media: i) no more than 0.005 gram of yeast extract, and ii) no more than 0.001 gram of CMR agent selected from boric acid and nitrilotriacetic acid, wherein the fed-batch medium when it is present is a medium that supplements the pre-growth and/or growth medium/media, and wherein more nanoparticles are produced in the growth step than in the pre-growth step.

11 Claims, 6 Drawing Sheets

(56) References Cited

OTHER PUBLICATIONS

Bazylinski et al., "Supplementary Methods. Collection, enrichment and isolation of strain MV-1", Jan. 1, 2012, pp. 1-5.
Xiang et al., "Purified and sterilized magnetosomes from Magnetospirillum gryphiswaldense MSR-1 were not toxic to mouse fibroblasts in vitro", Letters in Applied Microbiology, vol. 45, No. 1, Jul. 1, 2007, pp. 75-81.
Faivre et al., "Magnetotactic Bacteria and Magnetosomes", Chemical Reviews, vol. 108, No. 11, Nov. 12, 2008, pp. 4875-4898.
Search Report dated Aug. 23, 2019 in corresponding application No. FR1801033, 14 pgs.
Search Report dated Jul. 26, 2019 in corresponding application No. FR1801034, 25 pgs.
Matthew J. O'Hara et al: "Magnetic iron oxide and manganese-doped iron oxide nanoparticles for the collection of alpha-emitting radionuclides from aqueous solutions", RSC Advances, vol. 6, No. 107, (Jan. 1, 2016), pp. 105239-105251, 13 pgs.
Cynthia L. Warner et al: "Manganese Doping of Magnetic Iron Oxide Nanoparticles: Tailoring Surface Reactivity for a Regenerable Heavy Metal Sorbent", Langmuir, vol. 28, No. 8, (Feb. 13, 2012), pp. 3931-3937, 7 pgs.
Scott J. Kemp et al: "Monodisperse magnetite nanoparticles with nearly ideal saturation magnetization", RSC Advances, vol. 6, No. 81, (Aug. 8, 2016), pp. 77452-77464, 13 pgs.
Panchal Vineet et al: "Control ling magnetic properties of iron oxide nanoparticles using post-synthesis thermal treatment", Applied Physics A Materials Science & Processing, Springer Berlin Heidelberg, Berlin/Heidelberg, vol. 114, No. 2, (Jan. 12, 2013), pp. 537-544, 9 pgs.
Zhang Z J et al: Magnetic greigite (Fe3S4) nanomaterials: Shape-controlled solvothermal synthesis and their calcination conversion into hematite ($\alpha$-Fe2O3) nanomaterials, Journal of Alloys and Compounds, Elsevier Sequoia, Lausanne, CH, vol. 488, No. 1, (Nov. 20, 2009), pp. 339-345, 7 pgs.
Edouard Alphandery: "Applications of Magnetosomes Synthesized by Magnetotactic Bacteria in Medicine", Frontiers in Bioengineering and Biotechnology, vol. 2, (Mar. 11, 2014), 6 pgs.
Matsunaga T et al: "Enhancement of Magnetic Particle Production by Nitrate and Succinate Fed-Batch Culture of *Magnetospirillum* sp. AMB-1", Biotechnology Techniques, Chapman & Hall, vol. 10, No. 5, (Jan. 1, 1996), pp. 485-500, 6 pgs.
J. Heyen et al: "Growth and magnetosome formation by microaerophilic Magnetospirillum strains in anoxygen-controlled fermentor", Applied Microbiology and Biotechnology, vol. 61, No. 5-6, (Feb. 20, 2003), pp. 536-544, 9 pgs.
Jian-Bo Sun et al: "High-yield growth and magnetosome formation by Magnetospirillum gryphiswaldense MSR-1 in an oxygen-controlled fermenter supplied solely with air", Applied Microbiology and Biotechnology, Springer, Berlin, DE, vol. 79, No. 3, (Apr. 19, 2008), pp. 389-397, 9 pgs.
Yang Chen-Dong et al: "Effects of growth medium composition, iron sources and atmospheric oxygen concentrations on production of luciferase-bacterial magnetic particle complex by a recombinantMagnetospirillum magneticumAMB-1", Enzyme and Microbial Technology, Stoneham, MA, US, vol. 29, No. 1, (Apr. 23, 2017), pp. 13-19, 7 pgs.
Edouard Alphandéry et al: "Chains of Magnetosomes Extracted from AMB-1 Magnetotactic Bacteria for Application in Alternative Magnetic Field Cancer Therapy", HAL archives-ouvertes.fr, (Jun. 30, 2017), pp. 1-16, 18 pgs.
Jacob Jobin John et al: "Magnetotactic bacteria and magnetosomes—Scope and challenges", Materials Science and Engineering C, Elsevier Science S.A, CH, vol. 68, (Jul. 20, 2016), pp. 919-928, 10 pgs.
Dirk Schuler et al: "Iron-limited growth and kinetics of iron uptake in Magnetospirillum gryphiswaldense", Archives of Microbio, Springer Berlin Heidelberg, Berlin/Heidelberg, vol. 166, No. 5, (Nov. 1, 1996), pp. 301-307, 7 pgs.
Sarah Staniland et al., "Controlled cobalt doping of magnetosomes in vivo", Nature Nanotechnology, V. 3, p. 158 (2008), 5 pgs.
Notice of Defects dated May 31, 2021, in corresponding to Israeli Application No. 269755; 9 pages (with English Translation).
Notice Before Acceptance dated Jun. 7, 2022, in corresponding to Israeli Application No. 269755; 6 pages (with English Translation).
Notice of Acceptance dated Aug. 23, 2022, in corresponding to Israeli Application No. 269755; 2 pages (with English Translation).

* cited by examiner

CELLULAR PRODUCTION OF PURE IRON OXIDE NANOPARTICLES

FIELD

The field of the invention is that of biological production of nanoparticles comprising a low quantity of impurities.

BACKGROUND

Bacteria producing nanoparticle(s), such as magnetotactic bacteria, are known to accumulate impurities in their crystallized structure. For example, when magnetotactic bacteria are grown in the presence of cobalt, they produce magnetosomes comprising iron oxide and cobalt (S. Staniland et al, Nature nanotechnology, V. 3, P. 158 (2008)). For medical applications, it is desired that nanoparticle(s) contain(s) a low level of toxic impurities such as cobalt.

SUMMARY

The invention relates to a method for producing high purity iron oxide nanoparticles using nanoparticle-producing cells, comprising:
   a) A pre-growth step comprising amplifying the nanoparticle-producing cell(s) in a pre-growth and/or fed-batch medium/media preferentially such that nanoparticle-producing cell(s) produce(s) essentially no nanoparticles, and
   b) A growth step comprising amplifying the nanoparticle-producing cell(s) originating from the pre-growth step in a growth and/or fed-batch medium/media preferentially such that nanoparticle-producing cell(s) produce nanoparticles, wherein the pre-growth and/or growth and/or fed-batch medium/media comprise(s), per kilogram or liter of pre-growth and/or growth and/or fed-batch medium/media:
      i) no more than $5.10^5$, $5.10^3$, 50, 5, 0.5, 0.005, 0.0005, 0.00005 or $5.10^{-10}$ gram of yeast extract, and/or
      ii) no more than $10^5$, $10^3$, 10, 1, 0.1, 0.001, $10^{-5}$ or $10^{-10}$ gram of CMR agent preferentially selected from the group consisting of boric acid and nitrilotriacetic acid,
wherein preferentially the fed-batch medium when it is present is a medium that supplements the pre-growth and/or growth medium/media,
wherein preferentially more nanoparticles are produced in the growth step than in the pre-growth step, preferentially by a factor of at least 0, 0.1, 0.5, 2, 5, 10, $10^3$, $10^5$ or $10^{10}$, where this factor is preferentially $Q_2/Q_1$, where $Q_1$ and $Q_2$ are preferentially the quantities of nanoparticles produced in/during the pre-growth and growth steps or sub-steps, respectively, and/or
wherein preferentially the pre-growth and/or growth and/or fed-batch medium/media comprise(s) at least another compound, which is preferentially involved in bacterial growth and/or magnetosome production or synthesis, wherein preferentially the other compound is a source of carbon, nitrogen, calcium, vitamin, oxygen, iron, phosphate, phosphorous, and/or magnesium.

DETAILED DESCRIPTION

Figure 1:
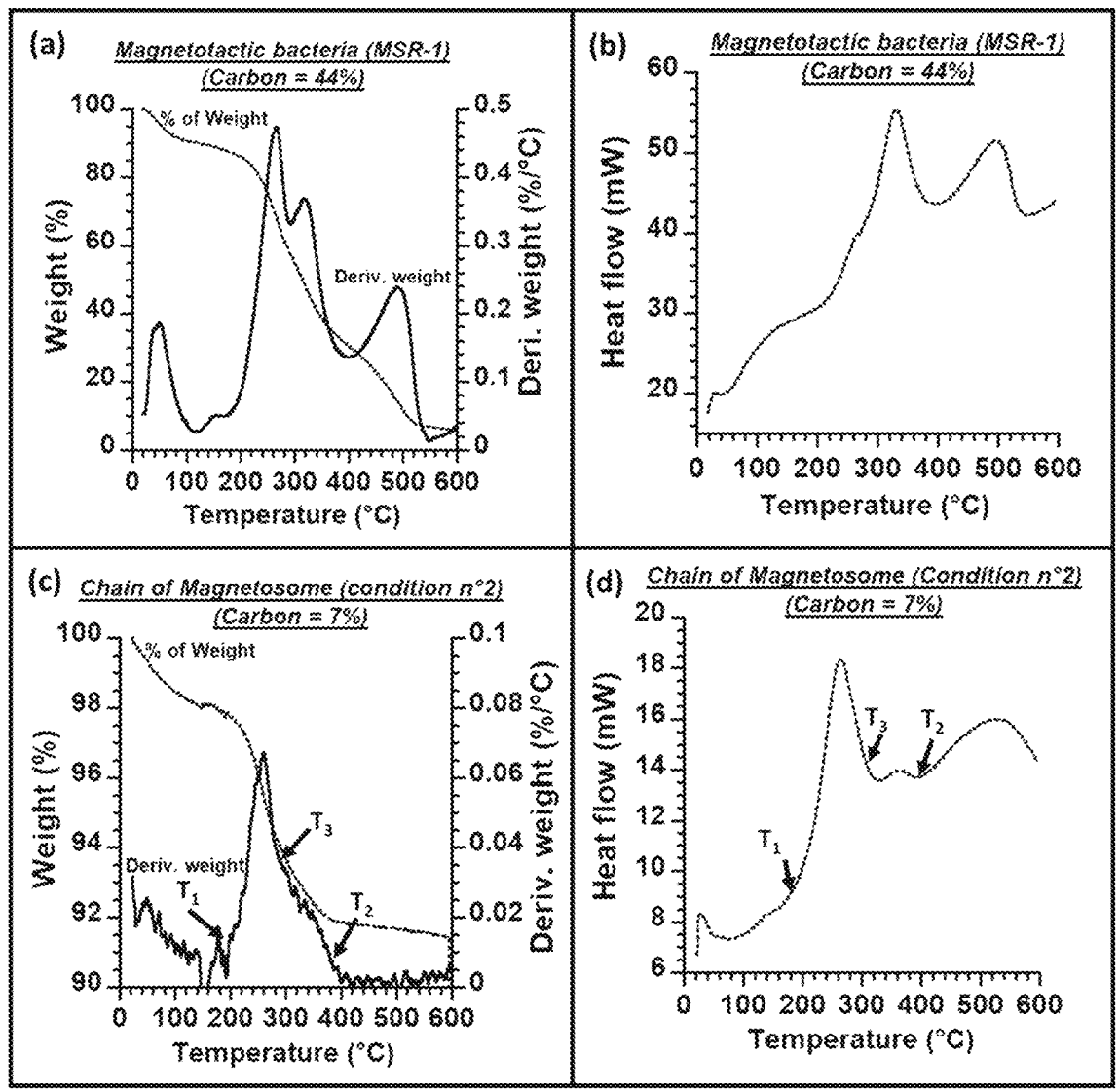
FIG. 1: TGA-DSC analysis of whole magnetotactic bacteria and magnetosomes extracted from magnetotactic bacteria according to condition 2 of lysis. (a), The variation of the percentage in weight as a function of temperature as well as the derivative of this variation as a function of temperature for a sample comprising 3 mg of lyophilized magnetotactic bacteria when it is heated between 20° C. and 600° C. at a rate of 6° C./min. (b), Heat flow in mW as a function of temperature produced by a sample comprising 3 mg of lyophilized magnetotactic bacteria when it is heated between 20° C. and 600° C. at a rate of 6° C./min. (c), The variation of the percentage in weight as a function of temperature as well as the derivative of this variation as a function of temperature for a sample comprising 3 mg of lyophilized magnetosomes extracted from whole bacteria according to condition 2 of lysis when the sample is heated between 20° C. and 600° C. at a rate of 6° C./min. (d), Heat flow in mW as a function of temperature produced by a sample comprising 3 mg of lyophilized magnetosomes extracted from whole bacteria according to condition 2 of lysis when the sample is heated between 20° C. and 600° C. at a rate of 6° C./min. Concerning (a) and (c), the y axis can be replaced by the percentage in mass, leading to the same plots.

In one embodiment of the invention, the nanoparticle-producing cells are cells, preferentially eukaryotic or prokaryotic ones, that have the faculty or ability to produce or synthesize nanoparticles, preferentially when they are inserted or amplified in a medium that comprises at least one compound that is comprised in the nanoparticle, preferentially at a concentration larger than $10'$, 1 or $10^6$ µM.

In one embodiment of the invention, nanoparticle-producing cell(s) produce(s) essentially no nanoparticles when these cells produce less than $10^{50}$, $10^{10}$, $10^5$, $10^3$, 10, 1, $10^{-1}$, $10^{-3}$ or $10^{-5}$ mg of nanoparticles per liter of pre-growth and/or growth and/or fed-batch medium/media or when the pre-growth and/or growth and/or fed-batch medium/media preferentially comprising nanoparticle-cell(s) comprise(s) less than $10^{50}$, $10^{10}$, $10^5$, $10^3$, 10, 1, $10^{-1}$, $10^{-3}$ or $10^{-5}$ mg of nanoparticles per liter of pre-growth and/or growth and/or fed-batch medium/media.

In one embodiment of the invention, nanoparticle-producing cell(s) produce nanoparticles when these cells produce more than 0, $10^{-50}$, $10^{-20}$, $10^{-10}$, $10^{-5}$, $10^{-1}$, 1, 10, $10^3$ or $10^5$ mg of nanoparticles per liter of pre-growth and/or growth and/or fed-batch medium/media or when the pre-growth and/or growth and/or fed-batch medium/media preferentially comprising nanoparticle-cell(s) comprise(s) more than 0, $10^{-50}$, $10^{-20}$, $10^{-10}$, $10^{-5}$, $10^{-1}$, 1, 10, $10^3$ or $10^5$ mg of nanoparticles per liter of pre-growth and/or growth and/or fed-batch medium/media.

In one embodiment of the invention, the quantity of nanoparticles produced by the nanoparticle cells in the pre-growth step is equal to $Q_2-Q_1$, where $Q_1$ and $Q_2$ are the quantities of nanoparticles produced at times $t_1$ and $t_2$ of the pre-growth step, where $t_2$ is larger than $t_1$, preferentially $t_2/t_1$ is larger than 1, 2, 5, 10 or $10^3$, preferentially $t_2$ is the end of the pre-growth step and $t_1$ is the beginning of the pre-growth step.

In one embodiment of the invention, the quantity of nanoparticles produced by the nanoparticle cells in the growth step is equal to $Q'_2-Q'_1$, where $Q'_1$ and $Q'_2$ are the quantities of nanoparticles produced at times $t'_1$ and $t'_2$ of the growth step, where $t'_2$ is larger than $t'_1$, preferentially $t'_2/t'_1$ is larger than 1, 2, 5, 10 or $10^3$, preferentially $t'_2$ is the end of the growth step and $t'_1$ is the beginning of the growth step.

Preferentially, $Q'_2-Q'_1$ is larger than $Q_2-Q_1$, preferentially by a factor of at least 0, $10^{-10}$, $10^{-1}$, 1, 5, 10, $10^3$ or $10^5$.

Preferentially, the total quantity of nanoparticles produced by the nanoparticle-producing cells is equal to $Q_{total}=Q'_2-Q'_1+Q_2-Q_1$.

In some cases, $Q_{total}$ can be larger than $10^{-50}$, $10^{-10}$, $10^{-5}$, $10^{-3}$, $10^{-1}$, 0, 1, 5, 10 or 100 mg of nanoparticles, preferentially of iron comprised in nanoparticles, preferentially per liter of pre-growth and/or growth medium/media.

In some other cases, $Q_{total}$ can be lower than $10^{50}$, $10^{10}$, $10^5$, $10^3$, 100, 50, 10 or 1 mg of nanoparticles, preferentially of iron comprised in nanoparticles, preferentially per liter of pre-growth and/or growth medium/media.

In one embodiment of the invention, the yeast extract is one element selected from the group consisting of: i) whole yeast extract, ii) a medium comprising more than 1, 10, 50 or 90% of compounds from the whole yeast extract, and iii) a chemical equivalent of the yeast extract.

In one embodiment of the invention, the peptone is one element selected from the group consisting of: i) whole peptone, ii) a medium comprising more than 1, 10, 50 or 90% of compounds from the whole peptone, and iii) a chemical equivalent of peptone.

The invention relates to a method for producing high purity iron oxide nanoparticles using nanoparticle-producing cells, preferentially comprising a pre-growth step comprising amplifying the nanoparticle-producing cells preferentially in a pre-growth medium while preferentially producing essentially no nanoparticles, which is preferentially followed by a growth step, comprising amplifying the nanoparticle-producing cells preferentially originating from the pre-growth step preferentially in a growth medium while producing nanoparticles, wherein preferentially the growth step differs from the pre-growth step by at least one property selected from the group consisting of:
  i) a ratio $C_{FeGS}/C_{FePGS}$ that is larger than 0, $10^{-5}$, $10^{-3}$, 1, 10, $10^3$ or $10^5$, where $C^{FeGS}$ and $C_{FePGS}$ are concentrations in iron or iron source of the growth medium and pre-growth medium, respectively,
  ii) a ratio $C_{CGS}/C_{CPGS}$ that is larger than 0, $10^{-5}$, $10^{-3}$, 1, 10, $10^3$ or $10^5$, where $C_{CGS}$ and $C_{CPCS}$ are the concentrations in carbon or carbon source of the growth medium and pre-growth medium, respectively,
  iii) a ratio $C_{NGS}/C_{NPGS}$ that is larger than 0, $10^{-5}$, $10^{-3}$, 1, 10, $10^3$ or $10^5$, where $C_{NGS}$ and $C_{NPGS}$ are the concentrations in nitrogen or nitrogen source of the growth medium and pre-growth medium, respectively,
  iv) a ratio $\Delta_p H_{GS}/\Delta pH_{PGS}$ that is lower than 0, $10^{10}$, $10^5$, $10^3$, $10^2$, 1, 0.5 or 0.1, where $\Delta_{pHGS}$ and $\Delta pH_{PGS}$ are the pH variations of the growth medium and pre-growth medium, respectively,
  v) a ratio $Q_{GGS}/Q_{GPGS}$ that is larger than 0, $10^{10}$, $10^5$, $10^3$, $10^2$, 1, 0.5 or 0.1, where $Q_{GGS}$ and $Q_{GPGS}$ are quantities of gas, oxygen or air brought in or bubbled through the growth medium and pre-growth medium, respectively,
  vi) a ratio $N_{SSGS}/N_{SSPGS}$ that is lower than 0, $10^{-5}$, $10^{-3}$, 1, 10, $10^3$ or $10^5$, where $N_{SSGS}$ and $N_{SSPGS}$ are numbers of sub-steps of the growth step and numbers of sub-steps of the pre-growth step, respectively, where two sub-steps are separated by each other by a transfer of nanoparticle-producing cells from a first sub-step to a second sub-step, and
  vii) the growth medium is supplemented by a fed-batch medium, whereas the pre-growth medium is not supplemented by such medium, and/or wherein preferentially the pre-growth, growth, and/or fed-batch medium/media does/do not comprise:
  I) at least one compound or assembly of compounds comprised in or originating from yeast extract selected in the group consisting of:
    I.1) more than 0, $10^{-10}$, $10^{-5}$, $10^{-1}$, 1, $10^3$ or $10^5$ gram per liter of pre-growth and/or growth and/or fed-batch medium/media of protein,
    I.2) more than 0, $10^{-10}$, $10^{-6}$, $10^{-1}$, 1, $10^3$ or $10^5$ gram per liter of pre-growth and/or growth and/or fed-batch medium/media of nucleic acids,
    I.3) more than 0, $10^{-10}$, $10^{-5}$, $10^{-1}$, 1, $10^3$ or $10^5$ gram per liter of pre-growth and/or growth and/or fed-batch medium/media of glutathione,
    I.4) more than 0, $10^{-10}$, $10^{-7}$, $10^{-1}$, 1, $10^3$ or $10^5$ gram per liter of pre-growth and/or growth and/or fed-batch medium/media of at least one the compounds selected from the group consisting of: dextran, mannan, trehalose, flavoring nucleotide, B vitamins, biotin, and volatile aromatic compounds, I.5) more than 0, $10^{-10}$, $10^{-7}$, $10^{-1}$, 1, $10^3$ or $10^5$ gram per liter of pre-growth and/or growth and/or fed-batch medium/media of calcium, I.6) more than 0, $10^{-10}$, $10^{-6}$, $10^{-1}$, 1, $10^3$ or $10^5$ gram per liter of pre-growth and/or growth and/or fed-batch medium/media of phosphorous, I.7) more than 0, $10^{-10}$, $10^{-8}$, $10^{-1}$, 1, $10^3$ or $10^5$ gram per liter of pre-growth and/or growth and/or fed-batch medium/media of zinc, I.8) more than 0, $10^{-10}$, $10^{-1}$, 1, $10^3$ or $10^5$ gram per liter of pre-growth and/or growth and/or fed-batch medium/media of chrome, I.9) more than 0, $10^{-10}$, $10^{-7}$, $10^{-1}$, 1, $10^3$ or $10^5$ gram per liter of pre-growth and/or growth and/or fed-batch medium/media of potassium, I.10) more than 0, $10^{-10}$, $10^{-1}$, 1, $10^3$ or $10^5$ gram per liter of pre-growth and/or growth and/or fed-batch medium/media of cobalt, I.11) more than 0, $10^{-10}$, $10^{-9}$, $10^{-1}$, 1, $10^3$ or $10^5$ gram per liter of pre-growth and/or growth and/or fed-batch medium/media of manganese, I.12) more than 0, $10^{-10}$, $10^{-1}$, 1, $10^3$ or $10^5$ gram per liter of pre-growth and/or growth and/or fed-batch medium/media of strontium, I.13) more than 0, $10^{-10}$, $10^{-7}$, $10^{-1}$, 1, $10^3$ or $10^5$ gram per liter of pre-growth and/or growth and/or fed-batch medium/media of magnesium, I.14) more than 0, $10^{-10}$, $10^{-4}$, $10^{-1}$, 1, $10^3$ or $10^5$ gram per liter of pre-growth and/or growth and/or fed-batch medium/media of yeast extract, and I.15) more than 0, 1, 5, 10, 15, 20 or 50 different components originating from yeast extract;

II. at least one compound or assembly of compounds comprised in or originating from peptone selected in the group consisting of:

II.1) more than 0, $10^{-10}$, $10^{-4}$, $10^{-1}$, 1, $10^3$ or $10^5$ gram per liter of pre-growth and/or growth and/or fed-batch medium/media of ashes, II.2) more than 0, $10^{-10}$, $10^{-3}$, $10^{-1}$, 1, $10^3$ or $10^5$ gram per liter of pre-growth and/or growth and/or fed-batch medium/media of proteins, II.3) more than 0, $10^{-10}$, $10^{-4}$, $10^{-1}$, 1, $10^3$ or $10^5$ gram per liter of pre-growth and/or growth and/or fed-batch medium/media of sucrose, II.4) more than 0, $10^{-10}$, $10^{-5}$, $10^{-1}$, 1, $10^3$ or $10^5$ gram per liter of pre-growth and/or growth and/or fed-batch medium/media of raffinose, II.5) more than 0, $10^{-10}$, $10^{-4}$, $10^{-1}$, 1, $10^3$ or $10^5$ gram per liter of pre-growth and/or growth and/or fed-batch medium/media of neutral detergent fiber, II.6) more than 0, $10^{-10}$, $10^{-5}$, $10^{-1}$, 1, $10^3$ or $10^5$ gram per liter of pre-growth and/or growth and/or fed-batch medium/media of Ethereal Extract, II.7) more than 0, $10^{-10}$, $10^{-5}$, $10^{-1}$, 1, $10^3$ or $10^5$ gram per liter of pre-growth and/or growth and/or fed-batch medium/media of peptone, and II.8) more than 0, 1, 5, 10, 15, 20 or 50 different components originating from peptone;

III. at least one compound or assembly of compounds comprised in or originating from Wolf's minerals or mineral elixir selected in the group consisting of:

III.1) more than 0, $10^{-20}$, $10^{-5}$, $10^{-1}$, 1, $10^3$ or $10^5$ mol per liter of pre-growth and/or growth and/or fed-batch medium/media of nitrilotriacetic acid, III.2) more than 0, $10^{-20}$, $10^{-6}$, $10^{-1}$, 1, $10^3$ or $10^5$ mol per liter of pre-growth and/or growth and/or fed-batch medium/media of magnesium sulfate, III.3) more than 0, $10^{-20}$, $10^{-5}$, $10^{-1}$, 1, $10^3$ or $10^5$ mol per liter of pre-growth and/or growth and/or fed-batch medium/media of sodium chloride, III.4) more than 0, $10^{-20}$, $10^{-5}$, $10^{-1}$, 1, $10^3$ or $10^5$ mol per liter of pre-growth and/or growth and/or fed-batch medium/media of manganese sulfate, III.5) more than 0, $10^{-20}$, $10^{-6}$, $10^{-1}$, 1, $10^3$ or $10^5$ mol per liter of pre-growth and/or growth and/or fed-batch medium/media of ferrous sulfate, III.6) more than 0, $10^{-20}$, $10^{-6}$, $10^{-1}$, 1, $10^3$ or $10^5$ mol per liter of pre-growth and/or growth and/or fed-batch medium/media of cobalt nitrate, III.7) more than 0, $10^{-20}$, $10^{-6}$, $10^{-1}$, 1, $10^3$ or $10^5$ mol per liter of pre-growth and/or growth and/or fed-batch medium/media of calcium chloride, III.8) more than 0, $10^{-20}$, $10^{-6}$, $10^{-1}$, 1, $10^3$ or $10^5$ mol per liter of pre-growth and/or growth and/or fed-batch medium/media of zinc sulfate, III.9) more than 0, $10^{-20}$, $10^{-7}$, $10^{-1}$, 1, $10^3$ or $10^5$ mol per liter of pre-growth and/or growth and/or fed-batch medium/media of copper sulfate, III.10) more than 0, $10^{-20}$, $10^{-7}$, $10^{-1}$, 1, $10^3$ or $10^5$ mol per liter of pre-growth and/or growth and/or fed-batch medium/media of aluminium potassium sulfate originating from Wolf's minerals or mineral elixir, III.11) more than 0, $10^{-20}$, $10^{-7}$, $10^{-1}$, 1, $10^3$ or $10^5$ mol per liter of pre-growth and/or growth and/or fed-batch medium/media of boric acid, III.12) more than 0, $10^{-20}$, $10^{-8}$, $10^{-1}$, 1, $10^3$ or $10^5$ mol per liter of pre-growth and/or growth and/or fed-batch medium/media of sodium molybdate, III.13) more than 0, $10^{-20}$, $10^{-9}$, $10^{-1}$, 1, $10^3$ or $10^5$ mol per liter of pre-growth and/or growth and/or fed-batch medium/media of sodium selenite, III.14) more than 0, $10^{-20}$, $10^{-7}$, $10^{-1}$, 1, $10^3$ or $10^5$ mol per liter of pre-growth and/or growth and/or fed-batch medium/media of sodium tungstate, III.15) more than 0, $10^{-20}$, $10^{-7}$, $10^{-1}$, 1, $10^3$ or $10^5$ mol per liter of pre-growth and/or growth and/or fed-batch medium/media of nickel chloride, III.16) more than 0, $10^{-20}$, $10^{-8}$, $10^{-1}$, 1, $10^3$ or $10^5$ mol per liter of pre-growth and/or growth and/or fed-batch medium/media of Wolf's mineral or mineral elixir, and III.17) more than 0, 10 different components of Wolf's mineral or mineral elixir;

IV) more than 0, $10^{-20}$, $10^{-5}$, $10^{-1}$, 1, $10^3$ or $10^5$ mol per liter of pre-growth and/or growth and/or fed-batch medium/media of EDTA;

and/or

V) at least one compound or assembly of compounds comprised in or originating from Wolf's vitamins selected in the group consisting of:

V.1) more than 0, $10^{-20}$, $10^{-9}$, $10^{-1}$, 1, $10^3$ or $10^5$ mol per liter of pre-growth and/or growth and/or fed-batch medium/media of biotin, V.2) more than 0, $10^{-20}$, $10^{-8}$, $10^{-1}$, 1, $10^3$ or $10^5$ mol per liter of pre-growth and/or growth and/or fed-batch medium/media of calcium pantothenate, V.3) more than 0, $10^{-20}$, $10^{-9}$, $10^{-1}$, 1, $10^3$ or $10^5$ mol per liter of pre-growth and/or growth and/or fed-batch medium/media of folic acid, V.4) more than 0, $10^{-20}$, $10^{-9}$, $10^{-1}$, 1, $10^3$ or $10^5$ mol per liter of pre-growth and/or growth and/or fed-batch medium/media of inositol, V.5) more than 0, $10^{-20}$, $10^{-8}$, $10^{-1}$, 1, $10^3$ or $10^5$ mol per liter of pre-growth and/or growth and/or fed-batch medium/media of nicotinic acid, V.6) more than 0, $10^{-20}$, $10^{-8}$, $10^{-1}$, 1, $10^3$ or $10^5$ mol per liter of pre-growth and/or growth and/or fed-batch medium/media of p-Aminobenzoic acid, V.7) more than 0, $10^{-20}$, $10^{-9}$, $10^{-1}$, 1, $10^3$ or $10^5$ mol per liter of pre-growth and/or growth and/or fed-batch medium/media of pyridoxine HCl, V.8) more than 0, $10^{-20}$, $10^{-9}$, $10^{-1}$, 1, $10^3$ or $10^5$ mol per liter of pre-growth and/or growth and/or fed-batch medium/media of riboflavin, V.9) more than 0, $10^{-20}$, $10^{-9}$, $10^{-1}$, 1, $10^3$ or $10^5$ mol per liter of pre-growth and/or growth and/or fed-batch medium/media of Thiamine HCl, V.10) more than 0, $10^{-20}$, $10^{-8}$, $10^{-1}$, 1, $10^3$ or $10^5$ mol per liter of pre-growth and/or growth and/or fed-batch medium/media of thiotic acid, V.11) more than 0, $10^{-20}$, $10^{-9}$, $10^{-1}$, 1, $10^3$ or $10^5$ mol of at least one component of Wolf's vitamin, and V.12) more than 0, 1, 5, 10, 15 or 20 different Wolf's vitamin; and/or preferentially wherein the pre-growth, growth, and/or fed-batch medium/media does/do not comprise, preferentially as measured per mg or per gram or per milliliter or per liter of pre-growth, growth and/or fed-batch medium/media, more than:

1) 0, $10^{-20}$, $10^{-10}$, $10^{-5}$, $10^{-3}$ or 1 gram of protein preferentially originating from yeast extract,
2) 0, $10^{-20}$, $10^{-10}$, $10^{-6}$, $10^{-3}$ or 1 gram of nucleic acids preferentially originating from yeast extract,
3) 0, $10^{-20}$, $10^{-10}$, $10^{-5}$, $10^{-1}$ or 1 gram of glutathione preferentially originating from yeast extract,
4) 0, $10^{-20}$, $10^{-10}$, $10^{-7}$, $10^{-1}$ or 1 gram of at least one the compounds preferentially originating from yeast extract selected from the group consisting of: dextran, mannan, trehalose, flavoring nucleotide, B vitamins, biotin, and volatile aromatic compounds.
5) 0, $10^{-20}$, $10^{-10}$, $10^{-7}$, $10^{-1}$ or 1 gram of calcium preferentially originating from yeast extract,
6) 0, $10^{-20}$, $10^{-10}$, $10^{-6}$, $10^{-1}$ or 1 gram of phosphorous preferentially originating from yeast extract,
7) 0, $10^{-20}$, $10^{-10}$, $10^{-8}$, $10^{-1}$ or 1 gram of zinc preferentially originating from yeast extract,
8) 0, $10^{-20}$, $10^{-10}$, $10^{-5}$, $10^{-1}$ or 1 gram of chrome preferentially originating from yeast extract,
9) 0, $10^{-20}$, $10^{-10}$, $10^{-7}$, $10^{-5}$, $10^{-1}$ or 1 gram of potassium preferentially originating from yeast extract,
10) 0, $10^{-20}$, $10^{-10}$, $10^{-5}$, $10^{-1}$ or 1 gram of cobalt preferentially originating from yeast extract,
11) 0, $10^{-20}$, $10^{-9}$, $10^{-5}$, $10^{-1}$ or 1 gram of manganese preferentially originating from yeast extract,
12) 0, $10^{-20}$, $10^{-10}$, $10^{-5}$, $10^{-1}$ or 1 gram of strontium preferentially originating from yeast extract,
13) 0, $10^{-20}$, $10^{-10}$, $10^{-7}$, $10^{-3}$, $10^{-1}$ or 1 gram of magnesium preferentially originating from yeast extract,
14) 0, $10^{-20}$, $10^{-10}$, $10^{-4}$, $10^{-1}$ or 1 gram of yeast extract,
15) 0, 1, 5, 10 or 15 different components originating from yeast extract,
16) 0, $10^{-20}$, $10^{-10}$, $10^{-4}$, $10^{-1}$ or 1 gram of ashes preferentially originating from peptone,
17) 0, $10^{-20}$, $10^{-10}$, $10^{-3}$, $10^{-1}$ or 1 gram of proteins preferentially originating from peptone,
18) 0, $10^{-20}$, $10^{-10}$, $10^{-4}$, $10^{-1}$ or 1 gram of sucrose preferentially originating from peptone,
19) 0, $10^{-20}$, $10^{-10}$, $10^{-5}$, $10^{-1}$ or 1 gram of raffinose preferentially originating from peptone,
20) 0, $10^{-20}$, $10^{-10}$, $10^{-4}$, $10^{-1}$ or 1 gram of neutral detergent fiber preferentially originating from peptone,
21) 0, $10^{-20}$, $10^{-10}$, $10^{-5}$, $10^{-1}$ or 1 gram of Ethereal Extract preferentially originating from peptone,
22) 0, $10^{-20}$, $10^{-10}$, $10^{-5}$, $10^{-1}$ or 1 gram of peptone,
23) 0, 1, 5, 7, 10 or 15 different components originating from peptone,
24) 0, $10^{-20}$, $10^{-10}$, $10^{-5}$, $10^{-1}$ or 1 mol of nitrilotriacetic acid preferentially originating from Wolf's minerals or mineral elixir,
25) 0, $10^{-20}$, $10^{-10}$, $10^{-6}$, $10^{-1}$ or 1 mol of magnesium sulfate preferentially originating from Wolf's minerals or mineral elixir,
26) 0, $10^{-20}$, $10^{-10}$, $10^{-5}$, $10^{-1}$ or 1 mol of sodium chloride preferentially originating from Wolf's minerals or mineral elixir,
27) 0, $10^{-20}$, $10^{-10}$, $10^{-5}$, $10^{-1}$ or 1 mol of manganese sulfate preferentially originating from Wolf's minerals or mineral elixir,
28) 0, $10^{-20}$, $10^{-10}$, $10^{-6}$, $10^{-1}$ or 1 mol of ferrous sulfate preferentially originating from Wolf's minerals or mineral elixir,
29) 0, $10^{-20}$, $10^{-10}$, $10^{-6}$, $10^{-1}$ or 1 mol of cobalt nitrate preferentially originating from Wolf's minerals or mineral elixir,
30) 0, $10^{-20}$, $10^{-10}$, $10^{-6}$, $10^{-1}$ or 1 mol of calcium chloride preferentially originating from Wolf's minerals or mineral elixir,
31) 0, $10^{-20}$, $10^{-10}$, $10^{-6}$, $10^{-1}$ or 1 mol of zinc sulfate preferentially originating from Wolf's minerals or mineral elixir,
32) 0, $10^{-20}$, $10^{-10}$, $10^{-7}$, $10^{-1}$ or 1 mol of copper sulfate preferentially originating from Wolf's minerals or mineral elixir,
33) 0, $10^{-20}$, $10^{-10}$, $10^{-7}$, $10^{-1}$ or 1 mol of aluminium potassium sulfate preferentially originating from Wolf's minerals or mineral elixir,
34) 0, $10^{-20}$, $10^{-10}$, $10^{-7}$, $10^{-1}$ or 1 mol of boric acid preferentially originating from Wolf's minerals or mineral elixir,
35) 0, $10^{-20}$, $10^{-10}$, $10^{-8}$, $10^{-3}$, $10^{-1}$ or 1 mol of sodium molybdate preferentially originating from Wolf's minerals or mineral elixir,
36) 0, $10^{-20}$, $10^{45}$, $10^{-9}$, $10^{-3}$, $10^{-1}$ or 1 mol of sodium selenite preferentially originating from Wolf's minerals or mineral elixir,
37) 0, $10^{-20}$, $10^{-7}$, $10^{-3}$, $10^{-1}$ or 1 mol of sodium tungstate preferentially originating from Wolf's minerals or mineral elixir,
38) 0, $10^{-20}$, $10^{-7}$, $10^{-3}$, $10^{-1}$ or 1 mol of nickel chloride preferentially originating from Wolf's minerals or mineral elixir,
39) 0, $10^{-20}$, $10^{-8}$, $10^{-3}$, $10^{-1}$ or 1 mol of Wolf's mineral or mineral elixir,
40) 0, 1, 5, 10 or 20 different components of Wolf's mineral or mineral elixir,
41) 0, $10^{-20}$, $10^{-10}$, $10^{-5}$, $10^{-1}$ or 1 mol of EDTA,
42) 0, $10^{-50}$, $10^{-30}$, $10^{-9}$, $10^{-3}$, $10^{-1}$ or 1 mol of biotin preferentially originating from Wolf's vitamins,
43) 0, $10^{-50}$, $10^{-30}$, $10^{-8}$, $10^{-3}$, $10^{-1}$ or 1 mol of Cacium pantothenate preferentially originating from Wolf's vitamins,
44) 0, $10^{-50}$, $10^{-30}$, $10^{-9}$, $10^{-3}$, $10^{-1}$ or 1 mol of folic acid preferentially originating from Wolf's vitamins, 45) 0, $10^{-50}$, $10^{-30}$, $10^{-9}$, $10^{-3}$, $10^{-1}$ or 1 mol of inositol preferentially originating from Wolf's vitamins,
46) 0, $10^{-50}$, $10^{-30}$, $10^{-10}$, $10^{-8}$, $10^{-3}$, $10^{-1}$ or 1 mol of nicotinic acid preferentially originating from Wolf's vitamins,
47) 0, $10^{-50}$, $10^{-30}$, $10^{-8}$, $10^{-3}$, $10^{-1}$ or 1 mol of p-Aminobenzoic acid preferentially originating from Wolf's vitamins,
48) 0, $10^{-50}$, $10^{-30}$, $10^{-9}$, $10^{-3}$, $10^{-1}$ or 1 mol of pyridoxine HCl preferentially originating from Wolf's vitamins,
49) 0, $10^{-50}$, $10^{-30}$, $10^{-9}$, $10^{-3}$, $10^{-1}$ or 1 mol of riboflavin preferentially originating from Wolf's vitamins,
50) 0, $10^{-50}$, $10^{-30}$, $10^{-9}$, $10^{-3}$, $10^{-1}$ or 1 mol of Thiamine HCl preferentially originating from Wolf's vitamins,
51) 0, $10^{-50}$, $10^{-30}$, $10^{-8}$, $10^{-3}$, $10^{-1}$ or 1 mol of thiotic acid preferentially originating from Wolf's vitamins,
52) 0, $10^{-50}$, $10^{-30}$, $10^{-9}$, $10^{-3}$, $10^{-1}$ or 1 mol of at least one component of Wolf's vitamin,
53) 0, 1, 5, 10 or 20 different Wolf's vitamins,
54) 0, 1, 2, 3, 6, 10 or 100 different vitamins,
55) 0, $10^{-50}$, $10^{-20}$, $10^{-9}$, $10^{-8}$, $10^{-7}$, $10^{-5}$, $10^{-3}$, $10^{-1}$ or 1 mol of at least one vitamin,
56) 0, $10^{-50}$, $10^{-20}$, $10^{-10}$, $10^{-5}$, $10^{-4}$, $10^{-2}$, $10^{-1}$, 1, 10 or $10^3$ g of yeast extract,
57) 0, $10^{-50}$, $10^{-20}$, $10^{-9}$, $10^{-3}$, $10^{-1}$, 1, 5 or 10 mol of at least one component of yeast extract,
58) 0, 1, 2, 5, 10 or 100 different components of yeast extract,
59) 0, $10^{-50}$, $10^{-10}$, $10^{-5}$, $10^{-1}$, 1, 10 or $10^3$ g of peptone,
60) 0, $10^{-50}$, $10^{-9}$, $10^{-5}$, $10^{-3}$, $10^{-1}$, 1 or 10 mol of at least one component of peptone,
61) 0, 1, 2, 5, 10 or 100 different components of peptone,
62) 0, 1, 2, 5, 10 or 100 different CMR agents,
63) 0, $10^{-50}$, $10^{-9}$, $10^{-5}$, 0.05, $10^{-1}$, 1, 10, $10^3$ or $10^6$ mg of at least one CMR agent,
64) 0, 1, 2, 5, 10 or 100 different chelating agents,
65) 0, $10^{-50}$, $10^{-20}$, $10^{-9}$, $10^{-8}$, $10^{-3}$, $10^{-1}$, 1, 5, 10 or $10^3$ mol of at least one chelating agent,
66) 0, 1, 2, 5, 10 or 100 different amino acids,
67) 0, $10^{-50}$, $10^{-10}$, $10^{-5}$, $10^{-3}$, 1, 10, $10^3$, $10^5$ or $10^{10}$ mg of at least one amino acid,
68) 0, 1, 2, 5, 10 or 100 different toxic or cytotoxic compounds,
69) 0, $10^{-50}$, $10^{-10}$, $10^{-5}$, $10^{-3}$, $10^{-1}$, 1, 10, $10^3$ or $10^5$ mg of at least one toxic or cytotoxic compound,
70) 0, 1, 3 or 7 different heavy metals different from iron,
71) 0, $10^{-50}$, $10^{-10}$, $10^{-5}$, $10^{-3}$, $10^{-1}$, 1, 10, $10^3$ or $10^5$ mg of at least one heavy metal different from iron,
72) 0, 1, 2, 3, 4, 5, 6, 7, 8, 9, 10 metal(s) or chemical element(s) chosen among cadmium, lead, arsenic, mercury, cobalt, vanadium, nickel, lithium, antimony, and copper,
73) 1 mg of cadmium, lead, arsenic, mercury, cobalt, vanadium, nickel, lithium, antimony, and/or copper,
74) 0, $10^{-50}$, $10^{-10}$, 0.5, 1, 5, 10, $10^3$ or $10^6$ mL or $10^{-50}$, $10^{-30}$, $10^{-10}$, $10^{-8}$, $10^{-5}$, $10^{-3}$, 1, 10, $10^3$ or $10^6$ mol of Wolf's vitamin,
75) $10^{-50}$, $10^{-20}$, $10^{-9}$, $10^{-5}$, $10^{-1}$, 1, 5, 10, $10^3$ or $10^5$ mol of at least one component of Wolf's vitamin,
76) 0, 1, 2, 5, 10 or 100 different components of Wolf's vitamin,
77) 0, $10^{-50}$, $10^{-10}$, 0.5, 1, 5, 10, $10^3$ or $10^6$ mL or $10^{-50}$, $10^{-30}$, $10^{-10}$, $10^{-8}$, $10^{-5}$, $10^{-3}$, 1, 10, $10^3$ or $10^6$ mol of Wolf's mineral,
78) $10^{-50}$, $10^{-20}$, $10^{-9}$, $10^{-5}$, $10^{-1}$, 1, 5, 10, $10^3$ or $10^5$ mol of at least one component of Wolf's mineral,
79) 0, 1, 2, 5, 7, 10, 15 or 100 different components of Wolf's mineral,
80) $10^{-50}$, $10^{-20}$, $10^{-9}$, $10^{-5}$, $10^{-1}$, 1, 5, 10, $10^3$ or $10^5$ mol of mineral elixir,
81) $10^{-50}$, $10^{-20}$, $10^{-9}$, $10^{-5}$, $10^{-1}$, 1, 5, 10, $10^3$ or $10^5$ mol of at least one component of mineral elixir, and/or
82) 0, 1, 2, 5, 10, 14 or 100 different components of mineral elixir.

The invention also relates to the method according to the invention, wherein the fed-batch medium comprises at least one compound that is selected from the group consisting of: iron, iron source, carbon, carbon source, nitrogen, nitrogen source, and combination thereof and the concentration of the at least one compound in the fed-batch medium is larger than $10^{-6}$ μM, 1 μM, and/or $10^6$ μM.

In one embodiment of the invention, at least one vitamin, component of Wolf's vitamin or vitamin solution is selected from the group consisting of: folic acid, folates, pyridoxine, pyridoxamine, pyridoxal, riboflavin, biotin, thiamine, nicotinic acid, pantothenic acid, vitamin B12, amino benzoic acid, thiotic acid, all-trans-Retinol, Retinals, alternative provitamin A-functioning Carotenoids including all-trans-beta-carotene, Niacin, Niacinamide, Nicotinamide, riboside, cyanocobalamin, hydroxocobalamin, methylcobalamin, adenosylcobalamin, ascorbic acid, cholecalciferol, ergocalciferol, tocopherols, tocotrienols, phylloquinone, menaquinones, vitamin A, vitamin $B_1$, vitamin $B_2$, vitamin $B_3$, vitamin $B_5$, vitamin $B_6$, vitamin $B_7$, vitamin $B_9$, vitamin $B_{12}$, vitamin C, vitamin D, vitamin $D_2$, vitamin $D_3$, vitamin E, vitamin K, vitamin $V_i$ where V can be any letter from A to Z and i can be any integer between 1 and 100, and derivatives thereof.

In another embodiment of the invention, at least one component of Wolf's mineral is selected from the group consisting of: nitrilotriacetic acid, magnesium sulfate, sodium chloride, manganese sulfate, ferrous sulfate heptahydrate, cobalt nitrate, calcium chloride, zinc sulfate heptahydrate, hydrate copper sulfate, aluminum potassium sulfate dodecahydrate, boric acid, sodium molybdate, sodium selenite, sodium tungstate dihydrate, nickel chloride, and derivatives thereof.

In another embodiment of the invention, at least one component of yeast extract is selected from the group consisting of: i) at least one protein, ii) at least one nucleic acid, iii) at least one functional peptide, iv) glutathione, v) dextran, vi) mannan, vii) trehalose, viii) flavoring nucleotide, ix) B vitamin, x) biotin, x) at least one volatile aromatic compound, xi) calcium, xii) Phosphorus, xiii) Zinc, xiv) Iron, xv) Chromium, xvi) Potassium, xvii) Cobalt, xviii) Manganese, xix) Strontium, xx) Magnesium, and xxi) derivatives thereof.

In another embodiment of the invention, at least one component of Mineral elixir is selected from the group consisting of: nitrilotriacetic acid, $MgSO_4$, $MnSO_4$, NaCl, $FeSO_4$, $CoSO_4$, $CaCl_2$, $ZnSO_4$, $CuSO_4$, $KAl(SO_4)_2$, $H_3BO_3$, $Na_2MoO_4$, $NiCl_2$, $Na_2SeO_3$, and derivatives thereof.

In one embodiment of the invention, it is equivalent to say that the pre-growth, growth, and/or fed-batch medium/media does/do not comprise more than a certain quantity or concentration or number of at least one compound than to say that the pre-growth, growth, and/or fed-batch medium/media comprise(s) less than a certain quantity or concentration or number of at least one compound.

In one embodiment of the invention, the nanoparticle-producing cells are amplified or grown in the pre-growth and/or growth and/or fed-batch medium/media, preferentially in the pre-growth and/or growth medium/media and not in the fed-batch medium.

In one embodiment of the invention, the growth and/or pre-growth medium/media comprise(s) the growth and/or pre-growth medium/media either: i) without/before the fed-batch medium is inserted in the growth and/or pre-growth medium/media or ii) with/after the fed-batch medium is inserted in the growth and/or pre-growth medium/media.

In one embodiment of the invention, the fed-batch medium is the fed-batch medium or medium before it is inserted in the growth and/or pre-growth medium/media.

In another embodiment of the invention, the fed-batch medium is part of the pre-growth and/or growth medium/media after it is inserted in the growth and/or pre-growth medium/media.

In one embodiment of the invention, the parameters $C_{FEGS}$, $C_{FePGS}$, $C_{CGS}$, $C_{CPGS}$, $C_{NGS}$, $C_{NPGS}$, $\Delta_pH_{GS}$, and/or $\Delta pH_{PGS}$, exist or is/are measured in the pre-growth, growth and/or fed-batch medium/media.

In one embodiment of the invention, the parameters $Q_{GGS}$, $Q_{GPGS}$, $N_{SSGS}$, and $N_{SSPGS}$, as well as the situation during which the growth medium is supplemented by a fed-batch medium, whereas the pre-growth medium is not supplemented by such medium, occur during, at the beginning or at the end of the pre-growth and/or growth step(s).

In one embodiment of the invention, the derivative thereof is a derivative of at least one first compound selected in the group consisting of: i) a second compound differing from the at least one first compound by at least one different atom or functional group, preferentially originating from the at least one first compound after transformation of the at least one first compound, preferentially with at least one atom or functional group in common with the at least one first compound, ii) a non-hydrated form of the at least one first compound, iii) a hydrated form of the at least one first compound, iv) a reduced form of the at least one first compound, v) an oxidized form of the at least one first compound, vi) an acidic form of the at least one first compound, vii) a basic form of the at least one first compound, viii) a crystalline or solid form of the at least one first compound, ix) a soluble or solubilized form of the at least one first compound, and x) a salt of the at least one first compound.

The invention relates to the method according the invention, wherein the growth step differs from the pre-growth step by at least one property selected from the group consisting of:

i) a ratio $C_{FeGS}/C_{FePGS}$ that is larger than $10^{-5}$, $10^{-3}$, 1, 10, $10^3$ or $10^5$, where $C_{FeGS}$ and $C_{FePGS}$ are concentrations in iron or iron source of the growth medium and pre-growth medium, respectively, ii) a ratio $C_{CGS}/C_{CPGS}$ that is larger than $10^{-5}$, $10^{-3}$, 1, 10, $10^3$ or $10^5$, where $C_{CGS}$ and $C_{CPGS}$ are the concentrations in carbon or carbon source of the growth medium and pre-growth medium, respectively, iii) a ratio $C_{NGS}/C_{NPGS}$ that is larger than $10^{-5}$, $10^{-3}$, 1, 10, $10^3$ or $10^5$, where $C_{NGS}$ and $C_{NPGS}$ are the concentrations in nitrogen or nitrogen source of the growth medium and pre-growth medium, respectively, iv) a ratio $\Delta_pH_{GS}/\Delta pH_{PGS}$ that is lower than $10^{10}$, $10^5$, $10^3$, $10^2$, 1, 0.5 or 0.1, where $\Delta_{pHGS}$ and $\Delta pH_{PGS}$ are the pH variations of the growth medium and pre-growth medium, respectively, v) a ratio $Q_{GGS}/Q_{GPGS}$ that is larger than $10^{10}$, $10^5$, $10^3$, $10^2$, 1, 0.5 or 0.1, where $Q_{GGS}$ and $Q_{GPGS}$ are quantities of gas, oxygen or air brought in or bubbled through the growth medium and pre-growth medium, respectively, vi) a ratio $N_{SSGS}/N_{SSPGS}$ that is lower than $10^{-5}$, $10^{-3}$, 1, 10, $10^3$ or $10^5$, where $N_{SSGS}$ and $N_{SSPGS}$ are numbers of sub-steps of the growth step and numbers of sub-steps of the pre-growth step, respectively, where two sub-steps are separated by each other by a transfer of nanoparticle-producing cells from a first sub-step, preferentially associated to the growth of nanoparticle-producing cells in a first volume, to a second sub-step, preferentially associated to the growth of nanoparticle-producing cells in a second volume, and vii) the growth medium is supplemented by a fed-batch medium, whereas the pre-growth medium is not supplemented by such medium.

The invention also relates to the method according to the invention, wherein the pre-growth and/or growth and/or fed-batch medium/media comprise(s), preferentially per kilogram or liter of pre-growth and/or growth and/or fed-batch medium/media, less than:

i) $10^3$% in mass or volume, or 1% in mass or volume, or $10^{-2}$% in mass or volume, or $5.10^{-3}$% in mass or volume, or $10^3$ gram, or $10^2$ gram, or 10 gram, or $10^{10}$ mL, or $10^5$ mL, or $10^3$ mL, or 10 mL, or 5 mL, or 1 mL, or 0.5 mL, or $10^{-5}$ mL, or $10^3$ mol, or 10 mol, or 1 mol, or $10^{-5}$ mol, or $10^{-8}$ mol, or $10^{-9}$ mol, or $10^{-10}$ mol of vitamins, preferentially Wolf's vitamins, or chemical components selected from the group consisting of: folic acid, folates, pyridoxine, Pyridoxine HCl, pyridoxamine, pyridoxal, riboflavin, biotin, thiamine, thiamine HCl, nicotinic acid, pantothenic acid, calcium pantothenate, inositol, p-Aminobenzoic acid, amino benzoic acid, thiotic acid, all-trans-Retinol, Retinals, alternative provitamin A-functioning Carotenoids including all-trans-beta-carotene, Niacin, Niacinamide, Nicotinamide, riboside, cyanocobalamin, hydroxocobalamin, methylcobalamin, adenosylcobalamin, ascorbic acid, cholecalciferol, ergocalciferol, tocopherols, tocotrienols, phylloquinone, menaquinones, vitamin A, vitamin B1, vitamin B2, vitamin B3, vitamin B5, vitamin B6, vitamin B7, vitamin B9, vitamin B12, vitamin C, vitamin D, vitamin D2, vitamin D3, vitamin E, vitamin K, vitamin Vi where V can be any letter from A to Z and i can be any integer between 1 and 100, and derivatives thereof, ii) 1, 5, 6, 10 or 20 different vitamins, preferentially Wolf's vitamins, or chemical components, which are selected from the group consisting of: folic acid, folates, pyridoxine, Pyridoxine HCl, pyridoxamine, pyridoxal, riboflavin, biotin, thiamine, thiamine HCl, nicotinic acid, pantothenic acid, calcium pantothenate, inositol, p-Aminobenzoic acid, amino benzoic acid, thiotic acid, all-trans-Retinol, Retinals, alternative provitamin A-functioning Carotenoids including all-trans-beta-carotene, Niacin, Niacinamide, Nicotinamide, riboside, cyanocobalamin, hydroxocobalamin, methylcobalamin, adenosylcobalamin, ascorbic acid, cholecalciferol, ergocalciferol, tocopherols, tocotrienols, phylloquinone, menaquinones, vitamin A, vitamin B1, vitamin B2, vitamin B3, vitamin B5, vitamin B6, vitamin B7, vitamin B9, vitamin B12, vitamin C, vitamin D, vitamin D2, vitamin D3, vitamin E, vitamin K, vitamin Vi where V can be any letter from A to Z and i can be any integer between 1 and 100, and derivatives thereof, iii) $10^3$% in mass or volume, or 10% in mass or volume, or 1% in mass or volume, or $10^{-2}$% in mass or volume, or $10^{-5}$% in mass or volume, or $10^3$ gram, or 10 gram, or 1 gram, or $10^5$ mL, or $10^3$ mL, or 10 mL, or 1 mL, or $10^{-3}$ mL, or $10^3$ mol, or 10 mol, or 1 mol, or $10^{-3}$ mol, or $10^{-7}$ mol, or $10^{-8}$ mol, or $10^{-10}$ mol of minerals, preferentially Wolf's mineral or mineral elixir, or chemical components selected from the group consisting of: nitrilotriacetic acid, magnesium sulfate, sodium chloride, manganese sulfate, ferrous sulfate, ferrous sulfate heptahydrate, cobalt nitrate, calcium chloride, zinc sulfate, zinc sulfate heptahydrate, copper sulfate, hydrate copper sulfate, aluminum potassium sulfate, aluminum potassium sulfate dodecahydrate, boric acid, sodium molybdate, sodium selenite, sodium tungstate, sodium tungstate dihydrate, nickel chloride, EDTA, $MgSO_4$, $MnSO_4$, NaCl, $FeSO_4$, $CoSO_4$, $CaCl_2$, $ZnSO_4$, $CuSO_4$, $KAl(SO_4)_2$, $H_3BO_3$, $Na_2MoO_4$, $NiCl_2$, $Na_2SeO_3$, and derivatives thereof, iv) 1, 3, 7 or 10 different components of minerals, preferentially Wolf's mineral or mineral elixir, or chemical components selected from the group consisting of: nitrilotriacetic acid, magnesium sulfate, sodium chloride, manganese sulfate, ferrous sulfate, ferrous sulfate, ferrous sulfate heptahydrate, cobalt nitrate, calcium chloride, zinc sulfate, zinc sulfate heptahydrate, copper sulfate, hydrate copper sulfate, aluminium potassium sulfate, aluminum potassium sulfate dodecahydrate, boric acid, sodium molybdate, sodium selenite, sodium tungstate, sodium tungstate dihydrate, nickel chloride, EDTA, $MgSO_4$, $MnSO_4$, NaCl, $FeSO_4$, $CoSO_4$, $CaCl_2$, $ZnSO_4$, $CuSO_4$, $KAl(SO_4)_2$, $H_3BO_3$, $Na_2MoO_4$, $NiCl_2$, $Na_2SeO_3$, and derivatives thereof, v) $10^{-50}$ gram, or $10^{-10}$ gram, or $10^{-5}$ gram, or 0.005 gram, or $10^{-1}$ gram, or 1 gram, or 10 gram, or $10^5$ gram, or $10^{-50}$ M, or $10^{-8}$ M, or $10^{-3}$ M, or $10^{-1}$ M, or 1 M, or $10^3$ M of at least one component of yeast extract or at least one compound originating from yeast extract selected from the group of compounds consisting of: at least one protein, at least one nucleic acid, at least one functional peptide, glutathione, dextran, mannan, trehalose, flavoring nucleotide, B vitamin, biotin, at least one volatile aromatic compound, calcium, Phosphorus, Zinc, Iron, Chrome or Chromium, Potassium, Cobalt, Manganese, Strontium, Magnesium, and derivatives thereof, vi) 1, 2, 3, 5, 10, 15, 20 or 50 different components of yeast extract or compounds originating from yeast extract selected from the group consisting of: at least one protein, at least one nucleic acid, at least one functional peptide, glutathione, dextran, mannan, trehalose, flavoring nucleotide, B vitamin, biotin, at least one volatile aromatic compound, calcium, Phosphorus, Zinc, Iron, Chrome or Chromium, Potassium, Cobalt, Manganese, Strontium, Magnesium, and derivatives thereof, vii) $10^{-50}$ gram, or $10^{-10}$ gram, or $10^{-3}$ gram, or 0.01 gram, or 1 gram, or 5 gram, or 10 gram or $10^5$ gram, or $10^{-50}$ M, or $10^{-20}$ M, or $10^{-8}$ M, or $10^{-3}$ M, or $10^{-1}$ M, or 1 M, or 10 M, or $10^3$ M of at least one component of peptone or at least one compound originating from peptone selected from the group consisting of: ashes, proteins, sucrose, stachyose, raffinose, neutral detergent fiber, Ethereal Extract, and derivatives thereof, viii) 1, 3, 5, 10, 20 or 50 different components of peptone or compounds originating from peptone selected from the group consisting of: ashes, proteins, sucrose, stachyose, raffinose, neutral detergent fiber, Ethereal Extract, and derivatives thereof, ix) $10^{-50}$, $10^{-10}$, $10^{-5}$, 0.001, $10^{-1}$, 1, 10, $10^3$ or $10^5$ gram of EDTA, x) $10^{-50}$, $10^{-10}$, $10^{-5}$, 0.001, $10^{-1}$, 1, 10, $10^3$ or $10^5$ gram of at least one amino acid, xi) 1, 3, 5, 10, 20 or 50 different amino acids, xii) 1, 5, 7, 12, 15, 20 or 50 different CMR, toxic or cytotoxic compounds selected from the group consisting of: nitrilotriacetic acid, manganese sulfate, cobalt nitrate, zinc sulfate, copper sulfate, aluminum potassium sulfate, boric acid, sodium molybdate, sodium selenite, sodium tungstate, nickel chloride, and derivatives thereof, xiii) 1, 2, 5, 10, 50 or 100 different chemical elements or heavy metal selected in the group consisting of: cadmium, lead, arsenic, mercury, cobalt, vanadium, nickel, lithium, antimony, and copper, and derivatives thereof, xiv) $10^{-50}$, $10^{-10}$, $10^{-5}$, $10^{-1}$, 1, 10, $10^3$ or $10^5$ gram of at least one chemical element or heavy metal selected in the group consisting of: cadmium, lead, arsenic, mercury, cobalt, vanadium, nickel, lithium, antimony, and copper, and derivatives thereof, xv) $10^{-50}$, $10^{-10}$, $10^{-5}$, $10^{-1}$, 1, 10, $10^3$ or $10^5$ gram of at least one CMR, toxic or cytotoxic compound selected from the group consisting of: nitrilotriacetic acid, manganese sulfate, cobalt nitrate, zinc sulfate, copper sulfate, aluminum potassium sulfate, boric acid, sodium molybdate, sodium selenite, sodium tungstate, nickel chloride, and any derivative thereof, and/or xvi) $10^{-50}$, $10^{-10}$, $10^{-5}$, 0.01, $10^{-1}$, 1, 10, $10^3$ or $10^5$ gram of peptone.

The invention also relates to the method according to the invention, wherein at least one compound of the pre-growth and/or growth medium/media has a concentration $C_2$ or a concentration $C_{total}=C_1+C_2$, wherein:

$C_1$ is a concentration of the at least one compound of the pre-growth and/or growth medium/media not consumed by the nanoparticle-producing cells, $C_2$ is a concentration of the at least one compound of the pre-growth and/or growth medium/media consumed by nanoparticle-producing cells, $C_1$ and/or $C_2$ is/are preferentially measured or separated or differentiated by using a method that enables isolating the at least one compound consumed by the nanoparticle-producing cells from the at least one compound not consumed by the nanoparticle-producing cells, such as centrifugation or tangential filtration, and $C_1$ and/or $C_2$ is/are preferentially measured or considered at the beginning, during or at the end of the pre-growth and/or growth step(s).

In one embodiment of the invention, one compound of the pre-growth and/or growth medium/media consumed by nanoparticle-producing cells is one compound that is comprised in the nanoparticle cells, preferentially when nanoparticle-producing cells consume such compound.

In another embodiment of the invention, one compound of the pre-growth and/or growth medium/media not consumed by nanoparticle-producing cells is one compound that is comprised outside of the nanoparticle cells, preferentially when nanoparticle-producing cells do not consume such compound.

In one embodiment, a method is used to separate consumed and non-consumed compounds. This method preferentially separates whole bacteria from the pre-growth and/or growth medium/media that do(does) not comprise such bacteria. This method can be centrifugation or filtration, preferentially tangential filtration, or a method that enables separating whole bacteria from liquid medium, based on a separation between elements of low size and/or low weight comprised in the pre-growth and/or growth medium/media and elements of large size and/or large weight in whole bacteria.

The invention also relates to the method according to the invention, wherein the concentration of at least one compound comprised in the fed-batch medium, preferentially, iron, iron source, carbon, carbon source, nitrogen, and/or nitrogen source, is larger than $10^{-6}$ µM, 1 µM, and/or $10^6$ µM.

The invention also relates to the method according to the invention, wherein the pre-growth, growth, and/or fed-batch medium/media do(does) not comprise the at least one compound at a concentration that affects the growth of nanoparticle-producing cells and/or nanoparticle production, and/or wherein the pre-growth, growth, and/or fed-batch medium/media are(is) substantially free of the at least one compound, wherein the at least one compound is selected from the group consisting of: 1) Wolf's Vitamin or a medium that comprises more than half of the total number of different components of Wolf's vitamin, 2) one component of Wolf's vitamin, 3) folic acid, 4) pyridoxine, 5) riboflavin, 6) biotin, 7) thiamin, 8) nicotinic acid, 9) pantothenic acid, 10) vitamin $B_{12}$, 11) amino benzoic acid, 12) thiotic acid, 13) Wolf's mineral or a medium that comprises more than half of the total number of different components of Wolf's mineral, 14) nitrilotriacetic acid, 15) magnesium sulfate, 16) sodium chloride, 17) manganese sulfate, 18) ferrous sulfate heptahydrate, 19) cobalt nitrate, 20) calcium chloride, 21) zinc sulfate heptahydrate, 22) hydrate copper sulfate, 23) aluminum potassium sulfate dodecahydrate, 24) boric acid, 25) sodium molybdate, 26) sodium selenite, 27) sodium tungstate dihydrate, 28) yeast extract or a medium that comprises more than half of the total number of different components of yeast extract, 29) equivalent of yeast extract or a medium that comprises more than half of the total number of different components of the equivalent of yeast extract, 30) 1, 2 or 5 protein(s) originating from or comprised in yeast extract, 31) 1, 2 or 5 nucleic acid(s) originating from or comprised in yeast extract, 32) 1, 2 or 5 peptide(s) or functional peptide(s) originating from or comprised in yeast extract, 33) glutathione, 34) dextran, 35) mannan, 36) trehalose, 37) flavoring nucleotide originating from or comprised in yeast extract, 38) B vitamin, 39) biotin, 40) 1, 2 or 5 volatile aromatic compound(s) originating from or comprised in yeast extract, 41) Chromium, 42) Cobalt, 43) Strontium, 44) nickel chloride, 45) or a medium that comprises more than half of the total number of different components of mineral elixir, 46) $MnSO_4$, 47) NaCl, 48) $FeSO_4$, 49) $CoSO_4$, 50) $CaCl_2$, 51) $ZnSO_4$, 52) $CuSO_4$, 53) $KAl(SO_4)_2$, 54) $H_3BO_3$, 55) $Na_2MoO_4$, 56) $NiCl_2$, 57) $Na_2SeO_3$, 58) peptone or a medium that comprises more than half of the total number of different components of peptone, 59) one component of peptone, 60) 1, 2 or 5 protein(s) originating from or comprised in peptone, 61) a sugar originating from or comprised in peptone, 62) one amino acid originating from or comprised in peptone, 63) ashes originating from or comprised in peptone, 64) one fiber originating from or comprised in peptone, 65) one CMR agent, 66) boric acid, 67) one amino acid, 68) alanine, 69) arginine, 70) asparagine, 71) aspartic acid, 72) cysteine, 73) glutamine, 74) glutamic acid, 75) glycine, 76) histidine, 77) isoleucine, 78) leucine, 79) lysine, 80) methionine, 81) phenylalanine, 82) proline, 83) serine, 84) threonine, 85) tryptophan, 86) tyrosine, 87) valine, 88) one cytotoxic or toxic compound, 89) manganese sulfate, 90) copper sulfate, 91) aluminum potassium sulfate, 92) boric acid, 93) sodium tungstate, 94) one heavy metal different from iron, 95) Titanium, 96) Vanadium, 97) Manganese, 98) Nickel, 99) Copper, 100) Zinc, 101) Gallium, 102) Germanium, 103) Arsenic, 104) Zirconium, 105) Niobium, 106) Molybdenum, 107) Technetium, 108) Ruthenium, 109) Rhodium, 110) Palladium, 111) Silver, 112) Cadmium, 113) Indium, 114) Tin, 115) Tellurium, 116) Lutetium, 117) Hafnium, 118) Tantalum, 119) Tungsten, 120) Rhenium, 121) Osmium, 122) Iridium, 123) Platinum, 125) Gold, 126) Mercury, 127) Thallium, 128) Lead, 129) Bismuth, 130) Polonium, 131) Astatine, 132) Lanthanum, 133) Cerium, 134) Praseodymium, 135) Neodymium, 136) Promethium, 137) Samarium, 138) Europium, 139) Gadolinium, 140) Terbium, 141) Dysprosium, 142) Holmium, 143) Erbium, 144) Thulium, 145) Ytterbium, 146) Actinium, 147) Thorium, 148) Protactinium, 149) Uranium, 150) Neptunium, 151) Plutonium, 152) Americium, 153) Curium, 154) Berkelium, 155) Californium, 156) Einsteinium, 157) Fermium, 158) Nobelium, 159) Radium, 160) Lawrencium, 161) Rutherfordium, 162) Dubnium, 163) Seaborgium, 164) Bohrium, 165) Hassium, 166) Meitnerium, 167) Darmstadtium, 168) Roentgenium, 169) Copernicium, 170) Elements 113-118, 171) Helium, 172) Lithium, 173) Beryllium, 174) Bore, 175) Fluor, 176) Aluminum, 177) Silicon, 178) Argon, 179) Scandium, 180) Chrome, 181) Nickel, 182) Copper, 183) Selenium, 184) Brome, 185) Krypton, 186) Rubidium, 187) Yttrium, 188) Sn, 189) Antimony, 190) Iodine, 191) Xenon, 192) Cesium, 193) Barium, 194) Lutecium, 195) Astate, 196) Radon, 197) Francium, 198) Mendelevium, 199) Mount, 200) Ununbium, 201) Ununtrium, 202) Ununquadium, 203) Ununpentium, 204) Ununhexium, 205) Ununseptium, 206) Ununoctium, 207) salts of these compounds 1) to 206), and 208) derivatives thereof.

The invention also relates to the method according to the invention, wherein the concentration of the compound that affects the growth of nanoparticle-producing cells and/or nanoparticle production, is a concentration in the pre-growth, growth and/or fed-batch medium/media that is: i) larger than 1 pico-Molar, 1 micro-Molar, 1 mili-Molar, $10^{-50}$ M, $10^{-10}$ or $10^{-5}$ M, or ii) larger than $10^{-50}$, $10^{-10}$, $10^{-5}$ or $10^{-3}$ gram of compound per liter of pre-growth, growth and/or fed-batch medium/media.

In one embodiment of the invention, the concentration of the compound that affects the growth of nanoparticle-producing cells and/or nanoparticle production, is a concentration in the pre-growth, growth and/or fed-batch medium/media that is: i) smaller than $10^{50}$, 1, $10^{-5}$, $10^{-6}$ or $10^{-9}$ M, or ii) smaller than $10^{10}$, 1, $10^{-10}$ or $10^{-20}$ gram of compound per liter of pre-growth, growth and/or fed-batch medium/media.

The invention relates to the method according to the invention, wherein the growth medium and/or fed-batch medium/media is/are supplemented by a fed-batch medium and:

i) the fed-batch medium has a pH that is lower, preferentially by at least $10^{-5}$, 0.1, 0.5, 1, 2, 3 or 5 pH unit(s), than a pH of the pre-growth and/or growth medium/media, and/or ii) the concentration of at least one of the chemical elements, preferentially selected from the group consisting of: a) the phosphorous or phosphate source, b) the potassium source, c) the magnesium source, d) the iron source, e) the vitamin source, f) the calcium source, g) $KH_2PO_4$, h) $MgSO_4$, i) $FeCl_3$, j) thiamine, k) $CaCl_2$, and l) derivatives thereof, is larger in the fed-batch medium than in the pre-growth and/or growth medium/media, preferentially by a factor of at least $10^{-50}$, $10^{-10}$, 0, 1.1, 5, 10 or $10^3$.

In one embodiment, the above conditions i) and ii) are verified by considering the pH and concentration of at least one compound:
  i) before the fed-batch medium has been inserted in the pre-growth and/or growth medium/media for the fed-batch medium, and/or
  ii) before, during or after the fedbatch medium has been inserted in the pre-growth and/or growth medium/media for the pre-growth and/or growth medium/media.

The invention also relates to the method according to the invention, wherein:
  the nanoparticle-producing cells are magnetotactic bacteria, and/or
  the nanoparticles are magnetosomes.

In another embodiment of the invention, the nanoparticles are the nanoparticle-producing cells of high purity.

In another embodiment of the invention, the nanoparticles are high purity nanoparticles, preferentially high purity iron oxide based nanoparticles, where high purity nanoparticles are preferentially nanoparticles that comprise less than 100, 99, 90, 50, 20, 10, 1 or 0.1% in mass or number of atoms selected in the group consisting of: cadmium, lead, arsenic, mercury, cobalt, vanadium, nickel, lithium, antimony, copper and derivatives, where high purity iron oxide based nanoparticles are preferentially high purity nanoparticles that comprise more than 1, 50, 90, 93 or 99% in number of atoms or mass of iron and/or oxygen and/or iron oxide.

The invention also relates to the method according to the invention, wherein the pre-growth and/or growth medium/media comprise(s) a source of calcium, a source of carbon, a source of nitrogen, a source of phosphate or phosphorous, a source of sulfur, a source of iron, a source of vitamin, and a source of calcium, and:
  the concentration of the source of carbon in the pre-growth and/or growth medium/media is larger, preferentially by a factor of at least 0, 0.5, 1.1, 2, 4, 10 or 100, than the concentrations of at least one compound selected from the group consisting of: the source of phosphate or phosphorous, the source of sulfur, the source of vitamin, and the source of calcium in the pre-growth and/or growth medium/media, and/or
  the concentration of the source of nitrogen in the pre-growth and/or growth medium/media is larger, preferentially by a factor of at least 0, 0.5, 1.1, 2, 4, 10 or 100, than the concentrations of at least one compound selected from the group consisting of: the source of phosphate or phosphorous, the source of sulfur, the source of vitamin, and the source of calcium in the pre-growth and/or growth medium/media.

The invention also relates to the method according to the invention, further comprising a step of storing, amplifying, preparing, or inserting in the pre-growth and/or growth and/or fed-batch medium/media a bank of nanoparticle-producing cells, where such bank is preferentially stored, amplified, prepared in a bank medium that preferentially comprises at least $10^{-50}$, $10^{-10}$, $10^{-1}$, 0, 1, 5, 10, 50, 70, 90 or 99%, preferentially in number of compounds, of the same compounds as those of the pre-growth and/or growth and/or fed-batch medium/media, and preferentially at least one compound that is different from that of the pre-growth and/or growth and/or fed-batch medium/media, such as a vitamin, a mineral, a chelating agent, sucrose, and/or a cryo-protectant that is/are: i) not in the pre-growth and/or growth and/or fed-batch medium/media or ii) at a lower concentration in the pre-growth and/or growth and/or fed-batch medium/media than in the bank medium.

In one embodiment of the invention, the bank of nanoparticle-producing cells is a master, working or research cell bank of the nanoparticle-producing cells. In some cases, such bank comprises more than 1, 10, $10^3$, $10^{10}$ or $10^{20}$ nanoparticle-producing cell(s), preferentially per milliliter or liter of pre-growth and/or growth and/or fed-batch medium. In some other cases, such bank comprises less than $10^{100}$, $10^{50}$, $10^{20}$, $10^{10}$ or $10^3$ nanoparticle-producing cell(s).

In another embodiment of the invention, the cell bank is an assembly of at least one cell that is used to start the amplification of the nanoparticle-producing cells in the pre-growth and/or growth and/or fed-batch medium.

In one embodiment of the invention, the cell bank is prepared in the same or similar conditions as those of the pre-growth and/or growth step(s).

In another embodiment of the invention, the cell bank is prepared by bubbling or inserting a gas in the bank medium that comprises a low oxygen concentration, preferentially less than 50, 10 or 1% of oxygen, preferentially relatively to the volume of the bank medium.

The invention relates to the method according to the invention, further comprising a purifying step for obtaining high purity iron oxide based nanoparticle(s), preferentially starting from nanoparticles that are isolated from the nanoparticle-producing cells obtained at the end of the growth step, the purifying step preferentially comprising removal at least one impurity(ies) from the nanoparticle(s) produced in the growth step using at least one heating step in which the temperature of the nanoparticles according to the invention, which are preferentially produced in the growth step or essentially in the growth step, have a temperature that is increased to a temperature T and is then maintained at $T_i$ during a heating time $t_{hi}$, which is preferentially comprised between 1 second and 20 years, where $T_i$ is preferentially comprised between 50° C. and 700° C.

In one embodiment of the invention, $T_i$ is larger than −273, −100, −50, 0, 1, 10, 20, 50, 100, 200, 500, 700 or $10^{3}$° C.

In one embodiment of the invention, $T_i$ is smaller than $10^{20}$, $10^{10}$, $10^5$, $10^3$, 100, 50, 10, 0, −10 or −50° C.

In still another embodiment of the invention, $T_i$ is between 10 and $10^5$, 50 and $10^4$, 100 and $10^3$, 150 and 700, or between 200 and 500° C.

In one embodiment of the invention, $t_{hi}$ is larger than $10^{-50}$, $10^{-10}$, $10^{-5}$, $10^{-1}$, 1, 10, $10^2$, $10^3$, $10^5$ or $10^{10}$ second(s).

In another embodiment of the invention, $t_{hi}$ is lower than $10^{100}$, $10^{50}$, $10^{10}$, $10^5$, $10^3$, 10, 5, 2 or, 1 second.

In still another embodiment of the invention, $t_{hi}$ is comprised between $10^{-5}$ seconds and 1 year, 1 second and 20 years, 1 second and 1 year, 1 second and 1 month, 1 second and 1 week, 1 second and day, or between 1 second and 1 hour.

In one embodiment of the invention, the time to increase the temperature to T preferentially from an initial temperature that preferentially corresponds to the temperature of the nanoparticles when they are inserted in the equipment used to heat them, is lower, preferentially by a factor of at least 1.1, 5, 10 or $10^3$, than $t_{hi}$.

In another embodiment of the invention, the time to increase the temperature to $T_i$, is larger, preferentially by a factor of at least 1.1, 5, 10 or $10^3$, than $t_{hi}$.

In one embodiment of the invention, iron oxide based nanoparticles are nanoparticles that comprise more than 1%, 50%, 70%, 90% or 99%, preferentially in mass of iron oxide, preferentially without considering in this percentage coating or excipient material.

The invention also relates to nanoparticle-producing cells of high purity preferentially obtained by the method according to the invention, the nanoparticle-producing cells of high purity comprising more than $10^{-10}$, 1, 5, 10, 50, 75, 80, 90, 95, 99 or 99.9% of:
i) iron based on a ratio $M_{FeC}/M_{MC}$, where $M_{FeC}$ is the mass of iron in the nanoparticle-producing cells of high purity and $M_{MC}$ is the mass of iron and metals or metalloids other than iron in the nanoparticle-producing cells of high purity,
ii) iron and at least one other metal than iron selected in the group consisting of: Sodium, Magnesium, Aluminum, Potassium, Calcium, Scandium, Titanium, Chromium, Manganese, Zinc, Gallium, Strontium, Yttrium, Zirconium, Niobium, Molybdenum, Technetium, Indium, Cesium, Barium, Lanthanum, Cerium, Praseodymium, Neodymium, Samarium, Europium, Gadolinium, Terbium, Dysprosium, Holmium, Erbium, Thulium, Lutetium, Hafnium, Rhenium, and Tungstate, based on a ratio of $M_1/M_2$, where $M_1$ is the mass in the high purity iron oxide nanoparticle(s) of iron and of at least one other metal selected in the above group, and $M_2$ is the mass of all metals comprised in the high purity iron oxide nanoparticle(s), and/or
iii) iron and at least one other non-metal selected in the group consisting of: Hydrogen, Carbon, Nitrogen, Phosphorus, Sulfur, Fluorine, Chlorine, Bromine, Iodine, Helium, Neon, Argon, Krypton, Xenon, Radon, and Oxygen, based on a ratio $M_3/M_4$, where $M_3$ is the mass in the high purity iron oxide nanoparticle(s) of iron and of at least one other metal selected in the above group and $M_4$ is the mass of all chemical elements comprised in the high purity iron oxide nanoparticle(s).

The invention also relates to nanoparticle-producing cells of high purity or high purity iron oxide based nanoparticle(s) obtained by amplifying or growing nanoparticle-producing cells in a pure medium that comprises less than 1, $10^{-3}$, $10^{-6}$ or $10^{-9}$% of at least one heavy metal selected in the group consisting of: Cobalt, Manganese, Zinc, Nickel, Silver, Aluminum, Arsenic, Barium, Cadmium, Chrome, Copper, Molybdate, lead, Antimony, Selenium, Silica, Titan, Thallium, mercury, vanadium, gold, iridium, osmium, rhodium, ruthenium, platinum, lithium, antimony, Tin, Tungsten, and derivatives thereof, where this percentage is based on the ratio $C_{FeM}/C_{MM}$, where $C_{FeM}$ is the concentration of iron in the pure medium and $C_{MM}$ is the concentration of iron and metals or metalloids other than iron in the pure medium.

The invention also relates to high purity iron oxide based nanoparticle(s) preferentially obtained by the method according to the invention, the high purity iron oxide based nanoparticle(s) comprising more than $10^{40}$, 1, 5, 10, 50, 75, 80, 90, 93, 95, 99 or 99.9% of:
i) iron based on a ratio of $M_{FeN}/M_{Mn}$, where $M_{FeN}$ is the mass of iron in the high purity iron oxide nanoparticle(s) and $M_{MN}$ is the mass of iron and metals or metalloids other than iron in the high purity iron oxide nanoparticle(s),
ii) iron and at least one other metal than iron selected in the group consisting of: Sodium, Magnesium, Aluminum, Potassium, Calcium, Scandium, Titanium, Chromium, Manganese, Zinc, Gallium, Strontium, Yttrium, Zirconium, Niobium, Molybdenum, Technetium, Indium, Cesium, Barium, Lanthanum, Cerium, Praseodymium, Neodymium, Samarium, Europium, Gadolinium, Terbium, Dysprosium, Holmium, Erbium, Thulium, Lutetium, Hafnium, Rhenium, and Tungstate, based on a ratio of $M_1/M_2$, where $M_1$ is the mass in the high purity iron oxide nanoparticle(s) of iron and of at least one other metal selected in the above group, and $M_2$ is the mass of all metals comprised in the high purity iron oxide nanoparticle(s), and/or
iii) iron and at least one other non-metal selected in the group consisting of: Hydrogen, Carbon, Nitrogen, Phosphorus, Sulfur, Fluorine, Chlorine, Bromine, Iodine, Helium, Neon, Argon, Krypton, Xenon, Radon, and Oxygen, based on a ratio $M_3/M_4$, where $M_3$ is the mass in the high purity iron oxide nanoparticle(s) of iron and of at least one other metal selected in the above group and $M_4$ is the mass of all non-metals comprised in the high purity iron oxide nanoparticle(s).

The invention also relates to the nanoparticle-producing cells of high purity according to the invention and/or the high purity iron oxide based nanoparticle(s) according to the invention, wherein the metals or metalloids other than iron in the high purity iron oxide nanoparticle(s) and/or nanoparticle-producing cells of high purity are selected in the group consisting of: Sodium, Magnesium, Aluminum, Potassium, Calcium, Scandium, Titanium, Chromium, Manganese, Zinc, Gallium, Strontium, Yttrium, Zirconium, Niobium, Molybdenum, Technetium, Indium, Cesium, Barium, Lanthanum, Cerium, Praseodymium, Neodymium, Samarium, Europium, Gadolinium, Terbium, Dysprosium, Holmium, Erbium, Thulium, Lutetium, Hafnium, Rhenium, and Tungstate, at least 5 different metals or metalloids, and derivatives thereof.

The invention also relates to the high purity iron oxide based nanoparticle(s) according to the invention, wherein the high purity iron oxide based nanoparticles are magnetosomes.

The invention also relates to a composition comprising the high purity iron oxide based nanoparticles according to the invention.

The invention also relates to the nanoparticle-producing cells of high purity, also designated as highly pure nanoparticle-producing cells, according to the invention, wherein highly pure nanoparticle-producing cells are magnetotactic bacteria.

The invention also relates to a composition comprising the highly pure nanoparticle-producing cells according to the invention.

The invention also relates to a composition comprising highly pure nanoparticle-producing cells and high purity iron oxide nanoparticles preferentially obtained by the method according to the invention, wherein:

the highly pure nanoparticle-producing cells comprise more than 0, 1, 10, 50, 70, 90, 95 or 99% of:
i) iron based on a ratio $M_{FeC}/M_{MFe}$, where $M_{Fe}c$ is the mass of iron in the highly pure nanoparticle-producing cells and $M_{MC}$ is the mass of iron and metals or metalloids other than iron in the highly pure nanoparticle-producing cells,
ii) iron and at least one other metal than iron selected in the group consisting of: Sodium, Magnesium, Aluminum, Potassium, Calcium, Scandium, Titanium, Chromium, Manganese, Zinc, Gallium, Strontium, Yttrium, Zirconium, Niobium, Molybdenum, Technetium, Indium, Cesium, Barium, Lanthanum, Cerium, Praseodymium, Neodymium, Samarium, Europium, Gadolinium, Terbium, Dysprosium, Holmium, Erbium, Thulium, Lutetium, Hafnium, Rhenium, and Tungstate, based on a ratio of $M_1/M_2$, where $M_1$ is the mass in the high purity iron oxide nanoparticle(s) of iron and of at least one other metal selected in the above group, and $M_2$ is the mass of all metals comprised in the high purity iron oxide nanoparticle(s), and/or iii) iron and at least one other non-metal selected in the group consisting of: Hydrogen, Carbon, Nitrogen, Phosphorus, Sulfur, Fluorine, Chlorine, Bromine, Iodine, Helium, Neon, Argon, Krypton, Xenon, Radon, and Oxygen, based on a ratio $M_3/M_4$, where $M_3$ is the mass in the high purity iron oxide nanoparticle(s) of iron and of at least one other non-metal selected in the above group and $M_4$ is the mass of all non-metallic elements comprised in the high purity iron oxide nanoparticle(s), and the high purity iron oxide based nanoparticle(s) comprise more than 0, 1, 10, 50, 75, 93, 99 or 99.9% of:

i) iron based on a ratio of $M_{FeN}/M_{MN}$, where M is the mass of iron in the high purity iron oxide nanoparticle(s) and $M_{MN}$ is the mass of iron and metals or metalloids other than iron in the high purity iron oxide nanoparticle(s), ii) iron and at least one other metal than iron selected in the group consisting of: Sodium, Magnesium, Aluminum, Potassium, Calcium, Scandium, Titanium, Chromium, Manganese, Zinc, Gallium, Strontium, Yttrium, Zirconium, Niobium, Molybdenum, Technetium, Indium, Cesium, Barium, Lanthanum, Cerium, Praseodymium, Neodymium, Samarium, Europium, Gadolinium, Terbium, Dysprosium, Holmium, Erbium, Thulium, Lutetium, Hafnium, Rhenium, and Tungstate, based on a ratio of $M_1/M_2$, where $M_1$ is the mass in the high purity iron oxide nanoparticle(s) of iron and of at least one other metal selected in the above group, and $M_2$ is the mass of all metals comprised in the high purity iron oxide nanoparticle(s), and/or iii) iron and at least one other non-metal selected in the group consisting of: Hydrogen, Carbon, Nitrogen, Phosphorus, Sulfur, Fluorine, Chlorine, Bromine, Iodine, Helium, Neon, Argon, Krypton, Xenon, Radon, and Oxygen, based on a ratio $M_3/M_4$, where $M_3$ is the mass in the high purity iron oxide nanoparticle(s) of iron and of at least one other non-metal selected in the above group and $M_4$ is the mass of all non-metallic elements comprised in the high purity iron oxide nanoparticle(s).

The invention also relates to a composition comprising highly pure nanoparticle-producing cells and/or high purity iron oxide nanoparticles, wherein:

the nanoparticle-producing cells of high purity comprise more than 0, $10^{-50}$, $10^{-10}$, $10^{-5}$, $10^{-2}$, 1, 5, 10, 25, 50, 75, 90, 95, 99 or 99% of:

i) iron based on a ratio $M_{FeC}/M_{MC}$, where $M_{FeC}$ is the mass of iron in the nanoparticle-producing cells of high purity and $M_{MC}$ is the mass of iron and metals or metalloids other than iron in the nanoparticle-producing cells of high purity, ii) iron and at least one other metal than iron selected in the group consisting of: Sodium, Magnesium, Aluminum, Potassium, Calcium, Scandium, Titanium, Chromium, Manganese, Zinc, Gallium, Strontium, Yttrium, Zirconium, Niobium, Molybdenum, Technetium, Indium, Cesium, Barium, Lanthanum, Cerium, Praseodymium, Neodymium, Samarium, Europium, Gadolinium, Terbium, Dysprosium, Holmium, Erbium, Thulium, Lutetium, Hafnium, Rhenium, and Tungstate, based on a ratio of $M_1/M_2$, where $M_1$ is the mass in the high purity iron oxide nanoparticle(s) of iron and of at least one other metal selected in the above group, and $M_2$ is the mass of all metals comprised in the high purity iron oxide nanoparticle(s), and/or iii) iron and at least one other non-metal selected in the group consisting of: Hydrogen, Carbon, Nitrogen, Phosphorus, Sulfur, Fluorine, Chlorine, Bromine, Iodine, Helium, Neon, Argon, Krypton, Xenon, Radon, and Oxygen, based on a ratio $M_3/M_4$, where $M_3$ is the mass in the high purity iron oxide nanoparticle(s) of iron and of at least one other non-metal selected in the above group and $M_4$ is the mass of all non-metallic elements comprised in the high purity iron oxide nanoparticle(s), and the high purity iron oxide based nanoparticle(s) comprise more than 0, $10^{-50}$, $10^{-10}$, $10^{-5}$, $10^{-3}$, $10^{-1}$, 0, 1, 5, 10, 25, 50, 75, 93, 95, 99 or 99.9% of:

i) iron based on a ratio of $M_{FeN}/M_{MN}$, where M is the mass of iron in the high purity iron oxide nanoparticle(s) and $M_{MN}$ is the mass of iron and metals or metalloids other than iron in the high purity iron oxide nanoparticle(s), ii) iron and at least one other metal than iron selected in the group consisting of: Sodium, Magnesium, Aluminum, Potassium, Calcium, Scandium, Titanium, Chromium, Manganese, Zinc, Gallium, Strontium, Yttrium, Zirconium, Niobium, Molybdenum, Technetium, Indium, Cesium, Barium, Lanthanum, Cerium, Praseodymium, Neodymium, Samarium, Europium, Gadolinium, Terbium, Dysprosium, Holmium, Erbium, Thulium, Lutetium, Hafnium, Rhenium, and Tungstate, based on a ratio of $M_1/M_2$, where $M_1$ is the mass in the high purity iron oxide nanoparticle(s) of iron and of at least one other metal selected in the above group, and $M_2$ is the mass of all metals comprised in the high purity iron oxide nanoparticle(s), and/or iii) iron and at least one other non-metal selected in the group consisting of: Hydrogen, Carbon, Nitrogen, Phosphorus, Sulfur, Fluorine, Chlorine, Bromine, Iodine, Helium, Neon, Argon, Krypton, Xenon, Radon, and Oxygen, based on a ratio $M_3/M_4$, where $M_3$ is the mass in the high purity iron oxide nanoparticle(s) of iron and of at least one other non-metal selected in the above group and $M_4$ is the mass of all non-metallic elements comprised in the high purity iron oxide nanoparticle(s), wherein the nanoparticle-producing cells of high purity and/or the high purity iron oxide based nanoparticle(s) are preferentially obtained by cultivating the nanoparticle-producing cells in a growth medium, which is substantially free of at least one metal or non-metal or comprises less than 10 M, or 1 M, or $10^{-1}$ M, or $10^{-3}$ M, or $10^{-6}$ M, or 1 nano-Molar of at least one metal or non-metal, wherein the at least one metal or non-metal is selected in the group consisting of: 1) cadmium, 2) lead, 3) arsenic, 4) mercury, 5) cobalt, 6) vanadium, 7) nickel, 8) lithium, 9) antimony, 10) copper, 11) Valadium, 12) Molybdate, 13) Selenium, 14) Baryum, 15) Chrome, 16) Strontium, 17) a radioactive chemical element, 18) Beryllium, 19) Rubidium, 20) Ruthenium, 21) Rhodium, 22) Palladium, 23) Promethium, 24) Ytterbium, 25) Tantalum, 26) Osmium, 27) Iridium, 28) Bismuth, 29) Polonium, 30) Francium, 31) Radium, 32) Actinium, 33) Thorium, 34) Protactinium, 35) Uranium, 36) Neptunium, 37) Plutonium, 38) Americium, 39) Curium, 40) Berkelium, 41) Californium, Einsteinium, 42) Fermium, 43) Mendelevium, 44) Nobelium, 45) Lawrencium, 46) Rutherfordium, 47) Dubnium, 48) Seaborgium, 49) Bohrium, 50) Hassium, 51) Meitnerium, 52) Darmstadtium, 53) Roentgenium, 54) Copernicium, 55) Nihonium, 56) Flerovium, 57) Moscovium, 58) Livermorium, 59) Astatine, 60) Tennessine, 61) Oganesson, and 62) derivatives thereof.

In one embodiment of the invention, the nanoparticle-producing cells of high purity and/or the high purity iron oxide based nanoparticle(s) are obtained by cultivating and/or amplifying the nanoparticle-producing cells in:

a) the pre-growth growth and/or growth medium/media, and/or b) a medium that does not comprise or does not comprise at a concentration that affects the growth of the nanoparticle-producing cells, at least one metal or metalloid other than iron preferentially selected in the group consisting of: Cobalt, Manganese, Zinc, Nickel, Silver, Aluminum, Arsenic, Barium, Cadmium, Chrome, Copper, Molybdate, lead, Antimony, Selenium, Silica, Titan, Thallium, mercury, vanadium, gold, iridium, osmium, rhodium, ruthenium, platinum, lithium, antimony, Tin, Tungsten, and derivatives thereof.

The invention also relates to the nanoparticle-producing cells of high purity according to the invention, and/or the high purity iron oxide based nanoparticle(s) preferentially obtained from the nanoparticle-producing cells of high purity according to the invention, wherein:

the nanoparticle-producing cell(s) of high purity is/are magnetotactic bacterium/bacteria, and/or the high purity iron oxide nanoparticles is/are magnetosome(s).

The invention also relates to a composition, a medical device, a drug, a preparation, a suspension, a cosmetic composition, a plant composition, a biological composition, a mineral composition, and/or a nanoparticle composition, comprising the nanoparticle-producing cells of high purity according to the invention and/or the high purity iron oxide nanoparticle(s) according to the invention.

The invention also relates to the nanoparticle-producing cells of high purity preferentially comprising more than 1, 25, 50, 75, 90 or 99% of iron based on a ratio $M_{FeC}/M_{MC}$, where $M_{FeC}$ is the mass of iron in the nanoparticle producing cells of high purity and $M_{MC}$ is the mass of iron and metals or metalloids other than iron in the nanoparticle-producing cells of high purity and/or the high purity iron oxide based nanoparticle(s) preferentially comprising more than 1, 10, 50, 75, 93 or 99% of iron based on a ratio of $M_{FeN}/M_{MN}$, where $M_{FeN}$ is the mass of iron in the high purity iron oxide nanoparticle(s) and $M_{MN}$ is the mass of iron and metals or metalloids other than iron in the high purity iron oxide nanoparticle(s), wherein the nanoparticle-producing cells of high purity and/or the high purity iron oxide based nanoparticle(s) are preferentially obtained by cultivating the nanoparticle-producing cells in a growth medium, which is substantially free of metals selected in the group consisting of: cadmium, lead, arsenic, mercury, cobalt, vanadium, nickel, lithium, antimony, and copper. The term "substantially free" herein refers to substances that are not intentionally added to the medium but could be present as impurities.

In some cases, $M_{FeN}/M_{MN}$ and/or $M_{FeN}/M_{MN}$ can be smaller than 100, 99, 95, 90, 50, 25, 10, 5 or 1%.

The invention also relates to a method, preferentially the method according to the invention, for producing high purity iron oxide nanoparticles using nanoparticle-producing cells amplified in a pre-growth step followed by a growth step, wherein:

a) the pre-growth step is characterized by at least one of the following properties:

a1) it comprises at least one sub-step i, during which nanoparticle-producing cells are amplified in a volume $V_{PGSi}$ comprising a pre-growth medium, a2) $V_{PGSi}$ does not vary by more than 1, 10, 50, 80, 90 or 99% between the beginning and the end of the sub-step i;

a3) i is preferentially comprised between 1 and 5, 1 and 10, or between 1 and 1000;

a4) $V_{PGSi+1}/V_{PGSi}$ is comprised between 1.001 and 1000 or between 1.1 and 50;

a5) each sub-step i lasts for a length of time comprised between 1 second and 1 year, 1 minute and 1 month, 10 minutes and 1 week, or between 60 minutes and 3 days;

a6) at least one sub-step i lasts for more than 1 second or 1 hour;

a7) the temperature of the pre-growth medium of at least one sub-step is comprised between 10 and 60° C., 20 and 50° C., or between 30 and 40° C.;

a8) The concentration of oxygen or air or compressed air in the pre-growth medium decreases:

from: a8i) an oxygen, air, or compressed air partial pressure that is preferentially larger than 50 mbar, most preferentially equal to 210 mbar, at the beginning of at the least one sub-step i, or a8ii) an oxygen or air or compressed air percentage in volume relative to the maximum volume occupied by oxygen, air, or compressed air, in saturated pre-growth medium, which is preferentially equal to a percentage comprised between 25 and 100% at the beginning of the at least one sub-step i, or a8iii) an oxygen or air or compressed air volume relative to the volume of the pre-growth medium, which is preferentially comprised between 5 to 25% at the beginning of the at least one sub-step i, down to: a8iv) an oxygen, air, or compressed air partial pressure that is preferentially lower than 100 mbar, most preferentially equal to 0 mbar, at the end of the at least one sub-step i, or a8v) an oxygen or air or compressed air percentage in volume relative to the maximum volume occupied by oxygen, air, or compressed air, in saturated pre-growth medium, which is preferentially equal to a percentage comprised between 0 and 50%, at the end of the at least one sub-step i, or a8vi) an oxygen or air or compressed air volume relative to the volume of the pre-growth medium, which is preferentially equal to 0 to 10% at the end of the at least one sub-step i.

a9) The quantity of oxygen or air or compressed air brought to the Volume VPGS1 during at least one sub-step i of the pre-growth step is lower than 100 liters, 1000 mL or 100 mL of oxygen or air or compressed air per minute, preferentially during at least 0, 1, 5, 10 or 50% in time of the whole duration of the at least one sub-step i;

a10) The pre-growth medium is agitated at a speed comprised between 0 and 100 rotations per minute or between 0 and $10^3$ meter per minute, where this speed is preferentially that of at least one compound, whether in liquid, gaseous, or solid state, of the pre-growth medium, during the whole or part of sub-step i;

a11) the pH of the pre-growth medium is not maintained at a fixed pH, preferentially by not adding to the pre-growth medium a fed-batch medium preferentially comprising a source of iron or another medium than the pre-growth medium preferentially comprising a source of iron;

a12) the pH of the pre-growth medium varies by more than $10^{-5}$, $10^{-1}$, 0.5 or 1 pH unit between the beginning and the end of the at least one sub-step i, preferentially from a minimum value that is preferentially lower than 7 to a maximum value that is preferentially larger than 7.

a13) the pH of the pre-growth medium is maintained at a pH comprised between 3 and 11 or between 6 and 8 by adding to the pre-growth medium a fed-batch medium comprising less than $10^5$, $10^3$, $10^2$, 10 or 2 μM of iron or source of iron;

a14) the pre-growth medium comprises a total concentration in at least one of iron, iron source, carbon, carbon source, nitrogen, and nitrogen source, which vary(ies) by less than 100, 50, 20, 10, 5 or 1% between the beginning and the end of the at least one sub-step i;

a15) the pre-growth medium comprises a total concentration in iron or iron source that is lower than $10^5$ mM, $10^3$ mM, 10 mM, 2 mM of iron or iron source or $10^5$, $10^3$, $10^2$, 50, 10, 5, 2, 1, 0.5 g of iron or iron source per liter of pre-growth medium;

a16) the pre-growth medium comprises a total concentration in iron or iron source that is larger than $10^{-50}$ M or 1 pM of iron or iron source or 0.4 ng of iron or iron source per liter of pre-growth medium;

a17) the pre-growth medium comprises a total concentration in carbon or carbon source that is lower than 2 M or 260 g of carbon or carbon source per liter of pre-growth medium;

a18) the pre-growth medium comprises a total concentration in carbon or carbon source that is larger than 0.1 nM or 0.1 ng of carbon or carbon source per liter of pre-growth medium;

a19) the pre-growth medium comprises a total concentration in nitrogen or nitrogen source that is lower than 740 mM or 40 g of nitrogen or nitrogen source per liter of pre-growth medium;

a20) the pre-growth medium comprises a total concentration in nitrogen or nitrogen source that is larger than 0.1 nM or 0.1 ng of nitrogen or nitrogen source per liter of pre-growth medium;

a21) the quantity or concentration or percentage of carbon or carbon source consumed by the nanoparticle-producing cells between the beginning and the end of the at least one sub-step i is larger than:

$10^{-50}$, 0.01, 1 or 10 g of carbon or carbon source per liter of pre-growth medium or 1 mM of carbon or carbon source, and/or $10^{-10}$, 1, 50 or 75%, where this percentage is preferentially based on the ratio $(Q_{Cf}-Q_{Ci})/Q_{Ci}$, where $Q_{Cf}$ and $Q_{Ci}$ are the quantities of carbon contained in the pre-growth medium at the end and beginning of the at least one sub-step i, respectively, a22) the quantity or concentration or percentage of nitrogen or nitrogen source consumed by the nanoparticle-producing cells between the beginning and the end of the at least one sub-step i is larger than:

$10^{-50}$, 0.001, 1 or 10 g of nitrogen or nitrogen source per liter of pre-growth medium or 0.1 mM of nitrogen or nitrogen source, and/or $10^{-10}$, 1, 50 or 75%, where this percentage is preferentially based on the ratio $(Q_{Nf}-Q_{Ni})/Q_{Ni}$, where $Q_{Nf}$ and $Q_{Ni}$ are the quantities of nitrogen contained in the pre-growth medium at the end and beginning of the at least one sub-step i, respectively, a23) the quantity or concentration or percentage of iron or iron source consumed by the nanoparticle-producing cells between the beginning and the end of the at least one sub-step i is larger than:

$10^{-10}$, 0.0001, 1, 10 or $10^{10}$ mg of iron or iron source per liter of pre-growth medium or 0.5 µM of iron or iron source, and/or $10^{-10}$, 1, 20, 50 or 75%, where this percentage is preferentially based on the ratio $(Q_{Fef}-Q_{Fei})/Q_{Fei}$, where $Q_{Fef}$ and $Q_{Fei}$ are the quantities of iron contained in the pre-growth medium at the end and beginning of the at least one sub-step i, respectively.

a24) the quantity of carbon, carbon source, nitrogen, nitrogen source, iron, and/or iron source consumed by the nanoparticle-producing cells between the beginning and the end of the at least one sub-step i is smaller than the total concentration in carbon, carbon source, nitrogen, nitrogen source, iron, and/or iron source of the pre-growth medium;

a25) the total concentration in carbon, carbon source, nitrogen, nitrogen source, iron, and/or iron source of the pre-growth medium does(do) not vary by more than 1, 10, 20, 50, 80 or 99% between the beginning and the end of the sub-step i;

a26) the concentration in carbon, carbon source, nitrogen, nitrogen source, iron, and/or iron source consumed by the nanoparticle-producing cells of increases by more than 1, 10, 20, 50, 80, 90 or 99% between the beginning and the end of the sub-step i; wherein such conditions preferentially result in nanoparticle-producing cell(s) having at least one of the following properties:

a27) the nanoparticle-producing cell(s) produce essentially no nanoparticles or the nanoparticle-producing cell(s) produce less than $10^{10}$, $10^5$, 1, $10^{-3}$ or $10^{-6}$ mg of nanoparticles per liter of pre-growth medium, where this quantity is preferentially the quantity of nanoparticles produced at the end of the at least one sub-step i or the difference between the quantity of nanoparticles produced at the end of the at least one sub-step i and the quantity of nanoparticles produced at the beginning of at least one sub-step i;

a28) the nanoparticle-producing cells, preferentially without being concentrated at the end of the at least one sub-step i, lead to an optical density, preferentially measured between 0 and $10^5$ nm, most preferentially at 565 nm, which is characterized by at least one of the following properties:

a28i) it varies within a range of optical densities comprised between $10^{-20}$ and $10^{20}$ or between 0.0001 and 40 during the at least one sub-step i of the pre-growth step;

a28ii) it increases by a factor of more than 0, 0.5, 1, 1.1, 5, 10, $10^3$ or $10^5$ between the beginning and the end of the at least one sub-step i, where this factor is preferentially the ratio between the optical density measured at the end of sub-step i and the optical density measured at the beginning of sub-step i;

a28iii) it increases by a factor of less than $10^{10}$, $10^5$, 2000, $10^3$, $10^2$, 10, 5, 2 or 1 between the beginning and the end of the at least one sub-step i;

a28iv) it has a maximum value at the end of the at least one sub-step i that is lower than $10^5$, $10^3$ or 100;

a28v) it has a minimum value at the beginning of the at least one sub-step i that is larger than 0, $10^{-50}$, $10^{-10}$, 0.0001, $10^{-3}$ or $10^{-1}$;

a29) the nanoparticle producing-cells are characterized by a doubling time or a duration for being multiplied in number by a factor of 2, preferentially during at least one sub-step i of the pre-growth step, which is:

a29i) larger than $10^{-50}$, $10^{-5}$, 1, 10, $10^2$ or $10^3$ minute(s);

a29ii) smaller than $10^3$, 10, 1 or 0.1 month; and/or a29iii) comprised between 1 second and 1 month or between 1 minute and 1 month;

b) a growth step comprising amplifying the nanoparticle-producing cell(s) originating from the pre-growth step and/or produced during the pre-growth step in at least one growth step, preferentially only one growth step, most preferentially a number of growth steps smaller than the number of sub-steps i of the pre-growth step, wherein the at least one growth step is characterized by at least one property selected from the group consisting of:

b1) The nanoparticle-producing cells are amplified in a volume $V_{GS}$ comprising a growth medium;

b2) $V_{GS}$ is larger, preferentially by a factor of at least 0, 1, 1.1, 5, 10 or $10^3$ than the volume of at least one sub-step i of the pre-growth step;

b3) $V_{GS}$ is equal to: $V_{GS0}+V_{FB}$, where $V_{GS0}$ is the volume comprising the growth medium at the beginning of the growth step and $V_{FB}$ is the volume of fed-batch medium that is added to the growth medium during the growth step;

b4) $V_{GS}$ varies by more than $10^{-3}$, $10^{-1}$, 1, 5, 10, 25, 50 or 75% between the beginning and the end of the at least one growth step, preferentially by adding a fed-batch medium to the growth medium during the growth step;

b5) The volume comprising the growth medium at the beginning of the at least one growth step, $V_{GS0}$, is larger than the volume of fed-batch medium added to the growth medium during the at least one growth step, $V_{FB}$, preferentially by a factor of at least 0, 1, 1.1, 1.5, 2, 5, 10 or $10^3$;

b6) The duration of the at least one growth step is comprised between 1 minute and 1 month, preferentially between 40 hours and 15 days, b7) The duration of the at least one growth step is larger than the duration of the at least one sub-step i of the pre-growth step, preferentially by a factor of at least 0, 1, 1.1, 2, 5, 10 or $10^3$;

b8) The temperature of the growth medium is comprised between 10 and 60° C., 20 and 50° C., or between 30 and 40° C.;

b9) The concentration of oxygen or air or compressed air in the growth medium decreases:
from b9i) an oxygen, air, or compressed air partial pressure that is preferentially larger than 1 or 10 mbar, most preferentially equal to 210 mbar, at the beginning of at the least one growth step, or b9ii) an oxygen or air or compressed air percentage in volume relative to the maximum volume occupied by oxygen, air, or compressed air, in saturated growth medium, which is preferentially equal to a percentage comprised between 10 and 100%, at the beginning of the at least one growth step, or 9iii) an oxygen or air or compressed air volume relative to the volume of the growth medium, which is preferentially comprised between 1 to 25% at the beginning of the at least one growth step,
down to b9iv) an oxygen, air, or compressed air partial pressure that is preferentially lower than 50 or 500 mbar, most preferentially equal to 0 mbar, at the end of the at least one growth step, or b9v) an oxygen or air or compressed air percentage in volume relative to the maximum volume occupied by oxygen, air, or compressed air, in saturated growth medium, which is preferentially equal to a percentage comprised between 0 and 25%, at the end of the at least one growth step, or b9vi) an oxygen or air or compressed air volume relative to the volume of the pre-growth medium, which is preferentially comprised between 0 and 5% at the end of the at least one growth step.

b10) The quantity of oxygen or air or compressed air brought to the volume $V_{GS}$ during the whole growth step or part of the whole growth step is larger than 1, 10 or 200 mL of oxygen or air or compressed air per minute, preferentially during more that 1% in time of the whole duration of the growth step;

b11) The quantity of oxygen or air or compressed air brought to the volume $V_{GS}$ during the growth step is larger, preferentially by a factor of at least 0, 1, 1.1, 5, 10 or $10^3$ at the end than at the beginning of the growth step;

b12) The quantity of oxygen or air or compressed air brought to the volume $V_{GS}$ increases during the whole growth step or part of the whole growth step by an amount that is larger than $10^{-10}$, $10^{-5}$, 1, 10 or $10^5$ mL of oxygen or air or compressed air per minute;

b13) The growth medium is agitated at a higher speed than the growth medium, preferentially at a speed larger than 1, 10 or 100 rotations per minute or between 0 and $10^3$ meter per minute, where this speed is preferentially that of at least one compound, whether in liquid, gaseous, or solid state, of the growth medium, during the whole or part of the growth step;

b14) The pH of the growth medium varies less than the pH of the pre-growth medium or is maintained at a fixed pH comprised between 1 and 14 or between 6.5 and 7.5 or is prevented from varying by more than 0.1, 0.5 or 10 pH unit, preferentially by adding to the growth medium a fed-batch medium or another medium than the growth medium;

b15) The pH of the growth medium varies by less than 10, 0.5 or 0.1 pH unit between the beginning and the end of the growth step, preferentially from a minimum value that is preferentially lower than 7.5 to a maximum value that is preferentially larger than 6.5.

b16) The growth medium comprises a total concentration in carbon, carbon source, nitrogen, nitrogen source, iron, and/or iron source that vary(ies) by more than 0, $10^{-5}$, 1 or 50% between beginning and the end of the at least one growth step, b17) The growth medium comprises a total concentration in carbon or carbon source that is larger than $10^{-5}$ mM or 0.1 mM or $10^{-5}$ g or 0.01 g of carbon or carbon source per liter of growth medium;

b18) The growth medium comprises a total concentration in carbon or carbon source that is lower than $10^3$ M or 2 M or $10^3$ g or 180 g of carbon or carbon source per liter of growth medium;

b19) The growth medium comprises a total concentration in nitrogen or nitrogen source that is larger than $10^{-5\circ}$ mM or 0.01 mM or $5.10^{-10}$ g or 0.00005 g of nitrogen or nitrogen source per liter of growth medium;

b20) The growth medium comprises a total concentration in nitrogen or nitrogen source that is lower than $10^{10}$ mM or 111 mM or $10^5$ g or 6 g of nitrogen or nitrogen source per liter of growth medium;

b21) The growth medium comprises a total concentration in iron or iron source that is larger than $10^{-5}$ nM or 1 nM or $10^{-10}$ g or $3.10^{-7}$ g of iron or iron source per liter of growth medium;

b22) The growth medium comprises a total concentration in iron or iron source that is lower than $10^5$ or 1 mM or $10^5$ g or 0.3 g of iron or iron source per liter of growth medium;

b23) The quantity or concentration or percentage of carbon or carbon source consumed by the nanoparticle-producing cells between the beginning and the end of the at least one growth step is larger than:
$10^{-10}$, $10^{-5}$, 0.1, 1, 10 or $10^3$ g of carbon or carbon source per liter of growth medium or 1 mM of carbon or carbon or carbon source, and/or
$10^{-5\circ}$, $10^{-10}$, $10^{-5}$, $10^{-1}$, 1, 5, 10, 50 or 75%, where this percentage is based on the ratio $(Q_{Cf}-Q_{Ci})/Q_{Ci}$, where $Q_{Cf}$ and $Q_{Ci}$ are the quantities of carbon contained in the growth medium at the end and beginning of the at least one growth step, respectively, b24) the quantity or concentration or percentage of nitrogen or nitrogen source consumed by the nanoparticle-producing cells between the beginning and the end of the at least one growth step is larger than:

$10^{-10}$, $10^{-5}$, 0.01, 1 or 10 g of nitrogen or nitrogen source per liter of growth medium or 0.6 mM of nitrogen or nitrogen source, and/or $10^{-50}$, $10^{-10}$, $10^{-5}$, $10^{-1}$, 1, 5, 10, 50 or 75%, where this percentage is preferentially based on the ratio ($Q_{Nf}$-$Q_{Ni}$)/$Q_{Ni}$, where $Q_{Nf}$ and $Q_{Ni}$ are the quantities of nitrogen contained in the growth medium at the end and beginning of the at least one growth step, respectively, b25) the quantity or concentration or percentage of iron or iron source consumed by the nanoparticle-producing cells between the beginning and the end of the at least one growth step is larger than:

$10^{-10}$, $10^{-5}$, 0.01 or 1 mg of iron or iron source per liter of growth medium or 0.04 μM of iron or iron source, and/or $10^{-50}$, $10^{-10}$, $10^{-5}$, $10^{-1}$, 1, 5, 10, 50 or 75%, where this percentage is preferentially based on the ratio ($Q_{Fef}$-$Q_{Fei}$)/$Q_{Fei}$, where $Q_{Fef}$ and $Q_{Fei}$, are the quantities of iron contained in the growth medium at the end and beginning of the at least one growth step, respectively;

b26) The quantity of iron or iron source brought to the growth medium between the beginning and the end of the at least one growth step, preferentially by the fed-batch medium, is larger than $10^{-10}$ mg or 0.3 mg of iron or iron source per liter of growth medium or $10^{-3}$ μM or 1 μM of iron or iron source;

b27) The quantity of carbon or carbon source brought to the growth medium between the beginning and the end of the at least one growth step, preferentially by the fed-batch medium, is larger than $10^{-50}$, $10^{-10}$, $10^{-5}$ or 0.07 g of carbon or carbon source per liter of growth medium or larger than $10^{-10}$, $10^{-5}$, $10^{-3}$, 0.8, 1 or $10^3$ mM of carbon or carbon source;

b28) The quantity of nitrogen or nitrogen source brought to the growth medium between the beginning and the end of the at least one growth step, preferentially by the fed-batch medium, is larger than $10^{-10}$, 0.006 or 1 g of nitrogen or nitrogen source per liter of growth medium or 0.4 mM of nitrogen or nitrogen source;

b29) the quantity of carbon, carbon source, nitrogen, nitrogen source, iron, and/or iron source consumed by the nanoparticle-producing cells between the beginning and the end of the at least one growth step is smaller than the total concentration in carbon, carbon source, nitrogen, nitrogen source, iron, and/or iron source of the growth medium;

wherein such conditions preferentially result in nanoparticle-producing cell(s) having at least one of the following properties:

b30) the nanoparticle-producing cell(s) produce(s) nanoparticles or the nanoparticle-producing cell(s) produce more than $10^{-50}$, $10^{-10}$, 0.01 or 1 mg of nanoparticles per liter of growth medium, where this quantity is preferentially the quantity of nanoparticles produced at the end of the growth step or the difference between the quantity of nanoparticles produced at the end of the growth step and the quantity of nanoparticles produced at the beginning of the growth step;

b31) the nanoparticle-producing cells, preferentially without being concentrated at the end of the at least one growth step, lead to an optical density, preferentially measured between 0 and $10^4$ nm, most preferentially at 565 nm, which is characterized by at least one of the following properties:

b31i) the optical density at the end of the growth step is larger, preferentially by a factor of at least 0, 0.5, 1, 1.1, 1.5, 2, 5, 10 or $10^3$ than the optical density at the end of at least one sub-step i of the pre-growth step;

b3 lii) the optical density of the growth step varies within a range of optical density comprised between 0.001 and 300;

b3 liii) the optical density increases by a factor of more than 0, 0.5, 1, 1.1, 5, 10 or $10^3$ between the beginning and the end of the at least one growth step, where this factor is preferentially the ratio between the optical density measured at the end of the at least one growth step and the optical density measured at the beginning of the at least one growth step;

b31iv) the optical density increases by a factor of less than $10^{10}$, $10^4$ or 10 between the beginning and the end of the at least one growth step;

b31v) the optical density has a maximum value at the end of the at least one growth step that is smaller than $10^{10}$, $10^5$, 300 or 10;

b31vi) the optical density has a minimum value at the beginning of at least one growth step that is larger than $10^{-50}$, $10^{-10}$, 0.001 or 0.01; and/or b32) the nanoparticle-producing cells are characterized by a doubling time or a duration for being multiplied in number by a factor of 2, preferentially during the whole growth step or part of the whole growth step, which is b32i) larger than 1 minute;

b32ii) smaller than 1 month;

b32iii) comprised between 1 minute and 1 month; and/or b32iv) lower, preferentially by a factor of at least 1.1, than the doubling time of at least one sub-step i of the pre-growth step;

wherein preferentially the pre-growth, growth, and/or fed-batch medium/media does/do not comprise, preferentially as measured per liter of pre-growth, growth and/or fed-batch medium/media, more than: i) 1, 2, 3 or 6 different vitamins, ii) $10^{-9}$ mol of at least one vitamin, iii) $10^{-4}$ g of yeast extract, iv) $10^{-9}$ mol of at least one component of yeast extract, v) 1, 2, 5 or 10 components of yeast extract, vi) $10^{-5}$ g of peptone, vii) 1 or 2 different CMR agents, viii) 0.05 mg of at least one CMR agent, ix) 1, 2, or 5 different chelating agents, x) $10^{-8}$ mol of at least one chelating agent, xi) 1, 2 or 5 different amino acids, xii) 1 mg of at least one amino acid, xiii) 1, 2 or 5 different toxic or cytotoxic compounds, xiv) 1 mg of at least one toxic or cytotoxic compound, xv) 1, 3 or 7 different heavy metals different from iron, xvi) 1 mg of at least one heavy metal different from iron, xvii) more than 1, 2, 3, 4, 5, 6, 7, 8, 9, 10 metal(s) or chemical element(s) chosen among cadmium, lead, arsenic, mercury, cobalt, vanadium, nickel, lithium, antimony, and copper, xviii) 1 mg of cadmium, lead, arsenic, mercury, cobalt, vanadium, nickel, lithium, antimony, and/or copper, xix) 0.5 mL or $10^{-8}$ mol of Wolf's vitamin, xx) $10^{-9}$ mol of at least one component of Wolf's vitamin, xxi) 1, 2, 5 or 10 different components of Wolf's vitamin, xxii) 5 mL or $10^{-8}$ mol of Wolf's mineral, xxiii) $10^{-8}$ mol of at least one component of Wolf's mineral, xxiv) 1, 2, 5, 7, 10 or 15 different components of Wolf's mineral, xxv) $10^{-9}$ mol of mineral elixir, xxvi) $10^{-9}$ mol of at least one component of mineral elixir, and/or xxvii) 1, 2, 5, 10 or 14 different components of mineral elixir.

The invention also relates to the method according to the invention, wherein the end of the pre-growth and/or growth step(s) is/are characterized by at least one of the following properties:
  i) the optical density of the pre-growth and/or growth medium/media saturates or increases by less than 1 O.D. unit per hour of pre-growth and/or growth step(s);
  ii) the bio-mass of the pre-growth and/or growth medium/media saturates or increases by less than 1 g of nanoparticle-producing cells per hour of pre-growth and/or growth step(s);
  iii) the nanoparticle-producing cells stop producing nanoparticles or produce less than 0.01 mg of nanoparticles per hour of pre-growth and/or growth step(s);
  iv) the fed-batch medium is not anymore added to the pre-growth and/or growth medium/media; and
  v) oxygen is not anymore bubbled to the pre-growth and/or growth medium/media.

The invention also relates to the method according to the invention, wherein the beginning of the pre-growth and/or growth step(s) is/are characterized by at least one of the following properties:
  i) the optical density of the pre-growth and/or growth medium/media starts to increase, preferentially by more than 0.1 O.D. unit per day of pre-growth and/or growth step(s);
  ii) the bio-mass of the pre-growth and/or growth medium/media starts to increase, preferentially by more than 0.1 g of nanoparticle-producing cells per day of pre-growth and/or growth step(s);
  iii) the nanoparticle-producing cells start producing nanoparticles, preferentially more than 0.01 mg of nanoparticles per day of pre-growth and/or growth step(s);
  iv) the fed-batch medium is starts to be added to the pre-growth and/or growth medium/media;
  v) oxygen starts to be bubbled to the pre-growth and/or growth medium/media.

The invention also relates to the method according to the invention, wherein the pre-growth, growth, and/or fed-batch medium composition(s) is/are defined hereafter.

Preferentially, the pre-growth medium comprises at least 1, 2, 3, 4, 5, 6, or 7 of the following chemical element(s) or derivative(s), preferentially derivative(s) being or comprising a source of carbon, nitrogen, phosphate, manganese, potassium, calcium, vitamin, and/or chlorine: i) Na lactate or a source of carbon, preferentially at a concentration comprised between $10^{-20}$ or 0.0023 mol or gram of Na lactate or source of carbon per liter of pre-growth medium and 0.23 or $10^5$ mol or gram of Na lactate or source of carbon per liter of pre-growth medium, most preferentially at a concentration of 0.023±0.01 mol of Na lactate or source of carbon per liter of pre-growth medium, ii) ammonium chloride or source of nitrogen, preferentially at a concentration comprised between $10^{-20}$ or $7.4\ 10^{-4}$ mol or gram of ammonium chloride or source of nitrogen per liter of pre-growth medium and $7.4\ 10^{-2}$ or $10^5$ mol or gram of ammonium chloride or source of nitrogen per liter of pre-growth medium, most preferentially at a concentration of $(7.5\pm1).10^{-3}$ mol of ammonium chloride or source of nitrogen per liter of pre-growth medium, iii) $KH_2PO_4$ or source of potassium or source of phosphorous, preferentially at a concentration comprised between $10^{-20}$ or $1.55\ 10^{-5}$ mol or gram of $KH_2PO_4$ or source of potassium or source of phosphorous per liter of pre-growth medium and $1.55\ 10^{-3}$ or $10^5$ mol or gram of $KH_2PO_4$ or source of potassium or source of phosphorous per liter of pre-growth medium, most preferentially at a concentration of $(1.5\pm1).10^{-4}$ mol of $KH_2PO_4$ or source of potassium or source of phosphorous per liter of pre-growth medium, iv) $MgSO_4$ or source of magnesium, preferentially at a concentration comprised between $10^{-20}$ or $4.1.10^{-5}$ mol or gram of $MgSO_4$ or source of magnesium per liter of pre-growth medium and $4.1.10^{-3}$ or $10^5$ mol or gram of $MgSO_4$ or source of magnesium per liter of pre-growth medium, most preferentially at a concentration of $(4\pm1).10^{-4}$ mol of $MgSO_4$ or source of magnesium per liter of pre-growth medium, v) a source of iron or $FeCl_3$, preferentially at a concentration comprised between $10^{-20}$ or $2.10^{-7}$ mol or gram of $FeCl_3$ or source of iron per liter of pre-growth medium and $10^{-5}$ or $10^5$ mol or gram of $FeCl_3$ or source of iron per liter of pre-growth medium, most preferentially at a concentration of $(2\pm1)\ 10^{-6}$ mol of $FeCl_3$ or source of iron per liter of pre-growth medium, vi) thiamine or vitamin, preferentially at a concentration between $10^{-20}$ or $8.10^{-9}$ mol or gram of vitamin or thiamine per liter of pre-growth medium and $8.10^{-7}$ or $10^5$ mol or gram of vitamin or thiamine per liter of pre-growth medium, most preferentially at a concentration of $(8\pm2)\ 10^{-8}$ mol of vitamin or thiamine per liter of pre-growth medium, vii) $CaCl_2$ or source of calcium or chlorine, preferentially at a concentration between $10^{-20}$ or $10^{-5}$ mol or or gram of $CaCl_2$) or source of calcium or chlorine per liter of pre-growth medium and $10^{-3}$ or $10^5$ mol or gram of $CaCl_2$ or source of calcium or chlorine per liter of pre-growth medium, most preferentially at a concentration of $(1\pm0.8).10^{-4}$ mol of $CaCl_2$) or source of calcium or chlorine per liter of pre-growth medium.

Preferentially, the growth medium comprises, preferentially before adding the fed-batch medium to the growth medium, at least 1, 2, 3, 4, 5, 6, or 7 of the following chemical element(s) or derivative(s), preferentially derivative(s) being or comprising a source of carbon, nitrogen, phosphate, manganese, potassium, calcium, vitamin, and/or chlorine: i) Na lactate or a source of carbon, preferentially at a concentration comprised between $10^{-20}$ or 0.0014 mol or gram of Na lactate or source of carbon per liter of growth medium and 0.14 or $10^5$ mol or gram of Na lactate or source of carbon per liter of growth medium, most preferentially at a concentration of (0.014±0.01) mol of Na lactate or source of carbon per liter of growth medium, ii) ammonium chloride or source of nitrogen, preferentially at a concentration comprised between $10^{-20}$ or $4.1\ 10^{-4}$ mol or gram of ammonium chloride or source of nitrogen per liter of growth medium and $4.1\ 10^{-2}$ or $10^5$ mol or gram of ammonium chloride or source of nitrogen per liter of growth medium, most preferentially at a concentration of $(4.1\pm1).10^{-3}$ mol of ammonium chloride or source of nitrogen per liter of growth medium, iii) $KH_2PO_4$ or source of potassium or source of phosphorous, preferentially at a concentration comprised between $10^{-20}$ or $1.55\ 10^{-5}$ mol or gram of $KH_2PO_4$ or source of potassium or source of phosphorous per liter of growth medium and $1.55\ 10^{-3}$ or $10^5$ mol or gram of $KH_2PO_4$ or source of potassium or source of phosphorous per liter of growth medium, most preferentially at a concentration of $(1.5\pm1).10^{-4}$ mol of $KH_2PO_4$ per liter of growth medium, iv) $MgSO_4$ or source of magnesium, preferentially at a concentration comprised between $10^{-29}$ or $4.1.10^{-5}$ mol of $MgSO_4$ or source of magnesium per liter of growth medium and $4.1.10^{-3}$ or $10^5$ mol or gram of $MgSO_4$ or source of magnesium per liter of growth medium, most preferentially at a concentration of $(4\pm1).10^{-4}$ mol of $MgSO_4$ per liter of growth medium, v) a source of iron or $FeCl_3$, preferentially at a concentration comprised between $10^{-29}$ or $10^{-7}$ of $FeCl_3$ or source of iron per liter of growth medium and $10^{-5}$ or $10^5$ mol of $FeCl_3$ or source of iron per liter of growth medium, most preferentially at a concentration of $(2\pm1) \, 10^{-6}$ mol of $FeCl_3$ or source of iron per liter of growth medium, vi) thiamine or vitamin, preferentially at a concentration between $10^{-29}$ or $8.10^{-9}$ mol or gram of vitamin or thiamine per liter of growth medium and $8.10^{-7}$ or $10^5$ mol or gram of vitamin or thiamine per liter of growth medium, most preferentially at a concentration of $(8\pm2) \, 10^{-8}$ mol of vitamin or thiamine per liter of growth medium, vii) $CaCl_2$ or source of calcium or chlorine, preferentially at a concentration between $10^{-29}$ or $10^{-5}$ mol or gram of $CaCl_2$) or source of calcium or chlorine per liter of growth medium and $10^{-3}$ or $10^5$ mol or gram of $CaCl_2$ or source of calcium or chlorine per liter of growth medium, most preferentially at a concentration of $(1\pm0.8).10^{-4}$ mol of $CaCl_2$ or source of calcium or chlorine per liter of growth medium.

Preferentially, the fed-batch medium comprises, preferentially before being added to the growth medium, at least 1, 2, 3, 4, 5, 6, or 7 of the following chemical element(s) or derivative(s), preferentially derivative(s) being or comprising a source of carbon, nitrogen, phosphate, manganese, potassium, calcium, vitamin, and/or chlorine: i) lactic acid or a source of carbon, preferentially at a concentration comprised between $10^{-29}$ or $10^{-1}$ mol or gram of lactic acid or source of carbon per liter of fed-batch medium and 10 or $10^5$ mol or gram of lactic acid or source of carbon per liter of fed-batch medium, most preferentially at a concentration of $(1\pm0.5)$ mol of lactic acid or source of carbon per liter of fed-batch medium, ii) ammonia or source of nitrogen, preferentially at a concentration comprised between $10^{-29}$ or $2.8 \, 10^{-2}$ mol or gram of ammonia or source of nitrogen per liter of fed-batch medium and 2.8 or $10^5$ mol or gram of ammonia or source of nitrogen per liter of fed-batch medium, most preferentially at a concentration of $(2.8\pm1).10^{-1}$ mol of ammonia or source of nitrogen per liter of fed-batch medium, iii) $KH_2PO_4$ or a source of potassium or phosphorous, preferentially at a concentration comprised between $10^{-29}$ or $1.7 \, 10^{-3}$ mol of $KH_2PO_4$ or a source of potassium or phosphorous per liter of fed-batch medium and $1.7 \, 10^{-1}$ or $10^5$ mol or gram of $KH_2PO_4$ or a source of potassium or phosphorous per liter of fed-batch medium, most preferentially at a concentration of $(1.7\pm1).10^{-2}$ mol of $KH_2PO_4$ per liter of fed-batch medium, iv) $MgSO_4$ or a source of magnesium, preferentially at a concentration comprised between $10^{-29}$ or $2.10^{-4}$ mol or gram of $MgSO_4$ or a source of magnesium per liter of fed-batch medium and $2.10^{-2}$ or $10^5$ mol or gram of $MgSO_4$ or a source of magnesium per liter of fed-batch medium, most preferentially at a concentration of $(2\pm1).10^{-3}$ mol of $MgSO_4$ per liter of fed-batch medium, v) a source of iron or $FeCl_3$, preferentially at a concentration comprised between $10^{-20}$ or $10^{-4}$ mol or gram of $FeCl_3$ or source of iron per liter of fed-batch medium and $10^{-1}$ or $10^5$ mol or gram of $FeCl_3$ or source of iron per liter of fed-batch medium, most preferentially at a concentration of $(7\pm4) \, 10^{-3}$ mol of $FeCl_3$ or source of iron per liter of fed-batch medium, vi) thiamine or vitamin, preferentially at a concentration between $10^{-20}$ or $10^{-8}$ mol or gram of vitamin or thiamine per liter of fed-batch medium and $10^{-4}$ or $10^5$ mol or gram of vitamin or thiamine per liter of fed-batch medium, most preferentially at a concentration of $(2\pm1.5) \, 10^{-6}$ mol of vitamin or thiamine per liter of fed-batch medium, vii) $CaCl_2$ or source of calcium or chlorine, preferentially at a concentration between $10^{-20}$ or $10^{-5}$ of $CaCl_2$ mol or gram or source of calcium or chlorine per liter of fed-batch medium and $10^{-2}$ or $10^5$ mol or gram of $CaCl_2$ or source of calcium or chlorine per liter of fed-batch medium, most preferentially at a concentration of $(1\pm0.8).10^{-3}$ mol of $CaCl_2$ or source of calcium or chlorine per liter of fed-batch medium.

The invention also relates to the method according to the invention, wherein the pre-growth, growth, and/or fed-batch medium/media comprise(s) at least one of the sources selected from the group consisting of:
- a source of carbon selected from the group consisting of: at least one compound comprising at least one atom of carbon, lactic acid, Na lactate, lactic acid, acetate, glycolate, glucose, pyruvate, succinate, carbon dioxide, glycerol and combinations thereof, at a concentration preferentially comprised between 1 nM and 2 Mol/L;
- a source of iron selected from the group consisting of: at least one compound comprising at least one atom of iron, iron citrate, iron quinate, iron chloride, iron sulfate, FeCl3, and combinations thereof, at a concentration preferentially comprised between 1 nM and $2.10^{-3}$ Mol/L;
- a source of nitrogen selected from the group consisting of: at least one compound comprising at least one atom of nitrogen, nitrate salt, nitrogen gas, ammonium, ammonia, ammonium salt, urea, an amino acid, ammonia gas, and combinations thereof, at a concentration preferentially comprised between 1 nM and 4 Mol/L;
- a source of oxygen selected from the group consisting of: at least one compound comprising at least one atom of oxygen, oxygen or air or compressed air, preferentially in the form of a gas, the source of oxygen being in some cases bubbled or introduced to the growth medium, at a gas rate that is preferentially comprised between 5 mL of gas per minute and 50000 mL of gas per minute;
- a source of phosphate consisting of at least one compound comprising at least one atom of phosphate, at a concentration preferentially comprised between 1 nM and $2.10^{-1}$ Mol/L;
- a source of potassium consisting of at least one compound comprising at least one atom of potassium, at a concentration preferentially comprised between 1 nM and $2.10^{-1}$ Mol/L;
- a source of sulfur or sulfate consisting of at least one compound comprising at least one atom of sulfur or sulfate, at a concentration preferentially comprised between 1 nM and $4.10^{-1}$ Mol/L;
- a source of manganese consisting of at least one compound comprising at least one atom of manganese, at a concentration preferentially comprised between 1 nM and $4.10^{-1}$ Mol/L;
- a source of vitamin selected from the group consisting of: at least one compound comprising at least one vitamin, Biotin, Calcium, pantothenate, Folic acid, Inositol, Nicotinic acid, p-Aminobenzoic acid, Pyridoxine HCl, Riboflavin, Thiamine, Thiamine HCL and derivatives thereof and combinations thereof, at a concentration preferentially comprised between 1 nM and $10^{-4}$ Mol/L, and
- a source of calcium consisting of at least one compound comprising at least one atom of calcium, at a concentration preferentially comprised between 1 nM and $10^{-1}$ Mol/L.

In one embodiment of the invention, the source(s) of carbon, nitrogen, potassium, phosphorous, magnesium, calcium, vitamin, iron, oxygen, and/or chlorine comprise at least 1, 2, 5, 10 or $10^3$ atoms of carbon, nitrogen, potassium, phosphorous, magnesium, calcium, vitamin, iron, oxygen, and/or chlorine, preferentially within the chemical formula or molecule(s) or component(s) of these sources.

In still another embodiment of the invention, when a compound or quantity or element or property P1 is higher, longer, or larger than a compound or quantity or element or property P2, it means that that $P1=\alpha \cdot P2$, where $\alpha$ is preferentially a number or integer larger than 1, or $P1=\alpha+P2$, where $\alpha$ is preferentially a number or integer larger than 0.

In still another embodiment of the invention, when a compound or a quantity or element or property P1 is lower, shorter, or smaller than a compound or a quantity or element or property P2, it means that that P1=P2/oc, where c is preferentially a number or integer larger than 1, or $P1=P2-\alpha$, where $\alpha$ is preferentially a number or integer larger than 0.

In one embodiment of the invention, a CMR compound is a carcinogenic, mutagenic, and/or repro-toxic compound. In some cases, a carcinogenic compound is a compound that produces induces or is suspected to produce or induce a cancer, preferentially in a living organism or human. In some cases, a mutagenic compound is a compound that produces or induces or is suspected to produce or induce a mutation, modification, change in number or size of at least one gene, DNA, RNA, DNA strand, RNA strand, and/or nucleic acid, preferentially in a living organism or human. In some cases, a repro-toxic compound is a compound that produces or induces or is suspected to produce or induce a toxicity, mutation, modification, change of the reproductive organs, embryo, fetus, preferentially in a living organism or human.

In one embodiment of the invention, a toxic or cytotoxic compound is a compound that produces or induces or is suspected to produce or induce toxicity, death, loss of weight, damage towards organs, change in behavior, change in consumed food or water, necrosis, apoptosis, cellular internalization, change in number, shape and/or geometry of cell(s), preferentially in an individual or living organism.

In some cases, a compound is CMR or cytotoxic or toxic at a concentration that is larger than $10^{-6}$, $10^{-3}$, $10^{-1}$, 1, 10, $10^3$ or $10^6$ μM.

In some other cases, a compound is CMR or cytotoxic or toxic at a concentration that is lower than $10^{20}$, $10^6$, $10^3$, 10, 1, $10^{-1}$, $10^{-3}$ or $10^{-6}$ μM.

The invention relates to a method for producing high purity iron oxide nanoparticles using nanoparticle-producing cell(s), comprising:
i) a pre-growth step consisting in amplifying the nanoparticle-producing cell(s) in a pre-growth medium such that nanoparticle-producing cell(s) produce(s) essentially no nanoparticles, and
ii) a growth step consisting in amplifying the nanoparticle-producing cell(s) originating from the pre-growth step in a growth medium such that nanoparticle-producing cell(s) produce(s) nanoparticles.

The invention relates to a method for producing high purity iron oxide nanoparticles using nanoparticle-producing cell(s), comprising:
i) a pre-growth step consisting in amplifying the nanoparticle-producing cell(s) in a pre-growth medium such that nanoparticle-producing cell(s) produce(s) essentially no nanoparticles, and/or
ii) a growth step consisting in amplifying the nanoparticle-producing cell(s) originating from the pre-growth step in a growth medium such that nanoparticle-producing cell(s) produce(s) nanoparticles.

In one embodiment of the invention, the growth medium is supplemented by a fed-batch medium.

In one embodiment of the invention, the growth medium supplemented by the fed-batch medium is the growth medium.

In one embodiment of the invention, the growth medium has at least one property in common with the pre-growth and/or fed-batch medium.

In one embodiment of the invention, the growth medium and/or pre-growth medium comprise(s) at least one source selected in the group consisting of: i), a source of carbon or sodium or lactate, preferentially sodium lactate, ii) a source of ammonium, preferentially ammonium chloride, iii) a source of magnesium, preferentially magnesium sulfate, iv) a source of potassium, preferentially potassium phosphate, v) a source of vitamin vitamin, preferentially thiamin, vi) a source of calcium, preferentially calcium chloride, and vii) a source of iron, preferentially iron chloride. Each source is preferentially comprised in the growth and/or pre-growth medium at a concentration comprised between $10^{-6}$ and $10^3$, $10^{-3}$ and 100 mM, 0.01 and 10 mM, or between 0.1 and 10 mM.

In one embodiment of the invention, in the pre-growth medium and/or growth medium, the concentration of the vitamin and/or source of calcium and/or source of iron is smaller, by a factor of at least 0, 0.5, 1, 1.1, 1.2, 1.5, 5, 10, $10^3$ or $10^5$ than the concentration of the source of sodium and/or the source of ammonium and/or the source of magnesium and/or the source of potassium.

In one embodiment of the invention, the fed-batch medium comprises at least one source selected in the group consisting of: i), a source of carbon, preferentially lactic acid, ii), ammonia, iii) a source of potassium, preferentially potassium phosphate, iv) a source of magnesium, preferentially magnesium sulfate, v) a source of iron, preferentially iron chloride, vi) a source of vitamin, preferentially thiamine, vii) a source of calcium, preferentially calcium chloride, and viii) a source of iron, preferentially iron chloride. Each source is preferentially comprised in the growth and/or pre-growth medium at a concentration comprised between 0.001 and 100 mM, 0.01 and 10 mM, or between 0.1 and 10 mM.

In one embodiment of the invention, in the fed-batch medium, the concentration of the vitamin and/or source of calcium is smaller, by a factor of at least 0, 0.5, 1, 1.1, 1.2, 1.5, 5, 10, $10^3$ or $10^5$, than the concentration of the source of sodium and/or the source of ammonium and/or the source of magnesium and/or the source of potassium and/or source of iron.

In one embodiment of the invention, the nanoparticle(s) according to the invention is/are or comprise(s) assemblies of more than 1, 2, 5, 10, $10^3$, $10^5$, $10^{10}$, $10^{20}$, $10^{50}$ or $10^{100}$ nanoparticle(s), nanoparticles per liter of growth medium or nanoparticles per nanoparticle-producing cell. In some cases, iron oxide represents or is an assembly of more than 1, 10, $10^3$, $10^5$, $10^{10}$, $10^{20}$, $10^{50}$ or $10^{100}$ atom(s) of iron and/or more than 1, 10, $10^3$, $10^5$, $10^{10}$, $10^{20}$, $10^{50}$ or $10^{100}$ atom(s) of oxygen. In some other cases, the chemical element(s), and/or impurity(ies) comprised in the nanoparticles, are/is or represent(s) more than 1, 10, $10^3$, $10^5$, $10^{10}$, $10^{20}$, $10^{50}$ or $10^{100}$ chemical element(s), and/or impurity(ies) comprised in the nanoparticles.

In another embodiment of the invention, the nanoparticle(s) according to the invention is/are or comprise(s) assemblies of less than $10^{100}$, $10^{50}$, $10^{20}$, $10^{10}$, $10^5$, $10^3$, 100, 50, 10, 5 or 2 nanoparticle(s), nanoparticles per liter of growth medium or nanoparticles per nanoparticle-producing cell. In some cases, iron oxide represents or is an assembly of less than 1, 10, $10^3$, $10^5$, $10^{10}$, $10^{20}$, $10^{50}$ or $10^{100}$ atom(s) of iron and/or less than 1, 10, $10^3$, $10^5$, $10^{10}$, $10^{20}$, $10^{50}$ or $10^{100}$ atom(s) of oxygen. In still some other cases, the chemical element(s) and/or impurity(ies) comprised in the nanoparticles is/are or represent(s) less than $10^{100}$, $10^{50}$, $10^{20}$, $10^{10}$, $10^5$, $10^3$, 100, 50, 10, 5 or 2 chemical elements, and/or impurity(ies) comprised in the nanoparticles.

In one embodiment of the invention, at least one impurity is comprised in the nanoparticle.

In one embodiment of the invention, the high purity iron oxide nanoparticles comprise a low quantity of impurity(ies), for example when the method enables to obtain nanoparticles with a low quantity of impurity. In some cases, the nanoparticle(s) does/do not comprise at least one impurity or comprise(s) or comprise(s) less than $10^{50}$, $10^{20}$, $10^{10}$, $10^5$, $10^2$, 10, 5, 2, 5, 1, $10^{-2}$, $10^{-10}$, $10^{-20}$ or $10^{-50}$ impurity(ies) or impurity(ies) per gram of nanoparticles or gram of impurity(ies) per gram of nanoparticles. In some other cases, the percentage, preferentially in mass, of impurity(ies) comprised inside or at the surface of the nanoparticle(s) is lower than 100, 90, 80, 70, 60, 50, 30, 20, 10, 5, 1, 0.1 or 0.001%. According to the invention, this percentage of impurity(ies) can in some cases be defined as the ratio between the number of atoms, quantity, mass, or volume of impurity(ies) comprised in the nanoparticle(s) divided by the total number of atoms, quantity, mass, or volume of all chemical element(s) comprised in the nanoparticle(s). In some cases, all chemical element(s) comprised in the nanoparticle(s) can be the sum of the iron oxide, doping material, and impurity(ies), comprised in the nanoparticle(s). In still some other cases, the concentration of the impurity(ies) comprised inside or at the surface of the nanoparticle(s) is lower than $10^{50}$, $10^{30}$, $10^{10}$, $10^5$, $10^3$, 500, 100, 50, 10, 1, $10^{-1}$, $10^{-3}$, $10^{-5}$, $10^{-10}$ or $10^{-50}$ μg of impurity(ies) per gram of nanoparticle(s).

In another embodiment of the invention, the high purity iron oxide nanoparticles comprise a large quantity of impurity(ies), for example when the impurity(ies) is/are added or incorporated to the nanoparticles after the production of the nanoparticles by the method. In some cases, the nanoparticles comprise more than $10^{-50}$, $10^{-20}$, $10^{-10}$, $10^{-5}$, $10^{-2}$, 1, 2, 5, 10, $10^3$, $10^5$, $10^{10}$, $10^{20}$ or $10^{50}$ impurity(ies) or impurities per gram of nanoparticles or gram of impurity per gram of nanoparticles. In some cases, the nanoparticles comprise a large quantity of impurity(ies). In some cases, the percentage, preferentially in mass, of the impurity(ies) comprised inside or at the surface of the nanoparticle(s) is larger than $10^{-40}$, $10^{-20}$, $10^{-10}$, $10^{-5}$, $10^{-2}$, $10^{-1}$, 1, 5, 10, 25, 50, 75, 80 or 90%. In still some other cases, the concentration of impurity(ies) comprised inside or at the surface of the nanoparticle(s) is larger than $10^{-100}$, $10^{-50}$, $10^{-20}$, $10^{-10}$, $10^{-5}$, $10^{-3}$, $10^{-2}$, $10^{-1}$, 1, 10, 50, 100, $10^3$, $10^5$ or $10^{10}$ μg of impurity(ies) per gram of nanoparticle(s).

In some cases, the impurities can be the same impurities, i.e. preferentially impurities comprising the same chemical elements.

In some other cases, the impurities can be different impurities, i.e. preferentially impurities comprising at least one different chemical element.

In one embodiment of the invention, the chemical element(s) is selected from the group consisting of: actinide, actinium, aluminium, americium, antimony, argon, arsenic, astatine, barium, berkelium, beryllium, bismuth, bohrium, boron, bromine, caesium, calcium, californium, carbon, cerium, chlorine, chromium, cobalt, copernicum, cadmium, copper, curium, darmstadtium, dubnium, dysprosium, einsteinium, erbium, europium, fermium, fleovium, fluorine, francium, gadolinium, gallium, germanium, gold, hafnium, helium, hessium, holmium, hydrogen, indium, iodine, iridium, iron, krypton, lanthanide, lanthanum, lawrencium, lead, lithium, livermorium, lutetium, magnesium, manganese, meitherium, mendelevium, mercury, molybdenum, neodymium, neon, neptunium, nickel, niobium, nitrogen, nobelium, osmium, oxygen, palladium, phosphorus, platinum, plutonium, polonium, potassium, praseodymium, proctactinium, promethium, radium, radon, rhenium, rhodium, roentgenium, rubidium, ruthenium, rutherfordium, samarium, selenium, silicon, silver, sodium, strontium, sulphur, scandium, seaborgium, tellurium, terbium, thorium, thulium, tin, tantalum, technetium, thallium, titanium, tungsten, ununoctium, ununpentium, ununseptium, ununtrium, uranium, vanadium, xenon, ytterbium, yttrium, zinc, zirconium, and a combination of several of these chemical element(s).

The invention also relates to the method according to the invention, wherein the impurity(ies) is/are at least one chemical element different from iron, oxygen, and/or iron oxide.

The invention also relates to the method according to the invention, wherein the impurity is preferentially carbon or carbonaceous material.

In one embodiment of the invention, the carbonaceous material comprises at least one carbon atom, preferentially but not necessarily mixed or assembled with other chemical element(s) than carbon.

In still another embodiment of the invention, the carbon or carbonaceous material originates from, is produced by, or comes from nanoparticle-producing cell(s).

The invention also relates to the method according to the invention, wherein the nanoparticle(s) obtained by the method comprise(s) iron oxide, where the iron oxide has at least one of the following properties: i), it comprise at least one atom of iron and one atom of oxygen, ii), it forms a crystallized or mineral structure, iii), it can have the chemical formula $FeO$, $FeO_2$, $Fe_3O_4$, $Fe_4O_5$, $Fe_5O_6$, $Fe_5O_7$, $Fe_{25}O_{32}$, $Fe_{13}O_{19}$, $\alpha$-$Fe_2O_3$, $\beta$-$Fe_2O_3$, $\gamma$-$Fe_2O_3$, $\varepsilon$-$Fe_2O_3$, iv), it can be composed of wilstite, iron dioxide, magnetite, hematite, maghemite, v), it can be in the epsilon phase, alpha phase, beta phase, gamma phase, vi), it can be in various levels of oxidations, vii), it has the formula $Fe_\alpha O_\beta D_\gamma$, where $\alpha$, $\beta$ and/or $\gamma$ is/are coefficients, preferentially stoichiometric coefficients. In some cases, $\alpha$, $\beta$, and/or $\gamma$ is/are equal to 0, 1, 2, 3, 4, 5, 6, 7, 8, 9, 10, 11, 12, 13, 14, 15, 16, 18, 19 or 20. In some other cases, $\alpha$, $\beta$, and/or $\gamma$ is/are larger than 0, 1, 2, 3, 4, 5, 6, 7, 8, 9, 10, 11, 12, 13, 14, 15, 16, 18, 19 or 20. In still some other cases, $\alpha$, $\beta$, and/or $\gamma$ is/are lower than 0, 1, 2, 3, 4, 5, 6, 7, 8, 9, 10, 11, 12, 13, 14, 15, 16, 18, 19 or 20. In some other cases, D is the doping material of the nanoparticles. In some cases, the doping material can be selected from the group consisting of: Aluminum, antimonite, barium, chrome, copper, gold, manganese, silver, tin, titanium, and zinc.

In one embodiment of the invention, the iron oxide comprised in the nanoparticles is the predominant chemical element of the nanoparticle. In some cases, the high purity iron oxide nanoparticles can comprise a large quantity of iron oxide. In some cases, the percentage, preferentially in mass, of iron oxide comprised in the nanoparticle(s), is larger than $10^{-40}$, $10^{-20}$, $10^{-10}$, $10^{-5}$, $10^{-2}$, $10^{-1}$, 1, 5, 10, 25, 50, 75, 80, 90, 99 or 99.9%. According to the invention, this percentage of iron oxide can in some cases be defined as the ratio between the number of atoms, quantity, mass, or volume of iron oxide in the nanoparticle(s) divided by the total number of atoms, quantity, mass, or volume of all chemical element(s) comprised in the nanoparticle(s). In still some other cases, the concentration of iron oxide, comprised in the nanoparticle(s) is larger than $10^{-100}$, $10^{-50}$, $10^{-20}$, $10^{-10}$, $10^{-5}$, $10^{-3}$, $10^{-2}$, $10^{-1}$, 1, 10, 50, 100, $10^3$, $10^5$ or $10^{10}$ μg of iron oxide, per gram of nanoparticle(s).

In one embodiment of the invention, the high purity iron oxide nanoparticles comprise a low quantity of iron oxide, for example when the nanoparticles are treated and/or partly or fully destroyed and/or administered to an organism, or when the method does not enable to incorporate a large quantity of iron oxide in the nanoparticles. In some cases, the percentage, preferentially in mass, of iron oxide, comprised inside or at the surface of the nanoparticle(s), is lower than 100, 90, 80, 70, 50, 30, 10, 5, 1, 0.1 or 0.001%. In some other cases, the concentration of iron oxide, comprised in the nanoparticle(s) can be lower than $10^{50}$, $10^{30}$, $10^{10}$, $10^5$, $10^3$, 500, 100, 50, 10, 1, $10^{-1}$, $10^{-3}$, $10^{-5}$, $10^{-10}$, or $10^{-50}$ μg of iron oxide per gram of nanoparticle(s).

In another embodiment of the invention, the percentage, concentration, number of atoms, quantity, mass, or volume of iron oxide comprised in the nanoparticle(s) is larger, preferentially by a factor of 1.00001, 1.001, 1.1, 2, 5, 10, 50, $10^2$, $10^3$, $10^5$, $10^{10}$, $10^{20}$ or $10^{50}$, than the percentage, concentration, number of atoms, quantity, mass, or volume of impurity(ies) comprised in the nanoparticle(s).

In one embodiment of the invention, the iron oxide and/or impurity(ies) is/are comprised or inserted: i) inside the nanoparticle(s), ii) at the surface of the nanoparticle(s), iii) outside of the nanoparticle(s), iv) in the crystalline or amorphous structure of the nanoparticle(s), v) in a defect of the nanoparticle(s), and/or vi) in a vacancy of the nanoparticle(s).

In one embodiment of the invention, the iron oxide and/or impurity(ies) is/are in interaction, such as electrostatic, strong, weak, nuclear, metallic, Van der Waals, Debye, London, or hydrogen interactions with the nanoparticle(s).

In one embodiment of the invention, the iron oxide and/or impurity(ies) is/are located at a distance from the nanoparticle(s), preferentially from the center or surface of the nanoparticle(s), which is lower than $10^{50}$, $10^{20}$, $10^{10}$, $10^5$, $10^3$, 100, 10, 5 or 1 nm. In some cases, the center of the nanoparticles is the region or volume or location or assembly of chemical elements that is at the middle of the largest, lowest, and/or average dimension of the nanoparticle such as half of the diameter of a spherical nanoparticle or half of the largest, lowest, and/or average length of a nanoparticle. In some other cases, the surface of the nanoparticles is the region or location or assembly of chemical elements that is at the largest distance from the center of the nanoparticle while remaining in the nanoparticle.

In still another embodiment of the invention, the iron oxide and/or impurity(ies) is/are located at a distance from nanoparticle(s), preferentially from the center or surface of the nanoparticle(s), which is larger than 0.001, 0.01, 0.1, 1, 10, 100, $10^3$, $10^5$, $10^{10}$, $10^{20}$ or $10^{50}$ nm.

In another embodiment of the invention, the nanoparticle(s) according the invention comprise(s) a core and/or a coating, which preferentially surrounds the core of the nanoparticle(s).

In one embodiment of the invention, the core and/or coating of the nanoparticles possess at least one property in common with the nanoparticles such as the concentration in iron oxide and/or impurity(ies).

In one embodiment of the invention, the nanoparticle(s), the core and/or coating of the nanoparticle(s), has/have at least one of the following properties:

(a) magnetic, diamagnetic, superparamagnetic, ferromagnetic, ferrimagnetic, and/or paramagnetic behavior(s) or property(ies), preferentially observed under the application of magnetic field of strength preferentially larger than $10^{-50}$, $10^{-40}$, $10^{-20}$, $10^{-10}$, $10^{-5}$, $10^{-2}$ or $10^{-1}$ T, preferentially observed at temperatures lower than $10^{10}$, $10^5$, $10^3$, $10^2$, 10 or 1 K. In some cases, the core can have different magnetic property(ies) from the coating. For example, the core can be ferromagnetic or superparamagnetic while the coating can be diamagnetic or paramagnetic.

(b) a crystalline part or structure comprising at least 1, 2, 5, 10, 50, 100, $10^3$, $10^5$, $10^7$, $10^9$, $10^{20}$ or $10^{50}$ crystalline plane(s) or crystalline ordered structures, which can preferentially be observed or measured under electron microscopy. In some cases, the core can have a different crystalline structure from the coating. For example, the core can comprise more than 1, 5, 10, $10^3$ or $10^5$ crystalline plane(s) or crystalline ordered structure(s) while the coating can have less than $10^5$, $10^3$, 10, 5 or 2 crystalline planes or crystalline ordered structures.

(c) a composition made of metal(s) or metal oxide(s), preferentially iron oxide, most preferentially maghemite and/or magnetite. In some cases, the core comprises a different composition from the coating. For example, the core comprises more than 1, 5, 10, 25, 50, 75, 90, 95 or 99 percent or percent in mass of iron oxide while the coating comprises less than 99, 95, 90, 75, 50, 10, 5 or 1 percent or percent in mass of iron oxide. This percentage can be the ratio between the quantity, volume, number of atoms, mass of iron oxide comprised in the core and/or coating divided by the total quantity, total volume, total number of atoms, total mass, of all chemical element(s) comprised in the core and/or coating.

(d) single domain, or be magnetically mono-domain, (e) a magnetic microstructure, which can be characterized by the presence of magnetic field lines, which can be oriented in a preferential direction such as an axis of easy magnetization or a crystallographic direction of the core of the nanoparticle(s) such as [111], where such a magnetic microstructure can under certain conditions be observable, in particular by electronic holography, (f) a size comprised between 1 nm and $10^5$ μm, 1 nm and $10^3$ μm, 1 nm and 100 μm, 1 nm and 10 μm, 1 nm and 1 μm, 5 nm and 1 μm, 5 and 500 nm, 5 and 250 nm, 5 and 100 nm, 5 and 80 nm, 5 and 60 nm, 10 nm and 1 μm, 10 and 500 nm, 10 and 250 nm, 10 and 100 nm, 10 and 80 nm, 10 and 60 nm, 15 nm and 1 μm, 15 and 500 nm, 15 and 250 nm, 15 and 100 nm, 15 and 80 nm, 15 and 60 nm, 20 nm and 1 μm, 20 and 500 nm, 20 and 250 nm, 20 and 100 nm, 20 and 80 nm, or between 20 et 60 nm, (g) a size in some cases larger than 0.1, 1, 2, 5, 10, 15, 20, 25, 30, 35 or 40 nm, (h) a size in some other cases lower than $10^{10}$, $10^5$, $10^4$, 2000, 1000, 500, 400, 300, 200, 150, 120, 100, 95, 90, 80, 75, 70, 65, 60, 55, 50, 45, 40, 35, 30, 25, 20, 15, 10 or 5 nm, (i) a zeta potential, charge, or surface charge comprised between $-10^{10}$ mV and $10^{10}$ mV, $-10^5$ mV and $10^5$ mV, $-10^4$ mV and $10^4$ mV, $-10^3$ mV and $-10^2$ mV and $10^2$ mV, $-10$ and $10$ mV, preferentially at pH comprised between 0 and 14, 1 and 13, 2 and 12, 3 and 11, 4 and 10, 5 and 9, or between 6 and 8.

(j) a zeta potential, charge, or surface charge, which is in some cases larger than $-10^{50}$, $-10^{20}$, $-10^{10}$, $-10^{5}$, $-10^{3}$, $-10$, $-5$, $-1$, $0$, $5$, $10$, $20$, $50$, or $100$ mV, preferentially at pH larger than 0, 1, 2, 3, 4, 5, 6, 7, 8, 9, 10, 11, 12 or 13.

(k) a zeta potential, charge, or surface charge, which is in some other cases larger than $-10^{50}$, $-10^{20}$, $-10^{10}$, $-10^{5}$, $-10^{3}$, $-10$, $-5$, $-1$, $0$, $5$, $10$, $20$, $50$, or $100$ mV, preferentially at pH lower than 14, 13, 12, 11, 10, 9, 8, 7, 6, 5, 4, 3, 2, 1 or 0.

(l) a zeta potential, charge, or surface charge, which is in some other cases lower than $10^{50}$, $10^{20}$, $10^{10}$, $10^{5}$, $10^{3}$, $10$, $5$, $1$, $0$, $-5$, $-10$, $-20$, $-50$, or $-100$ mV, preferentially at pH larger than 0, 1, 2, 3, 4, 5, 6, 7, 8, 9, 10, 11, 12 or 13.

(m) a zeta potential, charge, or surface charge, which is in some other cases lower than $10^{50}$, $10^{20}$, $10^{10}$, $10^{5}$, $10^{3}$, $10$, $5$, $1$, $0$, $-5$, $-10$, $-20$, $-50$, or $-100$ mV, preferentially at pH lower than 14, 13, 12, 11, 10, 9, 8, 7, 6, 5, 4, 3, 2, 1 or 0.

(n) an isoelectric point comprised between 0 and 14, 1 and 13, 2 and 12, 3 and 11, 4 and 10, 5 and 9, or between 6 and 8, (o) in some cases, an isoelectric point in some cases larger than 0, 1, 2, 3, 4, 5, 6, 7, 8, 9, 10, 11, 12 or 13, and/or (p) in some other cases, an isoelectric point in some other cases lower than 14, 13, 12, 11, 10, 9, 8, 7, 6, 5, 4, 3, 2, 1 or 0.

In one embodiment of the invention, the core and/or coating is/are synthesized by the nanoparticle-producing cell(s).

In another embodiment of the invention, the core and/or coating is/are not synthesized by the nanoparticle-producing cell(s).

In one embodiment of the invention, the cell(s) producing the nanoparticle(s), also designated as nanoparticle-producing cell(s) or (the) cell(s), are eukaryotic or prokaryotic cell(s). In some cases, they are the cell(s) produced by or comprised in or amplified in the pre-growth and/or growth medium/media.

In one embodiment of the invention, less than 100, 80, 70, 50, 10, 20, 10, 5, 2, 1, 0.1 or $10^{-10}$% of nanoparticle-producing cells comprise or produce at least one nanoparticle. In some cases, this percentage can be the ratio between the number of cells comprised in the pre-growth and/or growth medium/media that comprise or produce at least one nanoparticle divided by the total number of cells in the pre-growth and/or growth medium/media.

In another embodiment of the invention, more than 100, 80, 70, 50, 10, 20, 10, 5, 2, 1, 0.1 or $10^{-10}$% of nanoparticle-producing cells comprise or produce at least one nanoparticle.

In one embodiment of the invention, the nanoparticle-producing cell(s) are whole cell(s).

In still another embodiment of the invention, the nanoparticle-producing cell(s) are parts of the cell(s) such as cell membrane, vesicle, enzyme, protein, lipid, DNA, RNA, organelle, compartment, cytoplasm, viruses, comprised in, originating from, replicating in, or produced by the synthetizing cell(s).

In one embodiment of the invention, the synthetizing cells are the cells synthesizing the nanoparticles, preferentially when they grow or divide or are comprised in the growth and/or fed-batch medium, preferentially not when they grow or divide or are comprised in the pre-growth medium.

In one embodiment of the invention, the nanoparticle(s) synthesized by the cell(s) is/are designated as cell-synthesized nanoparticle(s).

In one embodiment of the invention, the nanoparticle-producing cell(s) synthesize(s) the nanoparticle(s) inside the cell(s). Preferentially nanoparticle(s) is/are synthesized inside cell(s) when they are synthesized, assembled, crystallized, partly or fully: i), by or in or near or inside part of the cell such as an organelle, Golgi vesicle or apparatus, endosome, exosome, ribosome, endoplasmic reticulum, actin filament, nucleus, peroxisome, microtubule, lysosome, mitochondrion, filament, centrosome, flagellum, or the cell membrane, ii) in a region that is located inside the cell(s), or iii) in a region located at a distance from part of the cell(s) that is lower than $10^{5}$, $10^{3}$, 100, 10 or 1 nm.

In another embodiment of the invention, the nanoparticle-producing cell(s) synthesize(s) the nanoparticle(s) outside the cell(s). Preferentially nanoparticle(s) is/are synthesized outside the cell(s) when it/they is/are synthesized, assembled, crystallized, partly or fully: i) in a region that is located outside the cell(s), or ii) in a region located at a distance from part of the cell(s) that is larger 1, 10, 100, $10^{3}$ or $10^{5}$ nm.

In some cases, the cell(s) is/are assemblies of more than 1, 10, $10^{3}$, $10^{5}$, $10^{10}$, $10^{20}$, $10^{50}$ or $10^{100}$ cell(s), preferentially per liter of growth medium. In some other cases, the cell(s) is/are assemblies of less than $10^{100}$, $10^{50}$, $10^{20}$, $10^{10}$, $10^{5}$, $10^{3}$, 100, 50, 10, 5 or 2 cell(s), preferentially per liter of growth medium.

In one embodiment of the invention, the nanoparticle-producing cell(s) is/are eukaryotic cell(s), preferentially belonging to humans, animals, plants, trees, flours, branches, mushrooms, fungi, archae, birds, fishes, pigeons, trout, mammals, ants, bees, or insects.

In one embodiment of the invention, the nanoparticle-producing cell(s) is/are prokaryotic cell(s) or bacteria.

In some cases, the nanoparticle-producing cells can be Mycobacterium, preferentially Mycobacterium paratuberculosis, Shewanella, preferentially Shewanella oneidensi, Geothrix, preferentially Geothrix fermentans. These bacteria preferentially synthesize nanoparticle(s) outside the cells.

In some other cases, the nanoparticle-producing cells can be magnetotactic bacteria, such as *Magnetospirillum magneticum* strain AMB-1, magnetotactic coccus strain MC-1, three facultative anaerobic vibrios strains MV-1, MV-2 and MV-4, the *Magnetospirillum magnetotacticum* strain MS-1, the *Magnetospirillum gryphiswaldense* strain MSR-1, a facultative anerobic magnetotactic spirillum, *Magnetospirillum magneticum* strain MGT-1, and an obligate anaerobe, *Desulfovibrio magneticus* RS-1. These bacteria preferentially synthetize nanoparticle(s) inside the cell(s).

In one embodiment of the invention, the nanoparticle-producing cell(s) is/are cultivated in or using a pre-growth medium for/during the pre-growth step, and/or in or using a growth medium for/during the growth step, and/or in or using a fed-batch medium during the growth step. In some cases, the pre-growth and/or growth medium/media is/are the medium/media in which nanoparticle-producing cell(s) is/are amplified. In some cases, the fed-batch medium is the medium that is added to the growth medium, preferentially during the growth step.

In one embodiment of the invention, the total pre-growth and/or growth medium/media can comprise at least one source of chemical element, water, and nanoparticle-producing cells. In some other cases, the partial pre-growth and/or growth medium/media comprises at least one source of chemical element, water, without nanoparticle-producing cells. In still some other cases, the pre-growth and/or growth medium/media comprises only nanoparticle-producing cells.

In one embodiment of the invention, the pre-growth and/or growth and/or fed-batch medium/media comprise at least one source, preferentially one source of a chemical element, or comprise at least one chemical element, preferentially in a liquid, gaseous, and/or solid state. In some cases, the pre-growth and/or growth and/or fed-batch medium/media is/are in a liquid, gaseous, and/or solid state.

In one embodiment of the invention, the concentration of a chemical element such as iron in the pre-growth and/or growth medium/media is the concentration of this chemical element in: i) the total pre-growth and/or growth medium/media, ii) the partial pre-growth and/or growth medium/media, or iii) the nanoparticle-producing cells.

In one embodiment of the invention, a certain quantity or volume of cell(s) can be a certain quantity or volume of growth medium comprising these cell(s). In some other cases, a certain quantity or volume of cell(s) can be a certain quantity or volume of cell(s) without water or without the aqueous environment of the cell(s) or after water or the aqueous environment of the cell(s) has been removed, for example by lyophilization.

In one embodiment of the invention, the conditions of amplifications of cells during the pre-growth and/or growth steps enable preventing genetic modifications of the nanoparticle-producing cells. In some cases, the genetic modifications of the nanoparticle-producing cell are modifications of at least $10^{-50}$, $10^{-20}$, $10^{-10}$, $10^{-5}$, $10^{-3}$, $10^{-1}$, 1, 5, 10, 50, 75, 90 or 95% of gene(s), part(s) of genes, DNA portion(s), or nucleotide(s) This percentage can be the ratio between the number or quantity of gene(s), part(s) of genes, DNA portion(s), or nucleotide(s) that have been modified in the nanoparticle-producing cell(s) and the total number or quantity of all gene(s), part(s) of genes, DNA portion(s), nucleotide(s) that belong to the nanoparticle-producing cell(s).

In still another embodiment of the invention, the pre-growth and/or growth medium/media comprise a majority of water, preferentially of purified, deionized or ultrapure water, preferentially more than $10^{-50}$, $10^{-20}$, $10^{-10}$, $10^{-5}$, $10^{-3}$, 1, 10, 50, 75, 80, 90, 99, 99.99 or 99.99999 percent or percent in mass of water. This percentage can be the ratio between the quantity, mass, volume, or number of atoms of water comprised in the pre-growth and/or growth medium/media divided by the total quantity, mass, volume, or number of atoms of all chemical element(s) comprised in the pre-growth and/or growth medium/media.

In one embodiment of the invention, the pre-growth and/or growth medium/media comprise(s) at least one chemical element or one source of chemical element. In some cases, the concentration of a chemical element, such as iron, in the pre-growth and/or growth medium/media, is the concentration of this chemical element at any time of the pre-growth and/or growth step. In some cases, this concentration can be measured by estimating the number of moles, the mass, or the volume of/occupied by this chemical element divided by the total number of moles, total mass, or total volume of/occupied by all chemical elements in the pre-growth and/or growth medium/media In one embodiment of the invention, the pre-growth and/or growth medium/media comprise(s) at least one source of carbon. In some cases, the source of carbon comprises the chemical element of the periodic table C. In some cases, the source of carbon can be selected in the list consisting of: acetate, glycolate, glucose, lactate, pyruvate, succinate, carbon dioxide, glycerol, and a derivative or combination of these compounds.

In one embodiment of the invention, the growth and/or pre-growth medium/media comprise(s) at least one source of nitrogen. In some cases, the source of nitrogen comprises the chemical element of the periodic table N. In some cases, the source of nitrogen can be selected from the group consisting of: ammonium salts, nitrate salts, urea, amino acids, ammonium salts, ammonia, nitrogen gas, and a derivative or combination of these compounds.

In one embodiment of the invention, the pre-growth and/or growth medium/media comprise(s) at least one source of sulfur or sulfate. In some cases, the source of sulfur or sulfate comprises the chemical element of the periodic table S. In some cases, the source of sulfur or sulfate can be sulfate salts or hydrogen sulfide.

In one embodiment of the invention, the pre-growth and/or growth medium/media comprise(s) at least one source of phosphorous or phosphate. In some cases, the source of phosphorous or phosphate comprises the chemical element of the periodic table P. In some cases, the source of phosphorous or phosphate can be phosphate salts.

In one embodiment of the invention, the pre-growth and/or growth medium/media comprise(s) at least one source of calcium. In some cases, the source of calcium comprises the chemical element of the periodic table Ca. In some cases, the source of calcium can be a calcium salt.

In one embodiment of the invention, the pre-growth and/or growth medium/media comprise(s) at least one source of Potassium. In some cases, the source of Potassium comprises the chemical element of the periodic table K. In some cases, the source of Potassium is a Potassium salt.

In one embodiment of the invention, the pre-growth and/or growth medium/media comprise(s) at least one source of Magnesium. In some cases, the source of Magnesium comprises the chemical element of the periodic table Mg. In some cases, the source of Magnesium is a Magnesium salt.

In one embodiment of the invention, the pre-growth and/or growth medium/media comprise(s) at least one source of oxygen. In some cases, the source of oxygen comprises the chemical element of the periodic table O. In some cases, the source of oxygen is an organic compound, carbon dioxide, or di-oxygen.

In one embodiment of the invention, the pre-growth and/or growth medium/media comprise(s) at least one source of hydrogen. In some cases, the source of hydrogen comprises the chemical element of the periodic table H. In some cases, the source of hydrogen is an organic compound, or di-hydrogen.

In one embodiment of the invention, the pre-growth and/or growth medium/media comprise(s) at least one source of iron. In some cases, the source of iron comprises the chemical element of the periodic table Fe. In some cases, the source of iron is or consists of or comprises iron. In some cases, the source of iron is iron citrate, iron quinate, iron chloride, or iron sulfate.

In one embodiment of the invention, the pre-growth and/or growth medium/media comprise(s) at least one source of sulfur. In some cases, the source of sulfur comprises the chemical element of the periodic table S. In some cases, the source of sulfur is comprised in at least one vitamin.

In one embodiment of the invention, the sources of carbon, nitrogen, sulfur, sulfate phosphorous, phosphate, calcium, Potassium, Magnesium, Oxygen, hydrogen, or iron, comprise(s) more than $10^{-100}$, $10^{-50}$, $10^{-20}$, $10^{-10}$, $10^{-5}$, $10^{-3}$, $10^{-1}$, 1, 5, 10, 25, 50, 75, 80, 90 or 95 percent in mass of carbon, nitrogen, sulfur, sulfate, phosphorous, phosphate, calcium, Potassium, Magnesium, Oxygen, hydrogen, or iron, respectively. In some cases, they are in a gaseous, liquid, or solid state. In some other cases, they can be used to prepare the pre-growth and/or growth medium/media. In some cases, the pre-growth and/or growth medium/media comprise(s) more than 2, 3, 4, 5, 10, 50, 100, $10^3$, $10^5$, $10^{10}$ or $10^{50}$ different sources of carbon, nitrogen, sulfur, sulfate, phosphorous, phosphate, calcium, potassium, magnesium, oxygen, hydrogen, and/or iron. In some other cases, the pre-growth and/or growth medium/media comprise(s) less than 2, 3, 4, 5, 10, 50, 100, $10^3$, $10^5$, $10^{10}$ or $10^{50}$ different sources carbon, nitrogen, sulfur, sulfate, phosphorous, phosphate, calcium, potassium, magnesium, oxygen, hydrogen, and/or iron.

In one embodiment of the invention, at least one source of carbon, nitrogen, sulfur, sulfate, phosphorous, phosphate, calcium, potassium, magnesium, oxygen, hydrogen, and/or iron of the pre-growth medium is the same as that of the growth medium.

In another embodiment of the invention, at least one source of carbon, nitrogen, sulfur, sulfate, phosphorous, phosphate, calcium, potassium, magnesium, oxygen, hydrogen, and/or iron of the pre-growth medium is different from that of the growth medium.

In another embodiment of the invention, the pre-growth and/or growth medium/media comprise(s) the source(s) of carbon, nitrogen, sulfur, sulfate, phosphorous, phosphate, calcium, potassium, magnesium, oxygen, hydrogen, and/or iron at a concentration that is larger than $10^{-100}$, $10^{-50}$, $10^{-20}$, $10^{-10}$, $10^{-5}$, $10^{-3}$, $10^{-1}$, 1, 10, $10^2$, $10^3$, $10^5$ or $10^{10}$ mM.

In another embodiment of the invention, the pre-growth and/or growth medium/media comprise(s) the source(s) of carbon, nitrogen, sulfur, sulfate, phosphorous, phosphate, calcium, potassium, magnesium, oxygen, hydrogen, and/or iron, at a concentration that is lower than $10^{100}$, $10^{50}$, $10^{20}$, $10^{10}$, $10^5$, $10^3$, 10, 1, $10^{-1}$, $10^{-3}$, $10^{-6}$, $10^{-9}$, $10^{-20}$, $10^{-50}$ or $10^{-100}$ mM.

In an another embodiment of the invention, the pre-growth and/or growth medium/media is/are prepared using pharmaceutical grade or ultrapure chemicals or chemical element(s).

In still another embodiment of the invention, medium impurity(ies) is/are impurity(ies) comprised in the pre-growth and/or growth and/or fed-batch medium/media.

In one embodiment of the invention, the pre-growth and/or growth medium/media comprise(s) a low quantity of medium impurity(ies). In some cases, the percentage of medium impurity(ies) is lower than 100, $10^{20}$, $10^{10}$, $10^5$, $10^2$, 10, 5, 1, 0.1, or 0.001%. Preferentially, the pre-growth and/or growth medium/media comprise(s) a quantity or concentration of medium impurity(ies), which is lower, preferentially by a factor of at least 1.00001, 1.1, 1.5, 2, 5, 10, $10^3$, $10^{10}$ or $10^{20}$, than the quantity or concentration of at least one source of carbon, nitrogen, sulfur, sulfate, phosphorous, phosphate, calcium, potassium, magnesium, oxygen, hydrogen, and/or iron. According to the invention, the percentage in medium impurity(ies) can in some cases be defined as the ratio between the number of atoms, quantity, mass, or volume of medium impurity(ies) comprised in the pre-growth and/or growth medium/media divided by the total number of atoms, quantity, mass, or volume of all chemical element(s) comprised in the pre-growth and/or growth medium/media. In some other cases, the concentration of medium impurity(ies) comprised in the pre-growth and/or growth medium/media is lower than $10^{50}$, $10^{30}$, $10^{10}$, $10^5$, $10^3$, 500, 100, 50, 10, 1, $10^{-1}$, $10^{-3}$, $10^{-5}$, $10^{-10}$ or $10^{-50}$ µg of medium impurity(ies) per mL of pre-growth and/or growth medium/media.

In still another embodiment of the invention, the pre-growth and/or growth medium/media does/do not comprise at least one medium impurity.

In one embodiment of the invention, the pre-growth and/or growth medium/media comprise(s) a significant quantity of medium impurity(ies). In some cases, the percentage, preferentially in mass, of medium impurity(ies), is larger than 0, $10^{-40}$, $10^{-20}$, $10^{-10}$, $10^{-5}$, $10^{-2}$, $10^{-1}$, 1, 5, 10, 25, 50, 75, 80, or 90%. In some other cases, the concentration of medium impurity(ies) comprised in the pre-growth and/or growth medium/media is larger than $10^{-100}$, $10^{-50}$, $10^{-20}$, $10^{-10}$, $10^{-5}$, $10^{-3}$, $10^{-2}$, $10^{-1}$, 1, 10, 50, 100, $10^3$, $10^5$, or $10^{10}$ µg of medium impurity(ies) per mL of pre-growth and/or growth medium/media.

In some cases, the nanoparticles produced or obtained or resulting from the pre-growth and/or growth medium/media can be magnetosomes.

In one embodiment of the invention, the method according to the invention comprises a pre-growth step, which consists in amplifying the nanoparticle-producing cell(s) in a pre-growth medium so that nanoparticle-producing cell(s) produce(s) essentially no nanoparticles.

In one embodiment of the invention, the nanoparticle-producing cell(s) used to start the pre-growth step are cell(s) with at least one of the following properties: i) they are the cells before the pre-growth step, preferentially more than 0.001, 0.1, 1, 5, 10, $10^3$, $10^5$ or $10^{10}$ hour(s) before the beginning of the pre-growth step, ii) they are comprised in a cellular bank such as a master cell bank, a working cell bank, or a research cell bank, iii) they comprise more than 1, 5, 10, $10^3$, $10^5$ or $10^{10}$ nanoparticle(s) per cell, iv) they are comprised in a liquid or medium, preferentially identical or similar in composition to the pre-growth and/or growth medium/media, preferentially comprising a majority of water, v) they are comprised in a medium with a concentration in medium impurity(ies) lower than 100, 10, 1, $10^{-1}$, $10^{-2}$, $10^{-3}$, $10^{-5}$ or $10^{-10}$ vi) they are comprised in a medium or kept in conditions that enables maintaining or having less than 100, 10, 1, 0.1 or 0.01 gram of impurity(ies) per gram of nanoparticle(s), v) they are comprised in a volume comprised between $10^{-100}$ and $10^{100}$, $10^{-50}$ and $10^{50}$, $10^{-30}$ and $10^{30}$, $10^{-20}$ and $10^{20}$, $10^{-10}$ and $10^{10}$, $10^{-6}$ and $10^5$, $10^{-6}$ and $10^4$, $10^{-6}$ and $10^2$, or between $10^{-6}$ and 1 liter, vi) they are comprised in a volume at least 10 times lower than the volume of the first pre-growth step, vii) they are or represent a number of cell(s), preferentially per liter of pre-growth and/or growth medium/media, comprised between 1 and $10^{100}$, 2, and $10^{50}$, 3 and $10^{20}$, or between 10 and $10^{10}$ cells, vii) they have an optical density comprised between $10^{-50}$ and $10^{50}$, $10^{-20}$ and $10^{20}$, $10^{-10}$ and 10, $10^{-5}$ and $10^5$, $10^{-5}$ and $10^3$, $10^{-5}$ and $10^2$, $10^{-5}$ and 1, $10^{-5}$ and $10^{-1}$, $10^{-5}$ and $10^{-2}$, or between $10^{-5}$ and $10^{-3}$, viii) they have a number of cell division, preferentially per hour or per hour per liter of pre-growth and/or growth medium/media, which is lower than 1, 10, $10^3$, $10^5$, $10^{10}$, $10^{20}$, $10^{50}$ or $10^{100}$, ix) they are stored or kept at a temperature below 100, 50, 25 or 0° C., preferentially at 77 K or −20° C.

In one embodiment of the invention, the nanoparticle-producing cells used to start the pre-growth step have at least one of the following properties: i) they are comprised in a medium with a concentration in medium impurity larger than $10^{-50}$, $10^{-20}$, $10^{40}$, $10^{-5}$, $10^{-2}$, $10^{-1}$, 1 or 10 ii) they are comprised in a medium or kept in conditions that enable maintaining or having more than $10^{-40}$, $10^{-20}$ or $10^{-10}$ gram of impurity(ies) per gram of nanoparticle(s), iii) they have a number of cell division, preferentially per hour or per hour per liter of pre-growth and/or growth medium/media, which is larger than 1, 10, $10^3$, $10^5$, $10^{10}$, $10^{20}$, $10^{50}$ or $10^{100}$, iv) they comprise less than 1, 5, 10, $10^3$, $10^5$ or $10^{10}$ nanoparticle(s) per cell. This can be the case when/if they are maintained or originate from a medium that comprises a sufficiently low iron concentration to prevent the production of nanoparticles.

In one embodiment of the invention, at least one the property(ies) of the nanoparticle-producing cells used to start the pre-growth step enables preventing the death or destruction or disappearance or denaturation or inactivation of the nanoparticle-producing cell(s).

In an embodiment of the invention, the optical density of the cell(s) is measured when the cells are comprised in the pre-growth and/or growth medium/media, in a solution, or in water, preferentially after the growth medium has been removed and the cells have been re-suspended in water. In some cases, the optical density of the cell(s) is measured at a wavelength larger than 1, 2, 5, 10, 50, 100, 200, 300, 400, 450, 500, 550, 600, 900, $10^3$, $10^5$ or $10^7$ nm. In some other cases, the optical density of the cell(s) is measured at a wavelength lower than $10^7$, $10^5$, $10^3$, 900, 600, 550, 500, 450, 400, 300, 200, 100, 50, 10, 5, 2 or 1 nm. In sill some other cases, the optical density of the cells is measured at a wavelength comprised between 1 and $10^7$ nm, 50 and $10^5$ nm, 100 and $10^3$ nm, 200 and 900 nm, or between 400 and 800 nm.

In one embodiment of the invention, the number of cell amplification, between two time points to and $t_1$ of the pre-growth and/or growth step(s), is equal to or is proportional to: i), the ratio between the optical density measured at $t_1$ and the optical density measured at to and/or ii), the ratio between the number of cells at $t_1$, $n(t_1)$, and the number of cells at to, $n(t_0)$.

In one embodiment of the invention, the speed or rate of cell division is $[n(t_1)-n(t_0)]/(t_1-t_0)$.

In another embodiment, the speed or rate of cell division is: $n(t_1)-n(t_0)/[(t_1-t_0) \cdot V]$, where V is the volume of the pre-growth and/or growth medium in which the cells are cultured or amplified.

In one embodiment of the invention, the pre-growth step begins by thawing or heating, preferentially from a temperature below 100, 50, 25, 10 or 0° C. to a temperature above 0, 10, 25, 50 or 100° C., the nanoparticle-producing cell(s) used to start the pre-growth step. After that, the nanoparticle-producing cells are preferentially inserted or added the pre-growth medium. In some cases, this initial phase of the pre-growth step takes place during a lapse of time comprised between $10^{-50}$ and $10^{50}$, $10^{-50}$ and $10^{10}$, $10^{-30}$ and $10^5$, $10^{-20}$ and $10^3$, $10^{-10}$ and $10^2$, or between $10^{-5}$ and 10 hour(s).

In another embodiment of the invention, the pre-growth step is divided in sub-steps 0, 1, . . . , i, . . . , j, corresponding to the amplifications in the different, preferentially increasing, volumes $V_0$, $V_1$, $V_i$, . . . $V_j$, where i is an integer designating the number i of amplifications in different volumes (0<i<j), j is an integer designating the total number of amplifications in different volumes, $V_0$, $V_i$, and $V_j$ are the initial, $i^{th}$, and final volume of amplification, respectively. In some cases, cell amplification or the number of cell amplification in different volumes can be important during the pre-growth step, for example when the pre-growth step begins from a low quantity of cells, preferentially lower than $10^{100}$, $10^{50}$, $10^{20}$, $10^{10}$, $10^5$, $10^3$, $10^2$, 10, 5, 3 or 2 cells, preferentially comprised in one liter or one milliliter or one microliter of pre-growth medium or aqueous solution. In these cases, i and/or j can be larger than 1, 2, 3, 4, 5, 6, 7, 8, 9, 10, 15, 20, 10, $10^3$, $10^5$ or $10^{10}$. In some other cases, cell amplification or the number of cell amplification in different volumes can be low, for example when the pre-growth step begins from a large quantity of cells, preferentially larger than 2, 3, 5, 10, $10^2$, $10^3$, $10^5$, $10^{10}$, $10^{20}$, $10^{50}$ or $10^{100}$ cells, preferentially comprised in one liter or one milliliter or one microliter of pre-growth medium or aqueous solution. In these cases, i and/or j is/are lower than $10^{10}$, $10^5$, $10^3$, $10^2$, 10, 5, 4, 3, 2 or 1.

In one embodiment of the invention, the ratio $V_i/V_{i-1}$ is large, preferentially larger than $10^{-50}$, $10^{-30}$, $10^{-20}$, $10^{-10}$, $10^{-5}$, $10^{-3}$, $10^{-2}$, $10^{-1}$, 1, 1.00001, 1.0001, 1.001, 1.01, 1.1, 1.2, 1.5, 2, 3, 4, 5, 7, 10, $10^2$, $10^3$, $10^5$ or $10^{10}$. In some cases, $V_i/V_{i-1}$ is large when between the sub-step i-1 and the sub-step i of the pre-growth step: the number of cell division, preferentially per hour or per hour per liter of pre-growth medium, is larger than 1, 5, 10, $10^3$, $10^{10}$ or $10^{20}$, or when the cell optical density increases by a factor of more than 1.00001, 1.1, 2, 5, 10, $10^3$, $10^5$ or $10^7$ per hour.

In another embodiment of the invention, the ratio $V_i/V_{i-1}$ is low, preferentially lower than $10^{100}$, $10^{50}$, $10^{10}$, $10^5$, $10^3$, $10^2$, 10, 5, 3, 2, 1.01, 1.001, 1.000001, 1, $10^{-5}$, $10^{-10}$ or $10^{-50}$. In some cases, $V_i/V_{i-1}$ is low when the number of cell division, preferentially per hour or per hour per liter of pre-growth medium, is lower than $10^{50}$, $10^{10}$, $10^3$, $10^2$, 10, 5 or 1, or when the cell optical density increases by a factor of less than 1.00001, 1.1, 2, 5, 10, $10^3$, $10^5$ or $10^7$ per hour.

In some cases, the number of pre-growth steps in different volumes can be increased by decreasing $V_i/V_{i-1}$. In some other cases, the number of pre-growth steps in different volumes can be decreased by increasing $V_i/V_{i-1}$.

In one embodiment of the invention, the pre-growth step and/or at least one of its sub-step(s) last(s) and/or take(s) place until the optical density of the bacterial suspension in volume $V_i$ (1<i<j) reaches a value that is: i), above $10^{-50}$, $10^{-30}$, $10^{-20}$, $10^{-10}$, $10^{-5}$, $10^{-3}$, $10^{-1}$, 1, 5, 10, 15, 50, $10^2$, $10^3$ or $10^5$, and/or ii), larger, preferentially by a factor of more than 1.000001, 1.0001, 1.01, 1.1, 1.5, 2, 5, 10, $10^2$, $10^3$, $10^5$, $10^{10}$ or $10^{20}$, at the end than at the beginning of the pre-growth step and/or at the end than at the beginning of at least one sub-step of the pre-growth step.

In one embodiment of the invention, the pre-growth step and/or at least one of its sub-step(s) last(s) and/or take(s) place until the optical density of the bacterial suspension in volume $V_i$ (1<i<j) reaches a value that is: i), lower than $10^{-50}$, $10^{-30}$, $10^{-20}$, $10^{-10}$, $10^{-5}$, $10^{-3}$, $10^{-1}$, 1, 5, 10, 15, 50, $10^2$, $10^3$ or $10^5$, and/or ii), lower, preferentially by a factor of more than 1.000001, 1.0001, 1.01, 1.1, 1.5, 2, 5, 10, $10^2$, $10^3$, $10^5$, $10^{10}$ or $10^{20}$, at the end than at the beginning of the pre-growth step and/or at the end than at the beginning of at least one sub-step of the pre-growth step.

In one embodiment of the invention, the beginning of the amplification in volume $V_0$ takes place at time $t_{PG0b}$, the end of the amplification in volume $V_0$ takes place at time $t_{PG0e}$, the beginning of the amplification in volume $V_i$ occurs at time $t_{PGib}$, the end of amplification in volume $V_i$ takes place at time $t_{PGie}$, the beginning of the amplification in volume $V_j$ takes place at time $t_{jb}$, and/or the end of the amplification in volume $V_j$ takes place at time $t_{PGje}$.

In one embodiment of the invention, the length of time that separates: i), the beginning of the pre-growth step, at time $t_{PG0b}$, and the end of the pre-growth step, at time $t_{PGje}$, which is equal to $t_{PGje}-t_{PG0b}$, and/or ii), the beginning of sub-step i, $t_{PGib}$, and the end of sub-step i, $t_{PGie}$, which is equal to $t_{PGie}-t_{PGib}$, is/are larger than or equal to $10^{-20}$, $10^{-10}$, $10^{-5}$, $10^{-3}$, $10^{-2}$, $10^{-1}$, 1, 2, 5, 10, 24, 100, $10^3$, $10^5$ or $10^7$ hour(s). In some cases, $t_{PGje}-t_{PG0b}$ and/or $t_{PGie}-t_{PGib}$ is/are large when the cells divide with difficulty or slowly, preferably at a speed or rate lower than $10^{-50}$, $10^{-20}$, $10^{-10}$, $10^{-5}$, $10^{-3}$, $10^{-1}$, 1, 10, $10^3$ or $10^5$ cellular division(s) per hour or cellular division(s) per hour per liter of pre-growth medium.

In still another embodiment of the invention, $t_{PGje}-t_{PG0b}$ and/or $t_{PGie}-t_{PGib}$ is/are lower than or equal to $10^{40}$, $10^{30}$, $10^{20}$, $10^{10}$, $10^5$, $10^3$, $10^2$, 10, 5, 2, 1, $10^{-1}$, $10^{-3}$, $10^{-5}$ or $10^{-10}$ hour(s). In some cases, $t_{PGje}-t_{PG0b}$ and/or $t_{PGie}-t_{PGib}$ is/are low when the cells divide easily or rapidly, preferably at a speed or rate larger than $10^{-50}$, $10^{-20}$, $10^{-10}$, $10^{-5}$, $10^{-3}$, $10^{-1}$, 1, 10, $10^3$ or $10^5$ cellular division(s) per hour(s) or cellular division(s) per hour per liter of pre-growth medium.

In one embodiment of the invention, the nanoparticle-producing cells are amplified during the pre-growth step by introducing at $t_{PGib}$ or $t_{PG0b}$ or by maintaining during the pre-growth step or at least one of its sub-step an iron concentration in the pre-growth medium that is lower than $10^{100}$, $10^{20}$, $10^5$, $10^3$, 10, 5, 1, $10^{-1}$, $10^{-3}$ or $10^{-5}$ μM, preferentially to avoid nanoparticle synthesis that could prevent cellular amplification.

In another embodiment of the invention, the nanoparticle-producing cells are amplified during the pre-growth step by introducing at $t_{PGib}$ or $t_{PG0b}$ or by maintaining during the pre-growth step or at least one of its sub-step an iron concentration in the pre-growth medium that is larger than $10^{-50}$, $10^{-20}$, $10^{-10}$, $10^{-5}$, $10^{-3}$, $10^{-2}$ or $10^{-1}$ μM, preferentially to enable efficient cellular metabolism.

In another embodiment of the invention, the nanoparticle-producing cells are amplified during the pre-growth step by introducing at $t_{PGib}$ or $t_{PG0b}$ or by maintaining during the pre-growth step or at least one of its sub-step an iron concentration in the pre-growth medium between $10^{-10}$ and $10^{10}$, $10^{-5}$ and $10^5$, $10^{-3}$ and $10^3$, $10^{-1}$ and 1 μM, $10^{-1}$ and 10 μM, or between $10^{-2}$ and 100 μM.

In another embodiment of the invention, the nanoparticle-producing cells are amplified during the pre-growth step or at least one of its sub-steps by consuming oxygen. In some cases, the percentage of oxygen in the pre-growth medium decreases from: i), a value above $10^{-50}$, $10^{-10}$, $10^{-5}$, $10^{-3}$, 1, 5, 10, 20, 50, 75, 90, 95, 99 or 99.9%, preferentially from 21% or a value comprised between 10 and 30%, at $t_{PGib}$ or $t_{PG0b}$, down to a value below 99.9, 95, 90, 80, 75, 50, 20, 5, 2, 1, $10^{-3}$, $10^{-5}$, $10^{-10}$ or $10^{-5\circ}$ %, preferentially 0% or a value comprised between 0 and 10%, at $t_{PGie}$ or $t_{PGje}$ and/or ii), the percentage of oxygen in the pre-growth medium decreases by a factor of more than 1.0001, 1.001, 1.1, 1.2, 1.5, 2, 5, 10, 50, $10^2$, $10^3$, $10^5$ or $10^{10}$, preferentially between $t_{PG0b}$ and $t_{PGje}$ and/or between $t_{PGib}$ and $t_{PGie}$. In some cases, oxygen is not added to the pre-growth medium during the pre-growth step or at least one of its sub-steps, resulting in a decrease in the percentage of oxygen in the pre-growth medium due to the consumption of oxygen by the bacteria. In some other cases, oxygen is added to the pre-growth medium during the pre-growth step or at least one of its sub-steps, resulting in a variation of oxygen percentage in the pre-growth medium that is due both to the consumption of oxygen by the bacteria and to the addition of oxygen to the pre-growth medium.

In one embodiment of the invention, the percentage of oxygen, preferentially $O_2$, in the pre-growth and/or growth medium/media is the percentage of dissolved oxygen, preferentially $O_2$, in the pre-growth and/or growth medium/media. In some cases, a percentage of 100% can correspond to the maximum quantity of $O_2$ solubilized in the pre-growth and/or growth medium/media, comprised between $10^{-5}$ and $10^{20}$ mg, preferentially comprised between 1 and 10 mg of dissolved $O_2$ per liter of pre-growth and/or growth medium/media.

In one embodiment of the invention, the pre-growth step consists in amplifying the cells, where such amplification is associated with, corresponds to, or is: i) a speed or rate or number of cell division, preferentially per unit volume such as one liter of pre-growth medium, which is larger, preferentially by a factor of more than 1.000001, 1.0001, 1.01, 1.1, 1.2, 1.5, 2, 5, 10, $10^2$, $10^3$, $10^5$, $10^{10}$, $10^{20}$ or $10^{50}$, at the beginning than end of the pre-growth step or one of its sub-step, or at $t_{PGie}$ or $t_{PGje}$ than at $t_{PGib}$ or $t_{PG0b}$, ii) a speed or rate or number of cell division, preferentially per unit volume such as one liter of pre-growth medium, which increases from a number of cells or cells per hour lower than or equal to $10^{100}$, $10^{50}$, $10^{20}$, $10^{10}$, $10^5$, $10^3$, $10^2$, 10, 5 or 2, at the beginning of the pre-growth step or one of its sub-step or at $t_{PGib}$ or $t_{PG0b}$, up to a number of cells or cells per hour larger than or equal to 2, 5, 10, $10^2$, $10^3$, $10^5$, $10^{10}$, $10^{20}$, $10^{50}$ or $10^{100}$, at the end of the pre-growth step or one of its sub-step or at $t_{PGie}$ or $t_{PGje}$, iii) an optical density, preferentially measured for cells comprised in a fixed pre-growth volume such as one liter, which is larger, preferentially by a factor of more than 1.00001, 1.1, 1.2, 1.5, 2, 5, 10, $10^3$, $10^5$, $10^{10}$, $10^{20}$ or $10^{50}$, at the end of the pre-growth step or one of its sub-step or at $t_{PGie}$ or $t_{PGje}$ than at the beginning of the pre-growth step or one of its sub-step or at $t_{PGib}$ or $t_{PG0b}$, or which increases from an optical density lower than or equal to 10, 1, $10^{-1}$, $10^{-2}$ or $10^{-3}$ at the beginning of the pre-growth step or one of its sub-step or at $t_{PGib}$ or $t_{PG0b}$ to an optical density larger than or equal to $10^{-10}$, $10^{-2}$, $10^{-1}$, 1 or 10 at the end of the pre-growth step or one of its sub-step or at $t_{PGie}$ or $t_{PGje}$.

In one embodiment of the invention, preferentially during, at the beginning, or at the end of the pre-growth step or of at least one of its sub-steps, cells that produce essentially no nanoparticles have or are characterized by at least one of the following properties: i) a number of nanoparticles comprised in the cells that is lower than $10^3$; $10^2$, 50, 20, 10, 5, 2 or 1, preferentially lower than 10 or 5, or between 0 and $10^3$, preferentially between 0 and 10 or between 0 and 5, ii) a percentage of cells with at least one nanoparticle that is lower than 100, 99, 90, 80, 50, 20, 10, 1, 0.1%, preferentially lower than 10 or 1% or comprised between 0 and 99%, 0 and 50, 0 and 10, preferentially between 0 and 5%, where this percentage is preferentially the ratio between the number of cells with at least one nanoparticle and the total number of cells, preferentially comprised in the pre-growth medium, iii) an optical density larger than $10^{-50}$, $10^{-20}$, $10^{-10}$, $10^{-5}$, $10^{-3}$, $10^{-2}$, 0.1, 0.2, 0.5, 1, 5, 10 or 100, iv) a number of cells larger than 1, 5, 10, $10^2$, $10^3$, $10^5$, $10^{10}$, $10^{20}$, $10^{50}$ or $10^{100}$, v) they are comprised in a volume larger than 0.0001, 0.001, 0.1, 1, 10, 50, $10^2$, $10^3$, $10^5$ or $10^{10}$ liter(s), vi) a number of cell generation comprised between 1 and $10^{10}$, 1 and $10^3$, preferentially between 50 and 300, vii) a ratio between the optical density measured at the end of the pre-growth step, $OD_{PGE}$, and the beginning of the pre-growth step, $OD_{PGB}$, $OD_{PGE}/OD_{PGB}$, larger than 1, 2, 5, 10, 15, 25, 50, 100, $10^3$, $10^5$, $10^{10}$, $10^{50}$ or $10^{100}$, and/or viii) the ratio between the optical density measured at the end of sub-step i of the pre-growth step, $OD_{PGiE}$, and the optical density measured at the beginning of sub-step i of the pre-growth step, $OD_{PGiB}$, $OD_{PGiE}/OD_{PGiB}$, larger than or equal to 1, 2, 5, 10, 15, 25, 50, 100, $10^3$, $10^5$, $10^{10}$, $10^{50}$ or $10^{100}$.

In one embodiment of the invention, the cells that produce essentially no nanoparticles are non-magnetic cells.

In one embodiment of the invention, preferentially during, at the beginning or at the end of the pre-growth step or at least one of its sub-steps, a percentage of non-magnetic cells larger than $10^{-50}$, $10^{-20}$, $10^{-10}$, $10^{-5}$, $10^{-3}$, $10^{-1}$, 1, 5, 10, 50 or 75%, is obtained. In some cases, the percentage of non-magnetic cells is based on the ratio $n_{NMC}/(n_{MC}+n_{NMC})$, where $n_{MC}$ and $n_{NMC}$ are the numbers of magnetic cells and non-magnetic cells, respectively.

In another embodiment of the invention, non-magnetic cells don't display a magnetic response, where the magnetic response can be the orientation of at least one cell parallel to a magnetic field or a movement of the cell at a speed that is proportional to the strength of the magnetic field, where the strength of the magnetic field can be larger than $10^{-9}$, $10^{-3}$, $10^{-1}$, 1, $10^3$ or $10^6$ mT and/or the magnetic field is preferentially applied on the cell(s).

In one embodiment of the invention, the method comprises a growth step consisting in amplifying the nanoparticle-producing cell(s) originating from the pre-growth step in a growth medium so that nanoparticle-producing cell(s) produce(s) nanoparticles. In some cases, the growth step is carried out in a fermenter or apparatus, which enables to control the temperature, pH, iron concentration, and/or concentration of oxygen of the growth medium.

In another embodiment of the invention, the growth step begins by inserting the cells obtained from the pre-growth step in the growth medium. In some cases, the growth step or at least one of its sub-steps takes place during a lapse of time comprised between $10^{-50}$ and $10^{50}$, $10^{-50}$ and $10^{10}$, $10^{-30}$ and $10^5$, $10^{-20}$ and $10^3$, $10^{-10}$ and $10^2$, or between $10^{-5}$ and 24 hour(s). In some other cases, the growth step or at least one of its sub-steps takes place during a lapse of time lower than $10^{20}$, $10^{10}$, $10^5$, $10^3$, $10^2$, 10, 5, 2, 1, $10^1$, $10^{-2}$, $10^{-3}$, $10^{-5}$, $10^{-10}$ or $10^{-20}$ hour(s). In still some other cases, the growth step or at least one of its sub-step takes place during a lapse of time larger than $10^{-20}$, $10^{-10}$, $10^{-5}$, $10^{-3}$, $10^{-2}$, $10^{-1}$, 1, 2, 5, 10, $10^2$, $10^3$, $10^5$, $10^{10}$ or $10^{20}$ hour(s).

In one embodiment of the invention, the growth step consists in amplifying the cells during successive sub-steps $GS_O \ldots GS_i \ldots GS_j$, where $t_{GS0b}$, $t_{GSib}$, $t_{GSjb}$, are the beginning of steps 0, i, and j, and $t_{GSOe}$, $t_{GSie}$, $t_{GSje}$, are the ends of steps 0, i, and j, where $0<i<j$. In some cases, i and/or j is/are larger than 1, 2, 3, 4, 5, 6, 7, 8, 9, 10, 15, 20, 10, $10^3$, $10^5$ or $10^{10}$. In some other cases, i and/or j is/are lower than 1, 2, 3, 4, 5, 6, 7, 8, 9, 10, 15, 20, 10, $10^3$, $10^5$ or $10^{10}$.

In one embodiment of the invention, each subset i consists in bubbling or bringing a different amount of oxygen to/in the growth medium and/or bringing a different quantity of iron to/in the growth medium, preferentially with the help of a fed-batch medium.

In one embodiment of the invention, the growth step comprises at least one of the following sub-steps during which a gas, such as compressed air or a gas comprising more than 1% of $O_2$, is introduced to the growth medium, preferentially under stirring conditions at 1 to $10^{10}$, 5 to $10^5$, 10 to $10^4$, 100 to $10^3$, or 100 to 300 rotations per minute, and wherein:

During the first sub-step that lasts for $10^{-3}$ to $10^3$ hours or preferentially for 2 to 16 hours, the debit of the gas is comprised between 0 and $10^{10}$, preferentially between 0.001 and 40 mL/min per liter of growth medium, resulting in an increase of the optical density of the cells, from a value comprised between $10^{-10}$ and $10^3$, preferentially between 0.08 and 0.12 at the beginning of the first sub-step to a value at the end of the first sub-step larger by a factor of more than 1.0000001, 1.1, 1.5, 2, 5, 10 or $10^3$ than the value at the beginning of the first sub-step or to a value comprised between $10^{-9}$ and $10^4$, preferentially between 0.2 and 1.

During the second sub-step that lasts for $10^{-3}$ to $10^3$ hours or preferentially for 2 to 120 hours, the debit of the gas is increased by a factor larger than 1.0000001, 1.1, 1.5, 2, 5, 10 or $10^3$ compared with the first sub-step or is comprised between 0 and $10^{10}$, preferentially between 1 and 50 mL/min per liter of growth medium, resulting in an increase of the optical density of the cells from a value at the beginning of the second sub-step that is equal to that obtained at the end of the first stub-step or that is comprised between $10^{-9}$ and $10^4$, preferentially between 0.2 and 1, to a value at the end of the second sub-step larger by a factor of more than 1.0000001, 1.1, 1.5, 2, 5, 10 or $10^3$ than the value at the beginning of the second sub-step or to a value comprised between $10^{-9}$ and $10^4$, preferentially comprised between 0.5 and 4.

During the third sub-step that lasts for $10^{-3}$ to $10^3$ hours or preferentially for 2 to 120 hours, the debit of the gas is increased by a factor larger than 1.0000001, 1.1, 1.5, 2, 5, 10 or $10^3$ compared with the second sub-step or is comprised between 0 and $10^{10}$, preferentially between 50 and 120 mL/min per liter of growth medium, resulting in an increase of the optical density of the cells from a value at the beginning of the third sub-step that is equal to that obtained at the end of the second sub-step or that is comprised between $10^{-9}$ and $10^4$, preferentially between 0.5 and 4 to a value at the end of the third sub-step larger by a factor of more than 1.0000001, 1.1, 1.5, 2, 5, 10 or $10^3$ than the value at the beginning of the third sub-step or to a value comprised between $10^{-9}$ and $10^4$, preferentially comprised between 1 and 8 at the end of the third sub-step.

During the fourth sub-step that lasts for $10^{-3}$ to $10^3$ hours, preferentially for 2 to 120 hours, the debit of the gas is increased by a factor larger than 1.0000001, 1.1, 1.5, 2, 5, 10 or $10^3$ compared with the third sub-step or is comprised between 0 and $10^{10}$, preferentially between 200 and 300 mL/min per liter of growth medium, resulting in an increase of the optical density of the cells from a value at the beginning of the fourth sub-step that is equal to that obtained at the end of the third sub-step or that is comprised between $10^{-9}$ and $10^4$, preferentially between 1 and 8 to a value preferentially at the end of the fourth sub-step larger by a factor of more than 1.0000001, 1.1, 1.5, 2, 5, 10 or $10^3$ than the value at the beginning of the fourth sub-step or to a value comprised between $10^{-9}$ and $10^4$, preferentially between 2 and 16 at the end of the fourth sub-step.

During the fifth sub-step that lasts for $10^{-3}$ to $10^3$ hours, preferentially for 2 to 120 hours, the debit of the gas is increased by a factor larger than 1.0000001, 1.1, 1.5, 2, 5, 10 or $10^3$ compared with the fourth sub-step or is comprised between 0 and $10^{10}$, preferentially between 300 and 500 mL/min per liter of growth medium, resulting in an increase of the optical density of the cells from a value at the beginning of the fifth sub-step that is equal to that obtained at the end of the fourth sub-step or that is comprised between $10^{-9}$ and $10^4$, preferentially between 2 and 16 to a value at the end of the fifth sub-step larger by a factor of more than 1.0000001, 1.1, 1.5, 2, 5, 10 or $10^3$ than the value at the beginning of the fifth sub-step or to a value comprised between $10^{-9}$ and $10^4$, preferentially comprised between 4 and 32 at the end of the fifth sub-step.

In one embodiment of the invention, during sub-step i, preferentially sub-steps 2 to 5: i) the percentage of oxygen is maintained above 0.01% or 0.1 mBar by the debit of air and below 0.9% or 9 mBar due to the consumption of oxygen by the cells, ii) the debit of the gas is comprised between 0 and $10^{10}$, 1 and $10^5$, 5 and $10^4$, 10 and $10^3$ mL/min per liter of growth medium, iii) the growth medium is stirred at a speed comprised between 1 and $10^5$, 10 and $10^4$, 50 and $10^3$, or between 100 and 500 rotations per minute, iv) the debit of the gas can be decreased by increasing the stirring rate of the media, v) the debit of the gas can be increased by decreasing the stirring rate of the media, and/or vi) the optical density of the cells increases from a value preferentially comprised between $10^{-50}$ and $10^3$ at the beginning of sub-step i to a value preferentially comprised between $10^{-20}$ and $10^5$ at the end of sub-step i.

In one embodiment of the invention, the growth step comprises at least one sub-step during which: i) the pH of the growth medium is maintained at a fixed or determined or chosen pH, comprised between 0 and 14, 2 and 13, 4 and 11, 5 and 10, preferentially comprised between 5 and 8, most preferentially equal to 6.9, preferentially by adding an acidic source of iron comprised in a fed-batch medium, preferentially under stirring conditions at 1 to $10^{10}$, preferentially 100 to 300 rotations per minute. In some cases, the growth medium comprises an iron concentration at the beginning of the growth step or one of its sub-step that is: i) lower than $10^{10}$, $10^5$ or $10^2$ µM, preferentially lower than 10 or 2 µM, and/or ii) comprised between $10^{-10}$ and $10^{10}$, $10^{-5}$ and $10^5$, $10^{-3}$ and $10^3$ µM, preferentially comprised between 0.2 and 20 µM. In some other cases, during the growth step or one of its sub-step, the iron concentration of the growth medium increases, preferentially with the addition of the fed-batch medium to the growth medium, to reach a value at the end of the growth step or one of its sub-step that is: i) larger than $10^{-10}$, $10^{-5}$, $10^{-1}$ or 1 µM, preferentially larger than 2 µM and/or ii) comprised between $10^{-10}$ and $10^{10}$ µM, preferentially between 2 µM and 5 mM or between 2 µM and 0.5 mM.

In one embodiment of the invention, the growth step comprises at least one of the following sub-step(s), wherein:
  During the first sub-step, which lasts for $10^{-3}$ to $10^3$, preferentially 2 to 16 hours, the insertion of the fed-batch medium to the growth medium yields an iron concentration in the growth medium comprised between $10^{-10}$ and $10^{10}$ µM, preferentially between 2 and 20 µM, in some cases without taking into account the consumption of iron by the bacteria, in some other cases by taking into account the consumption of iron by the bacteria. This preferentially results in a production of nanoparticles that increases by a factor larger than 1.0000001, 1.1, 1.5, 2, 5, 10 or $10^3$ from the beginning to the end of the first sub-step, or from a value comprised between $10^{-10}$ and $10^{10}$, preferentially between 0.001 and 0.1 mg of nanoparticles per liter of growth medium at the beginning of the first sub-step to a value comprised between $10^{-10}$ and $10^{10}$, preferentially between 1 and 10 mg of nanoparticles per liter of growth medium at the end of the first sub-step.
  During the second sub-step, which lasts for $10^{-3}$ to $10^3$, preferentially 2 to 120 hours, the insertion of the fed-batch medium to the growth medium yields an iron concentration in the growth medium comprised between $10^{-10}$ and $10^{10}$ µM, preferentially between 20 and 40 µM, in some cases without taking into account the consumption of iron by the bacteria, in some other cases by taking into account the consumption of iron by the bacteria. This preferentially results in a production of nanoparticles that increases by a factor larger than 1.0000001, 1.1, 1.5, 2, 5, 10 or $10^3$ from the beginning to the end of the second sub-step, or from a value comprised between $10^{-10}$ and $10^{10}$, preferentially 1 and 10 mg of nanoparticles per liter of growth medium at the beginning of the second sub-step to a value comprised between $10^{-10}$ and $10^{10}$, preferentially between 2 and 20 mg of nanoparticles per liter of growth medium at the end of the second sub-step.
  During the third sub-step, which lasts for $10^{-3}$ to $10^3$, preferentially 2 to 120 hours, the insertion of fed-batch medium to the growth medium yields an iron concentration in the growth medium comprised between $10^{-10}$ and $10^{10}$ µM, preferentially between 40 and 150 µM, in some cases without taking into account the consumption of iron by the bacteria, in some other cases by taking into account the consumption of iron by the bacteria. This preferentially results in a production of nanoparticles that increases by a factor larger than 1.0000001, 1.1, 1.5, 2, 5, 10 or $10^3$ from the beginning to the end of the third sub-step, or from a value comprised between $10^{-10}$ and $10^{10}$, preferentially between 2 and 20 mg of nanoparticles per liter of growth medium at the beginning of the third sub-step to a value comprised between $10^{-10}$ and $10^{10}$, preferentially 4 and 40 mg of nanoparticles per liter of growth medium at the end of the third sub-step.
  During the fourth sub-step of the growth step, which lasts for $10^{-3}$ to $10^3$, preferentially for 2 to 120 hours, the insertion of the fed batch medium to the growth medium yields an iron concentration in the growth medium comprised between $10^{-10}$ and $10^{10}$ µM, preferentially between 150 and 500 µM, in some cases without taking into account the consumption of iron by the bacteria, in some other cases by taking into account the consumption of iron by the bacteria. This preferentially results in a production of nanoparticles that increases by a factor larger than 1.0000001, 1.1, 1.5, 2, 5, 10 or $10^3$ from the beginning to the end of the fourth sub-step, or from a value comprised between $10^{-10}$ and $10^{10}$, preferentially from a value comprised between 4 and 40 mg of nanoparticles per liter of growth medium at the beginning of the fourth sub-step to a value comprised between $10^{-10}$ and $10^{10}$, preferentially between 8 and 80 mg of nanoparticles per liter of growth medium at the end of the fourth sub-step.
  During the fifth sub-step of the growth step, which lasts for $10^{-3}$ to $10^3$, preferentially 2 to 120 hours, the insertion of the fed batch medium to the growth medium yields an iron concentration in the growth medium comprised between $10^{40}$ to $10^{10}$ µM, preferentially between 500 and 1000 µM, in some cases without taking into account the consumption of iron by the bacteria, in some other cases by taking into account the consumption of iron by the bacteria. This preferentially results in a production of nanoparticles that increases by a factor larger than 1.0000001, 1.1, 1.5, 2, 5, 10 or $10^3$ from the beginning to the end of the second sub-step, or from a value comprised between $10^{-10}$ and $10^{10}$, preferentially between 8 and 80 mg of nanoparticles per liter of growth medium at the beginning of the fifth sub-step to a value comprised between $10^{40}$ and $10^{10}$, preferentially between 16 and 160 mg of nanoparticles per liter of growth medium at the end of the fifth sub-step.

In one embodiment of the invention, during the growth step or sub-step i of the growth step, preferentially sub-steps 1 to 5: i), the iron concentration of the growth medium is increased above $10^{40}$ µM, preferentially 2 µM, preferentially by adding a fed-batch medium comprising iron to the growth medium and below $10^{10}$ mM, preferentially 5 mM, due to the consumption of iron by the cells, ii), the total quantity of iron per liter of growth medium brought to the growth medium is comprised between $10^{-6}$ and 15, preferentially between $2.10^4$ and 1.5 g of iron per liter of growth medium, and/or iii) the quantity of nanoparticles increases from a value between 0 and 500 mg, preferentially between 0 and 80 mg of nanoparticles per liter of growth medium at the beginning of the growth step or one of its sub-step to a value comprised between 1 and $10^5$ mg, preferentially between 10 and 200 mg of nanoparticles per liter of growth medium at the end of the growth step or one of its sub-step.

In one embodiment of the invention, the grow step consists in amplifying the cells, were such amplification is associated with, or corresponds to: a speed or rate or number of cell division or an optical density, which is larger, preferentially by a factor of more than 1.000001, 1.0001, 1.01, 1.1, 1.2, 1.5, 2, 5, 10, $10^2$, $10^3$, $10^5$, $10^{10}$, $10^{20}$ or $10^{50}$ during the growth step or at least one of its sub-step than during the pre-growth step or at least one of its sub-step.

In one embodiment of the invention, preferentially during, at the beginning, or at the end of the growth step or of at least one of its sub-steps, nanoparticle-producing cells have or are characterized by at least one of the following properties: i) a number of nanoparticles comprised in the cells that is larger than 1, 2, 5, 10, 50, $10^2$ or $10^3$, preferentially larger than 0, 1 or 2, or between 0 and $10^3$, preferentially between 0 and 100 or between 0 and 10, ii) a percentage of cells with at least one nanoparticle that is larger than $10^4$, $10^{-2}$, $10^{-1}$, 1, 5, 10, 50, 75 or 95, preferentially larger than 10 or 50% or comprised between 0 and 99%, 10 and 75, 5 and 90, preferentially between 20 and 100%, iii) an optical density larger than $10^{-50}$, $10^{-20}$, $10^{-10}$, $10^{-5}$, $10^{-3}$, $10^{-2}$, 0.1, 0.2, 0.5, 1, 5, 10 or 100, iv) a number of cells larger than 1, 5, 10, $10^2$, $10^3$, $10^5$, $10^{10}$, $10^{20}$, $10^{50}$ or $10^{100}$, v) cells comprised in a volume larger than 0.0001, 0.001, 0.1, 1, 10, 50, $10^2$, $10^3$, $10^5$ or $10^{10}$ liter(s), vi) a number of cell generation comprised between 1 and $10^{10}$, 1 and $10^3$, preferentially between 50 and 300, vii) a ratio between the optical density measured at the end of the growth step, $OD_{GE}$, and the beginning of the growth step, $OD_{GB}$, $OD_{GE}/OD_{GB}$, which is larger than 1, 2, 5, 10, 15, 25, 50, 100, $10^3$, $10^5$, $10^{10}$, $10^{50}$ or $10^{100}$, or viii) a ratio between the optical density measured at the end of sub-step i of the growth step, $OD_{GiE}$, and the beginning of sub-step i of the growth step, $OD_{GiB}$, $OD_{GiE}/OD_{GiB}$, which is larger than 1, 2, 5, 10, 15, 25, 50, 100, $10^3$, $10^5$, $10^{10}$, $10^{50}$ or $10^{100}$.

In one embodiment of the invention, the cells that produce essentially no nanoparticles are non-magnetic cells.

In one embodiment of the invention, at the beginning, preferentially during, at the beginning or at the end of the growth step or at least one of its sub-steps, a percentage of magnetic cells larger than $10^{-50}$, $10^{-20}$, $10^{-10}$, $10^{-5}$, $10^{-3}$, $10^{-1}$, 1, 5, 10, 50 or 75%, is obtained. In some cases, the percentage of magnetic cells is equal to $n_{MC}/(n_{MC}+n_{NMC})$, where $n_{MC}$ and $n_{NMC}$ are the numbers of magnetic cells and non-magnetic cells, respectively.

In another embodiment of the invention, magnetic cells are cells that display a magnetic response.

In some cases, the pre-growth step, the growth step, or at least one of their sub-step, is carried out at a temperature larger than −250, −200, −150, −100, −50, −20, −10, −5, −2, −1, 0, 1, 2, 5, 10, 20, 50, 75, 100, $10^3$, $10^5$ or $10^{7°}$ C. or with a temperature variation larger than $10^{-5}$, $10^{-3}$, $10^{-2}$, 0.1, 1, 5, 10, 50, 100 or 150° C. In some other cases, the pre-growth step, growth step, or at least one of their sub-steps, is carried out at a temperature lower than $10^7$, $10^5$, $10^3$, 100, 75, 50, 40, 30, 20, 10, 5, 2, 1, 0, −1, −2, −5, −10, −20, −50, −100, −150, −200 or −250° C. or with a temperature variation lower than $10^5$, $10^3$, $10^2$, 50, 20, 10, 5, 2, 1 or 0.1° C.

In some cases, the pre-growth step, growth step, or at least one of their sub-steps, is carried out at a pH larger than 1, 2, 3, 4, 5, 6, 7, 8, 9, 10, 11, 12, 13 or 14. pH or with a pH variation larger than $10^{-10}$, $10^{-7}$, $10^{-5}$, $10^{-4}$, $10^{-3}$, $10^{-1}$, 1, 2, 3, 4, 5, 6, 7, 8, 9, 10, 11, 12, 13 or 14 pH unit(s). In some other cases, the pre-growth step, the growth step, or at least one of their sub-steps, is carried out at a pH lower than 1, 2, 3, 4, 5, 6, 7, 8, 9, 10, 11, 12, 13 or 14 or with a pH variation lower than $10^{-10}$, $10^{-7}$, $10^{-5}$, $10^{-4}$, $10^{-3}$, $10^{-1}$, 1, 2, 3, 4, 5, 6, 7, 8, 9, 10, 11, 12, 13 or 14 pH unit(s).

In some cases, the temperature, temperature variation, pH, or pH variation, is sufficiently large to enable at least 1, 5, 10, $10^3$, $10^5$, $10^{10}$ or $10^{50}$ cell division(s) or cell divisions(s) per hour.

In some other cases, the temperature, temperature variation, pH, or pH variation, is sufficiently low to prevent the destruction, disappearance, or denaturation of more than 1, 5, 10, $10^3$, $10^5$, $10^{10}$ or $10^{50}$ cell(s) or cell(s) per hour.

The invention also relates to the method according to the invention, wherein the pre-growth medium does not comprise iron or at least one source of iron.

The invention relates to the method according to the invention, wherein the pre-growth medium comprises iron or at least one source of iron, wherein the nature and/or the quantity of iron or source of iron, preferentially essentially, does not allow the production of the nanoparticles by the cells while allowing cell growth.

In one embodiment of the invention, the nature of the source of iron is the composition, chemical formula, type of iron source, or is the iron source itself. In some cases, the iron source is a ferric or ferrous iron source. In some cases, it can be or comprise or be made of or have the chemical formula $Cl_3Fe$, $C_{10}H_{12}FeN_2NaO_8$, $Fe_2O_{12}S_3$, $C_6H_8FeNO_7$, $C_6H_5FeO_7$, $FeH_{18}N_3O_{18}$, $C_{30}H_{21}FeN_3O_{15}^{-3}$, $FeO_4P$, $C_6H_7FeO_8$, $Fe_2H_2O_{13}S_3$, $Fe_2H_{12}O_{18}S_3$, $C_{10}H_{12}FeN_2NaO_8$, $C_{10}H_{13}FeN_2O_8$, $FeH_{28}NO_{20}S_2$, $C_{10}H_{15}FeN_2NaO_8$, $C_{10}H_{14}FeN_2NaO_8^{+4}$, $C_{14}H_{21}FeN_3O_{10}$, $C_{18}Fe_7N_{18}$, $Fe_4H_2O_{22}S_5$, $Fe_4O_{21}P_6$, $F_3Fe$, $C_6H_{11}FeNO_7^{+3}$, $C_6H_1FeNO_7$, $C_{18}H_{15}FeO_9$, $C_{12}H_{29}Fe_5Na_2O_{23}$, $C_{12}H_{22}Fe_2O_{14}$, $C_{15}H_{21}FeO_6$, $C_{15}H_{24}FeO_6$, $C_6H_5FeO_7$, $C_{10}H_{16}FeN_3O_8$, $C_4H_{10}FeO_5$, $C_{54}H_{105}FeO_6$, $AsFeH_{13}O_9^+$, $AsFeO_4$, $Fe^{+3}$, $C_6H_{12}FeN_3O_{12}$, $C_6H_{18}As_3FeO_6$, $FeH_2O_5P$, $C_{21}H_{21}FeO_9S_3$, $C_6H_{11}FeNa_7^{+3}$, $C_{14}H_{22}FeN_3NaO_{10}$, $FeNaO_7P_2$, $C_3H_9As_3Fe_3O_9$, $C_{18}H_{24}Fe_4O_{42}P_6$, $C_6H_{11}FeO_{10}$, $C_9H_{18}FeN_3S_6$, $Cl_3FeO_{12}$, $C_6H_9FeNO_7^+$, $Cr_3Fe_2O_{12}$, $C_6H_{10}FeNO_8$, $FeH_3O_3$, $C_{15}H_{30}FeN_3S_6$, $C_{30}H_{27}FeN_3O_{15}$, $C_3FeN_3S_3$, $C_6H_{12}FeKO_6^{+4}$, $FeH_3O_3$, $FeN_3O_9$, $C_3H_3FeO_6$, $C_6H_8FeO_7$, $C_{24}H_{45}FeO_6$, $FeO_6P_3$, $Fe_2H_{14}O_{19}S_3$, $C_{18}H_{33}FeO_{21}$, $C_6H_9FeO_9$, $C_{18}H_{27}FeO_{24}$, $C_6FeN_6^3$, $C_{10}H_{12}FeN_2O_8^-$, $C_{22}H_{36}N_4O_{13}$, $C_3FeN_3$, $C_6H_{12}FeN_3O_{12}$, $C_6H_9FeO_6$, $C_{15}H_{27}FeO_6$, $FeH_4O_6P$, $C_{21}H_{15}FeO_9$, $FeH_8O_8P$, $C_6H_6FeNO_6$, $C_4FeKO_8$, $C_{12}H_{12}Fe_2O_{18}$, $C_{33}H_{35}FeN_4O_4$, $Cl_3FeH_4O_2$, $C_{24}H_{45}FeO_6$, $C_{10}H_{15}FeN_2O_7$, $FeH_4NO_8S_2$, $C_{32}H_{31}FeN_4O_5$, $Fe_2H_6O_3$, $AlF_6Fe$, $C_4H_4FeNO_8$, $C_{81}H_{84}FeN_3O_{33}$, $Fe_2S_3$, $Cl_3FeH_{14}O_7$, $C_{18}H_6FeN_9O_{21}$, $Cl_3FeO_9$, $FeI_3$, $C_6H_{14}FeO_{10}$, $C_6H_{10}FeO_8$, $C_{55}H_{80}FeN_{17}O_{21}S_3$, $C_{10}H_{16}FeN_5O_{13}P_3$, $C_{18}H_{34}FeO_{16}^{+3}$ $C_{12}H_{12}Fe_2O_{15}$, $C_6FeNa_3O_{12}$, $C_{10}H_{12}FeKN_2O_8$, $C_{21}H_{24}FeN_3O_9$, $C_6H_6Fe_2O_{12}$, $C_6Fe_2O_{12}$, AsFe, $C_{35}H_{33}FeN_5O_{11}^{-3}$, $Cl_3FeH_2O$, $C_{18}H_{30}Fe_2N_6O_{12}$, $FeI_3O_9$, $C_{10}H_{18}FeN_2NaO_{11}$, $Cl_3FeH_{18}O_9$, $Cr_2FeH_4NO_8$, $C_9H_{21}Fe_2O_{18}P_3$, $C_{18}H_{34}FeO_2$, $C_{30}H_{27}FeO_6$, $C_{30}H_{24}FeN_3O_{15}$, $C_{54}H_{102}FeO_6$, $Fe_4H_{18}O_{30}P_6$, $Fe_2Se_3$, $C_{54}H_{99}FeO_6$, $C_{15}H_{21}FeO_6$, $C_{10}H_{18}FeN_2O_7^{+2}$, $C_{10}H_{18}FeN_2O_7^{+2}$, $C_{10}H_{19}FeN_3O_8$, $C_{22}H_{14}FeO_4$, $C_{39}H_{63}FeN_6O_{15}^{+3}$, $C_{10}H_{19}FeN_3O_8$, $C_4FeNaO_8$, $FeO_4V$, $C_6H_{15}FeN_3O_{12}$, $C_6Fe_2O_{12}$, $C_{18}H_{24}Fe_2O_{24}^{-6}$, $C_{18}H_{19}FeN_2NaO_6$, $C_{18}H_{19}FeN_2NaO_6$, $C_{12}H_{18}Fe_2O_{12}$, $C_6FeK_3N_6$, $C_{24}H_{47}FeO_{25}^-$, $C_{18}H_{38}FeO_{19}$, $C_{15}H_{21}FeO_6$, $C_{18}H_{39}FeO_{24}$, $C_6H_{11}FeNO_7$, $C_6H_{12}FeO_6$, $C_{12}H_{28}FeO_{14}$, $FeHO_2$, $C_{45}H_{36}FeN_3O_6$, $Fe_3H_2O_4$, $Fe_2O_3$, $C_{36}H_{72}FeO_6$, $C_{12}H_{18}Fe_2O_{15}$, $C_9H_{18}FeO_9$, $FeH_6O_3$, $C_{54}H_{102}FeO_6$, $C_{42}H_{84}FeO_6$, $C_{16}H_{31}Fe\ O_2^2$, $C_{36}H_{69}FeO_6$, $Fe_3H_8O_4$, $C_8H_{15}Fe_2O_2^{+4}$, $C_{12}H_{48}Fe_2N_{12}O_{12}S_3$, $C_{48}H_{96}FeO_6$, $C_9H_{15}FeO_9$, $C_{35}H_{39}FeN_5O_{11}$, $C_{42}H_{81}FeO_6$, $C_{48}H_{93}FeO_6$, $C_{10}H_{24}O_2$, $Fe_2H_{18}O_{21}S_3$, $FeH_{12}N_3O_{15}$, $C_{24}H_{23}FeN_{10}O_6S_2$, $C_{18}H_{14}Cl_3FeN_{10}S_2$, $C_{21}H_{15}FeO_6$, $Fe_2H_{10}O_{17}S_3$, $C_{10}H_{19}FeN_3O_8$, $C_{18}H_{20}FeN_2NaO_6$, $C_3F_9FeO_9S_3$, $C_5H_{14}FeO_4$, $C_6H_{19}FeNO_{11}$, $C_{18}H_{16}FeN_2NaO_6$, $C_{32}H_{36}N_4O_9$, $C_{15}H_{30}FeO_6$, $C_{15}H_{24}FeO_6$, $C_{15}H_{15}F_9FeO_6$, $C_{21}H_{21}Cl_3FeIS$, $C_6H_{12}Fe_2O_{18}$, $C_6H_{18}FeO_{12}$, $C_6H_{15}FeO_{12}$, $C_6H_{18}Fe_2O_{18}$, $C_6H_8FeO_7$, $C_6H_{13}FeO_{11}$, $C_6H_4Fe_2N_7$, $FeH_2O_4S$, $C_{42}H_{60}N_{12}O_{16}$, $C_6Fe_2N_6$, $C_3Fe_2O_9$, $C_{162}H_{297}FeO_{27}^{-6}$, $C_{21}H_{27}Cl_4FeN_2O$, $C_6H_4FeNaO_7$, $C_{27}H_{50}FeN_6O_{10}$, $C_{25}H_{48}FeN_{608}$, $C_{27}H_{48}FeN_6O_9$, $C_6H_7FeO_6^{+2}$, $Fe_2H_2O_4$, $C_{14}H_{26}FeN_5O_{10}$, $Cl_4FeH_4N$, $Cl_3FeH_{12}O_{18}$, $C_6H_{17}FeN_2NaO_7^{+3}$, $C_{10}H_{11}FeNO_6$, $C_{15}H_{15}F_9FeO_6$, $C_6Fe_2N_6Na$, $C_9H_{21}Fe_2O_{18}P_3$, $C_{21}H_{27}C_1N_2O$, $C_2H_3FeO$, $C_{10}H_{12}Fe_2N_2O_8$, $FeH_3O_3P$, $C_7H_5FeO_2$, $C_7H_5FeO_2$, $FeI_3O_{12}$, $C_3H_4FeNO_2S$, $C_2H_2FeNO_2$, $C_{12}H_{12}Fe_2O_{12}$, $C_8H_7FeNO_3$, $C_2HFe$, $C_6H_7FeO_2S_4$, $C_6H_{11}FeO_6$, $C_{14}H_{19}FeO_{12}$, $BFeH_3O_3$, $C_{21}H_{18}FeO_{15}$, $C_{35}H_{56}FeN_6O_{13}$, $C_{12}H_{30}FeO_3$, $CHFe$, $C_{47}H_{48}FeNO_{14}$, $Fe_2H_6O_3$, $Fe_2O_9Sn_3$, $C_{18}H_{18}FeO_3$, $Fe_2O_9Se_3$, $Fe_2O_9Si_3$, $Fe_2O_9S_3$, $Br_3FeO_9$, $FeN_3O_6$, $C_{24}H_{54}FeO_3$, $C_{66}H_{129}FeO_6$, $FeP$, $C_6H_{18}FeO_{24}P_6^{+3}$, $C_{33}H_{72}FeO_3$, $C_{40}H_{75}FeO_4$, $C_2H_3FeS$, $C_3FeN_3$, $C_{21}H_{39}FeO_6$, $FeSi$, $C_{30}H_{29}FeN_3O_{16}$, $C_{22}H_{36}FeN_4O_{13}$, $C_{30}H_{57}FeO_6$, $C_{60}H_{117}FeO_6$, $C_{18}H_{12}FeN_3O_6$, $C_{18}H_{31}FeO_2^{+2}$, $FeS_2$, $C_6H_{11}FeN_4O_2$, $C_6H_5FeO_7$, $C_6H_5FeS$, $C_{10}H_{13}FeN_2O_{10}^-$, $C_8H_{13}FeOS_2$, $C_{27}H_{51}FeO_6$, $C_{24}H_{44}FeO_{25}^-$, $C_6H_{15}FeN_3O_6$, $C_6H_{12}FeO_9$, $Cl_3FeO_9S_3$, $CFeNS$, $Fe_4H_{12}O_{12}Si_3$, $C_3H_6FeO_{12}$, $C_4H_3FeO_4S_2$, $C_4H_4FeO_6$, $C_6H_3FeN_3O_6$, $C_5H_5FeO_2$, $C_{10}H_{24}FeN_4O_9$, $C_{14}H_{19}FeN_3NaO_{10}$, $C_{10}H_{14}FeN_2Na_2O_8$, $C_{36}H_{44}FeN_4$, $C_6FeNa_3O_{12}$, $Fe_2H_3OS_3$, $C_{16}H_{27}FeO_4$, $C_6H_8Fe_2O_{13}$, $C_6H_7FeO_3$, $C_4H_4FeO_6S_2$, $C_2H_5FeN_2$, $C_5H_7FeOS_2$, $C_{18}H_{18}FeNa_6O_{21}$, $C_3H_9FeO_9S_3$, $C_{24}H_{54}FeO_{12}P_3$, $C_{36}H_{55}FeN_6O_{11}$, $Fe_2H_2O_{10}Si_3$, $C_2H_4FeNO_2$, $C_4H_{11}FeN_2O_4$, $AsFeH_2O_5$, $C_{12}H_{13}FeO_{13}$, $C_{36}H_{67}FeO_6$, $C_{12}H_{13}FeO_{13}$, $C_3H_6FeN_3O_6$, $C_{18}H_{15}FeO_9S_3$, $C_{36}H_{75}FeO_{12}S_3$, $Fe_2H_4O_5$, $C_{28}H_{24}FeN_4^{+3}$, $F_3Fe$, $C_{30}H_{30}FeO_6$, $BFe$, $C_2H_8N_2O_4$, $C_8H_5FeN_2O_5$, $Fe_2H_4O_{11}Se_3$, $C_6H_7FeO_6S_4$, $C_4H_{10}FeN_3$, $C_6H_{12}Fe_2O_{15}$, $C_{15}H_{23}FeO_5$, $C_8H_{12}FeNO_{12}$, $C_{49}H_{56}C_1FeN_4O_6$, $FeH_1NO_8S_2$, $C_{36}H_{75}FeO_9S_3$, $B_3F_{12}Fe$, $FeP$, $Fe_2H_{20}O_{22}S_3$, $Cl_3FeH_{12}O_{15}$, $C_{18}H_9FeN_6$, $Fe_2H_{12}O_{15}Se_3$, $C_{56}H_{51}FeN_4$, $Fe_2H_8O_{13}Se_3$, $C_{44}H_{27}FeN_4$, $C_{33}H_{30}FeN_4O_6^{-2}$, $CrFeO_3$, $C_{18}H_{12}FeN_3O_{15}S_3$, $Cl_3FeH_{18}O_{21}$, $C_6H_5FeNa_3O_{13}$, $C_{18}H_{14}FeN_{13}O_9S_2$, $C_{15}H_{24}FeO_6$, $C_{24}H_{27}FeO_9S_3$, $C_{27}H_{54}FeN_3S_6$, $Cl_3FeH_{12}O_6$, $C_{16}H_{36}Pb$, $C_8H_{18}Fe_2O_{12}P_2$, $Cl_3FeH_{24}O_{12}$, $C_{24}H_{30}FeO_9S_3$, $C_{21}H_{24}FeO_9S_3$, $C_{18}H_{15}FeO_{12}S_3$, $Cl_3FeH_{20}O_{10}$, $C_{28}H_{24}FeN_6O_6^+$, $C_{66}H_{121}Fe_2NaO_{65}$, $Cr_3FeH_3O_{12}$, $C_{12}H_{28}Fe_2O_{14}$, $C_3H_8FeNS_2Zn^-$, $F_3FeH_6O_3$, $C_{30}H_{51}FeO_6$, $C_{30}H_{48}Fe_4N_6O_{24}$, $C_{30}H_{18}FeN_3O_6$, $C_{20}H_{36}FeO_4$, $C_6H_6FeK_3O_{15}$, $C_{15}H_6F_{18}FeO_6$, $C_{10}H_{13}FeN_2O_8$, $C_6FeN_6$, $C_{15}H_3F_{18}FeO_6$, $C_{15}H_{12}FeN_3O_3S_3$, $C_{21}H_{23}FeO_{10}S_3$, $FeH_2O^{+3}$, $C_{24}H_{44}FeNaO_{28}$, $Cr_3FeO_6$, $Fe_2H_2O^{+6}$, $C_6H_{12}FeN_9$, $FeH_5NO_4S$, $C_2K_2O_4$, $C_{18}H_{13}FeN_6$, $C_{30}H_{27}FeO_6$, $C_{34}H_{38}N_4O_4$, $Cl_3FeH_{15}O_{18}$, $C_6H_{18}FeO_6P_3S_6$, $C_6H_{11}ClFeNO_{10}S_2$, $C_5H_4F_3FeO_2^{+2}$, $C_6H_6Cr_2O_{12}$, $C_4H_3CrKO_8$, $C_2MgO_4$, $C_{12}H_{25}FeO_{14}$, $C_2H_2MgO_4^{+2}$, $C_2CrO_4^+$, $C_2HNaO_4$, $C_2HKO_4$, $C_6Cr_2O_{12}$, $C_2H_2FeO_4$, $C_2H_4MgO_6$, $C_6AlO_{12}^3$, $C_6Al_2O_{12}$, $C_2Li_2O_4$, $C_2MgO_4$, $C_{44}H_{30}N_4O_{12}S_4$, $C_{10}H_{19}FeN_2NaO_{10}$, $C_5H_4CuFeN_6O_3$, $C_{10}H_{14}FeN_2NaO_9$, $C_{30}H_{15}FeN_3Na_3O_{15}S_3$, $C_{27}H_{15}FeN_{12}O_6$, $C_9H_{18}FeN_3S_6$, $C_{30}H_{30}FeN_3O_{15}^{+3}$, $C_9H_{18}FeN_3S_6$, $C_6FeN_6$, $C_{18}Fe_7N_{18}$, $C_{18}H_{18}FeN_2NaO_6$, $C_{30}H_{21}FeN_{12}O_6$, $C_{44}H_{30}FeN_4^{+3}$, $C_{14}H_{18}FeK_2N_3O_{10}$, $C_{10}H_{16}FeN_2NaO_8$, $C_{33}H_{29}FeNO_{11}^+$, $C_{25}H_{18}FeN_4O_6S^+$, $C_{35}H_{24}FeN_6O_2S^+$, $C_{32}H_{32}C_1FeN_4O_6$, $C_{30}H_{12}F_9FeN_{12}O_6$, $C_{30}H_{18}Cl_3FeN_{12}O_9$, $C_{60}H_{72}FeN_9O_9^{+3}$, $C_{60}H_{66}FeN_9O_9^{+3}$, $C_{15}H_{24}FeO_6$, $C_{22}H_{25}Cl_2FeN_3O_9^+$, $C_{18}H_{23}Cl_3FeN_3O_{12}$, $C_{11}H_{24}FeNO_{11}$, $C_{49}H_{54}FeN_4O_9^+$, $C_{42}H_{54}C_{18}Fe_2N_4O_2$, $C_{44}H_{26}Cl_4FeN_4^{+3}$, $C_{34}H_{32}FeN_4O_4^+$, $C_{44}H_{38}FeN_8^{+7}$, $C_9H_{11}Cl_2FeN_4O_2S$, $C_{18}H_{32}FeN_4O_8^{+3}$, $C_{34}H_{32}ClFeN_4O_6$, or $C_{19}H_{25}FeN_4O_6$. In some other cases, the iron source can be or comprise or be made of or have the chemical formula: $Fe^{+2}$, $FeH_{14}O_{11}S$, $FeH_8N_2O_8S_2$, $FeO_4S$, $Cl_2Fe$, $FeS$, $C_4H_2FeO_4$, $C_{12}H_{26}FeO_{16}$, $C_4H_5FeNO_4$, $C_{12}H_{10}Fe_3O_{14}$, $C_{16}H_{30}FeO_4$, $FeH_2O_5S$, $C_{10}H_{12}FeN_2Na_2O_8$, $As_2Fe_3O_8$, $CFeO_3$, $C_6H_{12}FeO_6$, $FeH_{12}N_2O_{12}$, $C_{12}H_{10}Fe_3O_{14}$, $C_6H_5FeNaO_7$, $C_{34}H_{32}FeN_4O_4$, $C_{12}H_{22}FeO_{14}$, $C_{12}H_{14}FeO_{12}$, $C_6H_{10}FeO_6$, $C_4H_8FeN_2O_4$, $C_{12}H_{28}FeO_{16}$, $FeI_2$, $FeH_4N_2O_6S_2$, $C_{34}H_{32}FeN_4O_{41}^{-2}$, $C_{34}H_{32}FeN_4O_4$, $F_2Fe$, $C_6H_{18}FeO_9$, $C_6H_5FeO_7^-$, $C_2FeO_4$, $C_4H_4FeO_4$, $C_{12}FeO_8$, $Fe_3O_8P_2$, $FeO$, $B_2F_8Fe$, $FeH_8O_8S$, $C_4H_6FeO_4$, $C_4H_4FeO_4$, $C_{12}H_{10}FeNa_4O_{14}$, $C_{22}H_{14}FeO_4$, $C_2H_4FeO_6$, $C_{12}H_{24}FeO_{14}$, $C_{14}H_{20}FeN_3O_{10}^-$, $C_{12}FeH_8O_4$, $C_{12}H_8FeN_2O_4$, $C_4H_8FeO_4$, $C_5H_7FeNO_4$, $C_8H_{12}FeN_2O_8$, $C_{12}H_{10}Fe_3O_{14}$, $C_6H_{16}FeO_9$, $C_{19}H_{19}FeN_7O_{10}S$, $C_{10}H_{16}FeN_2O_8$, $C_{12}H_{10}Ca_2FeO_{14}$, $C_2H_6FeO_6$, $C_{36}H_{70}FeO_4$, $C_6H_6FeO_7$, $C_4H_2FeO_4$, $C_{36}H_{21}Cl_2FeNgO_{14}$, $C_{32}H_{62}FeO_4$, $FeH_2O_2$, $C_4H_6FeO_6$, $C_6H_8CaFeO_7^{+4}$, $C_4H_{10}Cl_2FeN_2O_4$, $C_{36}H_{24}Cl_2FeN_6O_8$, $C_6H_{14}FeO_7$, $C_{12}H_{16}FeO_{12}$, $BFe$, $C_{32}H_{16}FeN_8$, $C_{12}H_{26}FeO_{15}$, $C_{12}H_{10}Fe_3O_{14}$, $FeH_8I_2O_4$, $C_4H_{10}FeN_2O_8S$, $C_{30}H_{24}C_{12}FeN_6O_8$, $C_{39}H_{30}C_{12}FeN_6O_8$, $C_{12}H_{14}FeO_{12}$, $C_{30}H_{24}FeN_6^{+2}$, $C_4H_2FeO_4^{-2}$, $C_4H_4FeO_4$, $C_{10}H_{16}FeO_4$, $C_{36}H_{24}FeN_6O_4S$, $C_2H_4FeO_6$, $C_2H_2FeO_6$, $C_8H_{15}Fe_2O_2^{+4}$, $C_{32}H_{16}FeN_8$, $C_{12}H_{16}Fe_3O_{14}$, $C_{12}H_{24}FeO_{14}$, $C_2FeN_2S_2$, $C_{12}H_{16}FeN_6O_4$, $C_{14}H_{20}FeN_3O_{10}$, $C_{12}H_7FeN_3O_6S$, $C_{20}H_{12}FeN_4$, $C_{12}H_{16}Ca_2FeO_{14}$, $C_{46}H_{54}FeO_9$, $C_6H_5FeO_7$, $FeH_4O_6S$, $C_{10}H_{15}FeN_2NaO_7$, $C_{10}H_6FeN_4O_8$, $Fe_2P$, $C_4H_4FeO_6$, $C_{14}H_{26}FeO_{16}$, $C_{12}FeH_{12}O_{14}$, $C_4H_8C_{12}FeN_2O_4$, $C_6Fe_3N_6$, $C_4H_{12}As_2FeO_8$, $C_{10}H_{16}FeO_4$, $FeH_{20}N_2O_{14}S_2$, $C_{16}H_{30}FeO_4$, $C_{40}H_{40}FeN_8O_4^+$, $Fe_2Na_8O_{21}P_6$, $C_{14}H_8FeO_{10}$, $C_{14}H_8FeO_4$, $C_{12}H_{20}FeO_4$, $C_8H_8FeS$, $C_5H_4FeO$, $C_2H_3FeNO_2$, $C_{10}H_{14}FeN_2O_8$, $C_6H_2FeN_3O_7^+$, $C_2H_2Fe$, $C_{10}H_6FeN_2$, $C_6H_{15}FeN_3O_7$, $C_{72}H_{124}FeO_8^{-2}$, $FeH_{22}N_2O_{15}S_2$, $C_{40}H_{78}FeO_4$, $FeH_1N_2O_6^{+2}$, $C_{44}H_{86}FeO_4$, $C_{10}H_{20}FeN_2O_8S_2$, $C_{20}H_{38}FeO_4$, $C_{36}H_{66}FeO_4$, $C_{24}H_{46}FeO_4$, $C_{29}H_{26}FeP^+$, $C_{36}H_{64}FeO_6$, $C_{14}H_{26}FeO_4$, $C_{26}H_{28}FeNP$, $C_{28}H_{54}FeO_4$, $C_{36}H_{32}FeN_4O_4$, $C_{36}H_{36}FeN_4O_8$, $C_6H_9FeNO_7^+$, $C_5H_6FeO_2$, $C_4H_{11}BFeO_4$, $C_8H_{19}BFeO_4$, $C_4FeO_4S_2$, $C_6H_6FeO_7$, $C_{18}H_{34}FeO_4$, $C_{12}H_{20}FeO_{13}$, $C_4H_4FeO_6$, $C_5H_7FeNO_3$, $Fe_3H_8O_4$, $C_2FeN_2S_2$, $FeH_2O_2$, $Fe_3H_2O_4$, $C_{44}H_{28}FeN_4$, $C_2H_6FeO_5$, $Fe_2H_6O_{11}S_2$, $C_3H_4FeN_2O_3$, $Fe_3H_2O_9P_2$, $C_6H_{14}Fe_3N_3O_7^{-3}$, $C_4H_{10}FeN_2O_6$, $C_{12}FeH_2O$, $FeO_4W$, $C_6H_5FeO_3P$, $C_6H_8FeO_7$, $FeTe$, $C_4H_2FeO_4$, $C_{20}H_{20}C_{12}FeN_8$, $C_{14}H_{12}FeO_6$, $C_3H_3FeO_7P$, $C_4H_7FeNO_4$, $FeO_3Si$, $C_{12}FeH_{12}O_6$, $C_{12}FeH_2O_9$, $FeH_{10}O_9S$, $FeH_{12}O_{10}S$, $C_8H_{17}FeO_3P$, $C_4H_{14}FeO_8$, $Fe_3H_{16}O_{16}P_2$, $F_6FeSi$, $C_{72}H_{42}FeN_6Na_6O_{22}S_7$, $FeH_4O_5S$, $C_{39}H_{30}FeN_6O_4S$, $C_{40}H_{50}O_4$, $C_4H_{10}FeN_2O_4$, $C_2H_4FeN_2O_4S$, $Br_2FeH_2O$, $C_{98}H_{20}OFeN_{10}$, $C_{36}H_{21}FeN_9O_{10}S$, $C_{10}H_{10}Fe$, $C_2H_6FeN_2$, $F_6FeH_{12}O_6Si$, $C_{48}H_{48}FeN_6O_4S$, $FeO_4S$, $C_2H_{10}FeN_2O_8S_2$, $C_{44}H_{27}FeN_5O$, $C_{30}H_{24}FeN_6O_4S$, $C_6H_8O_6$, $C_6H_7NaO_6$, $FeH_4O_2^{+2}$, $FeH_2O^{+2}$, $C_3H_7FeNO_7S$, $C_{30}H_{18}FeN_3NaO_6$, $C_2H_{18}FeN_2O_{12}S_2$, $C_4H_4FeO_4$, $C_7H_7FeN_4O^+$, $Br_2Fe$, $C_{18}H_{22}C_{12}FeN_2$, $C_{32}H_{28}FeN_6O_6S_2$, $C_{12}H_{14}MgO_{12}$, $C_2H_5FeNO_6S$, $C_{45}H_{60}FeN_2O_8$, $C_{30}H_{22}C_{12}FeN_2$, $C_{38}H_{26}FeN_8O_2S_2$, $C_{30}H_{28}FeN_2O_6$, $C_{14}H_{12}C_{16}FeO_4$, $C_{12}H_{14}Fe$, $C_{36}H_{36}Cl_2FeN_6O_8$, $C_{17}H_{14}FeN_4O_4S$, $C_{24}H_{30}FeN_4O_4$, $C_{34}H_{32}ClFeN_4O_6$, $C_{12}H_{12}Fe$, $Fe_3H_{14}O_{12}P_2^{+6}$, $C_{32}H_{16}FeN_8$, $FeS_2$, $C_{16}H_{15}FeNO_2^{+2}$, $C_{29}H_{20}FeO_6$, $C_{23}H_{28}FeO_2$, $C_{11}H_{10}FeO_2$, $C_{13}H_{14}FeO_2$, $C_{12}H_{12}FeO_2$, $C_{46}H_{48}FeN_4O_6^{+2}$, $C_{47}H_{59}FeN_{13}O_8^{+2}$, $C_{46}H_{59}FeN_{13}O_8^{+2}$, $C_{48}H_{62}FeN_{12}O_8S^{+2}$, $C_{50}H_{65}FeN_{13}O_8^{+2}$, $C_{48}H_{63}FeN_{13}O_8^{+2}$, $C_{48}H_{62}FeN_{12}O_8S_1^{+2}$, $C_{55}H_{76}FeN_{14}O_9^{+2}$, $C_{25}H_{19}FeN_3$, $C_{15}H_{17}FeN_3OS^{+2}$, $C_{22}H_{23}FeN_3OS^{+2}$, $C_{26}H_{28}ClFeN_3$, $C_{28}H_{33}ClFeN_4$, $C_{27}H_{31}ClFeN_4$, $C_{29}H_{35}ClFeN_4$, $C_{30}H_{37}ClFeN_4$, $C_{28}H_{33}ClFeN_4$, $C_{27}H_{30}ClFeN_3$, $C_{26}H_{28}ClFeN_3$, $C_{29}H_{35}ClFeN_4$, $C_{27}H_{30}ClFeN_5O^{+2}$, $C_{41}H_{38}ClFeN_5O_3^{+2}$, $C_{42}H_{41}FeN_5O_3^{+2}$, $C_{41}H_{38}FFeN_5O_3^{+2}$, $C_{42}H_{47}FeN_5O_3^{+2}$, $C_{43}H_{49}FeN_5O_3^{+2}$, $C_{42}H_{41}FeN_5O_3^{+2}$, $C_{42}H_{40}ClFeN_5O_3^{+2}$, $C_{42}H_{40}ClFeN_5O_3^{+2}$, $C_{42}H_{40}FFeN_5O_3^{+2}$, $C_{41}H_{45}FeN_5O_3^{+2}$, $C_{42}H_{47}FeN_5O_3^{+2}$, $C_{41}H_{39}FeN_5O_3^{+2}$, $C_{22}H_{25}FeN_5O_5^{+2}$, $C_{24}H_{23}ClFeN_4O_2^{+2}$, $C_{24}H_{23}FFeN_4O_2^{+2}$, $C_{24}H_{24}FeN_4O_2^{+2}$, $C_{15}H_{21}FeN_3S^{+2}$, $C_{29}H_{34}FeN_4O_2^{+2}$, $C_{28}H_{31}ClFeN_4O_2^{+2}$, $C_{28}H_{31}FFeN_4O_2^{+2}$, $C_{30}H_{35}ClFeN_4O_3^{+2}$, $C_{30}H_{35}FeN_4O_3^{+2}$, $C_{28}H_{32}FeN_4O_2^{+2}$, $C_{27}H_{30}FeN_4O_2^{+2}$, $C_{26}H_{27}ClFeN_4O_2^{+2}$, $C_{30}H_{36}FeN_4O_3^{+2}$, $C_{28}H_{31}ClFeN_4O_3^{+2}$, $C_{28}H_{31}FFeN_4O_3^{+2}$, $C_{28}H_{32}FeN_4O_3^{+2}$, $C_{27}H_{29}ClFeN_4O_3^{+2}$, $C_{26}H_{27}FFeN_4O_2^{+2}$, $C_{26}H_{28}FeN_4O_2^{+2}$, $C_{26}H_{28}FeN_4O_2^{+2}$, $C_{27}H_{29}FFeN_4O_3^{+2}$, $C_{27}H_{30}FeN_4O_3^{+2}$, $C_{26}H_{27}ClFeN_4O_3^{+2}$, $C_{26}H_{27}FFeN_4O_3^{+2}$, $C_{26}H_{28}FeN_4O_3^{+2}$, $C_{25}H_{25}ClFeN_4O_3^{+2}$, $C_{25}H_{25}FFeN_4O_3^{+2}$, $C_{25}H_{26}FeN_4O_3^{+2}$, $C_{24}H_{23}ClFeN_4O_3^{+2}$, $C_{24}H_{23}FFeN_4O_3^{+2}$, $C_{24}H_{24}FeN_4O_3^{+2}$, $C_{25}H_{25}ClFeN_4O_2^{+2}$, $C_{25}H_{25}FFeN_4O_2^{+2}$, $C_{25}H_{26}FeN_4O_2^{+2}$, $C_{25}H_{26}FeN_4O_2^{+2}$, $C_{29}H_{32}ClFeN_7^{+2}$, $C_{33}H_{32}ClFeN_7^{+2}$, $C_{22}H_{27}ClFeN_3RuS^+$, $C_{18}H_{19}ClFeN_3RuS^+$, $C_{19}H_{19}BFeO_3^{+2}$, $C_{28}H_{25}ClFeN_4O^{+2}$, $C_{31}H_{38}FeN_4O_3$, $C_{29}H_{34}FeN_4O_3$, $C_{31}H_{41}FeN_3O$, $C_{28}H_{32}FeN_4O_3$, $C_{26}H_{29}FeN_3O_2$, $C_{26}H_{30}FeN_2O$, $C_{31}H_{36}FeN_4O_3$, $C_{30}H_{35}FeN_5O_4$, $C_{29}H_{35}FeN_5O_3$, $C_{32}H_{41}FeN_5O_3$, $C_{35}H_{38}FeN_4O_3$, $C_{32}H_{40}FeN_4O_3$, $C_{19}H_{13}BBr_2F_2FeO_2$, $C_{19}H_{14}BClF_2FeO_2$, $C_{19}H_{14}BBrF_2FeO_2$, $C_{19}H_{15}BF_2FeO_2$, $C_{21}H_{20}FeO_4$, $C_{20}H_{18}FeO_3$, $C_{20}H_{18}FeO_3$, $C_{20}H_{18}FeO_3$, $C_{19}H_{14}F_2FeO_2$, $C_{19}H_{14}Br_2FeO_2$, $C_{19}H_{15}BrFeO_2$, $C_{14}H_{12}FeO_3$, $C_{21}H_{19}BF_2FeO_4$, $C_{20}H_{17}BF_2FeO_3$, $C_{20}H_{17}BF_2FeO_3$, $C_{20}H_{17}BF_2FeO_3$, $C_{19}H_{13}BF_4FeO_2$, $C_{19}H_{13}BCl_2F_2FeO_2$, $C_{21}H_{29}AuCl_2FeN_4S^+$, $C_{30}H_{24}C_{12}FeN_6^{+2}$, $C_{22}H_{21}Cl_2FeN_3^{+2}$, $C_{23}H_{22}FeN_6^{+2}$, $C_{21}H_{19}FeN_7^{+2}$, $C_{23}H_{24}FeN_6O^{+2}$, $C_{47}H_{64}FeN_{14}O_9$, $C_{46}H_{60}FeN_{12}O_{10}$, $C_{41}H_{53}FeN_{11}O_7$, $C_{47}H_{65}FeN_{15}O_8$, $C_{45}H_{59}FeN_{13}O_9$, $C_{42}H_{54}FeN_{12}O_7$, $C_{43}H_{67}FeN_{15}O_8$, $C_{48}H_{65}FeN_{13}O_8$, $C_{47}H_{26}FeN_{12}O_8$, $C_{54}H_{77}FeN_{17}O_9$, $C_{51}H_7FeN_{15}O_{10}$, $C_{19}H_{16}FeO_2$, $C_{44}H_{48}FeN_9O_{17}P_3$, $C_{13}H_9C_{12}FeN_3O_6S$, $C_{19}H_{15}FeNO_3$, $C_{20}H_{18}FeO_2$, $C_{20}H_{18}FeO_3$, $C_{21}H_{20}FeO_3$, $C_{17}H_{20}FeN_2O_2$, $C_{18}H_{15}FeNO$, $C_{17}H_{14}FeOS$, $C_{17}H_{14}FeOS$, $C_{17}H_{14}FeO_2$, $C_{22}H_{22}FeO_4$, $C_{20}H_{18}FeO_2$, $C_{20}H_{18}FeO_2$, $C_{19}H_{14}C_{12}FeO_5$, $C_{21}H_{20}FeO_3$, $C_{48}H_{28}FeN_4O_8$, $C_{17}H_{15}FeNS$, $C_{34}H_{30}FeN_4O_4^{-2}$, $C_{30}H_{26}Br_2FeN_4O_4$, $C_{10}H_{18}FeN_2O_7^{+2}$, $C_{14}H_{12}FeO_4$, $C_{44}H_{20}C_{18}FeN_4$, $C_{64}H_{64}FeN_8O_{12}S_4$, $C_{56}H_{26}FeN_8O_8S_4$, $C_{26}H_{44}Br_8FeN_4$, $Cs_6H_{52}FeN_4$, $C_{52}H_{40}FeN_8O_{12}S_4$, $C_{44}H_{32}FeN_8O_8S_4$, or $C_{44}H_{28}FeN_4$. In some other cases, the source of iron has the chemical formula $C_aH_bFe_cO_dN_eS_fBr_gCl_hP_iNa_jAs_kK_lAl_mCr_nV_oI_pB_qF_rTe_sW_t$, where a, b, c, d, e, f, g, h, I, j, k l, m, n, o, p, q, r, s, t are coefficients that can be equal to 0, 1, 2, 3, 4, 5, 6, 7, 8, 9, 10, 11, 12, 13, 14, 15, 16, 17, 18, 19, 20, or any other integer between 21 and 1000000000000, where the C, H, Fe, O, N, S, Br, C, P, Na, As, K, Al, Cr, V, I, B, F, Te, and W atoms preferentially occupy the first, second, third, fourth, fifth, sixth, seventh, eighth, ninth, tenth, eleventh, twelve, thirteen's, fourteenth, fifteenth, sixteen's, seventeenth, eighteens, nineteenth, twentieth position, respectively. In some cases, the at least one atom of the chemical formula can occupy any one of the 20 positions of the formula. In some other cases, the source of iron can comprise the chemical functional groups selected in the group consisting of: Hydrocarbons, Alkane (R(CH$_2$)nH), Alkene (R$_2$C=CR$_2$), Alkyne (RC CR'), Benzene derivative (RC$_6$H$_5$); Groups containing halogen, Haloalkane (RX), Groups containing oxygen, Alcohol (ROH), Carbonyl (RCOR'), Aldehyde (RCHO), Acyl halide (RCOX), Carbonate (ROCOOR'), Carboxylate (RCOO), Carboxylic acid (RCOOH), Ester (RCOOR'), Methoxy (ROCH$_3$), Hydroperoxide (ROOH), Peroxide (ROOR'), Ether (ROW), Hemiacetal (RCH(OR')(OH)), Hemiketal (RC(OR")(OH)R'), Acetal (RCH(OR')(OR")), Ketal (RC(OR")(OR''')R'), Orthoester (RC(OR')(OR")(OR''')), Heterocycle (PhOC-OPh), Orthocarbonate ester (C(OR)(OR')(OR")(OR)), Groups containing nitrogen, Amide (RCONR$_2$), Amines (RNH$_2$, R$_2$NH, R$_3$N, R$_4$N+), Imine (RC(=NH)R', RC(=NR")R', RC(=NH)H, RC(=NR')H, Imide ((RCO)$_2$NR'), Azide (RN3), Azo compound (RN$_2$R'), Cyanates (ROCN, RNCO), Nitrate (RONO$_2$), Nitrile (RCN, RNC), Nitrite (RONO), Nitro compound (RNO$_2$), Nitroso compound (RNO), Oxime (RCH=NOH), Pyridine derivative (RC$_5$H$_4$N), Groups containing sulfur, Thiol (RSH), Sulfide (RSR), Disulfide (RSSR'), Sulfoxide (RSOR'), Sulfone (RSO$_2$R'), Sulfinic acid (RSO$_2$H), Sulfonic acid (RSO$_3$H), Thiocyanate (RSCN, RNCS), Thioketone (RCSR'), Thial (RCSH), Groups containing phosphorus, Phosphine (R$_3$P), Phosphonic acid (RP(=O)(OH)$_2$), Phosphate (ROP(=O) (OH)$_2$), Phosphodiester (HOPO(OR)$_2$), Groups containing boron, Boronic acid (RB(OH)$_2$), Boronic ester (RB(OR)$_2$), Borinic acid (R$_2$BOH), Borinic ester (R$_2$BOR), and a combination of several of these groups. In some other cases, the iron source can be an iron chelating agent.

In some cases, the quantity of the iron source is the quantity or concentration of the iron source or of iron, preferentially originating from the iron source, preferentially in the pre-growth and/or growth medium/media.

The invention also relates to the method according to the invention, wherein iron or the source of iron in the pre-growth medium consists of or comprises Fe$^{2+}$ and/or Fe$^{3}$±.

In some cases, a source of iron comprises Fe$^{2+}$ when it comprises Fee in its chemical formula.

In some other cases, a source of iron comprises Fe$^{3+}$ when it comprises Fe$_3$ in its chemical formula.

The invention relates to the method according to the invention, wherein the concentration of iron or of the iron source in the pre-growth medium is lower than 20 µM. In some cases, the concentration of iron or of the iron source in the pre-growth medium is lower than $10^{100}$, $10^{50}$, $10^{20}$, $10^{10}$, $10^5$, $10^3$, $10^2$, or 20 µM. In some other cases, the concentration of iron or of the iron source in the pre-growth medium is larger than 0, $10^{-50}$, $10^{-20}$, $10^{-5}$, $10^{-1}$, 1, 5, 10 or 20 µM. In still some other cases, the concentration of iron or of the iron source in the pre-growth medium is between $10^{-50}$ and $10^{50}$, $10^{-10}$ and $10^{10}$, $10^{-10}$ and $10^5$, $10^{-10}$ and $10^3$, or between $10^{-10}$ and 1 µM.

The invention relates to the method according to the invention, wherein the growth medium comprises iron or at least one source of iron, wherein the nature and/or quantity of iron or source of iron allows the production of the nanoparticles by the nanoparticle-producing cells and/or cell growth.

The invention relates to the method according to the invention, wherein the source of iron of the growth medium is the same as the source of iron of the pre-growth medium.

The invention relates to the method according to the invention, wherein the concentration of iron or source of iron in the growth medium is larger or equal than the concentration of iron or source of iron in the pre-growth medium.

In some cases, the concentration of iron or of the iron source in the growth medium is lower than $10^{100}$, $10^{50}$, $10^{20}$, $10^{10}$, $10^5$, $10^3$, $10^2$, or 20 µM. In some other cases, the concentration of iron or of the iron source in the growth medium is larger than 0, $10^{-50}$, $10^{-20}$, $10^{-5}$, $10^{-1}$, 1, 5, 10 or 20 µM. In still some other cases, the concentration of iron or of the iron source in the growth medium is between $10^{-50}$ and $10^{50}$, $10^{-10}$ and $10^{10}$, $10^{40}$ and $10^5$, $10^{40}$ and $10^3$, or between $10^{-10}$ and 1 µM.

The invention relates to the method according to the invention, wherein the growth medium is supplemented by a fed-batch medium.

In one embodiment of the invention, the fed-batch medium comprises at least one source in common with the pre-growth and/or growth medium/media. In some cases, the concentration of this source is equal or at least 1.00001, 1.1, 2, 5, 10, $10^3$ or $10^5$ larger in the fed-batch medium than in the pre-growth and/or growth medium/media. In some other cases, the concentration of this source is at least $10^5$, $10^3$, 10, 1, 1.1 or 1.00000001 lower in the fed-batch medium than in the pre-growth and/or growth medium/media.

The invention relates to the method according to the invention, wherein the fed-batch medium comprises iron or a source of iron with at a concentration larger than $10^{-50}$, $10^{-20}$, $10^{-10}$, $10^{-5}$, $10^{-1}$, 1, 5, 10, 20, 50, 100, $10^3$ or $10^5$ µM. In some other cases, the fed-batch medium comprises iron or a source of iron at a concentration lower than $10^{50}$, $10^{20}$, $10^{10}$, $10^5$, $10^2$, $10^{-2}$, $10^{-10}$ or $10^{-20}$ µM. In still some other cases, the fed-batch medium comprises iron or a source of iron at a concentration comprised between $10^{-50}$ and $10^{50}$, $10^{-15}$ and $10^{15}$, $10^{-10}$ and $10^5$, $10^{-5}$ and $10^5$, between $10^{-3}$ and $10^3$ µM, or between 0.5 nM and 50 M, preferentially before adding the fed-batch medium to the growth medium.

In one embodiment of the invention, the fed-batch medium is acidic or has a pH lower than 7, 6, 5, 4 or 3, preferentially lower than 2. In some cases, the fed-batch medium has a pH larger than 0 or 1.

The invention relates to the method according to the invention, wherein the fed-batch medium is introduced in the growth medium at a rate comprised between $10^{-15}$ liter per hour and $10^{15}$ liter(s) per hour or between $10^{-15}$ µM of iron per hour and $10^{15}$ µM of iron per hour. In some cases, the fed-batch is added to the growth medium at a low rate, preferentially at a rate that is lower than $10^{100}$, $10^{50}$, $10^{20}$, $10^{10}$, $10^5$, $10^2$, 10, 5, 1, $10^{-2}$, $10^{-3}$, $10^{-5}$ or $10^{-10}$ liter(s) of fed-batch medium per minute or µM of iron per minute, preferentially when the number of cell division in the growth medium is low, preferentially lower than $10^{20}$, $10^{10}$, $10^5$, $10^3$, 10, 1 cell division(s) per second or hour or day or month. In some other cases, the fed-batch medium is added to the growth medium a high rate, preferentially at a rate larger than $10^{-100}$, $10^{-50}$, $10^{-20}$, $10^{-10}$, $10^{-5}$, $10^{-2}$, 1, 5, 10, $10^2$, $10^3$, $10^5$ or $10^{10}$ liter(s) of fed-batch medium per minute or µM of iron per minute, preferentially when the number of cell division in the growth medium is large, preferentially larger than 1, 2, 5, 10, $10^3$, $10^5$, $10^{10}$ or $10^{20}$ cell division(s) per second or hour or day or month In some cases, between two sub-steps of the growth step, the debit of the fed-batch medium decreases, preferentially by a factor of more than 1.0000001, 1.00001, 1.0001, 1.01, 1.1, 1.2, 1.5, 2, 5, 10, $10^3$, $10^5$, $10^7$ or $10^9$. In some other cases, between two sub-steps of the growth step, the debit of the fed-batch medium increases, preferentially by a factor of more than 1.0000001, 1.00001, 1.0001, 1.01, 1.1, 1.2, 1.5, 2, 5, 10, $10^3$, $10^5$, $10^7$ or $10^9$.

In one embodiment of the invention, before being added to the growth medium, the fed-batch medium has an iron concentration that is larger by a factor of at least 1.000001, 1.001, 1, 1.5, 2, 5, 10, $10^2$, $10^3$ or $10^5$ than the iron concentration of the growth medium.

In another embodiment of the invention, preferentially after being added to the growth medium, the fed-batch medium becomes part of the growth medium.

The invention relates to the method according to the invention, wherein the pre-growth and/or growth medium/media according to the invention comprise(s) only one vitamin selected from the group consisting of Biotin, Calcium pantothenate, Folic acid, Inositol, Nicotinic acid, p-Aminobenzoic acid, Pyridoxine HCl, Riboflavin, Thiamine HCL, and any derivative of these vitamins.

In some cases, the pre-growth and/or growth medium/media can comprise less than $10^{50}$, $10^{20}$, $10^{10}$, $10^5$, $10^3$, 100, 75, 50, 25, 10, 5, 3, 2 or 1 vitamin(s) or different vitamins In some cases, different vitamins can be vitamins that comprise at least 1, 2, 5, 10, $10^2$, $10^3$, $10^5$, $10^{10}$, $10^{20}$, or $10^{50}$ different chemical element(s). In some other cases, the pre-growth and/or growth medium/media comprise(s) more than 1, 2, 5, 10, $10^2$, $10^3$, $10^5$ or $10^{10}$ vitamin(s) or different vitamins.

In some cases, the vitamin(s) can be water soluble vitamin(s). In some other cases, the vitamin(s) can be fat soluble vitamin(s). In still some other cases, the vitamin(s) can be belong to A, D, E, K, $B_1$, $B_2$, $B_3$, $B_5$, $B_6$, $B_7$, $B_9$, $B_{12}$, or C vitamin(s). In still some other cases, the vitamin is not produced by the nanoparticle-producing cells. In still some other cases, the vitamin is a vitamin used to treat a disease such as a disease caused by or associated with vitamin deficiency.

In still another embodiment of the invention, the vitamin(s) is/are selected from the group consisting of: Adenosylcobalamin, Aminobenzoic acid, Ascorbic acid, Biotin, Calcium D-(+)-pantothenate, Carotene Thiamine, Carotenoids beta, Cholecalciferol (D3), Cyanocobalamin, Cyanacobalamine, Ergocalciferol ($D_2$), Folates, Folic acid, Folinic acid, hydroxocobalamin, Inositol, Menaquinones ($K_2$), Methylcobalamin, Niacin, Niacinalide, Niacinamide, Nicotinamide riboside, Nicotinic acid, Pantothenic acid, Phylloquinone (KO, Pyridoxal, Pyridoxamine, Pyridoxine, p-Thioctic acid, Pyridoxal, Pyridoxamine, Pyridoxine, Pyridoxine hydrochloride, Retinal, Retinoic acid, Retinol, Riboflavin, Thiamine, Timaine, Tocopherol, or Tocotrienols, and a derivative or combination of one or several of this/these vitamin(s).

In still another embodiment of the invention, the at least one vitamin comprised in the growth medium is biotin, folic acid, riboflavin, nicotinic acid or thiamin HCl.

In some cases, the vitamin(s) comprised in the pre-growth medium is/are the same as the vitamin(s) comprised in the growth medium. In some other cases, the vitamin(s) comprised in the pre-growth medium is/are different from the vitamin(s) comprised in the growth medium.

The invention also relates to the method according to the invention, wherein the concentration of at least one vitamin comprised in the pre-growth and/or growth medium/media is lower than $10^{100}$, $10^{50}$, $10^{20}$, $10^{10}$, $10^{5}$, $10^{3}$, 10, 1, $10^{-1}$, $10^{-3}$, $10^{-4}$, $10^{-6}$, $10^{-9}$, $10^{-20}$, $10^{-50}$ or $10^{-100}$ M, or preferentially lower than 0.002 mol/L.

In another embodiment of the invention, the pre-growth and/or growth medium/media comprise(s) at least one vitamin or one chemical element comprised in at least one vitamin at a concentration that is larger than $10^{-100}$, $10^{-50}$, $10^{-20}$, $10^{-10}$, 10–5, $10^{-4}$, $10^{-3}$, or $10^{-1}$, 1, 10, $10^2$, $10^3$, $10^5$ or $10^{10}$ M.

The invention also relates to the method according to the invention, wherein the pre-growth and/or growth medium/media comprise at least one vitamin at a concentration, which is lower, preferentially by a factor of more than 1.0001, 1.2, 1.5, 2, 5, 10, $10^3$ or $10^5$, than the concentration of the source of carbon, nitrogen, sulfur, sulfate, phosphorous, phosphate, calcium, potassium, magnesium, oxygen, hydrogen, and/or iron. In some cases, the cells(s) do not require a large concentration of vitamins to grow, divide, and/or to synthetize nanoparticle(s).

The invention also relates to the method according to the invention, wherein the pre-growth and/or growth medium/media comprise(s), per gram or mL of growth or pre-growth medium, less than: i) 1 mg of yeast extract, ii) 1 mg of at least one component of yeast extract, iii) 1 mg of peptone, iv) 1 mg of at least one component of peptone, v) 1 mg of CMR agent, vi) 1 mg of at least one chelating agent, vii) 1 mg of at least one amino acid, viii) 1 mg of a toxic or cytotoxic compound, and/or ix) 1 mg of at least one heavy metal.

In one embodiment of the invention, the pre-growth and/or growth medium/media comprise(es) a concentration in yeast extract, peptone, CMR agent, chelating agent, amino acid, toxic or cytotoxic compound, and/or heavy metal, which is/are lower than $10^{100}$, $10^{50}$, $10^{20}$, $10^{10}$, $10^5$, $10^2$, 10, 1, $10^{-3}$ or $10^{-5}$ μg of yeast extract, peptone, CMR agent, chelating agent, amino acid, and/or heavy metal per liter or milliliter of pre-growth and/or growth medium/media. In some cases, this situation can occur when yeast extract, peptone, CMR agent, chelating agent, amino acid, toxic or cytotoxic compound, and/or heavy metal, has/have been removed from or are not comprised in the pre-growth and/or growth medium/media.

In one embodiment of the invention, the first and/or second medium/media comprise(s) a concentration in yeast extract, peptone, amino acid(s), and/or heavy metal(s), which is/are larger than $10^{-10}$, $10^{-50}$, $10^{-20}$, $10^{-10}$, $10^{-5}$, $10^{-2}$, $10^{-1}$, 1, 10, $10^3$ or $10^5$ μg of yeast extract, peptone, amino acid(s), and/or heavy metal(s) per liter or milliliter of pre-growth and/or growth medium/media. In some cases, this situation can occur when yeast extract, peptone, CMR agent, chelating agent, amino acid, and/or heavy metal, has/have been added, preferentially unwillingly, to the pre-growth and/or growth medium/media.

In one embodiment of the invention, the yeast extract is or comprise peptides, amino acids, purine bases, pyrimidine bases, and/or hydro-soluble vitamins of B group.

In one embodiment of the invention, the amino acid(s) is/are alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and/or valine.

In one embodiment of the invention, the heavy metal(s) is/are arsenic (As), cadmium (Cd), chrome (Cr), copper (Cu), mercury (Hg), nickel (Ni), lead (Pb), selenium (Se), and/or zinc (Zn).

In one embodiment of the invention, the agent(s) that is/are carcinogenic, mutagenic, or toxic for reproduction, also designated as CMR agent(s), is/are preferentially Nitriloacetic acid, Trisodium salt, and/or Boric acid.

In one embodiment of the invention, the toxic or cytoxic compound is a compound that produces the death of a cell or organism, preferentially of the nanoparticle-producing cells, preferentially when it is introduced in the pre-growth and/or growth medium/media, preferentially at a concentration larger than $10^{-10}$, $10^{-5}$, $10^{-2}$, 1, 5, 10, $10^3$, or 10 μM, preferentially at a concentration comprised between $10^{-10}$ and $10^{10}$ μM.

In one embodiment of the invention, the pre-growth and/or growth medium/media does/do not comprise the minerals selected in the group consisting of: selected in the group consisting of: $C_6H_6NO_6Na_3$, Nitriloacetic acid trisodium salt, $MnO_4S\ H_2O$, Manganese (II) sulfate monohydrate, NaCl, sodium chloride, $CoN_2O_6\ 6H_2O$, Cobalt (II) nitrate hexahydrate, $O_4SZn\ 7H_2O$, Zinc sulfate heptahydrate, $CuO_4S\ 5H_2O$, Copper(II) sulfate pentahydrate, $AlKO_8S_2\ 12H_2O$, Aluminium potassium sulfate dodecahydrate, $H_3BO_3$, Boric acid, $Na_2MoO_4\ 2H_2O$, Sodium molybdate dihydrate, $Cl_2Ni\ 6H_2O$, Nickel(II) chloride hexahydrate, $Na_2SeO_3$, Sodium selenite, and a derivative or combination one or several of these compounds.

In one embodiment of the invention, the pre-growth and/or growth medium/media comprise(s) a concentration in mineral(s), which is lower than $10^{100}$, $10^{50}$, $10^{20}$, $10^{10}$, $10^5$, $10^2$, 10, 1, $10^{-1}$, $10^{-3}$ or $10^{-5}$ μg of mineral(s) per liter or milliliter of growth medium. In some cases, this situation can occur when the minerals have been removed from the pre-growth and/or growth medium/media.

In one embodiment of the invention, the first (pre-growth) and/or second growth medium/media comprise(s) a concentration in mineral(s), which is larger than $10^{-100}$, $10^{-50}$, $10^{-20}$, $10^{-10}$, $10^{-5}$, $10^{-2}$, $10^{-1}$, 1, 10, $10^3$ or $10^5$ μg of mineral(s) per liter or milliliter of growth medium. In some cases, this situation can occur when the minerals have been removed, preferentially unwillingly, to the pre-growth and/or growth medium/media.

The invention also relates to the method accord to the invention, which comprises an additional step of purifying high purity iron oxide nanoparticle(s) by removing at least one impurity(ies) from the nanoparticle(s).

In one embodiment of the invention, the additional step of purifying high purity iron oxide nanoparticles consists in removing impurity(ies) from nanoparticle(s) and/or denaturing and/or destroying impurity(ies) comprised in the nanoparticles.

In one embodiment of the invention, the additional step of purifying the nanoparticles is preceded by a preceding step of isolating or extracting the nanoparticles from the cells. In some cases, the preceding step is a step of recovering the nanoparticles. In some cases, the preceding step is carried out by: i) mixing the cells, preferentially obtained from the growth step, with a detergent such as KOH or NaOH, ii) heating the cells at a temperature larger than −270, −250, −200, −150, −100, −50, −30, −10, −5, 0, 5, 10, 20, 30, 50, 75, 100, 150, 200, 500, $10^3$, $10^5$ or $10^{10°}$ C. or comprised between −270 and $10^{10}$, −100 and $10^5$, or between 0 and 100° C., iii) inducing a temperature gradient larger than $10^{-50}$, $10^{-20}$, $10^{-10}$, $10^{-5}$, $10^{-3}$, $10^{-1}$, 1, 2, 5, 10, $10^3$, $10^5$ or $10^{10°}$ C. per hour, minute or second, or comprised between $10^{-50}$ and $10^{10}$° C. per hour, minute or second, iii) applying a pressure on the cells, preferentially larger than 1, 10, 100, 500, $10^3$, $10^4$, $10^5$, $10^6$, $10^7$, $10^8$ or $10^9$ atmosphere(s), or comprised between 1 and $10^9$ atmosphere(s), using for example a French press, and/or iv) sonicating the cells, preferentially at a power larger than $10^{-50}$, $10^{-20}$, $10^{-5}$, $10^{-1}$, 1, 10, $10^2$, $10^3$, $10^5$ or $10^{10}$ W.

In another embodiment of the invention, the additional step of purifying the nanoparticles enables removing: i) a percentage in mass of impurity(ies) that is larger than $10^{-20}$, $10^{-10}$, $10^{-5}$, $10^{-2}$, $10^{-1}$, 1, 5, 10, 25, 50, 75, 80 or 90%, or ii) more than $10^{-50}$, $10^{-20}$, $10^{-10}$, $10^{-5}$, $10^{-1}$, 1, 5, 10, $10^3$, $10^5$ or $10^{10}$ μg of impurity(ies) per gram of nanoparticle(s).

In one embodiment of the invention, impurity(ies), preferentially removed by the additional step of purifying the nanoparticles, is/are carbon or carbonaceous material and/or is/are not iron oxide. Preferentially, this/these impurity(ies) are located in the coating of the nanoparticles.

In one embodiment of the invention, the impuritity(ies) is/are removed from the core and/or coating of the nanoparticles, preferentially from the coating of the nanoparticles. Preferentially, the impuritity(ies) that is/are removed is/are shallow impurity(ies). In some other cases, the impurity(ies) that is/are removed is/are deep impurity(ies).

The invention also relates to the additional step of the method of purifying the high purity iron oxide nanoparticles by removing at least one impurity(ies) from the nanoparticle(s), comprising at least one heating steps in which the temperature of the nanoparticles is increased to a temperature $T_0$, and is then maintained at $T_0$ during a heating time that is preferentially comprised between 1 second and 1 minute, 1 second and 1 hour, 1 second and 12 hours, 1 second and 1 day, 1 second and 1 week, 1 second and 1 month, or between 1 second and 1 year, where $T_0$ is preferentially comprised between −200 and $10^5$, −100 and $10^5$, −50 and $10^5$, −10 and $10^5$, 0 and $10^{5}$° C., 10 and $10^5$, 20 and $10^5$, 30 and $10^5$, 100 and $10^5$, 200 and $10^{5}$° C., 100 and $10^4$, 100 and $10^3$, or between 100 and 500° C.

The invention also relates to the additional step of the method of purifying the high purity iron oxide nanoparticles by removing at least one impurity(ies) from the nanoparticle(s), comprising at least two heating steps in which:

During step 1, the temperature of the nanoparticles is increased to a temperature $T_i$, and is then maintained at $T_1$ during a heating time that is comprised between 1 second and 20 years, where $T_1$ is comprised between 150° C. and 250° C.

During step 2, the temperature of the nanoparticles is increased to a temperature $T_2$, and is then maintained at $T_2$ during a heating time that is comprised between 1 second and 20 years, where $T_2$ is comprised between 350° C. and 450° C.

In some cases, the additional step of the method of purifying the high purity iron oxide nanoparticles or the heating step can be designated as purifying method.

The invention relates to the method for removing at least one impurity from high purity iron oxide nanoparticles, comprising an additional step between steps 1 and 2, in which the temperature of the nanoparticles is increased to a temperature $T_3$ and is then maintained at $T_3$ during a heating time that is comprised between 1 second and 20 years, where $T_3$ is comprised between 250° C. and 350° C.

In some cases, the temperature of the nanoparticles is maintained at the temperature $T_1$, $T_2$, and/or $T_3$, during a heating time that is smaller than 100 years, 50 years, 20 years, 10 years, 5 years, 2 years, 1 year, 11 months, 6 months, 3 months, 2 month, 1 month, 3 weeks, 2 weeks, 1 week, 6 days, 5 days, 3 days, 1 day, 23 hours, 12 hours, 6 hours, 1 hour, 50 minutes, 30 minutes, 20 minutes, 10 minutes, 5 minutes, 2 minutes, 1 minute, 50 seconds, 30 seconds, 10 seconds, 1 seconds, 1 millisecond or 1 microsecond. In some other cases, the temperature of the nanoparticles is maintained at the temperature $T_1$, $T_2$, and/or $T_3$, during a heating time that is larger than 1 microsecond, 1 millisecond, 1 second, 10 seconds, 30 seconds, 50 seconds, 1 minute, 2 minutes, 5 minutes, 10 minutes, 1 hour, 6 hours, 12 hours, 23 hours, 1 day, 3 days, 5 days, 6 days, 1 week, 2 weeks, 3 weeks, 1 month, 2 months, 3 months, 6 months, 11 months, 1 year, 2 years, 5 years, 10 years, 20 years, 50 years or 100 years. In still some other cases, the temperature of the nanoparticles is maintained at temperature $T_1$, $T_2$, and/or T3, during a heating time that is comprised between 1 microsecond and 100 years, 1 second and 20 years, 1 second and 1 year, 1 second and 1 month, 1 second and 1 day, 1 minute and 1 day, 5 minutes and 1 day, 10 minutes and 12 hours, 30 minutes and 6 hours, or between 30 minutes and 3 hours.

In an embodiment of the invention, the heating time is larger than the time during which the temperature is increased to $T_1$, $T_2$, and/or $T_3$, preferentially by a factor of more than 1.001, 1.1, 1.5, 2, 5, 10, $10^3$, $10^5$ or $10^{10}$.

In some cases, $T_1$ is comprised between −273° C. and 250° C., −200° C. and 250° C., −100 and 250° C., 0 and 250° C., 50 and 250° C., 150 and 250° C., or between 180 and 220° C. In some other cases, $T_2$ is comprised between 200 and $10^5$, 250 and $10^5$, 300 and $10^5$, 350 and $10^5$, 350 and $10^3$, 350 and 500, 350 and 450, or between 360 and 400° C. In still some cases, $T_3$ is comprised between −273 and $10^5$, −200 and $10^3$, −100 and 500, −50 and 200, 0 and 500, 100 and 500, 200 and 500, 200 and 400, or between 250 and 350° C.

In still another embodiment of the invention, $T_3$ is comprised between $T_1$ and $T_2$. In some cases, $T_3$ is lower than $T_2$, preferentially by a factor of more than 1.0001, 1.1, 1.2, 1.5, 2, 5, 10, $10^3$ or $10^5$. In some other cases, $T_3$ is larger than $T_1$, preferentially by a factor of more than 1.0001, 1.1, 1.2, 1.5, 2, 5, 10, $10^3$ or $10^5$.

In one embodiment of the invention, the temperature of the nanoparticles is the temperature of the heating apparatus or furnace used to heat the nanoparticles and/or comprising the nanoparticles, preferentially before, during, or after the treatment of the nanoparticles by the purifying method.

In one embodiment of the invention, the interval of temperatures that separates $T_1$ and $T_2$, designated as $[T_1, T_2]$, is such that: i), the nanoparticles display the largest variation or loss of weight or mass as a function of temperature and/or ii), the derivative of the variation or loss of weight or mass of the nanoparticles as a function of temperature is the largest.

In one embodiment of the invention, the ratio [% $W(T_2)$−% $W(T_1)$]/($T_2$−$T_1$), where % $W(T_2)$ and % $W(T_1)$ are the percentages in weight or mass of the nanoparticles at $T_2$ and $T_1$, respectively, is larger than $10^{-50}$, $10^{-30}$, $10^{-20}$, $10^{-10}$, $10^{-5}$, 0.01, 0.02, 0.03, 0.05, 0.1, 0.2, 0.3, 0.5, 1, 10 or $10^5$%/° C. In some cases, this ratio is large when the percentage in mass of carbon in the nanoparticles, preferentially before treating the nanoparticles by or with the purifying method, is large, preferentially larger than 10-20, 10-10, U⁵, $10^{-2}$, $10^{-1}$, 1, 5, 10, 20, 50, 75, 85, 95 or 100%/° C.

In another embodiment of the invention, the ratio [% $W(T_2)$−% $W(T_1)$]/($T_2$−$T_1$) is lower than $10^{50}$, $10^{30}$, $10^{20}$, $10^{10}$, $10^5$, 10, 5, 2, 1, 0.5, 0.05, $10^{-3}$, $10^{-5}$, $10^{-10}$ or $10^{-20}$%/° C. In some cases, this ratio is low when the percentage in mass of carbon in the nanoparticles, preferentially before treating the nanoparticles by or with the purifying method, is low, preferentially lower than 100, 95, 80, 70, 50, 30, 20, 10, 5, 2, 1, $10^{-1}$, $10^{-3}$, $10^{-5}$, $10^{-10}$ or $10^{-20}$%/° C.

In one embodiment of the invention, the temperature of the nanoparticles is maintained at $T_1$, $T_2$, and/or $T_3$, when $T_1$, $T_2$, and/or $T_3$ vary(ies) by less than $10^5$, $10^3$, 90, 80, 70, 60, 50, 40, 30, 20, 10, 5, 3, 2, 1, $10^{-5}$, $10^{-10}$ or $10^{-20}$%. In some cases, for each temperature $T_1$, $T_2$, and/or $T_3$, this percentage is equal to $T_{maxi} - T_{mini}/T_{avi}$, where $T_{maxi}$, $T_{mini}$, and $T_{avi}$ (i=1, 2, 3) are the maximum, minimum, and average temperatures reached during the heating time or during the heating step, preferentially after or when the temperature is maintained at a temperature $T_1$, $T_2$, and/or $T_3$. In some cases, this percentage is low when the furnace or heating apparatus enables to maintain the temperature stable without large fluctuations and/or when the nanoparticles are not prone to endothermic and/or exothermic reactions. In some cases, the endothermic reaction is a reaction in which heat or energy is transferred from the medium surrounding the nanoparticles to the nanoparticles. In some other cases, the exothermic reaction is a reaction in which heat or energy is transferred from the nanoparticles to the medium surrounding the nanoparticles.

In one embodiment of the invention, the temperature of the nanoparticles is not maintained at $T_1$, $T_2$, and/or $T_3$, when the temperature of the nanoparticles varies by more than $10^5$, $10^3$, 90, 80, 70, 60, 50, 40, 30, 20, 10, 5, 3, 2, 1, $10^{-5}$, $10^{-10}$ or $10^{-20}$%. In some cases, this percentage is large when the furnace or heating apparatus does not enable to maintain the temperature stable without large fluctuations and/or when the nanoparticles are prone to endothermic and/or exothermic reactions.

In one embodiment of the invention, the temperatures $T_1$ and/or $T_2$ is/are determined by:
i) measuring the variation of the percentage in weight or mass of the nanoparticles as a function of temperature when the nanoparticles are heated between two temperatures $T_{T<T1}$ and $T_{T>T2}$, where $T_{T<T1}$ is lower than $T_1$ and $T_{T>T2}$ is larger than $T_2$,
ii) measuring or representing or considering or examining or using at least one peak of the derivative of the variation of this percentage as a function of temperature,
iii) estimating or deducing from the variation of the percentage in weight or mass of the nanoparticles as a function of temperature, the interval of temperature in which this variation is maximum, where the minimum and maximum temperatures of this interval are $T_1$ and $T_2$, respectively,
iv) estimating or deducing from the position of at least one peak in the plot of the derivative of the variation of the percentage in weight or mass of the nanoparticles the two temperatures $T_1$ and $T_2$, resulting in the minimum values of the derivative at the beginning and end of the peak, respectively, and $T_3$ resulting in the maximum value of the derivative at the middle of the peak, and
v) estimating or deducing from the position of at least one peak in the plot of the variation of the heat flux of the nanoparticles as a function of temperatures, the temperatures $T_1$, $T_2$, $T_3$, preferentially located at the beginning of the at least one peak.

In some cases, the temperature where or for which or at which the peak starts to display a decrease of the derivative of the variation of the percentage in weight or mass of the nanoparticles as a function of temperature is at the beginning of the peak. In some other cases, the temperature where or for which or at which the peak stops to display an increase of the derivative of the variation of the percentage in weight or mass of the nanoparticles as a function of temperature is the end of the peak.

In another embodiment of the invention, the heat flux of the nanoparticles is the heat flux produced by the nanoparticles or released from the nanoparticles or originating from the nanoparticles, preferentially when the nanoparticles are heated with a heating apparatus such a furnace. Preferentially, the heat flux can be measured with an apparatus or using a thermo-analytical method, or using Differential thermo-analysis (DTA) or using differential scanning calorimetry (DSC).

In one embodiment of the invention, the heating step i, where i is preferentially an integer larger or equal to/than 0, of the purifying method according to the invention comprises at least one of the following phase(s), wherein:
during the first phase, the temperature of the nanoparticles is increased from a temperature $T_i$ up to a temperature $T_{iav}$, during a lapse of time $t_{i1p}$,
during the second phase, the temperature of the nanoparticles is maintained at the temperature $T_{iav}$, during a lapse of time $t_{i2p}$, and
during the third phase, the temperature of the nanoparticles is decreased from $T_{iav}$ to $T_f$ during a lapse of time $t_{i3P}$.

The invention also relates to a method of purification according to the invention comprising at least one heating step i, where the heating step comprises at least one of the following first, second and/or third phase(s), wherein:
during the first phase, the temperature of the nanoparticles is increased from a temperature $T_i$ up to a temperature $T_{iav}$, during a lapse of time $t_{i1P}$,
during the second phase, the temperature of the nanoparticles is maintained at the temperature $T_{iav}$, during a lapse of time $t_{i2P}$, and
during the third phase, the temperature of the nanoparticles is decreased from $T_{iav}$ to $T_f$ during a lapse of time $t_{i3P}$.

In some cases, $T_i$ and/or tip is/are at least 1.0001, 1.1, 1.5, 2, 5, 10 or 100 times lower than $T_{iav}$ and/or $t_{i2p}$. In some cases, $T_{iav}$ is equal to $T_1$, $T_2$, or $T_3$, and/or tap is equal to the time during which the temperature is increased to reach $T_i$. In still some other cases, $T_f$ and/or $t_{i3P}$ does/do not differ by a factor of more than 1.0001, 1.1, 1.5, 2, 5, 10, $10^2$ or $10^5$ from $T_i$ and/or $t_{i1P}$.

The invention also relates to the method, preferentially purifying method, according to the invention, wherein more than 10% in mass of carbon or carbonaceous material is removed from the nanoparticles, where this percentage is based on the ratio (% $C_{AT}$−% $C_{BT}$)/% $C_{BT}$, where % $C_{AT}$ and % $C_{BT}$ are the percentages of carbon or carbonaceous material after and before treating the nanoparticles with the method, respectively.

In some cases, (% $C_{AT}$−% $C_{BT}$)/% $C_{BT}$ is larger than $10^{-50}$, $10^{-20}$, $10^{-5}$, $10^{-2}$, $10^{-1}$, 1, 5, 10, 50, 75, 90, 95 or 99%. This can be the case when the purifying method is efficient or when the quantity of carbon or carbonaceous material comprised in the nanoparticle before treating the nanoparticles with the purifying method is lower than a certain threshold, preferentially lower than 99, 90, 70, 60, 50, 40, 30, 20, 10 or 1%.

In some other cases, (% $C_{AT}$−% $C_{BT}$)/% $C_{BT}$ is lower than 99, 90, 70, 60, 50, 40, 30, 20, 10 or 1%. This can be the case when the purifying method is not efficient or when the quantity of carbon or carbonaceous material comprised in the nanoparticle before treating the nanoparticles with the purifying method is larger than a certain threshold, preferentially larger than 99, 90, 70, 60, 50, 40, 30, 20, 10 or 1%.

In still some other cases, (% $C_{AT}$–% $C_{BT}$)/% $C_{BT}$ is between 0.1 and 100, 1 and 99, 10 and 99, 50 and 99, or between 80 and 99%.

The invention relates to high purity iron oxide based nanoparticle(s) obtained by the method according to the invention.

The invention also relates to high purity nanoparticle(s) or high purity nanoparticles that are not obtained by the method.

In one embodiment of the invention, the high purity nanoparticles, preferentially the coating of these nanoparticles, comprise: i), between 0.8 and 0.999999999 g of iron oxide per gram of nanoparticle, and/or ii) between $10^{-40}$ and $10^5$ μg of impurity(ies) per gram of nanoparticle.

In one embodiment of the invention, the high purity nanoparticles comprise a percentage in mass of carbon or carbonaceous material that is lower than 90, 10, 5, 2, preferentially 1, 0.5, 0.4 or 0.3%. In some cases, such a low percentage in mass of carbon enables to coat the nanoparticles with a coating that does not originates from the nanoparticle-producing cells.

In one embodiment of the invention, the SAR (specific absorption rate) of the high purity iron, oxide nanoparticles is larger than $10^{-100}$, $10^{-50}$, $10^{-20}$, $10^{-10}$, $10^{-5}$, $10^{-3}$, $10^{-1}$, 1, 10, $10^3$ or $10^5$ Watt per gram of nanoparticles. In some cases, the SAR of the nanoparticles is the largest when the quantity of impurities in the nanoparticles is the lowest. In some cases, the SAR of the high purity iron oxide nanoparticles is comprised between $10^{-100}$ and $10^{100}$, $10^{-1}$ and $10^5$, or between 0.1 and $10^3$ Watt per gram of nanoparticles. In some cases, the SAR of the nanoparticles is proportional to the slope, preferentially initial slope, of the temperature variation with time of the nanoparticles, ($\Delta T/\delta t$), preferentially surrounded by a medium such as water, biological material, body part, or tissue, where (AT/St) is preferentially estimated in °C./sec., where SAR=$\alpha(\Delta T/\delta t)$. In some cases, $\alpha = C_v/C_{nano}$, where $C_v$ is the specific heat capacity, preferentially of water, biological material, body part, or tissue, comprising the nanoparticles, and $C_{nano}$ the nanoparticle concentration or quantity or number of nano is nanoparticles, preferentially comprised in water, biological material, body part, or tissue. In some cases, the SAR is measured by exposing the high purity iron oxide nanoparticles to a radiation, preferentially a radiation that produces heat, preferentially a laser, magnetic field, alternating magnetic field, acoustic wave, ultrasound, radiofrequency.

In one embodiment of the invention, the high purity iron oxide nanoparticles have a size distribution that is lower than $10^{50}$, $10^{20}$, $10^{10}$, $10^5$, $10^3$, $10^2$, 10, 1, $10^{-1}$, $10^{-2}$ or $10^{-5}$ nm. In some cases, the nanoparticle size distribution is low when the method according to the invention enables the fabrication of nanoparticles with a low size distribution.

In another embodiment of the invention, the high purity iron oxide nanoparticles, preferentially at a concentration larger than $10^{-6}$, $10^{-3}$, $10^{-1}$, 1 or 10 mg of nanoparticles per ml or per mm$^3$ or per cell, destroy more than 1, 10, $10^3$, $10^6$ or $10^9$ cell(s).

The invention also relates to high purity iron oxide nanoparticle(s) that are produced at a yield larger than $10^{-50}$, $10^{-30}$, $10^{-10}$, $10^{-5}$, $10^{-2}$, $10^{-1}$, 1, 5, 10, 50, $10^2$, $10^3$ or $10^5$ mg of nanoparticle(s) or mg of iron comprised in nanoparticle(s), preferentially per cell, preferentially per liter of pre-growth and/or growth medium/media.

The invention also relates to the nanoparticle(s) obtained by the method according to the invention, wherein the yield of nanoparticle production is lower than $10^{50}$, $10^{30}$, $10^{10}$, $10^5$, $10^2$, 10, 5, 1, $10^{-1}$, $10^{-2}$, $10^{-3}$ or $10^{-5}$ mg of nanoparticle(s) or mg of iron comprised in nanoparticle(s), preferentially per cell, preferentially per liter of pre-growth and/or growth medium/media.

The invention also relates to high purity iron oxide based nanoparticle(s) according to the invention, wherein the high purity iron oxide nanoparticles is/are magnetosome(s).

In one embodiment of the invention, the magnetosomes are nanoparticles produced by magnetotactic bacteria that are preferentially treated following at least one of the following steps: i) nanoparticles are extracted and/or isolated from the bacteria, preferentially to obtain magnetosomes comprising crystallized minerals surrounded by a biological membrane, ii) the biological membrane is removed, preferentially using the purifying step, iii) the magnetosomes are coated with a coating that does not come from the nanoparticle-producing cell for stabilization, preferentially to avoid that the magnetosomes aggregate and/or sediment.

The invention also relates to a composition, drug, medical device, diagnostic composition, therapeutic composition, or cosmetic composition, comprising the high purity iron oxide nanoparticle(s) according to the invention.

In another embodiment of the invention, the high purity iron oxide nanoparticles yield: i) medical or therapeutic activity, for example by enabling the destruction of pathological cells, viruses, bacteria, cancer cells, or by being less toxic towards healthy tissues than pathological cells, viruses, bacteria, cancer cells, ii) diagnostic activity, for example by enabling the detection of pathological cells, viruses, bacteria, cancer cells, or by being less toxic towards healthy tissues, and/or, iii) cosmetic activity, for example by improving the appearance of a human.

In another embodiment of the invention, the high purity iron oxide nanoparticles are non-immunogenic or non-pyrogenic. In this case, they preferentially: i) attract or result in the appearance of a low number of immune cells, preferentially less than 1, 5, 10, $10^3$, $10^{10}$, $10^{50}$ or $10^{100}$ immune cells and/or ii) produce a temperature increase of a living organism lower than $10^5$, $10^3$, $10^2$, 50, 20, 10, 5, 2, 1 or 0.1° C.

The invention also relates to the nanoparticles according to the invention, preferentially the high purity iron oxide based nanoparticles, for use in the treatment of a disease, which is preferentially selected in the group consisting of: i) a disease associated with a proliferation of cells that is different from the cellular proliferation in a healthy individual, ii) a disease associated with the presence of pathological cells such as tumor or cancer cells in the body part or in the individual, iii) a disease associated with the presence of a pathological site, i.e a site comprising pathological cells, in an individual or body part, iv) a disease or disorder or malfunction of the body part, v) a disease associated with the presence of radio-resistant or acoustic-resistant or laser-resistant or magnetic field resistant cells, vi) an infectious disease, vii) an auto-immune disease, viii) a neuropathology, ix) a cancer, x) a tumor, xi) a disease comprising or due to at least one cancer or tumor cell, xii) a cutaneous condition, xiii) an endocrine disease, xiv) an eye disease or disorder, xv) an intestinal disease, xvi) a communication disorder, xvii) a genetic disorder, xviii) a neurological disorder, xix) a voice disorder, xx) a vulvovaginal disorder, xxi) a liver disorder, xxii) a heart disorder, xxiii) a heating disorder, xxiv) a mood disorder, xxv) anemia, preferentially iron anemia, xxvi) a personality disorder, xxvii) aids, notably neuro-aids, xxviii) Parkinson, xxix) Alzheimer, xxx) bacterial and/or fungi infection or contamination, xxxi) blood disease due for example to an absence or lack of efficient coagulation, and xxxii) a disease due to a deficiency in immune function or an immune disease.

In one embodiment of the invention, the cancer or tumor selected from the group consisting of: the cancer of an organ, cancer of blood, cancer of a system of a living organism, adrenal cancer, anal cancer, bile duct cancer, bladder cancer, bone cancer, brain cancer, breast cancer, cervical cancer, colon/rectum cancer, endometrial cancer, esophagus cancer, eye cancer, gallbladder cancer, heart cancer, kidney cancer, laryngeal and hypopharyngeal cancer, leukemia, liver cancer, lung cancer, nasal cavity and paranasal sinus cancer, nasopharyngeal cancer, neuroblastoma, non-Hodgkin lymphoma, oral cavity and oropharyngeal cancer, osteosarcoma cancer, ovarian cancer, pancreatic cancer, pancreatic penile cancer, prostate cancer, retinoblastoma, rhabdomyosarcoma, salivary gland cancer, sarcoma, skin cancer, small intestine cancer, stomach cancer, testicular cancer, thymus cancer, thyroid cancer, uterine cancer, uterine sarcoma cancer, vaginal cancer, vulvar cancer, waldenstrom macroglobulinemia wilms tumor, castleman disease ewing family of tumor, gastrointestinal carcinoid tumor, gastrointestinal stromal tumor, myelodysplastic syndrome pituitary tumor, and a cancerous disease such as gestational trophoblastic disease, Hodgkin disease, kaposi sarcoma, malignant mesothelioma, and multiple myeloma.

In still another embodiment of the invention, the treatment of the disease by the nanoparticles according to the invention occurs or is activated when the nanoparticles are exposed to a radiation and preferentially does not occur or is not activated when the nanoparticles are not exposed to a radiation.

In still another embodiment, the radiation is a laser, an acoustic wave such as an ultrasound, X-ray, gamma ray, and/or a magnetic field, preferentially an alternative magnetic field.

In still some other embodiment, the power or intensity of the radiation is between $10^{-50}$, $10^{-20}$, $10^{-10}$, $10^{-5}$, $10^{-1}$, 0, 1 mT, T, W, W/cm, W/cm$^2$ or W/cm$^3$ and 1, 5, 10, $10^3$, $10^5$, $10^{10}$, $10^{20}$ or $10^{50}$ mT, T, W, W/cm, W/cm$^2$ or W/cm$^3$.

In still another embodiment of the invention, the property(ies) or features, preferentially of the nanoparticle(s) or method, described in each individual embodiment or section or sentence of this patent application can be combined to result in a combination of property(ies) or features, preferentially of the nanoparticle(s) or method.

In still another embodiment of the invention, when a compound such as the nanoparticle or chemical element has a property in a condition 1 ($P_1$) that is higher, longer, or larger by a factor $\alpha$ than a property in a condition 2 ($P_2$), it means that $P_1 = \alpha \cdot P_2$ or $P_1 = \alpha + P_2$, where $\alpha$ is preferentially a number or integer larger than 1 or 0.

In still another embodiment of the invention, when a compound such as the nanoparticle or chemical element has a property in a condition 1 ($P_1$) that is smaller, or shorter by a factor $\alpha$ than a property in a condition 2 ($P_2$), it means that $P_1 = P_2/\alpha$ or $P_1 = P_2 - \alpha$, where $\alpha$ is preferentially a number or integer larger than 1 or 0.

The invention will be further disclosed by the following non-limiting examples.

EXAMPLES

Material and Methods:

Optical density measurements of suspensions of whole magnetotactic bacteria to assess bacterial growth: The optical density of the different suspensions of magnetotactic bacteria was measured at 565 nm, designated as $OD_{565\ nm}$, using a Secomam UviLine9400 spectrophotometer. The value of $OD_{565\ nm}$ is proportional to the concentrations of bacteria in the suspensions.

Measurement of the magnetic response of living magnetotactic bacteria using optical microscopic observations of these bacteria under the application of a magnetic field: 1 mL of a suspension of MSR-1 magnetotactic bacteria was centrifugated at 14500 rpm for 10 minutes. The growth medium was removed and replaced by a volume of PBS 0.1× to reach an $OD_{565\ nm}$ of 0.5. 1 μL of this suspension of MSR-1 magnetotactic bacteria was deposited on a parallelipedic microscope slide (Menzel-Glaser, 24 mm×60 mm, 0.13-16 mm thickness) for microscopic observation using a Zeiss Primo Vert optical microscope with X40 magnification. Four small cubic Neodinium magnets of strength 1.3 T (Supermagnet, N42 W-10-N 10×10×10 mm) were positioned on the microscope's platform at a distance from the suspension of bacteria of ~2 cm in such a way that it either generated a magnetic field parallel to the position of the observer or to the line between the two binoculars (position 1) or perpendicular to this position (position 2). 20 seconds after positioning the magnet in position 1 or 2, the percentage of bacteria aligned in the direction of the magnetic field was estimated, by considering 200 magnetotactic bacteria. The bacteria that were not aligned in the same direction as the magnetic field generated by the magnet were considered as non-magnetic. Their number is designated as $n_{BNM}$. The bacteria that were aligned in the direction of the magnetic field generated by the magnet were considered as magnetic. Their number was designated as $n_{BM}$. The percentage of magnetic bacteria was then given by $n_{BM}/(n_{BM}+n_{BNM})$. A positive magnetic response of magnetotatic bacteria corresponded to $n_{BM}/(n_{BM}+n_{BNM}) > 0.5$. A negative magnetic response of magnetotactic bacteria corresponds to $n_{BM}/(n_{BM}+n_{BNM}) < 0.5$.

In some cases, the percentage of magnetic bacteria can be measured by optical observation under microscope in the presence of a magnetic field.

Measurement of intracellular iron concentration: The iron concentration inside magnetotactic bacteria was determined by a destructive iron assay. For that, 2 mL of MSR-1 magnetotactic bacteria were centrifuged at 14500 g for 10 min. The bacterial pellet was then washed twice with 1×PBS and MilliQ water. After the second washing, the bacterial pellet was collected and 1 mL of 12N hydrochloric acid (HCl) was added to the pellet under the chemical hood. The sample was heated at 75° C. for 2 hours under stirring at 300 rpm to transform intracellular iron to $Fe^{3+}$ and $Fe^{2+}$ ions. The $Fe^{2+}$ ions were then oxidized to $Fe^{3+}$ with hydrogen peroxide ($H_2O_2$) at 20%. The presence of $Fe^{3+}$ ions was revealed by the addition of potassium thiocyanate (KCN, 2 mol/L) in an acidic medium, which led to the formation of a red-orange solution whose color depended on the concentration of $Fe^{3+}$ in the sample. As soon as the KCN was added, the absorbance of the solution was measured at 476 nm. The iron concentration in the sample was then estimated using a determined relation between the value of the absorbance measured at 476 nm and the concentration in iron (III) chloride. This method makes it possible to estimate the total intracellular iron concentration.

Analysis of the elemental chemical composition of the magnetosomes by ICP-AES: Following fermentation, MSR-1 magnetotactic bacteria were concentrated by tangential filtration in a volume of 5 L to reach an optical density between 25 and 30. Bacteria were then lysed during 1 hour in a 1 M KOH solution under stirring at 150 rpm at a temperature of 80° C. The bacterial lysate containing the magnetosomes was placed against a Neodynium magnet for 12 hours. The magnetosomes were then separated from the bacterial lysate and re-suspended in 10×PBS This washing procedure was repeated two times with 10×PBS and three times in MilliQ water. The magnetosomes were then lyophilized and heated in a muffle furnace in conditions described below to obtain a magnetosome powder comprising high purity iron oxide crystals with a low content of carbon. For the analysis of the elemental chemical composition, a solution of 500 µg of this powder was mixed with 200 µl of 12N HCl and 10 ml of 2% filtered $HNO_3$. The ICP-AES measurement of the powder gives the quantity of chemical elements comprised in the magnetosomes, in µg of these chemical elements (Ag, Al, As, Ba, Cd, Co, Cr, Cu, Mn, Mo, Ni, Pb, Sb, Se, Si, Sn, $T_1$, $T_1$, W, and Zn) per g of iron comprised in the magnetosomes.

Chemical products used for the preparation of the growth media: Aluminum potassium sulfate dodecahydrate (AlK$(SO_4)_2$12H$_2$O, ref. NFG A6435, Merck); Ammonia hydroxide ($NH_4OH$, ref. NFG 1336-21-6, Acros Organics; ref. FG 105422, Merck); Ammonium chloride ($NH_4Cl$, ref. NFG A9434, Merck; ref. FG 1011420001, Merck); Ammonium sulfate (($NH_4)_2SO_4$, ref. NFG A4418); Biotin ($C_{10}H_{16}N_2O_3S$, ref. NFG B4639, Merck; ref. FG B301, Merck); Boric acid ($H_3BO_3$, ref. NFG B6768, Merck); Calcium chloride ($CaCl_2$, ref. NFG 223506, Merck; ref. FG 1.42002, Merck); Calcium pantothenate ($HOCH_2C(CH_3)_2CH(OH)CONHCH_2CH_2CO_2.1/2Ca$, reference FG $C_{0400000}$, Merck); Cobalt(II) nitrate hexahydrate (Cobalt(II) nitrate hexahydrate, ref. FG 239267, Merck); Copper(II) sulfate pentahydrate ($CuO_4S.5H_2O$ 2O) (ref. NFG $C_{8027}$, Merck), DL-methionine ($CH_3SCH_2CH_2CH(NH_2)COOH$, ref. NFG $M_{2768}$, Merck); DL-tryptophan ($C_{11}H_{12}N_2O_2$, ref. NFG $T_{3300}$, Merck); EDTA (($HO_2CCH_2)_2NCH_2CH_2N(CH_2CO_2H)_2$, ref. NFG E6758, Merck); Ferric citrate ($C_6H_5FeO_7$, ref. NFG $F_{3388}$, Merck; ref. FG B301, Merck); Folic acid ($C_{19}H_{19}N_7O_6$, ref. NFG $F_{7876}$, Merck; ref. FG $F_{0300000}$, Merck); Inositol ($C_6H_{1206}$, ref. FG PHR1351, Merck); Iron(II) sulfate heptahydrate ($FeO_4S.7H_2O$, ref. NFG $F_{8633}$, Merck; ref. FG 1.03963, Merck); Iron(III) oxalate hexahydrate ($Fe_2(C_2O_4)_3.6H_2O$, ref. NFG 381446, Merck); L-histidine ($C_6H_9N_3O_2$, ref. FG PHR1108, Merck); Magnesium sulfate heptahydrate ($MgSO_4.7H_2O$, ref. NFG 63138, Merck; ref. FG 105882, Merck); Manganese(II) sulfate monohydrate ($MnO_4S·H_2O$, ref. NFG $M_{7899}$, Merck); Nickel(II) chloride hexahydrate ($Cl_2Ni.6H_2O$, ref. NFG N6136, Merck); Nicotinic acid ($C_6H_5NO_2$, ref. NFG N4126, Merck); Nitrilotriacetic acid trisodium salt ($C_6H_6NO_6Na_3$, ref. NFG N0253, Merck); p-Aminobenzoic acid ($H_2NC_6H_4CO_2H$, ref. NFG A9878, Merck); Potassium phosphate dibasic ($K_2HPO_4$, ref. NFG $P_{8281}$, Merck; ref. FG 105101, Merck); Potassium phosphate monobasic ($KH_2PO_4$, refe. NFG $P_{9791}$, Merck); Protoporphyrin IX ($C_{34}H_{34}N_4O_4$, ref. NFG $P_{8293}$, Merck); Pyridoxine HCl ($C_{12}H_{17}C_1N_4OS·HCl$, ref. NFG $P_{9755}$, Merck); Riboflavin ($C_{17}H_{20}N_4O_6$, ref. NFG R9504, Merck; ref. FG PHR1054, Merck); Sodium chloride (NaCl, ref. NFG 57653, Merck); Sodium lactate ($C_3H_5NaO_3$, ref. NFG L1375, Merck; ref. FG 106522, Merck); Sodium molybdate dihydrate ($Na_2Mo_4.2H_2O$, ref. NFG $M_{1003}$, Merck); Sodium selenite pentahydrate ($Na_2SeO_3.5H_2O$, ref. FG 89771, Merck); Thiamine HCL ($C_{12}H_{17}C_1N_4OS·HCl$, ref. NFG 47858, Merck, ref. FG PHR1037, Merck); Yeast extract (ref. NFG Y1625, Merck); Zinc sulfate heptahydrate ($O_4SZn.7H_2O$, ref. NFG Z0251, Merck). NFG designates Non-pharmaceutical grade chemicals used to prepare the growth media; FG designates Pharmaceutical grade chemicals used for the preparation of the growth media. We also used deionized water ($H_2O$), with a resistivity of 15 MΩ.

Composition of the different mineral elixirs: The composition of the different mineral elixirs (V0, CB1, V2, CB2, CB3, CB4, CB5, CB7, CB9, CB10, CB11, CB12, CB13) is given in table 6, where the quantity (in gram) of the different chemicals used to prepare 1 liter of these elixirs is indicated.

Composition of the different yeast extracts: The composition of the different yeast extracts (YE, YNBWAA, YNBWoAA, YNBWoAA.AS) is given in table 7, where the quantity (in gram) of the different chemicals used to prepare 1 liter of these yeast extracts is indicated. YNBWAA, YNBWoAA, YNBWoAA.AS designate reduced yeast extracts while YE designates non-reduced yeast extract (reference: Y0875, Sigma). YE comprises nitrogenous compounds, carbon, sulfur, trace nutrients, vitamin B complex and other important growth factors.

Composition of the different vitamin cocktails: The composition of the different vitamin cocktails (Vit1X, Vit5X, Vit10X, Vit0.5X, Vit0.1X) is given in table 8, where the quantity (in gram) of the different chemicals used to prepare 1 liter of these vitamin cocktails is indicated.

Composition of pre-growth media for condition 1 (table 1): One liter of pre-growth media comprises in one liter of deionized water 2.6 g of sodium lactate, 0.4 g of ammonium chloride, 0.1 g of magnesium sulfate heptahydrate, 0.5 g of potassium phosphate dibasic, 0.1 g of yeast extract YE (Table 7), and 0.5 mL of either one of the mineral elixirs V0, CB1, V2, CB2, CB3, CB4, CB5, CB7, CB9, CB10, CB11, CB12, or CB13 (Table 6).

Composition of growth media for condition 1 (table 1): One liter of growth media comprises in one liter of deionized water 2.6 g of sodium lactate, 0.4 g of ammonium chloride, 0.1 g of magnesium sulfate heptahydrate, 0.5 g of potassium phosphate dibasic, 0.1 g of yeast extract YE (Table 7), 0.5 mL of either one of the mineral elixirs V0, CB1, V2, CB2, CB3, CB4, CB5, CB7, CB9, CB10, CB11, CB12, or CB13 (Table 6), and 10 mL of ferric citrate (20 mM initial concentration).

Composition of pre-growth media for condition 2 (table 2): One liter of pre-growth media comprises in one liter of deionized water: 2.6 g of sodium lactate, 0.4 g of ammonium chloride, 0.1 g of magnesium sulfate heptahydrate, 0.5 g of potassium phosphate dibasic, 0.1 g of either one of yeast extract YE, YNBWAA, YNBWoAA, YNBWoAA.AS (Table 7), and 0.5 mL of mineral elixir CB3 (Table 6).

Composition of growth media for condition 2 (table 2): One liter of growth media comprises in one liter of deionized water 2.6 g of sodium lactate, 0.4 g of ammonium chloride, 0.1 g of magnesium sulfate heptahydrate, 0.5 g of potassium phosphate dibasic, 0.1 g of either one of yeast extracts YE, YNBWAA, YNBWoAA, or YNBWoAA.AS (Table 7,), 0.5 mL of mineral elixir CB3 (Table 6)., and 10 mL of ferric citrate (20 mM initial concentration).

Composition of pre-growth media for condition 3 (table 3): One liter of pre-growth media comprises in one liter of deionized water 2.6 g of sodium lactate, 0.4 g of ammonium chloride, 0.1 g of magnesium sulfate heptahydrate, 0.5 g of potassium phosphate dibasic, 0.1 mL of either one of vitamins Vit1X, Vit5X, Vit10X, Vit5X, Vit0.5X, or Vit0.1X (Table 8), and 0.5 mL of mineral elixir CB3 (Table 6).

Composition of growth media for condition 3 (table 3): One liter of growth media comprises in one liter of deionized water 2.6 g of sodium lactate, 0.4 g of ammonium chloride, 0.1 g of magnesium sulfate heptahydrate, 0.5 g of potassium phosphate dibasic, 0.1 mL of either one of vitamin cocktails Vit1X, Vit5X, Vit10X, Vit5X, Vit0.5X, or Vit0.1X (Table 8), 0.5 mL of mineral elixir CB3 (Table 6), and 10 mL of ferric citrate (20 mM initial concentration).

Composition of pre-growth media for condition 4 (table 4): One liter of pre-growth media comprises in one liter of deionized water 2.6 g of sodium lactate, 0.4 g of ammonium chloride, 0.1 g of magnesium sulfate heptahydrate, 0.5 g of potassium phosphate dibasic, 0.1 mL of either one of individual vitamins Bt, CP, FA, I, NA, AA, P, R, or T (Table 9), 0.5 mL of mineral elixir CB3 (Table 6).

Composition of growth media for condition 4 (table 4): One liter of growth media comprises in one liter of deionized water 2.6 g of sodium lactate, 0.4 g of ammonium chloride, 0.1 g of magnesium sulfate heptahydrate, 0.5 g of potassium phosphate dibasic, 0.1 mL of either one of the individual vitamins Bt, CP, FA, I, NA, AA, P, R, or T (Table 9), 0.5 mL of mineral elixir CB3 (Table 6), and 10 mL of ferric citrate (20 mM initial concentration).

Composition of pre-growth media for condition 5 (table 5): The composition of the different pre-growth media with various concentrations of the main components of the pre-growth media, i.e. sodium lactate, ammonium chloride, magnesium sulfate heptahydrate, potassium phosphate dibasic (N, SL0, SL0.5X, SL0.2X, SL0.1X, AC0, AC0.5X, AC0.2X, AC0.1X, MG0, MG0.5X, MG0, MG0.5X, MG0.2X, MG0.1X, P, $P_{0.5}X$, $P_{0.2}X$, $P_{0.1}X$) is given in table 5, where the quantity (in gram) of the different chemicals used to prepare 1 liter of these pre-growth media is indicated.

Composition of growth media for condition 5 (table 5): The composition of the different growth media with various concentrations of the main components of the pre-growth media, i.e. sodium lactate, ammonium chloride, magnesium sulfate heptahydrate, potassium phosphate dibasic (N, SL0, SL0.5X, SL0.2X, SL0.1X, AC0, AC0.5X, AC0.2X, AC0.1X, MG0, MG0.5X, MG0, MG0.5X, MG0.2X, MG0.1X, P, $P_{0.5}X$, $P_{0.2}X$, $P_{0.1}X$) is given in table 5, where the quantity (in gram) of the different chemicals used to prepare 1 liter of these growth media is indicated.

Composition of pre-growth media, growth media and fed-batch medium for condition 6, prepared using non-pharmaceutical grade chemicals (table 14(a)): The pre-growth media B1 and B4 comprise in one liter of deionized water 2.6 g of sodium lactate, 0.4 g of ammonium chloride, 0.1 g of magnesium sulfate heptahydrate, 0.5 g of potassium phosphate dibasic, 0.1 mL of vitamin cocktail Vit 0.1X (Table 8), and 0.5 mL of mineral elixir CB3 (Table 6). The growth media B1 and B4 comprise in one liter of deionized water 104 g of sodium lactate, 16 g of ammonium chloride, 1.2 g of magnesium sulfate heptahydrate, 2.8 g of potassium phosphate dibasic, 3.2 mL of vitamin cocktail Vit0.1X (Table 8), 2.8 mL of mineral elixir CB3 (Table 6). The fed-batch media B1 and B4 comprise in one liter of water 100 g of lactic acid, 4.8 g of ammoniac, 6 g of potassium phosphate dibasic, 2.4 of magnesium sulfate heptahydrate, 1 mL of vitamin cocktail Vit0.1X (Table 8), 7 mL of mineral elixir CB3 (Table 6), and either 1.8 g of ferric citrate (B1) or 2 g of iron III chloride (B4).

Composition of pre-growth media, growth media and fed-batch medium for condition 6, prepared using pharmaceutical grade chemicals (table 14(b)): The pre-growth media B2 and B3 comprise in one liter of deionized water 2.6 g of sodium lactate, 0.4 g of ammonium chloride, 0.1 g of magnesium sulfate heptahydrate, 0.5 g of potassium phosphate dibasic, 0.1 mL of vitamin cocktail Vit 0.1X (Table 8), and 0.5 mL of mineral elixir CB3 (Table 6). The growth media B1 and B4 comprise in one liter of deionized water 104 g of sodium lactate, 16 g of ammonium chloride, 1.2 g of magnesium sulfate heptahydrate, 2.8 g of potassium phosphate dibasic, 3.2 mL of vitamin cocktail Vit0.1X (Table 8), 2.8 mL of mineral elixir CB3 (Table 6). The fed-batch media B1 and B4 comprise in one liter of water 100 g of lactic acid, 4.8 g of ammoniac, 6 g of potassium phosphate dibasic, 2.4 of magnesium sulfate heptahydrate, 1 mL of vitamin cocktail Vit0.1X (Table 8), 7 mL of mineral elixir CB3 (Table 6), and either 1.8 g of ferric citrate (B2) or 2 g of iron III chloride (B3).

Stock of MSR-1 magnetotactic bacteria used for the different cultures: MSR-1 magnetotactic bacteria are commercialized by the company DSMZ under the reference DSM 6361. After reception, the MSR-1 bacterial suspensions were stored at an $OD_{565\ nm}$ (optical density measured at 565 nm) of 0.01, corresponding approximately to a bacterial concentration of $5.10^7$ bacteria per ml of culture medium (DSMZ Medium 380 used to grow the MSR1 Magnetospirillum Mediums strain DSMZ 6361) in a −80° C. freezer in 15 mL tubes (5 mL of bacterial suspension per tube) or in 1.5 mL Eppendorf tubes (600 μL of bacterial suspension per tube). Suspensions of MSR-1 bacteria stored in the freezer at −80° C. constitute the cellular stock. In some cases, the culture and/or pre-culture growth medium/media can be the same as the growth and/or pre-growth medium/media.

Notation: the number X after D in DX designates the number of day following the beginning of the pre-growth step, preferentially the day at which magnetotactic bacteria are inserted in the pre-growth medium for the first time or during the first sub-step of the pre-growth step.

Example 1: Determination of the Minimum Mineral Elixir Enabling Bacterial Growth and Magnetosome Synthesis This example describes the experimental protocol used to reduce as much as possible the mineral elixir composition while enabling the growth of MSR-1 magnetotactic bacteria and the synthesis of magnetosomes by these bacteria. In this example non-pharmaceutical grade chemicals were used for the preparation of the growth media. The composition of 1 liter of pre-growth and growth media used in this example (condition 1) are indicated in table 1. During the first day of the experiment (D1), a first step consisted in collecting the tubes of 15 ml containing 5 mL of MSR-1 cellular stock tube from the freezer at −80° C., in thawing the tubes by letting them at room temperature for 10 minutes. In a hood, we collected from these tubes 100 μl comprising $5.10^6$ MSR-1 magnetotactic bacteria that we have inserted in a 50 mL tube comprising 8 mL of filtered pre-growth medium. As a whole, 13 different culture conditions were tested corresponding to the 13 different mineral elixirs tested. The 50 ml tubes were incubated for 6 days between D1 and D6 in an incubator at 29.5° C. under shaking conditions at 150 rpm. A second step consisted in adding an iron source to the growth media to enable the synthesis of magnetosomes by MSR-1 bacteria. After 6 days of pre-growth, at D6, the 50 ml tubes were placed in a hood. 30 ml of filtered culture medium were then added to the 50 mL tubes and the bacteria grew between D6 and D13. A positive magnetic response at D13 and a ratio between the optical density at D13 and the optical density at D6 larger than 1 was observed for V0, V2, CB2, CB3, CB4, CB5, CB7, CB10, CB11, CB12, CB13 (condition 1). In contrast, no magnetic response for conditions CB1 and CB9, where the concentrations of chemical elements that comprise the mineral elixirs are lower than $10^{-5}$ g/l. In conclusion, the minimal mineral elixir that enables the growth of MSR-1 bacteria with a large increase in optical density ($OD_{565nmD13}/OD_{565\ nmD6}$ larger than 4.8) and the synthesis of magnetosomes (positive magnetic response) is CB13, composed only of iron sulfate heptahydrate at a concentration of 1 g/l and of calcium chloride at a concentration of 20 g/l.

Example 2: Determination of a Growth Medium without Yeast Extract, Enabling the Growth of Magnetotactic Bacteria and the Synthesis of Magnetosomes This example describes the experimental protocol used to determine the reduced medium replacing the yeast extract that enables the growth of MSR-1 magnetotactic bacteria and the synthesis of magnetosomes by these bacteria. In this example we used non-pharmaceutical grade chemicals for the preparation of the growth media. The compositions of pre-growth and growth media, in one liter of de-ionized water, are indicated in table 2 (condition 2), table 3 (condition 3), and table 4 (condition 4). During the first day of the experiment (D1), a first step consists in collecting the tubes of 15 ml containing 5 mL of MSR-1 cellular stock tube from the freezer at $-80°$ C., in thawing the tubes by letting them at room temperature for 10 minutes. In a hood, we collected from these tubes 100 µl comprising $5 \cdot 10^6$ MSR-1 magnetotactic bacteria that we have inserted in a 50 mL tube comprising 8 mL of filtered pre-growth medium of either condition 2 (table 2), condition 3 (table 3), or condition 4 (table 4). The 50 ml tubes were incubated for 6 days between D1 and D6 in an incubator at $29.5°$ C. under shaking conditions at 150 rpm. A second step consisted in adding an iron source to the growth media to enable the synthesis of magnetosomes by MSR-1 bacteria. After 6 days of pre-growth, at D6, the 50 ml tubes were placed in a hood. 30 ml of filtered growth medium were then added to the 50 mL tubes (condition 2, table 2, condition 3, table 3, condition 4, table 4) at D6 and the bacteria grew between D6 and D13. Tables 11 and 12 indicate that a magnetic response larger than 90% at D13 and a ratio between the optical density measured at D13 and the optical density measured at D6 larger than 1, was observed for yeast extracts YE, YNB-WAA, YNBWAA, YNBWoAA, YNBWoAA, YNBWoAA.AS (condition 2), for VitIX, Vit0.5X, Vit0.1X, (condition 3), Biotin (Bt), folic acid (FA), nicotinic acid (NA), Riboflavin (R), Thiamine HCl (T) (condition 4). In contrast, the magnetic response is 0 for conditions Vit5X, Vit10X (condition 3) and very low for conditions CP, I, AA, P (condition 4). In conclusion, the yeast extract can be replaced by a single vitamin, which is biotin, folic acid, riboflavin, nicotinic acid or thiamin HCl. These vitamins yield values of $OD_{565\ nmD13}/OD_{565\ nmD6}$ of 9.8 (biotin), 2.9 (folic acid), 4.8 (riboflavin), 2.4 (nicotinic acid), 5.8 (thiamin HCl) and 90% of magnetic response (table 11).

Example 3: Determination of the Minimal Concentrations of the Main Components of the Growth Media (Sodium Lactate, Ammonium Chloride, Magnesium Sulfate, Potassium Phosphate), Enabling the Growth of Magnetotactic Bacteria and the Synthesis of Magnetosomes by these Bacteria This example describes the experimental protocol used to determine the reduced growth medium, enabling the growth of MSR-1 magnetotactic bacteria and the synthesis of magnetosomes by these bacteria. In this example we used non-pharmaceutical grade chemicals for the preparation of the growth media. We varied the concentration of sodium lactate (conditions SL0, SL0.5X, SL0.2X, SL0.1X), ammonium chloride (AC0, AC0.5X, AC0.2X, AC0.1X), magnesium sulfate heptahydrate (MG0, MG0.5X, MG0.2X, MG0.1X), potassium phosphate dibasic (P0, P0.5X, P0.2X, P0.1X). The chemical compositions and concentrations of the pre-growth and growth media N, SL0, SL0.5X, SL0.2X, SL0.1X, AC0, AC0.5X, AC0.2X, AC0.1X, MG0, MG0.5X, MG0.2X, MG0.1X, P0, P0.5X, P0.2X, P0.1X, are summarized in table 5 for 1 liter of growth media. During the first day of the experiment (D1), a first step consists in collecting the tubes of 15 ml containing 5 mL of MSR-1 cellular stock tube from the freezer at $-80°$ C., in thawing the tubes by letting them at room temperature for 10 minutes. Under a hood, we collected from these tubes 100 µl comprising $5 \cdot 10^6$ MSR-1 magnetotactic bacteria that we have inserted in a 50 mL tube filled with 8 mL of pre-growth media (condition 5, table 5). The 50 ml tubes were incubated for 6 days between D1 and D6 in an incubator at $29.5°$ C. under shaking conditions at 150 rpm. A second step consisted in adding an iron source to the growth media to enable the synthesis of magnetosomes by MSR-1 bacteria. After 6 days of pre-growth, at D6, the 50 ml tubes were placed in a hood. 30 ml of filtered growth media were then added to the 50 mL tubes at D6 and the bacteria grew between D6 and D13. For conditions N, P0.5X, P0.2X, a growth ratio, or ratio between the optical density measured at D13 and the optical density measured at D6, was larger than 1, and a positive magnetic response (magnetic response>90%) was observed at D13. It indicates that these conditions enabled the bacteria to grow and produce magnetosomes. By contrast, for conditions SL0, SL0.5X, SL0.2X, SL0.1X, AC0, AC0.5X, AC0.2X, AC0.1X, MG0, MG0.5X, MG0.2X, MG0.1X, P0.1X, P0, the synthesis of the magnetosomes was very low (magnetic response<50%). In conclusion, the concentration of potassium phosphate can be reduced in the growth medium by a factor of 2 or 5 without affecting the growth and production of magnetosomes. Indeed, these conditions yield values of $OD_{565\ nmD13}/OD_{565\ nmD6}$ of 1.5 (condition P0.5X), 2.1 (condition P0.2X), and a percentage of positive magnetic response among bacteria larger than 90% (table 13). By contrast, the concentrations of the other chemicals of the medium (ammonium chloride, sodium lactate, magnesium phosphate) could not be reduced without significantly affecting the growth and/or the magnetic response of MSR-1 magnetotactic bacteria.

Example 4: Determination of the Iron Source in 1-Liter Fermenters Enabling the Growth of Magnetotactic Bacteria and the Synthesis of Magnetosomes by these Bacteria and of the Reduction of Impurities Obtained by Using High Pharmaceutical Grade Chemical Products for the Preparation of the Pre-Growth and/or Growth Medium/Media This example describes the experimental protocol used to determine the iron source, which enables the growth of MSR-1 magnetotactic bacteria and the synthesis of magnetosomes by these bacteria as well as the reduction of impurity(ies) comprised in the magnetosomes obtained by using pharmaceutical grade chemicals (condition 6). In this example we used pharmaceutical grade chemicals to prepare B2 and B3 growth media (table 14(b)) and non-pharmaceutical grade chemicals to prepare B1 and B4 growth media (table 14(a)). The compositions of the pre-growth medium, growth medium, and fed-batch medium are indicated for 1 liter of medium in tables 14(a) and 14(b). During the first day (D1), a first step of pre-growth consists in collecting 1 tube of 1.5 mL Eppendorf containing 600 μL of MSR-1 cellular stock tube from the freezer at −80° C., in thawing the tube by letting them at room temperature for 10 minutes. Under a hood, we collected from these tubes 300 μl comprising $1 \cdot 5 \cdot 10^7$ MSR-1 magnetotactic bacteria that we have inserted in a 500 mL sterile bottle filled with 250 mL of filtered pre-growth medium. The 500 ml bottle was incubated for 7 days between D1 and D7 in an incubator at 29.5° C. A second step of pre-growth was then carried out in a larger 2 L bottle. After 7 days of pre-growth, at D8, the 500 mL bottle was placed in a hood. The pre-growth medium containing the MSR-1 bacteria was manually transferred in a 2 L sterile bottle filled with 1.5 L of filtered pre-growth medium for the second step of pre-growth. The 2 L bottle was incubated for 1 day between D8 and D9 in an incubator at 29.5° C. under shaking conditions at 150 rpm. During the ninth day (D9), the growth step started. For that, 4 fermenters (conditions, B1, B2, B3, B4) of 1.5 L were filled with 780 mL of deionized water and autoclaved. The fermenters were then filled with 20 mL of filtered growth medium. Each of the 4 fermenters (conditions, B1, B2, B3, B4) was then filled with 200 mL of pre-growth medium containing the MSR-1 bacteria originating from the second step of pre-growth. Between day D9 and D11, an acidic fed-batch medium comprising an iron source was added to the growth medium to enable the synthesis of the magnetosomes by MSR-1 bacteria, while maintaining the pH of the growth medium at 6.9. During the growth step, the temperature was maintained at 29.5° C., airflow at 0.05 mL/min and agitation at 200 rpm. The optical densities, measured at 565 nm, of the bacterial suspensions at different days of the pre-growth step (D0 and D8) and growth step (D9, D10, D11) are indicated in table 15 for conditions B1, B2, B3, and B4. Following fermentation at D13, MSR-1 cells from fermenters B1, B2, B3, and B4 (conditions B1 to B4) were concentrated by centrifugation at 4000 rpm during 45 min. To lyse the bacteria, MSR-1 cells from fermenters B1, B2, B3, B4, were re-suspended in 15 mL of 1 M KOH solution and heated at 80° C. during 2 h in a sonicating bath at 25 kHz in 20 mL glass bottles. After bacterial lysis, magnetosomes from MSR-1 cells were separated from the organic material using a Neodymium magnet over-night. At D14, magnetosomes from conditions B1, B2, B3, B4 were washed two times using 15 mL of 10×Phosphate-buffered saline and two times using 15 mL of deionized water using a Neodymium magnet. During each wash, the magnetosome suspensions were positioned against a Neodymium magnet for 2 hours that attracts the magnetosomes. The supernate containing organic debris were discarded and replaced either by 15 mL of 10×Phosphate-buffered saline or 15 mL of deionized water. At D16, after the last wash the supernate were discarded and magnetosomes from conditions B1, B2, B3, B4 were transferred in ceramic cups and dried by positioning them against a Neodymium magnet over-day. At D17, the remaining liquid were discarded and magnetosomes were inserted in ceramic cups and positioned in a muffle furnace and heated at 200° C. for 30 min, 300° C. for 1 hour, and 380° C. for 1 hour. At D17, ~1 mg of purified magnetosomes from conditions B1, B2, B3, B4 were inserted in 15 mL tubes filled with 200 μL of HCL 12N. The tubes of 15 mL containing the magnetosomes were vortexed and incubated at room temperature for 2 hours and then filled with 9.8 mL of $HNO_3$ 2%. After that, the concentration in μg of elemental impurities per gram of nanoparticles were measured by ICP-AES. The results of these measurements are indicated in table 16 for conditions B1, B2, B3, B4, where elemental impurities are Ag (silver), Al (aluminium), As (arsenic), Ba (baryum), Cd (cadmium), Co (cobalt), Cr (chrome), Cu (copper), Mn (manganese), Mo (molybdenum), Ni (nickel), Pb (lead), Sb (antimony), Se (selenium), Si (silica), Sn (tin), $T_i$ (titanium), $T_i$ (tallium), W (tungstate), Zn (zinc). In conclusion, the condition B3 yields the largest value of $OD_{565\ nmD11}/OD_{565\ nmD9}$ of 26.8 and a percentage of positive magnetic response among bacteria (>90%) (table 15), indicating that Iron(III) chloride is the best iron source. Furthermore, except for Pb, elemental impurity concentrations are reduced in condition B3 where pharmaceutical grade chemicals were used compared with condition B4 where non-pharmaceutical grade chemicals were used (table 16).

Examples 5 (Purifying Method)

Materials and Methods:
Note: In this example, weight could be replaced by mass, preferentially leading to the same meaning.
Equipment Used to Analyze and Heat the Various Samples:
TGA-DSC: "Thermogravimetric analysis" (TGA) coupled to "Differential Scanning calorimetry" (DSC) is used to measure heat flow (in mW) or the percentage of mass loss of powders comprising lyophilized magnetosomes (treated or not) or lyophilized whole bacteria or lyophilized SIGMA nanoparticles as a function of the heating temperature of these powders. For the measurements, the powders are heated at a rate of 6° C. per minute between 20° C. and 600° C. The derivative of the percentage of mass variation of the powders is also plotted as a function of temperature. The TGA-DSC profiles make it possible to define the temperatures for which the material, preferentially organic material, located in or at the surface of the magnetosomes or nanoparticles will be degraded, removed from the nanoparticles, or transformed. ATG and DSC analyzes were performed with the SDT $Q_{600}$ (TA Instrument). It consists of a sealed enclosure, a furnace with temperature control, a micro-balance, and a thermocouple to measure the temperature. A mass of 3 mg of lyophilized bacteria, lyophilized magnetosomes, SIGMA nanoparticle powder, is used for TGA-DSC analysis CHNS: "Elemental Carbon, Hydrogen Nitrogen and Sulfur Analyzer" CHNS measurements are carried out using a CHNS analyzer (Flash Elemental Analyzer EA 1112 from Thermo Fischer scientific) using a mass of 3 mg per measurement of lyophilized magnetosomes (conditions of treatment n° 1, 2, 3, 4, 5, 6, 7, 8, 9, 10, 11), lyophilized whole bacteria, lyophilized SIGMA nanoparticles (not treated). CHNS measurements enable to determine the percentages in mass of carbon and nitrogen in the different powders. A mass of 3 mg of lyophilized bacteria, lyophilized magnetosomes, and SIGMA nanoparticle powder, is used for CHNS measurements.

Furnace: A muffle furnace (Nabertherm L9/11/B410) is used to heat 30 mg or 500 mg of magnetosomes extracted from magnetotactic bacteria following condition n° 1 or 2 without heat treatment above 200° C. or with heat treatment above 200° C. (following condition n° 3, 4, 5, 6, 7, 8, 9, 10 or 11). For that, the 30 or 500 mg powder of each sample is deposited in an uncovered porcelain cup and placed at the center of the furnace. A program is used to carry out the different heating conditions. The furnace enables to maintain the temperature of the nanoparticles or the temperature inside the furnace at a given temperature plus or minus 2° C., or the furnace enables to obtain a stable temperature between 20° C. and 380° C. with a fluctuation of 2° C. maximum.

Sample comprising whole magnetotactic bacteria (Sample 0): Magnetotactic bacteria obtained from condition 1 (mineral elixir V2, table 1) were collected and concentrated using a tangential filtration system to an optical density, measured at 565 nm (OD565 nm), between 100 and 200. Sample 0 comprises concentrated whole magnetotactic bacteria.

Samples Comprising Magnetosomes Extracted from Magnetotactic Bacteria without Heat Treatment Above 200° C. (Samples 1 and 2):

Condition 1 of lysis (Sample 1): 100 ml of sample 0, concentrated at an OD565 nm of 120, were mixed with 400 ml of 5 M NaOH and sonicated and heated at 60° C. for 1 hour using a sonic bath to lyse the bacteria. The treated magnetosomes were then isolated from the bacterial debris by placing a Neodinium magnet overnight against the wall of the container containing the lysed bacteria suspension and by replacing the supernatant containing the medium and bacterial debris by 1×PBS. The resulting suspension was then sonicated for 20 seconds at 101V in the presence of 1×PBS, placed against a Neodinium magnet for 15 minutes, the supernatant was removed and the treated magnetosomes were resuspended in 1×PBS. This sequence of sonication and magnetic separation was repeated four times. For an entire fermenter, this treatment was repeated 10 times in 10 different volumes. Pyrogenic magnetosome chains extracted from MSR-1 magnetotactic bacteria were thus obtained, i.e. approximately 500 mg in iron of magnetosomes comprised in 1.7 ml of water. Sample 1 comprises magnetosomes obtained from condition 1 of lysis.

Condition 2 of lysis (Sample 2): Concentrated magnetotactic bacteria were frozen at −80° C. for 48 hours. After thawing and dilution of the concentrate with MilliQ water to obtain an OD565 nm of 30, an amount of KOH was added to obtain to the concentrated bacteria to obtain a final KOH concentration of 1 M. This solution was transferred to a polypropylene (PP) bottle and placed in the water bath at 80° C. with stirring at 150 rpm with a mechanical stirring pad (Fisher Scientific), for 30 minutes. Then, the content of the bottle was transferred into 4 other glass bottles of 2 L. Each bottle was placed against a NdFeB magnet for 12 hours to magnetically separate the extracted magnetosomes from bacterial debris. The magnetosomes were then washed 6 times in 500 mL bottles by magnetic selection, until a clear supernatant was obtained. The first two washes were carried out with 10×PBS, which makes it possible to return to a neutral pH. Then the other four washes were carried out with water. After lysis, the basic pH of the lysate, caused by the KOH, was brought back to a neutral pH so as not to damage the magnetosomes. Pyrogenic magnetosome chains extracted from the strain MSR-1 were thus obtained, i.e. about 500 mg in iron of magnetosomes in 1.7 ml. Sample 2 comprises magnetosomes obtained after condition 2 of lysis.

Samples Comprising Magnetosome Extracted from Magnetotactic Bacteria and Treated with Phenol-Chloroform (Condition 3):

Condition 3 of treatment (Sample 3): 100 µl of the suspension containing 30 mg in iron of magnetosomes obtained following condition 1 of lysis were mixed with 200 ml of a solution containing 1% Triton X-100 and 1% SDS. The mixture was heated overnight at 50° C., was placed against a Neodinium magnet, the supernatant was removed and replaced with 80 mL of phenol at pH 8. The obtained suspension was heated for 2 hours under sonication at 60° C., held overnight at 60° C. without sonication, placed against a magnet, the supernatant of the suspension was removed and replaced with 80 mL of chloroform. The suspension containing the chloroform was placed against a magnet of Neodinium, the supernatant was removed and the residual chloroform adsorbed at the surface of the treated magnetosomes was removed by heating these magnetosomes for 2 hours under a hood. Finally, the cores of the magnetosomes thus obtained were desorbed from the glass wall from the tubes containing them by adding 80 ml of 1 M NaOH heated for 1 hour at 60° C. in a sonic bath. The suspension containing the cores of the magnetosomes was placed against a Neodinium magnet. The supernatant was removed and replaced with sterile MilliQ water. The suspension was sonicated for 20 seconds at 10 W. This washing sequence was repeated four times. Purified pyrogen-free magnetosomes were obtained in a small volume of pyrogen-free water. Sample 3 comprises magnetosomes obtained after condition 3 of treatment.

Samples Comprising Magnetosome Extracted from Magnetotactic Bacteria and Heated at Temperatures Above 200° C. (Samples 4 to 11):

Condition 4 of heat treatment (Sample 4): 100 µl of the suspension containing approximately 30 mg in iron of magnetosomes extracted from MSR-1 magnetotactic bacteria following condition 2 of lysis were lyophilized, introduced into a porcelain crucible, and baked in the furnace Nabertherm L9/11/B410. The heating protocol was as follows. The temperature of the furnace was increased from 20° C. to 200° C. at a rate of 6° C./min until the temperature of the furnace reaches 200° C. and the temperature of 200° C. in the furnace was maintained during one hour. Then the temperature of the furnace was decreased from 200° C. to 25° C. in 12 hours. Sample 4 comprises magnetosomes obtained after condition 4 of treatment.

Condition 5 of heat treatment (Sample 5): 100 µl of the suspension containing approximately 30 mg in iron of magnetosomes extracted from MSR-1 magnetotactic bacteria following condition 2 of lysis were lyophilized, introduced into a porcelain crucible, and baked in the furnace Nabertherm L9/11/B410. The heating protocol was as follows. The temperature of the furnace was increased from 20° C. to 400° C. at a rate of 6° C./min until the temperature of the furnace reaches 400° C. The temperature in the furnace was maintained at 400° C. for one hour. Then the temperature of the furnace was decreased from 400° C. to 25° C. in 20 hours. Sample 5 comprises magnetosomes obtained after condition 5 of treatment.

Condition 6 of heat treatment (Sample 6): 100 µl of a suspension comprising 30 mg in iron of magnetosomes prepared according to condition 2 of lysis, were lyophilized and then introduced into a porcelain crucible and heated in the furnace Nabertherm L9/11/B410. The heat treatment was as follows. The temperature of the furnace was increased from 20° C. to 200° C. in 20 min at a rate of 9° C./min. The temperature of the furnace was then maintained at 200° C. for 30 minutes. The temperature of the furnace was then increased from 200° C. to 300° C. in 10 min at a rate of 10° C./min. The temperature of the furnace was then maintained at 300° C. for 1 hour. Then the temperature of the furnace was decreased from 300° C. to 25° C. in 12 hours. Sample 6 comprises magnetosomes obtained after condition 6 of treatment.

Condition 7 of heat treatment (Sample 7): 100 µl of a suspension comprising 30 mg in iron of magnetosomes prepared according to condition 2 of lysis, were lyophilized and then introduced into a porcelain crucible and heated in the furnace Nabertherm L9/11/B410. The heat treatment was as follows. The temperature of the furnace was increased from 20° C. to 200° C. in 20 min at a rate of 9° C./min. The temperature of the furnace was then maintained at 200° C. for 30 minutes. The temperature of the furnace was then increased from 200° C. to 300° C. in 10 min at a rate of 10° C./min. The temperature of the furnace was then maintained at 300° C. for 1 hour. The temperature of the furnace was then increased from 300 to 380° C. in 10 min at a rate of 8° C./min. The temperature of the furnace was then maintained at 380° C. for 1 hour. The temperature of the furnace was then increased from 380° C. to 550° C. in 20 min at a rate of 8.5° C./min. The temperature of the furnace was then maintained at 550° C. for 1 h. Then the temperature of the furnace was decreased from 550° C. to 25° C. in 20 hours. Sample 7 comprises magnetosomes obtained after condition of treatment Condition 8 of heat treatment (Sample 8): 100 μl of the suspension containing 30 mg in iron of magnetosomes prepared according to condition 2 of lysis, were lyophilized and then introduced into a porcelain crucible and baked in the furnace Nabertherm L9/11/B410. The heat treatment was as follows. The temperature of the furnace was increased from 20° C. to 200° C. in 20 min at a rate of 9° C./min. The temperature of the furnace was then maintained at 200° C. for 30 minutes. The temperature of the furnace was then increased from 200° C. to 300° C. in 10 min at a rate of 10° C./min. The temperature of the furnace was then maintained at 300° C. for 1 hour. The temperature of the furnace was increased from 300° C. to 380° C. in 10 min at a rate of 8° C./min. The temperature of the furnace was then maintained at 380° C. for 1 h. Then the temperature of the furnace was decreased from 380° C. to 25° C. in 12 hours. Sample 8 comprises magnetosomes obtained after condition 8 of treatment.

Condition 9 of heat treatment (Sample 9): 100 μl of the suspension containing 30 mg in iron of magnetosomes prepared according to condition 1 of lysis, were lyophilized and then introduced into a porcelain crucible and heated in the furnace Nabertherm L9/11/B410. The heat treatment was as follows. The temperature of the furnace was increased from 20° C. to 200° C. in 20 min at a rate of 9° C./min. The temperature of the furnace was then maintained at 200° C. for 30 minutes. The temperature of the furnace was then increased from 200° C. to 300° C. in 10 min at a rate of 10° C./min. The temperature of the furnace was then maintained at 300° C. for 1 hour. The temperature of the furnace was increased from 300° C. to 380° C. in 10 min at a rate of 8° C./min. The temperature of the furnace was then maintained at 380° C. for 1 h. Then the temperature of the furnace was decreased from 380° C. to 25° C. in 12 hours. Sample 9 comprises magnetosomes obtained after condition 9 of treatment.

Condition 10 of heat treatment (Sample 10): 1.7 mL of a suspension containing 500 mg in iron of magnetosomes prepared according to condition n° 2 of lysis, were lyophilized and then introduced into a porcelain crucible and heated in the furnace Nabertherm L9/11/B410. The heat protocol was as follows. The temperature of the furnace was increased from 20° C. to 200° C. in 2 hours 30 min at a rate of 1.2° C./min. The temperature of the furnace was then maintained at 200° C. for 1 hour. The temperature of the furnace was then increased from 200° C. to 300° C. in 1 h 20 min at a rate of 1.25° C./min. The temperature of the furnace was then maintained at 300° C. for 2 hours. The temperature of the furnace was then increased from 300° C. to 380° C. in 1 hour 20 min at a rate of 1° C./min. The temperature of the furnace was then maintained at 380° C. for 2 h. Then the temperature of the furnace was decreased from 380° C. to 25° C. in 12 hours. Sample 10 comprises magnetosomes obtained after condition 10 of treatment.

Condition 11 of heat treatment (Sample 11): 1.7 mL of a suspension containing 500 mg in iron of magnetosomes prepared according to condition n° 1 of lysis, were lyophilized and then introduced into a porcelain crucible and heated in the furnace Nabertherm L9/11/B410. The heat treatment was as follows. The temperature of the furnace was increased from 20° C. to 200° C. in 2 hours and 30 minutes at a rate of 1.2° C./min. The temperature of the furnace was then maintained at 200° C. for 1 hour. The temperature of the furnace was then increased from 200° C. to 300° C. in 1 h 20 min at a rate of 1.25° C./min. The temperature of the furnace was then maintained at 300° C. for 2 hours. The temperature of the furnace was then increased from 300° C. to 380° C. in 1 hour 20 min at a rate of 1° C./min. The temperature of the furnace was then maintained at 380° C. for 2 h. Then the temperature of the furnace was decreased from 380° C. to 25° C. in 12 hours. Sample 11 comprises magnetosomes obtained after condition 11 of treatment.

Chemically synthesized nanoparticles (SIGMA, reference: 637106, batch n°: MKBK2270V): Powder of chemically synthesized nanoparticles have been purchased from SIGMA. They have a size of 35±13 nm and they comprise in addition to iron oxide, 198 ppm of Aluminum (Al), 600 ppm of Calcium (Ca) 74 ppm of Chromium (Cr), 72 ppm of Magnesium (Mg), 642.5 ppm of Manganese (Mn), 30 ppm of Nickel (Ni), 128 ppm of Sodium (Na), 34 ppm of Titanium ($T_i$), 8.3 ppm of Vanadium (V), 56.5 ppm of Zinc (Zn).

Results:

FIG. 1 (a) shows the percentage of weight loss of a sample comprising 3 mg of lyophilized whole MSR-1 magnetotactic bacteria (Sample 0) as a function of sample temperature, when the temperature of the sample is increased from 20° C. to 600° C. at a rate of 6° C. per minute, as well as the first derivative of this percentage. These measurements have been carried out with a combined TGA-DTA/DSC apparatus, measuring both heat flow using Differential Scanning calorimetry and weight changes using Thermogravimetry in a material as a function of temperature. CHNS measurements of 3 mg of lyophilized whole MSR-1 magnetotactic bacteria (Sample 0) have shown that they contain a large percentage of carbon of 44%, before being heated (table 19). The percentage in weight of this sample decreases from 100% at 20° C. down to 5.5% at 600° C., indicating that the sample loses most of weight between 20 and 600° C. More specifically, it appears in FIG. 1(a) that the slope of the variation of the percentage of weight as a function of temperature is the largest within two temperature ranges: between 200 and 400° C. (interval 1) and between 400 and 540° C. (interval 2). Between 200 and 400° C., the variation as a function of temperature of the slope of the percentage of weight as a function of temperature displays a double peak whose maximum are at 260° C. and 315° C. This double peak could be due to the loss by the whole magnetotactic bacteria of organic material, preferentially of type 1, for the peak centered at 260° C. and of organic material, preferentially of a different type than type 1 such as type 2, for the peak centered at 315° C. Between 400 and 540° C., the variation as a function of temperature of the slope of the percentage of weight variation as a function of temperature displays a peak. This peak could be due to the loss by the nanoparticles of organic material, preferentially of a different type than type 1 or type 2 such as type 3.

FIG. 1(b) shows the heat flow in milliwatt of a sample comprising 3 mg of lyophilized whole magnetotactic bacteria as a function of sample temperature, when the temperature of the sample is increased from 20° C. to 600° C. at a rate of 6° C. per minute. These measurements have been carried out with a TGA-DSC apparatus. FIG. 1(b) shows two peaks with maximum heat flow observed at temperatures of 330° C. and 500° C. The peak centered at 330° C. could be attributed to the combustion of the mass of nanoparticles that has been lost or removed from the nanoparticles or transformed between 200 and 400° C. The peak at 500° C. could be attributed to the combustion of the mass of nanoparticles that has been lost between 500 and 540° C.

FIG. 1(c) shows the percentage of variation of the weight of a sample comprising 3 mg of lyophilized chains of magnetosomes prepared according to condition 2 of lysis as a function of sample temperature, when the temperature of the sample is increased from 20° C. to 600° C. at a rate of 6° C. per minute, as well as the first derivative of this percentage. These measurements have been carried out with a TGA-DSC apparatus. CHNS measurements of lyophilized chains of magnetosomes (condition n° 2) have shown that they contain a percentage of carbon of 7%, before being heated, which is much lower than the percentage of carbon in whole magnetotactic bacteria (table 19). The percentage in weight of the sample comprising chains of magnetosomes decreases from 100% at 20° C. down to 91.4% at 600° C., indicating that the sample comprising chains of magnetosomes loses much less mass, i.e. 8.6%, than the sample comprising whole magnetotactic bacteria between 20° C. and 600° C. More specifically, it appears in FIG. 1(c) that the slope of the variation of the percentage in weight of the chains of magnetosomes as a function of temperature is the largest within the temperature range of 200 to 400° C. Between 200 and 400° C., the variation as a function of temperature of the slope of the percentage in weight of the chains of magnetosomes as a function of temperature displays a double peak whose maximum are at 260° C. and 315° C., similar positions than those of the double peak observed with whole bacteria. This double peak could be due to the loss by the chains of magnetosomes of organic material, preferentially organic material of type 1, for the peak centered at 260° C. and of organic material, preferentially organic material of type 2 for the peak centered at 315° C., where this organic material likely comes from the organic membrane layer surrounding the mineral iron oxide core of the magnetosomes. FIG. 1(d) shows the heat flow in milliwatt of a sample comprising 3 mg of lyophilized chains of magnetosomes as a function of the sample temperature, when the temperature of the sample is increased from 20° C. to 600° C. at a rate of 6° C. per minute. These measurements have been carried out with a TGA-DSC apparatus. FIG. 1(d) shows three peaks with maximum heat flow observed at temperatures of 250° C., 360° C., and 525° C. The peaks centered at 250° C. and 360° C. could be attributed to the combustion of the mass of nanoparticles that has been lost between 200 and 400° C. The peak at 525° C. could be attributed to the combustion of the mass of nanoparticles that has been lost above 500° C. and/or to the oxidation of the magnetosomes from an iron oxide composition of magnetite, maghemite, or an intermediate composition between magnetite and maghemite into hematite, which could result in heat flow possibly caused by an exothermic reaction.

Figure 2:
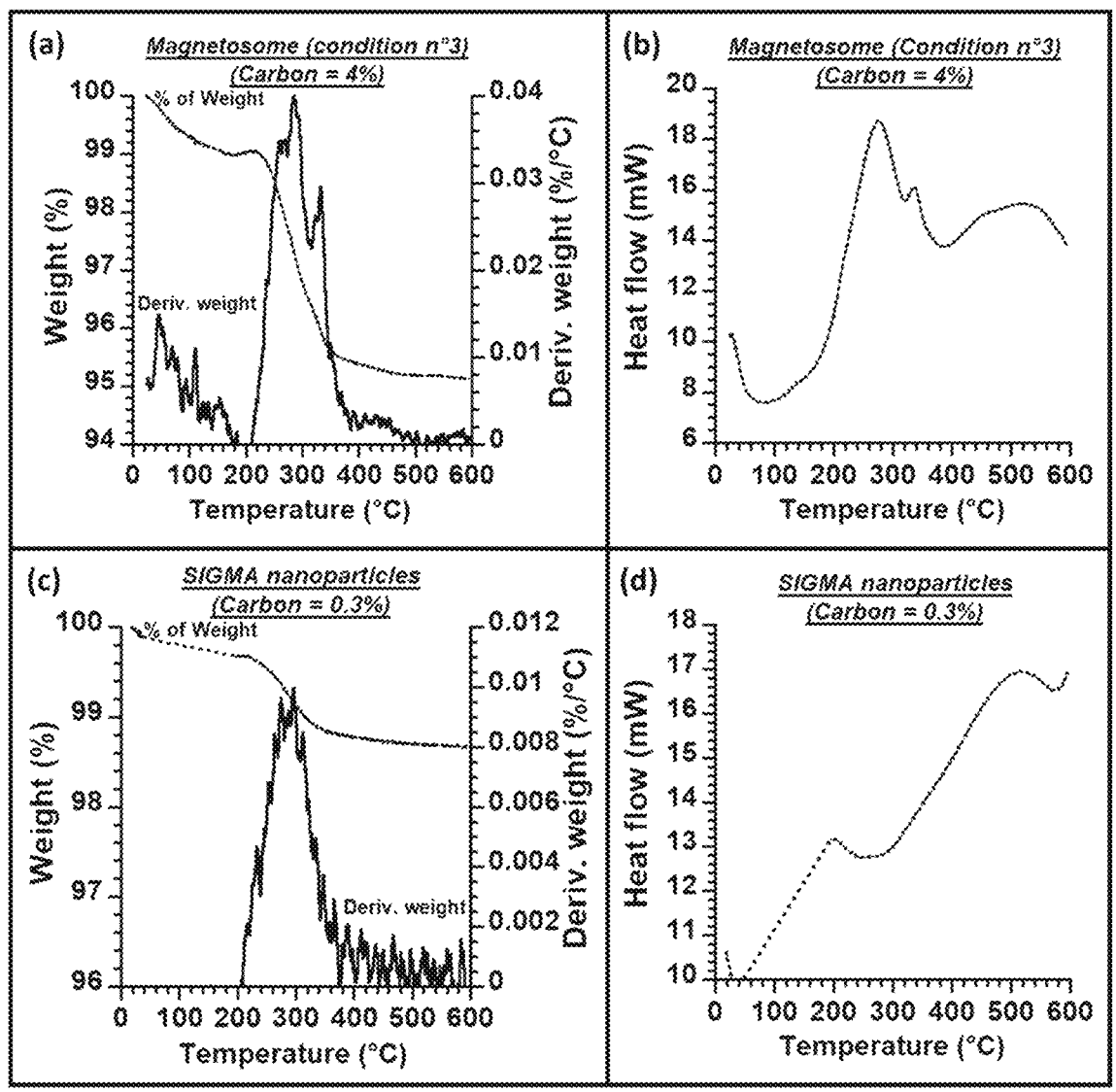
FIG. 2: TGA-DSC analysis of magnetosomes extracted from magnetotactic bacteria according to condition 3 and of chemically synthesized SIGMA nanoparticles. (a), Variation of the percentage in weight as a function of temperature as well as the derivative of this variation as a function of temperature for a sample comprising 3 mg of lyophilized magnetosomes extracted from magnetotactic bacteria according to condition 3. (b), Heat flow in mW as a function of temperature produced by a sample comprising 3 mg of lyophilized magnetosomes extracted from magnetotactic bacteria according to condition 3. (c), Variation of the percentage in weight as a function of temperature as well as the derivative of this variation as a function of temperature for a sample comprising 3 mg of lyophilized SIGMA nanoparticles. (d), Heat flow in mW as a function of temperature produced by a sample comprising 3 mg of lyophilized SIGMA nanoparticles. Concerning (a) and (c), the y axis can be replaced by the percentage in mass, leading to the same plots.
Figure 3:
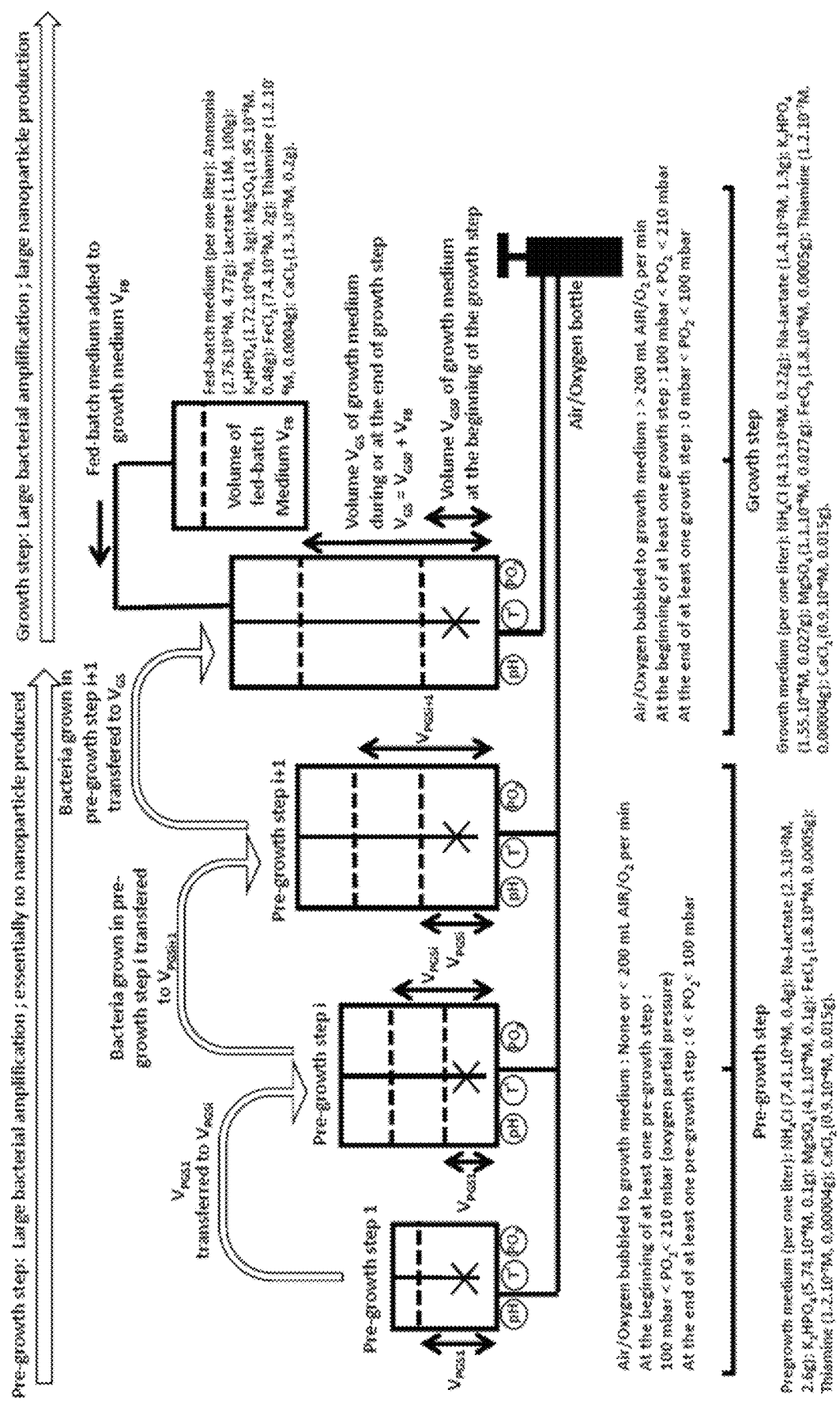
FIG. 3: An illustrative example of use of the method according to the invention, following a series of pre-growth step(s) 1, i, and i+1, where the pre-growth step is preferentially started by inserting nanoparticle-producing cells of the cell bank (typically $10^7$ cells) in the volume of pre-growth step $V_{PGS1}$ (typically ~50 mL), nanoparticle-producing cells are amplified in this volume typically during~7 days, nanoparticle-producing cells are then transferred from $V_{PGS1}$ to $V_{PGSi}$ ($V_{PGSi}$ typically ~500 mL), nanoparticle-producing cells are amplified in this volume during typically ~3 days, nanoparticle-producing cells are then transferred from $V_{PGSi}$ to $V_{PGSi+1}$ ($V_{PGSi+1}$ typically ~5 L), nanoparticle-producing cells are amplified in this volume during typically 3 days up to an OD of typically 1 and are then transferred to $V_{GS0}$ (typically 45 liters) where $V_{GS0}$ is supplemented by a fed-batch medium (typically 5-10 liters) during the growth step of preferentially ~5 days in the presence of oxygen bubbled through the growth medium to enable bacterial growth up to an OD of typically 5 to 40 and quantity of magnetosomes produced of 5 to 500 mg per liter of growth medium, where the pre-growth medium comprises a limited concentration of iron or iron source (preferentially <2 µM) preferentially to prevent the production of nanoparticles and the growth medium comprises iron or an iron source (preferentially >2 µM) preferentially to promote nanoparticle production.
Figure 4:
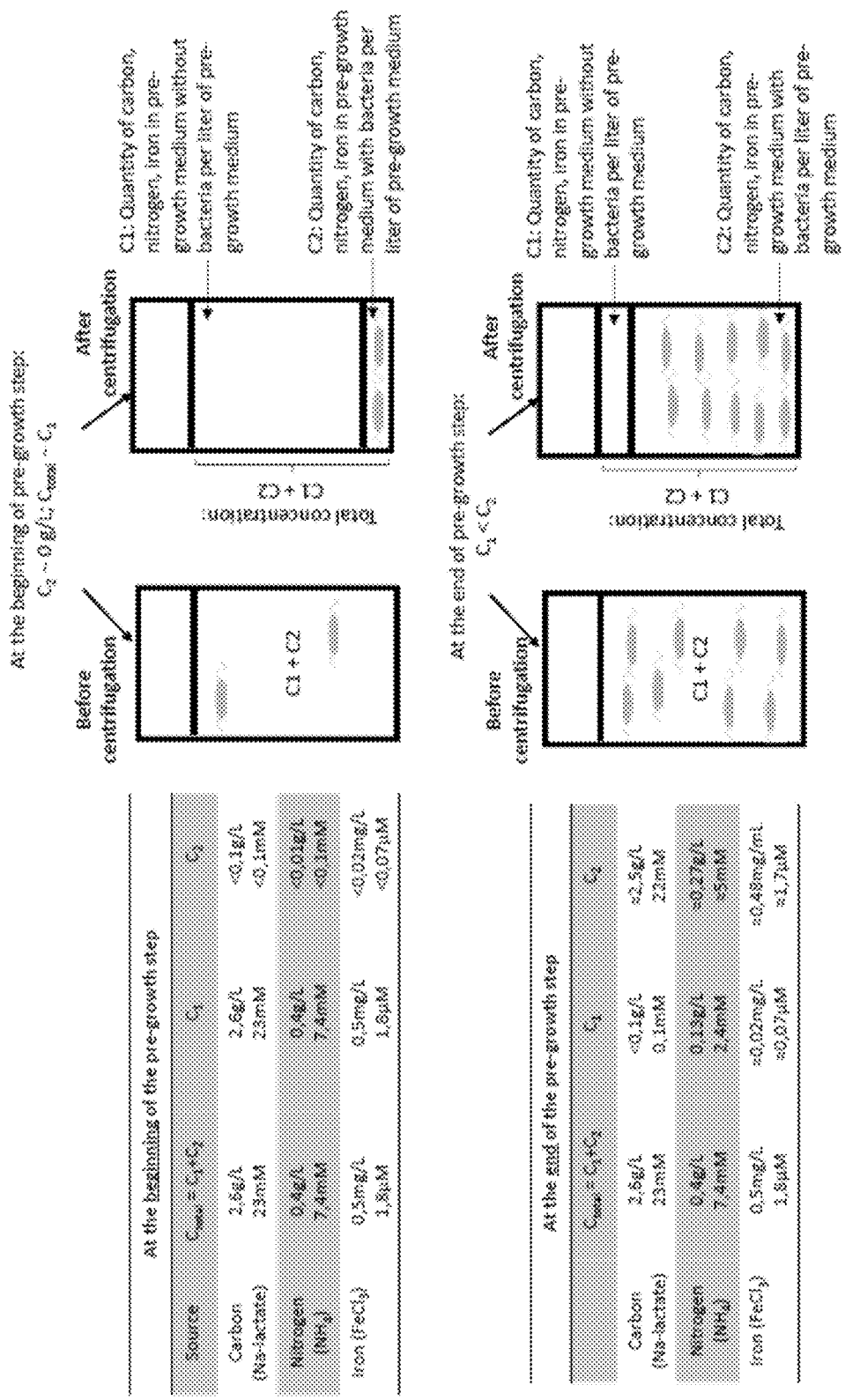
FIG. 4: Concentrations $C_1$ and $C_2$ of the carbon source, nitrogen source and iron source at the beginning and end of pre-growth step.
Figure 5:
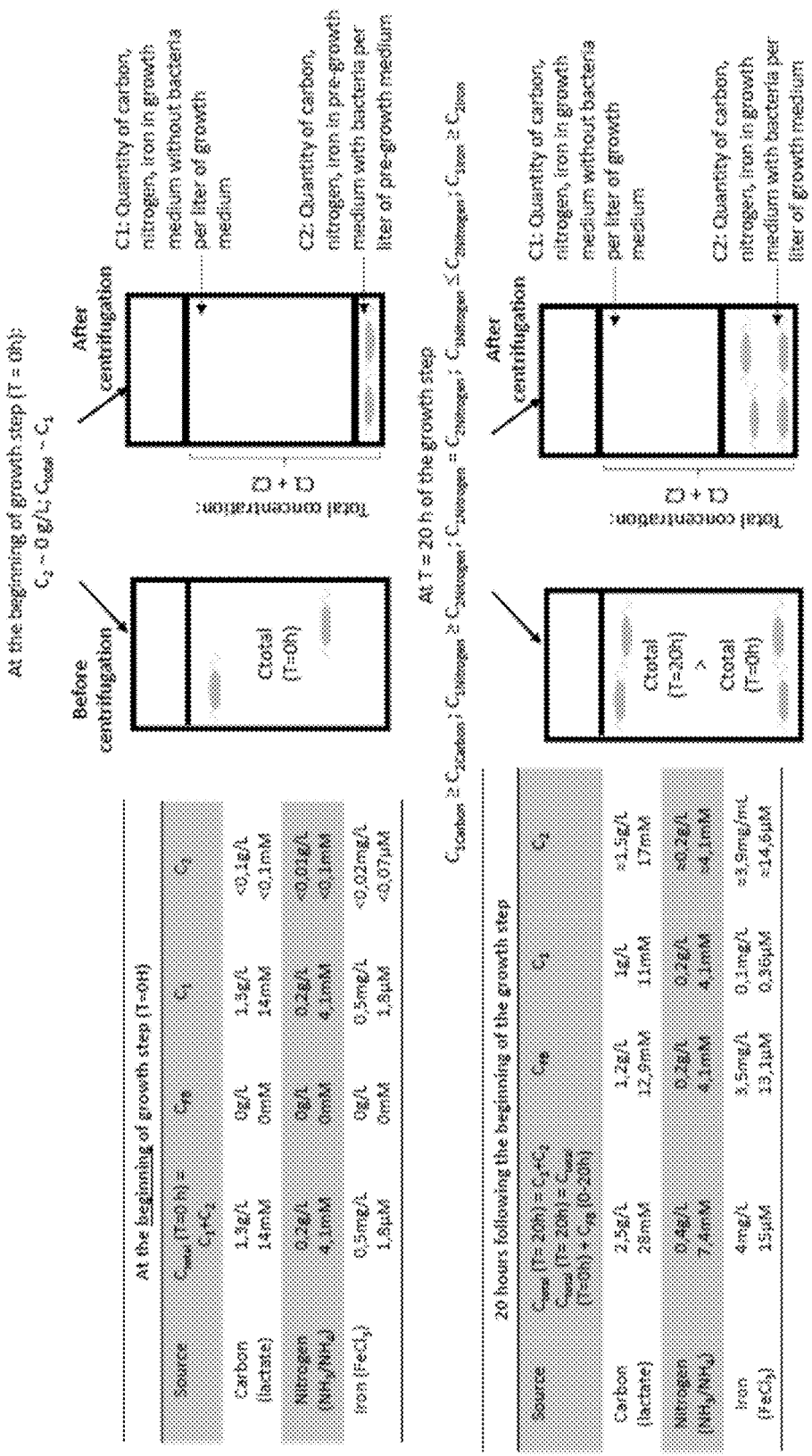
FIGS. 5 and 6: Concentrations $C_1$ and $C_2$ of the carbon source, nitrogen source and iron source at the beginning, 20 hours following the beginning, 40 hours following the beginning and more than 40 hours following the beginning of the growth step.
Figure 6:
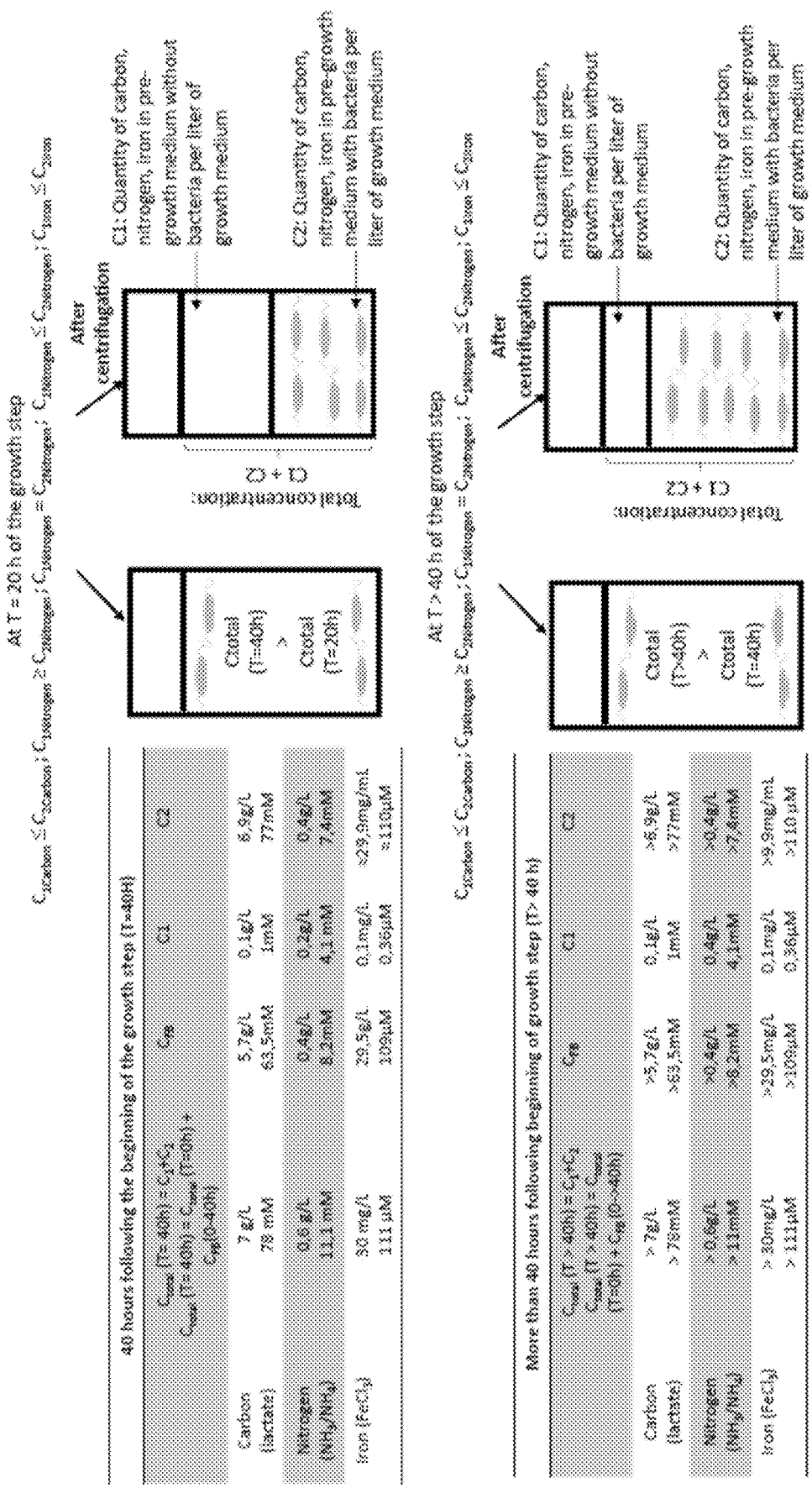

FIG. 2(a) shows the variation of the percentage in weight of a sample comprising 3 mg of lyophilized magnetosomes (Sample 3), prepared according to condition 3 as a function of the sample temperature, when the temperature of the sample is increased from 20° C. to 600° C. at a rate of 6° C. per minute, as well as the first derivative of this percentage. These measurements have been carried out with a TGA-DSC apparatus. CHNS measurements of lyophilized magnetosomes prepared according to condition 3 have shown that they contain a percentage of carbon of 4%, before being heated, which is lower than the percentage of carbon in magnetosomes prepared according to condition 2. The percentage in weight of the sample comprising magnetosomes (Sample 3) decreases from 100% at 20° C. down to 95.1% at 600° C., indicating that sample 3 comprising magnetosomes prepared according to condition 3 loses less weight, i.e. 4.9%, than sample 2 comprising magnetosomes prepared according to condition 2. More specifically, it appears in FIG. 2(a) that the slope of the variation of the percentage of weight as a function of temperature is the largest within the temperature range of 200 to 400° C. Between 200 and 400° C., the variation as a function of temperature of the slope of the percentage of weight as a function of temperature displays a quadruple peak whose maximum are at 264° C., 286° C., 325, and 331° C. The two peaks at 264° C. and 325° C. can be associated to peak shoulders. This quadruple peak could be due to the loss by the nanoparticles of organic material, preferentially of type 1, for the peak centered at 264° C., of organic material, preferentially of type 3, for the peak centered at 286° C., of organic material, preferentially of type 2 for the peak centered at 325° C., and of organic material, preferentially of type 4, for the peak centered at 331° C., where this organic material likely comes from some organic material surrounding or at the surface of the mineral iron oxide core of the magnetosomes. FIG. 2(b) shows the heat flow in milliwatt of a sample comprising 3 mg of lyophilized magnetosomes, prepared according to condition 3 (Sample 3), as a function of the sample temperature, when the temperature of the sample is increased from 20° C. to 600° C. at a rate of 6° C. per minute. These measurements have been carried out with out with a TGA-DSC apparatus. FIG. 2(b) shows four peaks with maximum heat flow observed at temperatures of 277° C., 335° C., 455° C. and 522° C. The peaks centered at 277° C. and 335° C. could be attributed to the combustion of the mass of nanoparticles that has been lost between 200 and 400° C. The peaks at 455 and 522° C. could be attributed to the combustion of the mass of nanoparticles that has been lost above 500° C. and/or to the oxidation of the magnetosomes from an iron oxide composition of magnetite, maghemite, or an intermediate composition between magnetite and maghemite into hematite, that could result in heat flow possibly caused by an exothermic reaction.

FIG. 2(c) shows the variation of the percentage in weight of a sample comprising 3 mg of powder of SIGMA nanoparticles, purchased from Merck Sigma, as a function of the sample temperature, when the temperature of the sample is increased from 20° C. to 600° C. at a rate of 6° C. per minute, as well as the first derivative of this percentage. These measurements have been carried out with a TGA-DSC apparatus. CHNS measurements of lyophilized SIGMA nanoparticles have shown that they contain a percentage of carbon of 0.3%, before being heated, which is lower than the percentage of carbon in magnetosomes prepared according to condition 3 (Sample 3). The percentage in weight of the sample comprising SIGMA nanoparticles decreases from 100% at 20° C. down to 98.7% at 600°

C., indicating that the sample comprising SIGMA nanoparticles loses less mass, i.e. 1.3%, than the magnetosomes prepared according to conditions 2 and 3. More specifically, it appears in FIG. 2(c) that the slope of the variation of the percentage in weight of SIGMA nanoparticles as a function of temperature is the largest within the temperature range of 200 to 400° C. Between 200 and 400° C., the variation as a function of temperature of the slope of the percentage of weight of SIGMA nanoparticles as a function of temperature displays a peak whose maximum is at 296° C. This peak could be due to the loss by the nanoparticles of organic material, preferentially of type 5, where this organic material could come from organic material adsorbed at the surface or comprised in or at the surface of the SIGMA nanoparticles. FIG. 2(d) shows the heat flow in milliwatt of a sample comprising 3 mg of powder of SIGMA nanoparticles as a function of the sample temperature, when the temperature of the sample is increased from 20° C. to 600° C. at a rate of 6° C. per minute. These measurements have been carried out with a TGA-DSC apparatus. FIG. 2(d) shows two peaks with maximum heat flow observed at temperatures of 200° C., and 515° C. The peak centered at 200° C. could be attributed to the combustion of the mass of nanoparticles that has been lost between 200 and 400° C. The peak centered at 515° C. could be attributed to the combustion of the mass of nanoparticles that has been lost above 500° C. and/or to the oxidation of the magnetosomes from an iron oxide composition of magnetite, maghemite, or an intermediate composition between magnetite and maghemite into hematite, that could result in heat flow possibly caused by an exothermic reaction resulting from the oxidation.

Determination of the different types of impurities, preferentially organic material, that can be removed, released, or dissociated from the nanoparticles: Each temperature corresponding or leading to the maximum value of the derivative of the variation of the percentage in weight of magnetosomes or Sigma nanoparticles as a function of temperature could be associated to a certain type of organic material that is removed from the nanoparticles. Hence, by knowing the values of these temperatures, it is possible to compare between different samples the type of organic material that can be removed from nanoparticles.

Determination of the temperatures at which the magnetosomes were heated in the furnace: In the different samples studied (whole magnetotactic bacteria, FIG. 1(a), chains of magnetosomes extracted from magnetotactic bacteria, FIG. 1(c), extracted and heated magnetosomes, FIG. 2(a)), the majority of organic material is removed or released from the magnetosomes extracted from magnetotactic bacteria between 200 and 400° C., i.e. the weight variation (%) and the derivative of the variation in weight (%/° C.) are the largest within this temperature range. We have therefore chosen to heat the magnetosomes extracted from magnetotactic bacteria at different temperatures comprised between 200 and 400° C.

Determination of the lysis method that leads to the lowest quantity of carbon in the magnetosomes: The magnetosomes extracted from magnetotactic bacteria with KOH have a lower quantity of carbon than the magnetosome extracted from magnetotactic bacteria with NaOH (7.1% with KaOH, Sample 2, compared with 14% with NaOH, Sample 1). The magnetosomes extracted from magnetotactic bacteria with KOH and heated at 200° C. for 30 min, 300° C. for 1 hour, and 380° C. for 1 hour have a lower percentage of carbon than the magnetosomes extracted from magnetotactic bacteria with NaOH and heated at 200° C. for 30 min, 300° C. for 1 hour, and 380° C. for 1 hour (0.3% with KOH, Sample 8, compared with 1% with NaOH, Sample 9). The magnetosomes extracted from magnetotactic bacteria with KOH and heated at 200° C. for 1 hour, 300° C. for 2 hours, and 380° C. for 2 hours have a lower percentage of carbon than the magnetosomes extracted from magnetotactic bacteria with NaOH and heated at 200° C. for 1 hour, 300° C. for 2 hours, and 380° C. for 2 hours (0.23% with KOH, Sample 10, compared with 0.8% with NaOH). This indicates that KOH is the best lysis method to yield a low percentage of carbon in the magnetosomes and therefore to have a high level of purification.

The magnetosomes extracted from magnetotactic bacteria with NaOH and then purified by a chemical method using phenol and chloroform possess a percentage in carbon, which is larger than that of the magnetosomes extracted from magnetoatctic bacteria with NaOH and heated at 200° C. during 30 minutes, 300° C. during 1 hour and 380° C. during 1 hour (1% of carbon with sample 9 compared with 5% of carbon with sample 3).

Determination of the heating temperature that leads to the lowest quantity of carbon in the magnetosomes: Considering the magnetosomes lysed with KOH, heating them at 400° C. during 1 hour leads to a lower quantity of carbon than heating them at 200° C. during 1 hour (3% of carbon at 400° C., Sample 5, compared with 5% of carbon at 200° C., Sample 4), indicating that increasing the heating temperature enables to remove more carbon.

Determination of the number of heating steps that leads to the lowest quantity of carbon in the magnetosomes: Considering the magnetosomes lysed with KOH, heating them at two different temperatures of 200 and 300° C. (Sample 6) or three different temperatures of 200° C., 300° C., and 380° C. (Sample 8), enables to remove more carbon than heating them at only one temperature (0.65% of carbon remains in the magnetosomes when they are heated at 200° C. and 300° C., Sample 6, and 0.3% of carbon remains in the magnetosomes when they are heated at 200, 300, and 380° C., Sample 8). This suggests that in order to reach a low level of carbon in the magnetosomes, magnetosomes can be heated at more than two different temperatures comprised between 200° C. and 380° C., such as 200° C., 300° C., and 380° C.

Determination of the heating time that leads to the lowest quantity of carbon in the magnetosomes: Considering the magnetosomes lysed with KOH and heated at 200° C., 300° C., and 380° C., increasing the heating time at 200° C. from 30 min to 1 hour and increasing the heating time at 300° C. and 380° C. from 1 hour to 2 hours slightly decreases the percentage of carbon that remains in the magnetosomes after heat treatment (0.23% for Sample 10 compared with 0.3% for Sample 8).

In conclusion, we have developed a method for heating nanoparticles, called magnetosomes, which are produced by specific cells called magnetotactic bacteria, which enables to reach a very low percentage in carbon, similar to that found in chemically synthesized nanoparticles, which are not synthesized by cells.

Tables:

Table 1: Compositions in one liter of water of the pre-growth and growth media used to grow MSR-1 magnetotactic bacteria in 50 milliliter tubes following condition 1. In this condition, 13 different pre-growth media and 13 different growth media were prepared using 13 different mineral elixirs (VO, CB1, V2, CB2, CB3, CB4, CB5, CB7, CB9, CB10, CB11, CB12, CB13), whose composition in one liter of deionized water is given in table 6.

Table 2: Compositions in one liter of water of the pre-growth and growth media used to grow MSR-1 magnetotactic bacteria in 50 milliliter tubes following condition 2. In this condition, 4 different pre-growth media and 4 different growth media were prepared using 4 different yeast extracts (YE, YNBWAA, YNBWoAA, YNBWoAA.AS), whose composition in one liter of deionized water is given in table 7.

Table 3: Compositions in one liter of water of the pre-growth and growth media used to grow MSR-1 magnetotactic bacteria in 50 milliliter tubes following condition 3. In this condition, 5 different pre-growth media and 5 different growth media were prepared using 5 different vitamin cocktails (Vit1X, Vit5X, Vit10X, Vit0.5X, Vit0.1X), whose composition in one liter of deionized water is given in table 8.

Table 4: Compositions in one liter of water of the pre-growth and growth media used to grow MSR-1 magnetotactic bacteria in 50 milliliter tubes following condition 4. In this condition, 9 different pre-growth media and 9 different growth media were prepared using 9 different individual vitamins (Bt, CP, FA, I, NA, AA, P, R, T), whose composition in one liter of deionized water is given in table 9.

Table 5: Compositions in one liter of water of the pre-growth and growth media used to grow MSR-1 magnetotactic bacteria in 50 milliliter tubes following condition 5. In this condition, 4 different concentrations of sodium lactate (SL0, SL0.5X, SL0.2X, SL0.1X), ammonium chloride (A0, A0.5X, A0.2X, A0.1X), Magnesium sulfate heptahydrate (MG0, MG0.5X, MG0.2X, MG0.1X), Potassium phosphate dibasic (P0, P0.5X, P0.2X, P0.1X) were tested.

Table 6: Compositions in one liter of water of the different mineral elixirs (V0, CB1, V2, CB2, CB3, CB4, CB5, CB7, CB9, CB10, CB11, CB12, CB13).

Table 7: Composition in one liter of water of the different yeast extracts (YE, YNBWAA, YNBWoAA, YNBWoAA.AS).

Table 8: Compositions in one liter of water of the different vitamin cocktails (Vit1X, Vit5X, Vit10X, Vit0.5X, Vit0.1X).

Table 9: Compositions in one liter of water of the different individual vitamins (Biotin Bt, Calcium pantothenate CP, Folic acid FA, Inositol I, Nicotinic acid NA, p-Aminobenzoic acid AA, Pyridoxine HCl P, Riboflavin R, Thiamine HCl T).

Table 10: For condition 1, optical density measured at the end of the pre-growth step, 6 days following the beginning of growth, $OD_{D6}$, or 13 days following the beginning of growth, $OD_{D13}$, ratio $OD_{D13}/OD_{D6}$, and percentage of magnetic response.

Table 11: For conditions 2 and 3, optical density measured at the end of the pre-growth step, 6 days following the beginning of growth, $OD_{D6}$, or 13 days following the beginning of growth, $OD_{D13}$, ratio $OD_{D13}/OD_{D6}$, and percentage of magnetic response.

Table 12: For condition 4, optical density measured at the end of the pre-growth step, 6 days following the beginning of growth, $OD_{D6}$, or 13 days following the beginning of growth, $OD_{D13}$, ratio $OD_{D13}/OD_{D6}$, and percentage of magnetic response.

Table 13: For condition 5, optical density measured at the end of the pre-growth step, 6 days following the beginning of growth, $OD_{D6}$, or 13 days following the beginning of growth, $OD_{D13}$, ratio $OD_{D13}/OD_{D6}$, and percentage of magnetic response.

Table 14(a): For condition 6 of growth of MSR-1 magnetotactic bacteria in one liter fermenter, compositions of pre-growth medium, growth medium, and fed-batch medium for B1 and B4, prepared using non-pharmaceutical grade chemicals.

Table 14(b): For condition 6 of growth of MSR-1 magnetotactic bacteria in one liter fermenter, compositions of pre-growth medium, growth medium, and fed-batch medium for B2 and B3, prepared using pharmaceutical grade chemicals.

Table 15: For condition 6, optical density and number of cells per mL measured at the beginning of the pre-growth step (D0) for bacteria inserted in a volume of 250 mL pre-growth media, at the end of the pre-growth step (D9) for bacteria grown in 1.5 liter pre-growth media, at the beginning of the growth step (D9) when bacteria are grown in 800 mL growth media, at D9 of the growth step, at D11 of the growth step. Ratio between the optical density of the bacteria measured at D11 and the optical density of the bacteria measured at D9. Percentage of magnetic response measured at D11.

Table 16: For magnetosomes produced under condition 6, extracted from magnetotactic bacteria and purified to remove more than 99% of carbonaceous material, concentration of impurities (Ag, Al, As, Ba, Cd, Co, Cr, Cu, Mn, Mo, Ni, Pb, Sb, Se, Si, Sn, $T_i$, W, Zn) in µg of impurities per gram of magnetosome, for media B1, B2, B3, and B4.

Table 17: For the fermenters B1, B2, B3, B4, the iron concentrations comprised in: i), the pre-growth medium at D0 (day 0), D8, D9, ii), the growth medium 0 h after the start of the growth step at D9, 6 h after the start of the growth step at D9, 12 h after the start of the growth step at D9, 24 h after the start of the growth step at D10, 48 h after the start of the growth step at D11, iii) volume of fed-batch medium introduced in the growth medium 0 h after the start of the growth step at D9, 6 h after the start of the growth step at D9, 12 h after the start of the growth step at D9, 24 h after the start of the growth step at D9, 48 h after the start of the growth step at D11.

Table 18: Conditions of treatments for the different samples (Sample 0 to sample 11), including the condition of lysis (using NaOH, KOH, or NaOH+Phenol and chloroform), the initial temperature before heating the sample ($T_i$), the temperature $T_1$, the rate $r_{i1}$ at which the temperature is increased from $T_i$ to $T_1$, the time $t_1$ during which the temperature is maintained at $T_1$, the temperature $T_2$, the rate $r_{12}$ at which the temperature is increased from $T_1$ to $T_2$, the rate $r_{i2}$ at which the temperature is increased from $T_i$ to $T_2$, the time $t_2$ during which the temperature is maintained at $T_2$, the temperature $T_3$, the rate $r_{13}$ at which the temperature is increased from $T_1$ to $T_3$, the rate $r_{32}$ at which the temperature is increased from $T_3$ to $T_2$, the time $t_3$ during which the temperature is maintained at $t_3$, the temperature $T_4$, the rate $r_{34}$ at which the temperature is increased from $T_3$ to $T_4$, the time $t_4$ during which the temperature is maintained at $T_4$, the final temperature $T_f$, the rate $r_{1f}$ at which the temperature is decreased from $T_1$ to $T_f$, the rate $r_{2f}$ at which the temperature is decreased from $T_2$ to $T_f$, the rate $r_{3f}$ at which the temperature is decreased from $T_3$ to $T_f$, the rate $r_{4f}$ at which the temperature is decreased from $T_4$ to $T_f$.

Table 19: For the different samples (Sample 3 to Sample 11), the percentages in mass of carbon (% C) and nitrogen (% N) after the treatment of the nanoparticles by conditions 3 to 11, the percentages in mass of carbon and (% Ci) and nitrogen (% Ni) for the magnetosomes extracted from magnetotactic bacteria following condition 1 or 2 before heat treatment (samples 4 to 11) or before treatment with phenol-chloroform (sample 3). Values of 4% C=% Ci−% C, 4% N=% Ni−% N, (100 Δ % C)/% Ci, (100·Δ % N)/Δ % Ni.

Condition 1: 13 Different Mineral Elixirs Tested

MSR-1 Magnetotactic Bacteria Grown in 50 mL Tubes

TABLE 1

|  | Name of chemicals | Chemical formula | Quantity | Concentration |
|---|---|---|---|---|
| Pregrowth medium | Sodium lactate | $C_3H_5NaO_3$ | 2.6 g | $2.30.10^{-2}$M |
|  | Ammonium chloride | $NH_4Cl$ | 0.4 g | $7.41.10^{-3}$M |
|  | Magnesium sulfate heptahydrate | $MgSO_4 \cdot 7H_2O$ | 0.1 g | $4.06.10^{-4}$M |
|  | Potassium phosphate dibasic | $K_2HPO_4$ | 0.5 g | $2.87.10^{-3}$M |
|  | Yeast extract (Table 7, YE) | / | 0.1 g | / |
|  | Mineral elixir: V0, CB1, V2, CB2, CB3, CB4, CB5, CB7, CB9, CB10, CB11, CB12, or CB13, Table 6 | / | 0.5 mL | / |
|  | Deionized water | $H_2O$ | 1 L | / |
| Growth medium | Sodium lactate | $C_3H_5NaO_4$ | 2.6 g | $2.30.10^{-2}$M |
|  | Ammonium chloride | $NH_4Cl$ | 0.4 g | $7.41.10^{-3}$M |
|  | Magnesium sulfate heptahydrate | $MgSO_4 \cdot 7H_2O$ | 0.1 g | $4.06.10^{-3}$M |
|  | Potassium phosphate dibasic | $K_2HPO_5$ | 0.5 g | $2.87.10^{-3}$M |
|  | Yeast extract (Table 7, YE) | / | 0.1 g | / |
|  | Mineral elixir: V0, CB1, V2, CB2, CB3, CB4, CB5, CB7, CB9, CB10, CB11, CB12, or CB13, Table 6 | / | 0.5 mL | / |
|  | Ferric citrate (20 mM) | $C_6H_5FeO_7$ | 10 mL | 200 μM |
|  | Deionized water | $H_2O$ | 1 L | / |

Condition 2: 4 Different Yeast Extracts Tested

MSR1 Magnetotactic Bacteria Grown in 50 mL Tubes

TABLE 2

|  | Name of chemicals | Chemical formula | Quantity | Concentration |
|---|---|---|---|---|
| Pregrowth medium | Sodium lactate | $C_3H_5NaO_3$ | 2.6 g | $2.30.10^{-2}$M |
|  | Ammonium chloride | $NH_4Cl$ | 0.4 g | $7.41.10^{-3}$M |
|  | Magnesium sulfate heptahydrate | $MgSO_4 \cdot 7H_2O$ | 0.1 g | $4.06.10^{-4}$M |
|  | Potassium phosphate dibasic | $K_2HPO_4$ | 0.5 g | $2.87.10^{-3}$M |
|  | Yeast extract: YE, YNBWAA, YNBWoAA, YNBWoAA.AS Table 7 | / | 0.1 g | / |
|  | Mineral elixir CB3 (Table 6) | / | 0.5 mL | $[FeO_4S \cdot 7H_2O] = 1.8.10^{-6}$M $[CaCl_2] = 1.4.10^{-3}$M |
|  | Deionized water | $H_2O$ | 1 L | / |
| Growth medium | Sodium lactate | $C_3H_5NaO_4$ | 2.6 g | $2.30.10^{-2}$M |
|  | Ammonium chloride | $NH_4Cl$ | 0.4 g | $7.41.10^{-3}$M |
|  | Magnesium sulfate heptahydrate | $MgSO_4 \cdot 7H_2O$ | 0.1 g | $4.06.10^{-4}$M |
|  | Potassium phosphate dibasic | $K_2HPO_5$ | 0.5 g | $2.87.10^{-3}$M |
|  | Yeast extract: YE, YNBWAA, YNBWoAA, YNBWoAA.AS Table 7 | / | 0.1 g | / |
|  | Mineral elixir CB3 (Table 6) | / | 0.5 mL | $[FeO_4S \cdot 7H_2O] = 1.8.10^{-6}$M $[CaCl_2] = 1.4.10^{-4}$M |
|  | Ferric citrate (20 mM) | $C_6H_5FeO_7$ | 10 mL | 200 μM |
|  | Deionized water | $H_2O$ | 1 L | / |

Condition 3: 7 Different Vitamin Cocktails Tested

MSR-1 Magnetotactic Bacteria Grown in 50 mL Tubes

TABLE 3

|  | Name of chemicals | Chemical formula | Quantity | Concentration |
|---|---|---|---|---|
| Pregrowth medium | Sodium lactate | $C_3H_5NaO_3$ | 2.6 g | $2.30.10^{-2}$M |
|  | Ammonium chloride | $NH_4Cl$ | 0.4 g | $7.41.10^{-3}$M |
|  | Magnesium sulfate heptahydrate | $MgSO_4 \cdot 7H_2O$ | 0.1 g | $4.06.10^{-4}$M |
|  | Potassium phosphate dibasic | $K_2HPO_4$ | 0.5 g | $2.87.10^{-3}$M |
|  | Vitamins coktail: Vit1X, Vit5X, Vit10X, Vit5X, Vit0.5X, or Vit0.1X Table 8 | / | 0.1 mL | $8.2.10^{-11}$M < [Vit] < $1.1.10^{-5}$M |

TABLE 3-continued

|   | Name of chemicals | Chemical formula | Quantity | Concentration |
|---|---|---|---|---|
|   | Mineral elixir CB3 (Table 6) | / | 0.5 mL | $[FeO_4S \cdot 7H_2O] = 1.8 \cdot 10^{-5}M$ $[CaCl_2] = 1.4 \cdot 10^{-3}M$ |
|   | Deionized water | $H_2O$ | 1 L | / |
| Growth medium | Sodium lactate | $C_3H_5NaO_4$ | 2.6 g | $2.30 \cdot 10^{-2}M$ |
|   | Ammonium chloride | $NH_4Cl$ | 0.4 g | $7.41 \cdot 10^{-3}M$ |
|   | Magnesium sulfate heptahydrate | $MgSO_4 \cdot 7H_2O$ | 0.1 g | $4.06 \cdot 10^{-4}M$ |
|   | Potassium phosphate dibasic | $K_2HPO_5$ | 0.5 g | $2.87 \cdot 10^{-3}M$ |
|   | Vitamins coktail: Vit1X, Vit5X, Vit10X, Vit5X, Vit0.5X, or Vit0.1X Table 8 | / | 0.1 mL | $8.2 \cdot 10^{-11}M < [Vit] < 1.1 \cdot 10^{-5}M$ |
|   | Mineral elixir CB3 (Table 6) | / | 0.5 mL | $[FeO_4S \cdot 7H_2O] = 1.8 \cdot 10^{-6}M$ $[CaCl_2] = 1.4 \cdot 10^{-4}M$ |
|   | Ferric citrate (20 mM) | $C_6H_5FeO_7$ | 10 mL | 200 µM |
|   | Deionized water | $H_2O$ | 1 L | / |

Condition 4: 9 Different Individual Vitamins Tested

MSR-1 Magnetotactic Bacteria Grown in 50 mL Tubes

TABLE 4

|   | Name of chemicals | Chemical formula | Quantity | Concentration |
|---|---|---|---|---|
| Pregrowth medium | Sodium lactate | $C_3H_5NaO_3$ | 2.6 g | $2.30 \cdot 10^{-2}M$ |
|   | Ammonium chloride | $NH_4Cl$ | 0.4 g | $7.41 \cdot 10^{-3}M$ |
|   | Magnesium sulfate heptahydrate | $MgSO_4 \cdot 7H_2O$ | 0.1 g | $4.06 \cdot 10^{-4}M$ |
|   | Potassium phosphate dibasic | $K_2HPO_4$ | 0.5 g | $2.87 \cdot 10^{-3}M$ |
|   | Individual vitamins: Bt, CP, FA, I, NA, AA, P, R, or T Table 9 | / | 0.1 mL | $8.2 \cdot 10^{-10}M < [Vit] < 1.1 \cdot 10^{-6}M$ |
|   | Mineral elixir CB3 (Table 6) | / | 0.5 mL | $[FeO_4S \cdot 7H_2O] = 1.8 \cdot 10^{-6}M$ $[CaCl_2] = 1.4 \cdot 10^{-4}M$ |
|   | Deionized water | $H_2O$ | 1 L | / |
| Growth medium | Sodium lactate | $C_3H_5NaO_4$ | 2.6 g | $2.30 \cdot 10^{-2}M$ |
|   | Ammonium chloride | $NH_4Cl$ | 0.4 g | $7.41 \cdot 10^{-3}M$ |
|   | Magnesium sulfate heptahydrate | $MgSO_4 \cdot 7H_2O$ | 0.1 g | $4.06 \cdot 10^{-4}M$ |
|   | Potassium phosphate dibasic | $K_2HPO_5$ | 0.5 g | $2.87 \cdot 10^{-3}M$ |
|   | Individual vitamins: Bt, CP, FA, I, NA, AA, P, R, or T Table 9 | / | 0.1 mL | $8.2 \cdot 10^{-10}M < [Vit] < 1.1 \cdot 10^{-6}M$ |
|   | Mineral elixir CB3 (Table 6) | / | 0.5 mL | $[FeO_4S \cdot 7H_2O] = 1.8 \cdot 10^{-6}M$ $[CaCl_2] = 1.4 \cdot 10^{-4}M$ |
|   | Ferric citrate (20 mM) | $C_6H_5FeO_7$ | 10 mL | 200 µM |
|   | Deionized water | $H_2O$ | 1 L | / |

Condition 5: Test of 4 Different Concentrations of the Main Constituents of the Growth Media MSR-1 Magnetotactic Bacteria Grown in 50 mL Tubes

TABLE 5

|   | Name of Chemicals | Chemical formula | N | SL0 | SL0.5X | SL0.2X | SL0.1X | AC0 | AC0.5X | AC0.2X | AC0.1X |
|---|---|---|---|---|---|---|---|---|---|---|---|
| Pregrowth medium | Sodium lactate | $C_3H_5NaO_3$ | 2.6 g | 0 g | 1.3 g | 0.52 g | 0.26 g | 2.6 g | 2.6 g | 2.6 g | 2.6 g |
|   | Ammonium chloride | $NH_4Cl$ | 0.4 g | 0.4 g | 0.4 g | 0.4 g | 0.4 g | 0 g | 0.2 g | 0.08 g | 0.04 g |
|   | Magnesium sulfate heptahydrate | $MgSO_4 \cdot 7H_2O$ | 0.1 g | 0.1 g | 0.1 g | 0.1 g | 0.1 g | 0.1 g | 0.1 g | 0.1 g | 0.1 g |
|   | Potassium phosphate dibasic | $K_2HPO_4$ | 0.5 g | 0.5 g | 0.5 g | 0.5 g | 0.5 g | 0.5 g | 0.5 g | 0.5 g | 0.5 g |
|   | Mineral elixir CB3 (Table 6) | / | 0.5 ml | 0.5 ml | 0.5 ml | 0.5 ml | 0.5 ml | 0.5 ml | 0.5 ml | 0.5 ml | 0.5 ml |
|   | Vitamins cocktail Vit0.1X (Table 8) | / | 0.1 ml | 0.1 ml | 0.1 ml | 0.1 ml | 0.1 ml | 0.1 ml | 0.1 ml | 0.1 ml | 0.1 ml |
|   | Deionized water | $H_2O$ | 1 l | 1 l | 1 l | 1 l | 1 l | 1 l | 1 l | 1 l | 1 l |
| Growth medium | Sodium lactate | $C_3H_5NaO_3$ | 2.6 g | 0 g | 1.3 g | 0.52 g | 0.26 g | 0.26 g | 2.6 g | 2.6 g | 2.6 g |
|   | Ammonium chloride | $NH_4Cl$ | 0.4 g | 0.4 g | 0.4 g | 0.4 g | 0.4 g | 0 g | 0.2 g | 0.08 g | 0.04 g |
|   | Magnesium sulfate heptahydrate | $MgSO_4 \cdot 7H_2O$ | 0.1 g | 0.1 g | 0.1 g | 0.1 g | 0.1 g | 0.1 g | 0.1 g | 0.1 g | 0.1 g |

TABLE 5-continued

|  |  |  |  |  |  |  |  |  |  |
|---|---|---|---|---|---|---|---|---|---|
|  | Potassium phosphate dibasic | $K_2HPO_4$ | 0.5 g | 0.5 g | 0.5 g | 0.5 g | 0.5 g | 0.5 g | 0.5 g | 0.5 g |
|  | Mineral elixir CB3 (Table 6) | / | 0.5 ml | 0.5 ml | 0.5 ml | 0.5 ml | 0.5 ml | 0.5 ml | 0.5 ml | 0.5 ml |
|  | Vitamins cocktail Vit0.1X (Table 8) | / | 0.1 ml | 0.1 ml | 0.1 ml | 0.1 ml | 0.1 ml | 0.1 ml | 0.1 ml | 0.1 ml |
|  | Ferric citrate (20 mM) | $C_6H_5FeO_7$ | 10 ml | 10 ml | 10 ml | 10 ml | 10 ml | 10 ml | 10 ml | 10 ml |
|  | Deionized water | $H_2O$ | 1 l | 1 l | 1 l | 1 l | 1 l | 1 l | 1 l | 1 l |

|  | Name of Chemicals | MG0 | MG0.5X | MG0.2X | MG0.1X | P0 | P0.5X | P0.2X | P0.1X |
|---|---|---|---|---|---|---|---|---|---|
| Pregrowth medium | Sodium lactate | 2.6 g | 2.6 g | 2.6 g | 2.6 g | 2.6 g | 2.6 g | 2.6 g | 2.6 g |
|  | Ammonium chloride | 0.04 g | 0.04 g | 0.04 g | 0.04 g | 0.04 g | 0.04 g | 0.04 g | 0.04 g |
|  | Magnesium sulfate heptahydrate | 0 g | 0.05 g | 0.02 g | 0.01 g | 0.01 g | 0.01 g | 0.01 g | 0.01 g |
|  | Potassium phosphate dibasic | 0.5 g | 0.5 g | 0.5 g | 0.5 g | 0 g | 0.25 g | 0.1 g | 0.05 g |
|  | Mineral elixir CB3 (Table 6) | 0.5 ml | 0.5 ml | 0.5 ml | 0.5 ml | 0.5 ml | 0.5 ml | 0.5 ml | 0.5 ml |
|  | Vitamins cocktail Vit0.1X (Table 8) | 0.1 ml | 0.1 ml | 0.1 ml | 0.1 ml | 0.1 ml | 0.1 ml | 0.1 ml | 0.1 ml |
|  | Deionized water | 1 l | 1 l | 1 l | 1 l | 1 l | 1 l | 1 l | 1 l |
| Growth medium | Sodium lactate | 2.6 g | 2.6 g | 2.6 g | 2.6 g | 2.6 g | 2.6 g | 2.6 g |  |
|  | Ammonium chloride | 0.04 g | 0.04 g | 0.04 g | 0.04 g | 0.04 g | 0.04 g | 0.04 g | 0.04 g |
|  | Magnesium sulfate heptahydrate | 0 g | 0.05 g | 0.02 g | 0.01 g | 0.01 g | 0.01 g | 0.01 g | 0.01 g |
|  | Potassium phosphate dibasic | 0.5 g | 0.5 g | 0.5 g | 0.5 g | 0 g | 0.25 g | 0.1 g | 0.05 g |
|  | Mineral elixir CB3 (Table 6) | 0.5 ml | 0.5 ml | 0.5 ml | 0.5 ml | 0.5 ml | 0.5 ml | 0.5 ml | 0.5 ml |
|  | Vitamins cocktail Vit0.1X (Table 8) | 0.1 ml | 0.1 ml | 0.1 ml | 0.1 ml | 0.1 ml | 0.1 ml | 0.1 ml | 0.1 ml |
|  | Ferric citrate (20 mM) | 10 ml | 10 ml | 10 ml | 10 ml | 10 ml | 10 ml | 10 ml | 10 ml |
|  | Deionized water | 1 l | 1 l | 1 l | 1 l | 1 l | 1 l | 1 l | 1 l | l: liter;
ml: milliliter

Compositions of the Different Tested Mineral Elixirs

TABLE 6

| Name of Chemicals | Chemical formula | V0 | CB1 | V2 | CB2 | CB3 |
|---|---|---|---|---|---|---|
| Nitrilotriacetic acid trisodium salt | $C_6H_5NO_6Na_3$ | 15 g | 0 g | 15 g | 0 g | 0 g |
| Magnesium sulfate heptahydrate | $MgSO_4 \cdot 7H_2O$ | 3 g | 0 g | 3 g | 3 g | 0 g |
| Manganese (II) sulfate monohydrate | $MnO_4S \cdot H_2O$ | 5 g | 0 g | 0.002 g | 0 g | 0 g |
| Sodium Chloride | NaCl | 10 g | 0 g | 10 g | 10 g | 0 g |
| Iron(II) sulfate heptahydrate | $FeO_4S \cdot 7H_2O$ | 1 g | 0 g | 1 g | 1 g | 1 g |
| Cobalt(II) nitrate hexahydrate | $CoN_2O_6 \cdot 6H_2O$ | 1.8 g | 0 g | 0.003 g | 0 g | 0 g |
| Calcium chloride | $CaCl_2$ | 30 g | 0 g | 30 g | 30 g | 30 g |
| Zinc sulfate heptahydrate | $O_4SZn \cdot 7H_2O$ | 1.8 g | 0 g | 0.003 g | 0 g | 0 g |
| Copper(II) sulfate pentahydrate | $CuO_4S \cdot 5H_2O$ | 0.1 g | 0 g | 0.002 g | 0 g | 0 g |
| Aluminum potassium sulfate dodecahydrate | $AlK(SO_4)_2 \cdot 12H_2O$ | 0.2 g | 0 g | 0.005 g | 0 g | 0 g |
| Boric acid | $H_3BO_3$ | 0.1 | 0 g | 0.1 | 0 g | 0 g |
| Sodium molybdate dihydrate | $Na_2MoO_4 \cdot 2H_2O$ | 0.1 g | 0 g | 0.1 g | 0 g | 0 g |
| Nickle(II) chloride hexahydrate | $Cl_2Ni \cdot 6H_2O$ | 0.25 g | 0 g | 0.002 g | 0 g | 0 g |
| Sodium selenite pentahydrate | $Na_2SeO_5 \cdot 5H_2O$ | 0.003 g | 0 g | 0.003 g | 0 g | 0 g |
| EDTA | $(HO_2CCH_2)_2NCH_2CH_2N(CH_2CO_2H)_2$ | 0 g | 0 g | 0 g | 0 g | 0 g |
| Iron(III) oxalate hexahydrate | $Fe_2(C_2O_4)_3 \cdot 6H_2O$ | 0 g | 0 g | 0 g | 0 g | 0 g |
| Protoporphyrin IX | $C_3H_3NaO_4$ | 0 g | 0 g | 0 g | 0 g | 0 g |
| Deionized water | $H_2O$ | 1 L | 1 L | 1 L | 1 L | 1 L |

| Name of Chemicals | CB4 | CB5 | CB7 | CB9 | CB10 | CB11 | CB12 | CB13 |
|---|---|---|---|---|---|---|---|---|
| Nitrilotriacetic acid trisodium salt | 0 g | 0 g | 15 g | $1.5 \cdot 10^{-6}$ g | 0 g | 0 g | 0 g | 0 g |

TABLE 6-continued

| | | | | | | | | |
|---|---|---|---|---|---|---|---|---|
| Magnesium sulfate heptahydrate | 3 g | 3 g | 3 g | $3 \cdot 10^{-6}$ g | 3 g | 3 g | 0 g | 0 g |
| Manganese (II) sulfate monohydrate | $2 \cdot 10^{-7}$ g | 0 g | 0 | $5 \cdot 10^{-8}$ g | 0 g | 0 g | 0 g | 0 g |
| Sodium Chloride | 10 g | 10 g | 10 g | $3 \cdot 10^{-5}$ g | 10 g | 10 g | 0 g | 0 g |
| Iron(II) sulfate heptahydrate | 1 g | 1 g | 1 g | $3 \cdot 10^{-5}$ g | 1 g | 1 g | 1 g | 1 g |
| Cobalt(II) nitrate hexahydrate | $3 \cdot 10^{-10}$ g | 0 g | 0 g | $10^{-6}$ g | 0 g | 0 g | 0 g | 0 g |
| Calcium chloride | 30 g | 30 g | 30 g | $2 \cdot 10^{-6}$ g | 30 g | 30 g | 15 g | 20 g |
| Zinc sulfate heptahydrate | 0.003 g | 0 g | 0 g | $2 \cdot 10^{-6}$ g | 0 g | 0 g | 0 g | 0 g |
| Copper(II) sulfate pentahydrate | 0.002 g | 0 g | 0 g | $10^{-7}$ g | 0 g | 0 g | 0 g | 0 g |
| Aluminum potassium sulfate dodecahydrate | 0.005 g | 0 g | 0 g | $2 \cdot 10^{-7}$ g | 0 g | 0 g | 0 g | 0 g |
| Boric acid | 0 g | 0 g | 0.1 g | $10^{-7}$ g | 0 g | 0 g | 0 g | 0 g |
| Sodium molybdate dihydrate | 0 g | 0 g | 0 g | $10^{-7}$ g | 0 g | 0 g | 0 g | 0 g |
| Nickle(II) chloride hexahydrate | 0 g | 0 g | 0 g | $2.5 \cdot 10^{-7}$ g | 0 g | 0 g | 0 g | 0 g |
| Sodium selenite pentahydrate | 0 g | 0 g | 0 g | $3 \cdot 10^{-9}$ g | 0 g | 0 g | 0 g | 0 g |
| EDTA | 0.4 g | 0.4 g | 0 g | 0 g | 0 g | 0 g | 0 g | 0 g |
| Iron(III) oxalate hexahydrate | 0 g | 1 g | 1 g | 0 g | 1 g | 0 g | 0 g | 0 g |
| Protoporphyrin IX | 0 g | 0 g | 0 g | 0 g | 0 g | 0.06 g | 0 g | 0 g |
| Deionized water | 1 L | 1 L | 1 L | 1 L | 1 L | 1 L | 1 L | 1 L |

Compositions of the Different Tested Yeast Extract

TABLE 7

| Chemical name | Chemical formula | YE | YNBWAA | YNBWoAA | YNBWoAA.AS |
|---|---|---|---|---|---|
| Yeast extract | / | 0.1 g | 0 g | 0 g | 0 g |
| Ammonium sulfate | $(NH_4)_2SO_4$ | 0 g | 5 g | 5 g | 0 g |
| L-histidine | $C_6H_9N_3O_2$ | 0 g | 0.01 g | 0 g | 0 g |
| DL-methionine | $CH_3SCH_2CH_2CH(NH_2)COOH$ | 0 g | 0.02 g | 0 g | 0 g |
| DL-tryptophan | $C_{11}H_{12}N_2O_2$ | 0 g | 0 g | 0 g | 0 g |
| Potassium phosphate monobasic | $KH_2PO_4$ | 0 g | 1 g | 1 g | 1 g |
| Magnesium sulfate | $MgSO_4$ | 0 g | 0.5 g | 0.5 g | 0.5 g |
| Sodium chloride | NaCl | 0 g | 0.1 g | 0.1 g | 0.1 g |
| Calcium chloride | $CaCl_2$ | 0 g | 0.1 g | 0.1 g | 0.1 g |
| Trace elements | $H^3BO^3$, $CuO_4S$, KI, $FeCl^3$, $Na^2MoO^4$, $O_4SZn$ | 0 g | $<4.10^{-4}$ g | $<4.10^{-4}$ g | $<4.10^{-4}$ g |
| Biotin | $C_{10}H_{16}N_2O_3S$ | 0 g | $2.10^{-6}$ g | $2.10^{-6}$ g | $2.10^{-6}$ g |
| Calcium pantothenate | $HOCH_2C(CH_3)_2CH(OH)CONHCH_2CH_2CO_2 \cdot 1/2Ca$ | 0 g | $4.10^{-4}$ g | $4.10^{-4}$ g | $4.10^{-4}$ g |
| Folic acid | $C_{19}H_{19}N_7O_6$ | 0 g | $2.10^{-6}$ g | $2.10^{-6}$ g | $2.10^{-6}$ g |
| Inositol | $C_6H_{12}O_6$ | 0 g | $2.10^{-3}$ g | $2.10^{-3}$ g | $2.10^{-3}$ g |
| Nicotinic acid | $C_6H_5NO_2$ | 0 g | $4.10^{-4}$ g | $4.10^{-4}$ g | $4.10^{-4}$ g |
| p-Aminobenzoic acid | $H_2NC_6H_4CO_2H$ | 0 g | $2.10^{-4}$ g | $2.10^{-4}$ g | $2.10^{-4}$ g |
| Pyridoxine HCl | $C_8H_{11}NO_3 \cdot HCl$ | 0 g | $4.10^{-4}$ g | $4.10^{-4}$ g | $4.10^{-4}$ g |
| Riboflavin | $C_{17}H_{20}N_4O_6$ | 0 g | $2.10^{-4}$ g | $2.10^{-4}$ g | $2.10^{-4}$ g |
| Thiamine HCL | $C_{12}H_{17}ClN_4OS \cdot HCl$ | 0 g | $4.10^{-4}$ g | $4.10^{-4}$ g | $4.10^{-4}$ g |
| Deionized water | $H_2O$ | 1 L | 1 L | 1 L | 1 L |

Compositions of the Different Vitamins Cocktails Tested

TABLE 8

| Chemical name | Chemical formula | Vit1X | Vit5X | Vit10X | Vit0.5X | Vit0.1X |
|---|---|---|---|---|---|---|
| Biotin | $C_{10}H_{16}N_2O_3S$ | $2 \cdot 10^{-6}$ g | $10^{-6}$ g | $2 \cdot 10^{-5}$ g | $10^{-6}$ g | $2 \cdot 10^{-7}$ g |
| Calcium pantothenate | $HOCH_2C(CH_3)_2CH(OH)CONHCH_2CH_2CO_2 \cdot \frac{1}{2}Ca$ | $4 \cdot 10^{-4}$ g | $2 \cdot 10^{-3}$ g | $4 \cdot 10^{-3}$ g | $2 \cdot 10^{-4}$ g | $4 \cdot 10^{-6}$ g |
| Folic acid | $C_{19}H_{19}N_7O_6$ | $2 \cdot 10^{-6}$ g | $2 \cdot 10^{-6}$ g | $2 \cdot 10^{-5}$ g | $10^{-6}$ g | $2 \cdot 10^{-7}$ g |
| Inositol | $C_6H_{12}O_6$ | $2 \cdot 10^{-3}$ g | $10^{-3}$ g | $2 \cdot 10^{-2}$ g | $10^{-3}$ g | $2 \cdot 10^{-4}$ g |
| Nicotinic acid | $C_6H_5NO_2$ | $4 \cdot 10^{-4}$ g | $2 \cdot 10^{-3}$ g | $4 \cdot 10^{-3}$ g | $2 \cdot 10^{-4}$ g | $4 \cdot 10^{-5}$ g |
| p-Aminobenzoic acid | $H_2NC_6H_4CO_2H$ | $2 \cdot 10^{-4}$ g | $10^{-3}$ g | $2 \cdot 10^{-3}$ g | $10^{-4}$ g | $2 \cdot 10^{-9}$ g |
| Pyridoxine HCl | $C_8C_{11}NO_3 \cdot HCl$ | $4 \cdot 10^{-4}$ g | $2 \cdot 10^{-3}$ g | $4 \cdot 10^{-3}$ g | $2 \cdot 10^{-4}$ g | $4 \cdot 10^{-5}$ g |
| Riboflavin | $C_{17}H_{20}N_4O_6$ | $2 \cdot 10^{-4}$ g | $10^{-3}$ g | $2 \cdot 10^{-3}$ g | $10^{-4}$ g | $2 \cdot 10^{-5}$ g |
| Thiamine HCL | $C_{12}H_{17}ClN_4OS \cdot HCl$ | $4 \cdot 10^{-4}$ g | $2 \cdot 10^{-3}$ g | $4 \cdot 10^{-3}$ g | $2 \cdot 10^{-4}$ g | $4 \cdot 10^{-5}$ g |
| Deionized water | $H_2O$ | 1 L | 1 L | 1 L | 1 L | 1 L |

Compositions of the Different Individual Vitamins Tested

TABLE 9

| Chemical name | Chemical formula | Bt | CP | FA |
|---|---|---|---|---|
| Biotin | $C_{10}H_{16}O_2O_3S$ | $2 \cdot 10^{-7}$ g | 0 g | 0 g |
| Calcium pantothenate | $HOCH_2C(CH_3)_2CH(OH)CONHCH_2CH_2CO_2 \cdot \frac{1}{2}Ca$ | 0 g | $4 \cdot 10^{-5}$ g | 0 g |
| Folic acid | $C_{19}H_{19}N_7O_6$ | 0 g | 0 g | $2 \cdot 10^{-7}$ g |
| Inositol | $C_6H_{12}O_6$ | 0 g | 0 g | 0 g |
| Nicotinic acid | $C_6H_5NO_2$ | 0 g | 0 g | 0 g |
| p-Aminobenzoic acid | $H_2NC_6H_4CO_2H$ | 0 g | 0 g | 0 g |
| Pyridoxine HCl | $C_8H_{11}NO_3 \cdot HCl$ | 0 g | 0 g | 0 g |
| Riboflavin | $C_{17}H_{20}N_4O_6$ | 0 g | 0 g | 0 g |
| Thiamine HCL | $C_{12}H_{17}ClN_4OS \cdot HCl$ | 0 g | 0 g | 0 g |
| Deionized water | $H_2O$ | 1 L | 1 L | 1 L |

| Chemical name | I | NA | AA | P | R | T |
|---|---|---|---|---|---|---|
| Biotin | 0 g | 0 g | 0 g | 0 g | 0 g | 0 g |
| Calcium pantothenate | 0 g | 0 g | 0 g | 0 g | 0 g | 0 g |
| Folic acid | 0 g | 0 g | 0 g | 0 g | 0 g | 0 g |
| Inositol | $2 \cdot 10^{-4}$ g | 0 g | 0 g | 0 g | 0 g | 0 g |
| Nicotinic acid | 0 g | $4 \cdot 10^{-5}$ g | 0 g | 0 g | 0 g | 0 g |
| p-Aminobenzoic acid | 0 g | 0 g | $2 \cdot 10^{-5}$ g | 0 g | 0 g | 0 g |
| Pyridoxine HCl | 0 g | 0 g | 0 g | $4 \cdot 10^{-5}$ g | 0 g | 0 g |
| Riboflavin | 0 g | 0 g | 0 g | 0 g | $2 \cdot 10^{-5}$ g | 0 g |
| Thiamine HCL | 0 g | 0 g | 0 g | 0 g | 0 g | $4 \cdot 10^{-6}$ g |
| Deionized water | 1 L | 1 L | 1 L | 1 L | 1 L | 1 L |

TABLE 10

| Condition | Mineral elixir | Optical density following pre-growth ($OD_{D6}$) | Optical density following growth ($OD_{D13}$) | Growth ratio ($OD_{D13}/OD_{D6}$) | Magnetic response % |
|---|---|---|---|---|---|
| 1 | V0 | 0.03 | 0.26 | 9.1 | >90 |
| 1 | CB1 | 0.03 | 0.12 | 3.6 | 0 |
| 1 | V2 | 0.02 | 0.18 | 9.0 | >90 |
| 1 | CB2 | 0.08 | 0.33 | 4.3 | >90 |
| 1 | CB3 | 0.08 | 0.62 | 7.6 | >90 |
| 1 | CB4 | 0.05 | 0.23 | 4.7 | >90 |
| 1 | CB5 | 0.04 | 0.23 | 5.4 | >90 |
| 1 | CB7 | 0.02 | 0.24 | 10.9 | >90 |
| 1 | CB9 | 0.04 | 0.1 | 2.3 | 0 |
| 1 | CB10 | 0.05 | 0.22 | 4.1 | >90 |
| 1 | CB11 | 0.03 | 0.25 | 10.0 | >90 |
| 1 | CB12 | 0.22 | 1.46 | 6.6 | >90 |
| 1 | CB13 | 0.32 | 1.52 | 4.8 | >90 |

TABLE 11

| Condition | Yeast extract/Vitamins cocktails | Optical density following pre-growth ($OD_{D6}$) | Optical density following growth ($OD_{D13}$) | Growth ratio ($OD_{D13}/OD_{D6}$) | Magnetic response |
|---|---|---|---|---|---|
| 2 | YE | 0.32 | 1.1 | 3.4 | >90 |
| 2 | YNBWAA | 0.31 | 0.82 | 2.6 | >90 |
| 2 | YNBWoAA | 0.32 | 0.76 | 2.4 | >90 |
| 2 | YNBWoAA.AS | 0.41 | 1.3 | 3.2 | >90 |
| 3 | Vit1X | 0.34 | 1.79 | 5.3 | >90 |
| 3 | Vit5X | 0 | 0 | | 0 |
| 3 | Vit10X | 0 | 0 | | 0 |
| 3 | Vit0.5X | 0.34 | 1.7 | 5.0 | >90 |
| 3 | Vit0.1X | 0.35 | 1.68 | 4.8 | >90 |

TABLE 12

| Condition | Vitamins | Optical density following pre-growth ($OD_{D6}$) | Optical density following growth ($OD_{D13}$) | Growth ratio ($OD_{D13}/OD_{D6}$) | Magnetic response (%) |
|---|---|---|---|---|---|
| 4 | Bt | 0.1 | 0.98 | 9.8 | >90 |
| 4 | CP | 0.3 | 0.98 | 3.3 | 5 |
| 4 | FA | 0.4 | 1.14 | 2.9 | 50 |
| 4 | I | 0.33 | 0.8 | 2.4 | 20 |
| 4 | NA | 0.27 | 0.65 | 2.4 | >90 |
| 4 | AA | 0.12 | 0.8 | 6.7 | 20 |
| 4 | P | 0.25 | 0.7 | 2.8 | 5 |
| 4 | R | 0.19 | 0.92 | 4.8 | >90 |
| 4 | T | 0.26 | 1.51 | 5.8 | >90 |

TABLE 13

| Condition | Chemicals | Optical density following pre-growth ($OD_{D6}$) | Optical density following growth ($OD_{D13}$) | Growth ratio ($OD_{D13}/OD_{D6}$) | Magnetic response (%) |
|---|---|---|---|---|---|
| 5 | N | 0.7 | 1.1 | 1.6 | >90 |
| 5 | SL0 | 0.12 | 0.1 | 0.8 | 0 |
| 5 | SL0.5X | 0.32 | 0.68 | 2.1 | 20 |
| 5 | SL0.2X | 0.1 | 0.23 | 2.3 | 20 |
| 5 | SL0.1X | 0.04 | 0.08 | 2.0 | 0 |
| 5 | AC0 | 0.15 | 0 | 0 | 0 |
| 5 | AC0.5X | 0.47 | 1.31 | 2.8 | 20 |
| 5 | AC0.2X | 0.27 | 0.99 | 3.7 | 5 |
| 5 | AC0.1X | 0.15 | 0.87 | 5.8 | 5 |
| 5 | MG0 | 0.16 | 0 | 0 | 0 |
| 5 | MG0.5X | 0.3 | 1.7 | 5.7 | 20 |
| 5 | MG0.2X | 0.003 | 0.002 | 0.7 | 5 |

TABLE 13-continued

| Condition | Chemicals | Optical density following pre-growth ($OD_{D6}$) | Optical density following growth ($OD_{D13}$) | Growth ratio ($OD_{D13}/OD_{D6}$) | Magnetic response (%) |
|---|---|---|---|---|---|
| 5 | MG0.1X | 0.003 | 0.006 | 2.0 | 5 |
| 5 | P0 | 1 | 0 | 0 | 0 |
| 5 | P0.5X | 0.54 | 0.83 | 1.5 | >90 |
| 5 | P0.2X | 0.5 | 1.07 | 2.1 | >90 |
| 5 | P0.1X | 0.55 | 1.16 | 2.1 | 50 |

Condition 6 in 1 L Fermenters with Non Pharmaceutical Grade Chemicals

TABLE 14(a)

| | Chemical name | Chemical formula | B1 (quantity) | B1 (concentration) | B4 (quantity) | B4 (concentration) |
|---|---|---|---|---|---|---|
| Pre-growth medium | Sodium lactate | $C_3H_5NaO_3$ | 2.6 g | $2.3 \cdot 10^{-2}$M | 2.6 g | $2.3 \cdot 10^{-2}$M |
| | Ammonium chloride | $NH_4Cl$ | 0.4 g | $7.4 \cdot 10^{-3}$M | 0.4 g | $7.4 \cdot 10^{-3}$M |
| | Magnesium sulfate heptahydrate | $MgSO_4 \cdot 7H_2O$ | 0.1 g | $4.1 \cdot 10^{-4}$M | 0.1 g | $4.1 \cdot 10^{-4}$M |
| | Potassium phosphate dibasic | $K_2HPO_4$ | 0.5 g | $2.9 \cdot 10^{-3}$M | 0.5 g | $2.9 \cdot 10^{-3}$M |
| | Mineral elixir CB3 (Table 6) | / | 0.5 mL | / | 0.5 mL | / |
| | Vitamins cocktail Vit0.1X (Table 8) | / | 0.1 mL | / | 0.1 mL | / |
| | Deionized water | $H_2O$ | 1 L | / | 1 L | / |
| Growth medium (NFG) | Sodium lactate | $C_3H_5NaO_3$ | 104 g | $0.9 \cdot 10^{-1}$M | 104 g | $0.9 \cdot 10^{-1}$M |
| | Ammonium chloride | $NH_4Cl$ | 16 g | $0.3 \cdot 10^{-1}$M | 16 g | $0.3 \cdot 10^{-1}$M |
| | Magnesium sulfate heptahydrate | $MgSO_4 \cdot 7H_2O$ | 1.2 g | $4.9 \cdot 10^{-3}$M | 1.2 g | $4.9 \cdot 10^{-3}$M |
| | Potassium phosphate dibasic | $K_2HPO_4$ | 2.8 g | $0.2 \cdot 10^{-2}$M | 2.8 g | $0.2 \cdot 10^{-2}$M |
| | Mineral elixir CB3 (Table 6) | / | 2.8 mL | / | 2.8 mL | / |
| | Vitamins cocktail Vit0.1X (Table 8) | / | 3.2 mL | / | 3.2 mL | / |
| | Deionized water | $H_2O$ | 1 L | / | 1 L | / |
| Fed-batch medium (NFG) | Lactic acid | $CH_3CH(OH)COOH$ | 100 g | $0.9 \cdot 10^{-1}$M | 100 g | $0.9 \cdot 10^{-1}$M |
| | Ammoniac | $NH_3$ | 4.8 g | $2.8 \cdot 10^{-1}$M | 4.8 g | $2.8 \cdot 10^{-1}$M |
| | Potassium phosphate dibasic | $K_2HPO_4$ | 6 g | $3.4 \cdot 10^{-2}$M | 6 g | $3.4 \cdot 10^{-2}$M |
| | Magnesium sulfate heptahydrate | $MgSO_4 \cdot 7H_2O$ | 2.4 g | $9.7 \cdot 10^{-3}$M | 2.4 g | $9.7 \cdot 10^{-3}$M |
| | Ferric citrate | $C_6H_5FeO_7$ | 1.8 g | $7.4 \cdot 10^{-3}$M | 0 g | 0M |
| | Iron III chloride | $Cl_3Fe$ | 0 g | 0M | 2 g | $7.4 \cdot 10^{-3}$M |
| | Mineral elixir CB3 (Table 6) | / | 7 mL | / | 7 mL | / |
| | Vitamins cocktail Vit0.1X (Table 8) | / | 1 mL | / | 1 mL | / |
| | Deionized water | $H_2O$ | 1 L | / | 1 L | / |

Condition 6 in 1 L Fermenters with Pharmaceutical Grade Chemicals

TABLE 14(b)

| | Chemical Name | Chemical formula | B2 (quantity) | B2 (concentration) | B3 (quantity) | B3 (concentration) |
|---|---|---|---|---|---|---|
| Pre-growth medium | Sodium lactate | $C_3H_5NaO_3$ | 2.6 g | $2.3 \cdot 10^{-2}$M | 2.6 g | $2.3 \cdot 10^{-2}$M |
| | Ammonium chloride | $NH_4Cl$ | 0.4 g | $7.4 \cdot 10^{-3}$M | 0.4 g | $7.4 \cdot 10^{-3}$M |
| | Magnesium sulfate heptahydrate | $MgSO_4 \cdot 7H_2O$ | 0.1 g | $4.1 \cdot 10^{-4}$M | 0.1 g | $4.1 \cdot 10^{-4}$M |
| | Potassium phosphate dibasic | $K_2HPO_4$ | 0.5 g | $2.9 \cdot 10^{-3}$M | 0.5 g | $2.9 \cdot 10^{-3}$M |
| | Mineral elixir CB3 (Table 6) | / | 0.5 mL | / | 0.5 mL | / |
| | Vitamins cocktail Vit0.1X (Table 8) | / | 0.1 mL | / | 0.1 mL | / |
| | Deionized water | $H_2O$ | 1 L | / | 1 L | / |
| Growth medium (FG) | Sodium lactate | $C_3H_5NaO_3$ | 104 g | $0.9 \cdot 10^{-1}$M | 104 g | $0.9 \cdot 10^{-1}$M |
| | Ammonium chloride | $NH_4Cl$ | 16 g | $0.3 \cdot 10^{-1}$M | 16 g | $0.3 \cdot 10^{-1}$M |
| | Magnesium sulfate heptahydrate | $MgSO_4 \cdot 7H_2O$ | 1.2 g | $4.9 \cdot 10^{-3}$M | 1.2 g | $4.9 \cdot 10^{-3}$M |
| | Potassium phosphate dibasic | $K_2HPO_4$ | 2.8 g | $0.2 \cdot 10^{-2}$M | 2.8 g | $0.2 \cdot 10^{-2}$M |
| | Mineral elixir CB3 (Table 6) | / | 2.8 mL | / | 2.8 mL | / |
| | Vitamins cocktail Vit0.1X (Table 8) | / | 3.2 mL | / | 3.2 mL | / |
| | Deionized water | $H_2O$ | 1 L | / | 1 L | / |
| Fed-batch medium (FG) | Lactic acid | $CH_3CH(OH)COOH$ | 100 g | $0.9 \cdot 10^{-1}$M | 100 g | $0.9 \cdot 10^{-1}$M |
| | Ammoniac | $NH_3$ | 4.8 g | $2.8 \cdot 10^{-1}$M | 4.8 g | $2.8 \cdot 10^{-1}$M |
| | Potassium phosphate dibasic | $K_2HPO_4$ | 6 g | $3.4 \cdot 10^{-2}$M | 6 g | $3.4 \cdot 10^{-2}$M |
| | Magnesium sulfate heptahydrate | $MgSO_4 \cdot 7H_2O$ | 2.4 g | $9.7 \cdot 10^{-3}$M | 2.4 g | $9.7 \cdot 10^{-3}$M |
| | Ferric citrate | $C_6H_5FeO_7$ | 1.8 g | $7.4 \cdot 10^{-3}$M | 0 g | 0M |
| | Iron III chloride | $Cl_3Fe$ | 0 g | 0M | 2 g | $7.4 \cdot 10^{-3}$M |
| | Mineral elixir CB3 (Table 6) | / | 7 mL | / | 7 mL | / |
| | Vitamins cocktail Vit0.1X (Table 8) | / | 1 mL | / | 1 mL | / |
| | Deionized water | $H_2O$ | 1 L | / | 1 L | / |

TABLE 15

| Growth Conditions | | Pre-growth (D0) V1 = 250 mL | | Pre-growth (D8) V2 = 1.5 L | | Growth (D9) V3 = 800 mL | | Growth (D10) V3 = 800 mL | | Growth (D11) V3 = 800 mL | | Growth ratio $OD_{D11}/OD_{D9}$ | Magnetic response at D11 (%) |
|---|---|---|---|---|---|---|---|---|---|---|---|---|---|
| | | Optical density | Number of cells/mL | Optical density | Number of cells/mL | Optical density | Number of cells/mL | Optical density | Number of cells/mL | Optical density | Number of cells/mL | | |
| 6 | B1 | 0.001 | $5 \cdot 10^6$ | 0.4 | $2 \cdot 10^9$ | 0.1 | $5 \cdot 10^8$ | 0.49 | $2.5 \cdot 10^9$ | 1.13 | $5.5 \cdot 10^9$ | 11.3 | 80 |
| 6 | B2 | 0.001 | $5 \cdot 10^6$ | 0.4 | $2 \cdot 10^9$ | 0.1 | $5 \cdot 10^8$ | 0.7 | $3.5 \cdot 10^9$ | 2 | $1 \cdot 10^{10}$ | 20.0 | 80 |
| 6 | B3 | 0.001 | $5 \cdot 10^6$ | 0.4 | $2 \cdot 10^9$ | 0.1 | $5 \cdot 10^8$ | 0.96 | $5 \cdot 10^9$ | 2.68 | $2.4 \cdot 10^{10}$ | 26.8 | 100 |
| 6 | B4 | 0.001 | $5 \cdot 10^6$ | 0.4 | $2 \cdot 10^9$ | 0.1 | $5 \cdot 10^8$ | 0.86 | $4.5 \cdot 10^9$ | 1.75 | $8.5 \cdot 10^9$ | 17.5 | 100 |

TABLE 16

| Growth Conditions | Element | Ag (µg/g) | Al (µg/g) | As (µg/g) | Ba (µg/g) | Cd (µg/g) | Co (µg/g) | Cr (µg/g) | Cu (µg/g) | Mn (µg/g) | Mo (µg/g) |
|---|---|---|---|---|---|---|---|---|---|---|---|
| B1 (NFG) | Elemental impureties (µg of impurity per g of iron in nanoparticle µg/g) | 169 | 307 | 0 | 1283 | 97 | 0 | 227 | 0 | 2751 | 0 |
| B2 (FG) | | 266 | 628 | 0 | 363 | 104 | 0 | 1627 | 0 | 785 | 0 |
| B3 (FG) | | 71 | 441 | 0 | 160 | 97 | 0 | 418 | 0 | 813 | 0 |
| B4 (NFG) | | 179 | 1390 | 0 | 418 | 118 | 0 | 3538 | 0 | 497 | 0 |

| Growth Conditions | Ni (µg/g) | Pb (µg/g) | Sb (µg/g) | Se (µg/g) | Si (µg/g) | Sn (µg/g) | Ti (µg/g) | Tl (µg/g) | W (µg/g) | Zn (µg/g) |
|---|---|---|---|---|---|---|---|---|---|---|
| B1 (NFG) | 473 | 367 | 0 | 0 | 0 | 0 | 625 | 0 | 0 | 0 |
| B2 (FG) | 660 | 677 | 0 | 0 | 0 | 12 | 1900 | 43 | 0 | 654 |
| B3 (FG) | 292 | 408 | 0 | 0 | 0 | 19 | 129 | 18 | 0 | 0 |
| B4 (NFG) | 727 | 379 | 0 | 0 | 0 | 21 | 197 | 48 | 0 | 3208 |

NFG: Non pharmaceutical grade chemicals in growth and fed-batch medium
FG: Pharmaceutical grade chemicals in growth and fed-batch medium

TABLE 17

| Growth Conditions | Chemicals | Pre-growth 1 (D0) | After pre-growth 1 (D8) | After pre-growth 2 (D9) | After 0 h of growth (D9) | After 6 h of growth (D9) | After 12 h of growth (D9) | After 24 h of growth (D10) | After 48 h of growth (D11) |
|---|---|---|---|---|---|---|---|---|---|
| B1 | Iron concentration Fed-batch medium | $1.8 \cdot 10^6$M | $1.8 \cdot 10^6$M | $1.8 \cdot 10^6$M | $1.8 \cdot 10^6$M 0 mL | $5.5 \cdot 10^6$M 0.4 mL | $1.3 \cdot 10^4$M 1.2 mL | $4.8 \cdot 10^4$M 5 mL | $2.1 \cdot 10^4$M 23 mL |
| B2 | Iron concentration Fed-batch medium | $1.8 \cdot 10^6$M | $1.8 \cdot 10^6$M | $1.8 \cdot 10^6$M | $1.8 \cdot 10^6$M 0 mL | $8.3 \cdot 10^6$M 0.7 mL | $2.2 \cdot 10^4$M 2.2 mL | $8.5 \cdot 10^4$M 9 mL | $3.7 \cdot 10^4$M 40 mL |
| B3 | Iron concentration Fed-batch medium | $1.8 \cdot 10^6$M | $1.8 \cdot 10^6$M | $1.8 \cdot 10^6$M | $1.8 \cdot 10^6$M 0 mL | $1.1 \cdot 10^4$M 1 mL | $2.9 \cdot 10^4$M 3 mL | $1.12 \cdot 10^4$M 12 mL | $4.9 \cdot 10^4$M 54 mL |
| B4 | Iron concentration Fed-batch medium | $1.8 \cdot 10^6$M | $1.8 \cdot 10^6$M | $1.8 \cdot 10^6$M | $1.8 \cdot 10^6$M 0 mL | $5.5 \cdot 10^6$M 0.6 mL | $1.8 \cdot 10^4$M 1.9 mL | $7.4 \cdot 10^4$M 7.8 mL | $3.2 \cdot 10^4$M 35 mL |

TABLE 18

| Samples | Lysis | Treatment | $T_i$ | $T_1, r_{i1}, t_1$ | $T_2, r_{i2}, t_2$ | $T_3, r_{13}, r_{32}, t_3$ | $T_4, r_{34}, t_4$ | $T_f, r_{1f}, r_{2f}, r_{3f}, r_{4f}$ |
|---|---|---|---|---|---|---|---|---|
| Sample 0 | None | No | 20° C. | NA | NA | NA | NA | 25° C. |
| Sample 1 | NaOH | No | 20° C. | NA | NA | NA | NA | 25° C. |
| Sample 2 | KOH | No | 20° C. | NA | NA | NA | NA | 25° C. |
| Sample 3 | NaOH | Phenol-chloroform | 20° C. | NA | NA | NA | NA | 25° C. |
| Sample 4 | KOH | Heat | 20° C. | $T_1$ = 200° C. $r_{i1}$ = 6° C./min $t_1$ = 1 hour | NA | NA | NA | $T_f$ = 25° C. $r_{1f}$ = 0.3° C./min |
| Sample 5 | KOH | Heat | 20° C. | NA | $T_2$ = 400° C. $r_{12}$ = 6° C./min $t_2$ = 1 hour | NA | NA | $T_f$ = 25° C. $r_{2f}$ = 0.3° C./min |
| Sample 6 | KOH | Heat | 20° C. | $T_1$ = 200° C. $r_{i1}$ = 9° C./min $t_1$ = 30 min | NA | $T_3$ = 300° C. $r_{13}$ = 10° C./min $t_3$ = 1 hour | NA | $T_f$ = 25° C. $r_{3f}$ = 0.4° C./min |

TABLE 18-continued

| Samples | Lysis | Treatment | $T_i$ | $T_1, r_{i1}, t_1$ | $T_2, r_{12}, r_{i2}, t_2$ | $T_3, r_{13}, r_{32}, t_3$ | $T_4, r_{34}, t_4$ | $T_f, r_{1f}, r_{2f}, r_{3f}, r_{4f}$ |
|---|---|---|---|---|---|---|---|---|
| Sample 7 | KOH | Heat | 20° C. | $T_1 = 200°$ C.<br>$r_{i1} = 9°$ C./min<br>$t_1 = 30$ min | $T_2 = 380°$ C.<br>$r_{12} = 8°$ C./min<br>$t_2 = 1$ hour | $T_3 = 300°$ C.<br>$r_{32} = 10°$ C./min<br>$t_3 = 1$ hour | $T_3 = 550°$ C.<br>$r_{34} = 8.5°$ C./min<br>$t_4 = 1$ hour | $T_f = 25°$ C.<br>$r_{4f} = 0.4°$ C./min |
| Sample 8 | KOH | Heat | 20° C. | $T_1 = 200°$ C.<br>$r_{i1} = 9°$ C./min<br>$t_1 = 30$ min | $T_2 = 380°$ C.<br>$r_{12} = 8°$ C./min<br>$t_2 = 1$ hour | $T_3 = 300°$ C.<br>$r_{32} = 10°$ C./min<br>$t_3 = 1$ hour | NA | $T_f = 25°$ C.<br>$r_{3f} = 0.5°$ C./min |
| Sample 9 | NaOH | Heat | 20° C. | $T_1 = 200°$ C.<br>$r_{i1} = 9°$ C./min<br>$t_1 = 30$ min | $T_2 = 380°$ C.<br>$r_{12} = 8°$ C./min<br>$t_2 = 1$ hour | $T_3 = 300°$ C.<br>$r_{32} = 10°$ C./min<br>$t_3 = 1$ hour | NA | $T_f = 25°$ C.<br>$r_{3f} = 0.5°$ C./min |
| Sample 10 | KOH | Heat | 20° C. | $T_1 = 200°$ C.<br>$r_{i1} = 1.2°$ C./min<br>$t_1 = 1$ hour | $T_2 = 380°$ C.<br>$r_{12} = 1°$ C./min<br>$t_2 = 2$ hours | $T_3 = 300°$ C.<br>$r_{32} = 1.25°$ C./min<br>$t_3 = 2$ hours | NA | $T_f = 25°$ C.<br>$r_{3f} = 0.5°$ C./min |
| Sample 11 | NaOH | Heat | 20° C. | $T_1 = 200°$ C.<br>$r_{i1} = 1.2°$ C./min<br>$t_1 = 1$ hour | $T_2 = 380°$ C.<br>$r_{12} = 81°$ C./min<br>$t_2 = 2$ hours | $T_3 = 300°$ C.<br>$r_{32} = 1.25°$ C./min<br>$t_3 = 2$ hours | NA | $T_f = 25°$ C.<br>$r_{3f} = 0.5°$ C./min |

$R_i$: rate of temperature increase to reach $T_i$
$T_i$: temperature maintained during step i
NA: Not applicable.

TABLE 19

| Samples | Lysis | Treatment | % C | % N | % $C_i$ | % $N_i$ | $\Delta$ % C = % $C_i$-% C | $\Delta$ % N = % $N_i$-% N | $\dfrac{100*\Delta\ \%\ C}{\%\ C_i}$ | $\dfrac{100*\Delta\ \%\ N}{\%\ N_i}$ |
|---|---|---|---|---|---|---|---|---|---|---|
| Sample 0 | None | No | 44 ± 4 | 9.9 ± 0.7 | | | | | | |
| Sample 1 | NaOH | No | 14 ± 6 | 2.5 ± 0.9 | 44 ± 4 | 9.9 ± 0.7 | −30 ± 10 | −7 ± 2 | −68 ± 17 | −75 ± 15 |
| Sample 2 | KOH | No | 7.1 ± 0.7 | 0.8 ± 0.2 | 44 ± 4 | 9.9 ± 0.7 | −37 ± 5 | −9.1 ± 0.9 | −84 ± 4 | −92 ± 3 |
| Sample 3 | NaOH | Phenol-chloroform | 5 ± 2 | 0.3 ± 0.2 | 14 ± 6 | 2.5 ± 0.9 | −9 ± 8 | −2 ± 1 | −64 ± 30 | −88 ± 8 |
| Sample 4 | KOH | Heat | 5 ± 1 | 0.28 ± 0.08 | 7.1 ± 0.7 | 0.8 ± 0.2 | −2 ± 2 | −0.5 ± 0.2 | −30 ± 25 | −65 ± 9 |
| Sample 5 | KOH | Heat | 3 ± 1 | 0.2 ± 0.1 | 7.1 ± 0.7 | 0.8 ± 0.2 | −4 ± 2 | −0.6 ± 0.3 | −58 ± 22 | −75 ± 19 |
| Sample 6 | KOH | Heat | 0.65 ± 0.01 | 0.099 ± 0.001 | 7.1 ± 0.7 | 0.8 ± 0.2 | −6.5 ± 0.7 | −0.7 ± 0.2 | −91 ± 1 | −88 ± 3 |
| Sample 7 | KOH | Heat | 0.3 ± 0.1 | 0.03 ± 0.01 | 7.1 ± 0.7 | 0.8 ± 0.2 | −6.8 ± 0.8 | −0.8 ± 0.2 | −96 ± 2 | −96 ± 1 |
| Sample 8 | KOH | Heat | 0.3 ± 0.1 | 0.03 ± 0.01 | 7.1 ± 0.7 | 0.8 ± 0.2 | −6.8 ± 0.8 | −0.8 ± 0.2 | −96 ± 2 | −96 ± 1 |
| Sample 9 | NaOH | Heat | 1.0 ± 0.3 | 0.4 ± 0.1 | 14 ± 6 | 2.5 ± 0.9 | −13 ± 1 | −2 ± 1 | −93 ± 33 | −84 ± 10 |
| Sample 10 | KOH | Heat | 0.23 ± 0.07 | 0.01 ± 0.01 | 7.1 ± 0.7 | 0.8 ± 0.2 | −6.9 ± 0.7 | −0.8 ± 0.2 | −96.8 ± 0.3 | −98.8 ± 0.3 |
| Sample 11 | NaOH | Heat | 0.8 ± 0.2 | 0.25 ± 0.03 | 14 ± 6 | 2.5 ± 0.9 | −13 ± 1 | −2.3 ± 0.9 | −94 ± 33 | −90 ± 4 |

The invention claimed is:

1. A method for producing high purity ferrimagnetic or ferromagnetic iron oxide nanoparticles using ferrimagnetic or ferromagnetic iron oxide nanoparticle-producing cells, which are magnetotactic bacteria, comprising:
 a) A pre-growth step comprising amplifying the ferrimagnetic or ferromagnetic iron oxide nanoparticle-producing cell(s) in a pre-growth and/or fed-batch medium/media, and
 b) A growth step comprising amplifying the ferrimagnetic or ferromagnetic iron oxide nanoparticle-producing cell(s) originating from the pre-growth step in a growth and/or fed-batch medium/media,
 wherein the pre-growth and/or growth and/or fed-batch medium/media comprise(s), per kilogram or liter of pre-growth and/or growth and/or fed-batch medium/media:
  i) no more than 0.005 gram of yeast extract, and
  ii) no boric acid and nitrilotriacetic acid, which are carcinogenic, mutagenic, and reprotoxic (CMR) agents,
 wherein the fed-batch medium in the pre-growth step and the growth step, when it is present, is a medium that supplements the pre-growth and/or growth medium/media,
 wherein more ferrimagnetic or ferromagnetic iron oxide nanoparticles are produced in the growth step than in the pre-growth step,
 wherein the ferrimagnetic or ferromagnetic iron oxide nanoparticles are produced inside the ferrimagnetic or ferromagnetic iron oxide nanoparticle-producing cells using an intracellular iron concentration, and
 wherein the ferrimagnetic or ferromagnetic iron oxide nanoparticle-producing cells have at least one property selected in the group consisting of:
  i) the ferrimagnetic or ferromagnetic iron oxide nanoparticle-producing cells are amplified at least partly under microaerobic conditions, and
  ii) ferrimagnetic or ferromagnetic iron oxide nanoparticle-producing cells are amplified at least partly under non-fully anerobic or non-fully aerobic conditions such that the pre-growth and/or growth and/or fed-batch medium/media comprises oxygen at a percentage in mass of oxygen, at a percentage in volume of oxygen, or at a percentage in number of oxygen atoms that is greater than 0% and strictly less than 100%,
 wherein the percentage in mass of oxygen is the mass of oxygen comprised in the pre-growth and/or growth and/or fed-batch medium/media relative to a maximum mass of oxygen comprised in the oxygen-saturated pre-growth and/or growth and/or fed-batch medium/media reached under fully aerobic conditions,
 wherein the percentage in volume of oxygen is the volume of oxygen comprised in the pre-growth and/or growth and/or fed-batch medium/media relative to a maximum volume of oxygen comprised in the oxygen-saturated pre-growth and/or growth and/or fed-batch medium/media reached under fully aerobic condition, and wherein the percentage in number of oxygen atoms is the number of oxygen atoms comprised in the pre-growth and/or growth and/or fed-batch medium/media relative to a maximum number of oxygen atoms comprised in the oxygen-saturated pre-growth and/or growth and/or fed-batch medium/media reached under fully aerobic conditions.

2. The method according to claim 1, wherein the growth step differs from the pre-growth step by at least one property selected from the group consisting of:
i) A ratio $C_{FeGS}/C_{FePGS}$ that is larger than 1, where $C_{FeGS}$ and $C_{FePGS}$ are concentrations in iron or iron source of the growth medium and pre-growth medium, respectively,
ii) A ratio $C_{CGS}/C_{CPGS}$ that is larger than 1, where $C_{CGS}$ and $C_{CPGS}$ are the concentrations in carbon or carbon source of the growth medium and pre-growth medium, respectively,
iii) A ratio $C_{NGS}/C_{NPGS}$ that is larger than 1, where $C_{NGS}$ and $C_{NPGS}$ are the concentrations in nitrogen or nitrogen source of the growth medium and pre-growth medium, respectively,
iv) A ratio $\Delta p_{HGS}/\Delta pH_{PGS}$ that is lower than 1, where $\Delta p_{HGS}$ and $\Delta pH_{PGS}$ are the pH variations of the growth medium and pre-growth medium, respectively,
v) A ratio $Q_{GGS}/Q_{GPGS}$ that is larger than 1, where $Q_{GGS}$ and $Q_{GPGS}$ are quantities of gas, oxygen or air brought in or bubbled through the growth medium and pre-growth medium, respectively,
vi) A ratio $N_{SSGS}/N_{SSPGS}$ that is lower than 1, where $N_{SSGS}$ and $N_{SSPGS}$ are numbers of sub-steps of the growth step and numbers of sub-steps of the pre-growth step, respectively, where two sub-steps are separated by each other by a transfer of ferrimagnetic or ferromagnetic iron oxide nanoparticle-producing cells from a first sub-step to a second sub-step, and
v) the growth medium is supplemented by a fed-batch medium, whereas the pre-growth medium is not supplemented by such medium,
wherein optionally the iron source has a chemical formula that comprises $Fe_cO_d$, wherein c and d are coefficients.

3. The method according to claim 1, wherein the pre-growth and/or growth and/or fed-batch medium/media comprises, per kilogram or liter of pre-growth and/or growth and/or fed-batch medium/media, less than:
i) $5.10^{-3}$% in mass or volume or 0.5 gram or 0.5 mL or $10^{-8}$ mol or $10^{-9}$ mol of vitamins or chemical components selected from the group consisting of: folic acid, folates, pyridoxine, Pyridoxine HCl, pyridoxamine, pyridoxal, riboflavin, biotin, thiamine, thiamine HCl, nicotinic acid, pantothenic acid, calcium pantothenate, inositol, p-Aminobenzoic acid, amino benzoic acid, thiotic acid, all-trans-Retinol, Retinals, alternative pro-vitamin A-functioning Carotenoids including all-trans-beta-carotene, Niacin, Niacinamide, Nicotinamide, riboside, cyanocobalamin, hydroxocobalamin, methylcobalamin, adenosylcobalamin, ascorbic acid, cholecalciferol, ergocalciferol, tocopherols, tocotrienols, phylloquinone, menaquinones, vitamin A, vitamin $B_1$, vitamin $B_2$, vitamin $B_3$, vitamin $B_5$, vitamin $B_6$, vitamin $B_7$, vitamin $B_9$, vitamin $B_{12}$, vitamin C, vitamin D, vitamin D2, vitamin D3, vitamin E, vitamin K, vitamin $V_i$ where V can be any letter from A to Z and i can be any integer between 1 and 100, and derivatives thereof,
ii) 6 different vitamins or chemical components, which are selected from the group consisting of: folic acid, folates, pyridoxine, Pyridoxine HCl, pyridoxamine, pyridoxal, riboflavin, biotin, thiamine, thiamine HCl, nicotinic acid, pantothenic acid, calcium pantothenate, inositol, p-Aminobenzoic acid, amino benzoic acid, thiotic acid, all-trans-Retinol, Retinals, alternative pro-vitamin A-functioning Carotenoids including all-trans-beta-carotene, Niacin, Niacinamide, Nicotinamide, riboside, cyanocobalamin, hydroxocobalamin, methylcobalamin, adenosylcobalamin, ascorbic acid, cholecalciferol, ergocalciferol, tocopherols, tocotrienols, phylloquinone, menaquinones, vitamin A, vitamin $B_1$, vitamin $B_2$, vitamin $B_3$, vitamin $B_5$, vitamin $B_6$, vitamin $B_7$, vitamin $B_9$, vitamin $B_{12}$, vitamin C, vitamin D, vitamin D2, vitamin D3, vitamin E, vitamin K, vitamin V, where V can be any letter from A to Z and i can be any integer between 1 and 100, and derivatives thereof,
iii) $10^{-2}$% in mass or volume or 1 gram or 1 mL or $10^{-7}$ mol or $10^{-8}$ mol of minerals or chemical components selected from the group consisting of: magnesium sulfate, sodium chloride, manganese sulfate, ferrous sulfate, ferrous sulfate heptahydrate, cobalt nitrate, calcium chloride, zinc sulfate, zinc sulfate heptahydrate, copper sulfate, hydrate copper sulfate, aluminum potassium sulfate, aluminum potassium sulfate dodecahydrate, sodium molybdate, sodium selenite, sodium tungstate, sodium tungstate dihydrate, nickel chloride, EDTA, $MgSO_4$, $MnSO_4$, NaCl, $FeSO_4$, $CoSO_4$, $CaCl_2$), $ZnSO_4$, $CuSO_4$, $KA_1(SO_4)_2$, $H_3BO_3$, $Na_2MoO_4$, $NiCl_2$, $Na_2SeO_3$, and derivatives thereof,
iv) 7 different minerals or chemical components selected from the group consisting of: magnesium sulfate, sodium chloride, ferrous sulfate, ferrous sulfate heptahydrate, cobalt nitrate, calcium chloride, zinc sulfate, zinc sulfate heptahydrate, copper sulfate, hydrate copper sulfate, aluminium potassium sulfate, aluminum potassium sulfate dodecahydrate, sodium molybdate, sodium selenite, sodium tungstate, sodium tungstate dihydrate, nickel chloride, EDTA, $MgSO_4$, $MnSO_4$, NaCl, $FeSO_4$, $CoSO_4$, $CaCl_2$, $ZnSO_4$, $CuSO_4$, $KAl(SO_4)_2$, $H_3BO_3$, $Na_2MoO_4$, $NiCl_2$, $Na_2SeO_3$, and derivatives thereof,
v) 0.005 gram or $10^{-8}$ M of at least one component of yeast extract or at least one compound originating from yeast extract selected from the group of compounds consisting of: at least one protein, at least one nucleic acid, at least one functional peptide, glutathione, dextran, mannan, trehalose, flavoring nucleotide, B vitamin, biotin, at least one volatile aromatic compound, calcium, Phosphorus, Zinc, Iron, Chrome or Chromium, Potassium, Cobalt, Manganese, Strontium, Magnesium, and derivatives thereof,
vi) 5 different components of yeast extract or compounds originating from yeast extract selected from the group consisting of: at least one protein, at least one nucleic acid, at least one functional peptide, glutathione, dextran, mannan, trehalose, flavoring nucleotide, B vitamin, biotin, at least one volatile aromatic compound, calcium, Phosphorus, Zinc, Iron, Chrome or Chromium, Potassium, Cobalt, Manganese, Strontium, Magnesium, and derivatives thereof,
vii) 0.01 gram or $10^{-8}$ M of at least one component of peptone or at least one compound originating from peptone selected from the group consisting of: ashes, proteins, sucrose, stachyose, raffinose, neutral detergent fiber, Ethereal Extract, and derivatives thereof,
viii) 5 different components of peptone or compounds originating from peptone selected from the group consisting of: ashes, proteins, sucrose, stachyose, raffinose, neutral detergent fiber, Ethereal Extract, and derivatives thereof, ix) 0.001 gram of EDTA, x) 0.001 gram of at least one amino acid, xi) 5 different amino acids, xii) 12 different CMR, toxic or cytotoxic compounds selected from the group consisting of: manganese sulfate, cobalt nitrate, zinc sulfate, copper sulfate, aluminum potassium sulfate, sodium molybdate, sodium selenite, sodium tungstate, nickel chloride, and derivatives thereof, xiii) 5 different chemical elements or heavy metal selected in the group consisting of: cadmium, lead, arsenic, mercury, cobalt, vanadium, nickel, lithium, antimony, and copper, and derivatives thereof, xiv) $10^{-5}$ gram of at least one chemical element or heavy metal selected in the group consisting of: cadmium, lead, arsenic, mercury, cobalt, vanadium, nickel, lithium, antimony, and copper, and derivatives thereof, xv) $10^{-5}$ gram of at least one CMR, toxic or cytotoxic compound selected from the group consisting of: manganese sulfate, cobalt nitrate, zinc sulfate, copper sulfate, aluminum potassium sulfate, sodium molybdate, sodium selenite, sodium tungstate, nickel chloride, and derivatives thereof, and/or xvi) 0.01 gram of peptone.

4. The method according to claim 1, wherein at least one compound of the pre-growth and/or growth medium/media has a concentration $C_2$ or a concentration $C_{total}=C_1+C_2$, wherein:

$C_1$ is a concentration of the at least one compound of the pre-growth and/or growth medium/media not consumed by the ferrimagnetic or ferromagnetic iron oxide nanoparticle-producing cells, $C_2$ is a concentration of the at least one compound of the pre-growth and/or growth medium/media consumed by ferrimagnetic or ferromagnetic iron oxide nanoparticle-producing cells, and $C_1$ and $C_2$ are measured or considered at the beginning, during or at the end of the pre-growth and/or growth step(s).

5. The method according to claim 1, wherein:

the pre-growth, growth, and/or fed-batch medium/media do(does) not comprise at least one compound at a concentration that affects the growth of ferrimagnetic or ferromagnetic iron oxide nanoparticle-producing cells and/or ferrimagnetic or ferromagnetic iron oxide nanoparticle production, and/or the pre-growth, growth, and/or fed-batch medium/media are(is) substantially free of at least one compound that affects the growth of ferrimagnetic or ferromagnetic iron oxide nanoparticle-producing cells and/or ferrimagnetic or ferromagnetic iron oxide nanoparticle production, and the at least one compound is selected from the group consisting of: 1) Wolf's Vitamin or a medium that comprises more than half of the total number of different components of Wolf's vitamin, 2) one component of Wolf's vitamin, 3) folic acid, 4) pyridoxine, 5) riboflavin, 6) biotin, 7) thiamin, 8) nicotinic acid, 9) pantothenic acid, 10) vitamin B12, 11) amino benzoic acid, 12) thiotic acid, 13) Wolf's mineral or a medium that comprises more than half of the total number of different components of Wolf's mineral, 14) magnesium sulfate, 15) sodium chloride, 16) manganese sulfate, 17) ferrous sulfate heptahydrate, 18) cobalt nitrate, 19) calcium chloride, 20) zinc sulfate heptahydrate, 21) hydrate copper sulfate, 22) aluminum potassium sulfate dodecahydrate, 24) boric acid, 23) sodium molybdate, 24) sodium selenite, 25) sodium tungstate dihydrate, 26) yeast extract or a medium that comprises more than half of the total number of different components of yeast extract, 27) equivalent of yeast extract or a medium that comprises more than half of the total number of different components of the equivalent of yeast extract, 28) 1, 2 or 5 protein(s) originating from or comprised in yeast extract, 29) 1, 2 or 5 nucleic acid(s) originating from or comprised in yeast extract, 30) 1, 2 or 5 peptide(s) or functional peptide(s) originating from or comprised in yeast extract, 31) glutathione, 32) dextran, 33) mannan, 34) trehalose, 35) flavoring nucleotide originating from or comprised in yeast extract, 36) B vitamin, 37) biotin, 38) 1, 2 or 5 volatile aromatic compound(s) originating from or comprised in yeast extract, 39) Chromium, 40) Cobalt, 41) Strontium, 42) nickel chloride, 43) or a medium that comprises more than half of the total number of different components of mineral elixir, 44) $MnSO_4$, 45) $NaCl$, 46) $FeSO_4$, 47) $CoSO_4$, 48) $CaCl_2$, 49) $ZnSO_4$, 50) $CuSO_4$, 51) $KAl(SO_4)_2$, 52) $H_3BO_3$, 53) $Na_2MoO_4$, 54) $NiCl_2$, 55) $Na_2SeO_3$, 56) peptone or a medium that comprises more than half of the total number of different components of peptone, 57) one component of peptone, 58) 1, 2 or 5 protein(s) originating from or comprised in peptone, 59) a sugar originating from or comprised in peptone, 60) one amino acid originating from or comprised in peptone, 61) ashes originating from or comprised in peptone, 62) one fiber originating from or comprised in peptone, 63) one CMR agent, 64) one amino acid, 65) alanine, 66) arginine, 67) asparagine, 68) aspartic acid, 69) cysteine, 70) glutamine, 71) glutamic acid, 72) glycine, 73) histidine, 74) isoleucine, 75) leucine, 76) lysine, 77) methionine, 78) phenylalanine, 79) proline, 80) serine, 81) threonine, 82) tryptophan, 83) tyrosine, 84) valine, 85) one cytotoxic or toxic compound, 86) manganese sulfate, 87) copper sulfate, 88) aluminum potassium sulfate, 89) sodium tungstate, 90) one heavy metal different from iron, 91) Titanium, 92) Vanadium, 93) Manganese, 94) Nickel, 95) Copper, 96) Zinc, 97) Gallium, 98) Germanium, 99) Arsenic, 100) Zirconium, 101) Niobium, 102) Molybdenum, 103) Technetium, 104) Ruthenium, 105) Rhodium, 106) Palladium, 107) Silver, 108) Cadmium, 109) Indium, 110) Tin, 111) Tellurium, 112) Lutetium, 113) Hafnium, 114) Tantalum, 115) Tungsten, 116) Rhenium, 117) Osmium, 118) Iridium, 119) Platinum, 120) Gold, 121) Mercury, 122) Thallium, 123) Lead, 124) Bismuth, 125) Polonium, 126) Astatine, 127) Lanthanum, 128) Cerium, 129) Praseodymium, 130) Neodymium, 131) Promethium, 132) Samarium, 133) Europium, 134) Gadolinium, 135) Terbium, 136) Dysprosium, 137) Holmium, 138) Erbium, 139) Thulium, 140) Ytterbium, 141) Actinium, 142) Thorium, 143) Protactinium, 144) Uranium, 145) Neptunium, 146) Plutonium, 147) Americium, 148) Curium, 149) Berkelium, 150) Californium, 151) Einsteinium, 152) Fermium, 153) Nobelium, 154) Radium, 155) Lawrencium, 156) Rutherfordium, 157) Dubnium, 158) Seaborgium, 159) Bohrium, 160) Hassium, 161) Meitnerium, 162) Darmstadtium, 163) Roentgenium, 164) Copernicium, 165) Elements 113-118, 166) Helium, 167) Lithium, 168) Beryllium, 169) Bore, 170) Fluor, 171) Aluminum, 172) Silicon, 173) Argon, 174) Scandium, 175) Chrome, 176) Nickel, 177) Copper, 178) Selenium, 179) Brome, 180) Krypton, 181) Rubidium, 182) Yttrium, 183) Sn, 184) Antimony, 185) Iodine, 186) Xenon, 187) Cesium, 188) Barium, 89) Lutecium, 190) Astate, 191) Radon, 192) Francium, 193) Mendelevium, 194) Mount, 195) Ununbium, 196) Ununtrium, 197) Ununquadium, 198) Ununpentium, 199) Ununhexium, 200) Ununseptium, 201) Ununoctium 202) salts of these compounds 1) to 201), and 203) derivatives thereof.

6. The method according to claim 5, wherein the concentration of the at least one compound that affects the growth of ferrimagnetic or ferromagnetic iron oxide nanoparticle-producing cells and/or ferrimagnetic or ferromagnetic iron oxide nanoparticle production, is a concentration in the pre-growth, growth and/or fed-batch medium/media that is larger than 1 pM, or 1 μM, or 1 mM, or $10^{-3}$ ng of compound per liter of pre-growth, growth and/or fed-batch medium/media, or 1 ng of compound per liter of pre-growth, growth and/or fed-batch medium/media, or $10^3$ ng of compound per liter of pre-growth, growth and/or fed-batch medium/media.

7. The method according to claim 1, wherein the growth medium and/or pre-growth medium is/are supplemented by a fed-batch medium and:
   i) the fed-batch medium has a pH that is lower than a pH of the pre-growth and/or growth medium/media, and/or
   ii) the concentration of at least one of the chemical elements selected from the group consisting of: a) the phosphorous or phosphate source, b) the potassium source, c) the magnesium source, d) the iron source, e) the vitamin source, f) the calcium source, g) $KH_2PO_4$, h) $MgSO_4$, i) $FeCl_3$, j) thiamine, k) $CaCl_2$, and 1) derivatives thereof, is larger in the fed-batch medium than in the pre-growth and/or growth medium/media.

8. The method according to claim 1, wherein:
   the ferrimagnetic or ferromagnetic iron oxide nanoparticles are magnetosomes.

9. The method according to claim 1, wherein the pre-growth and/or growth medium/media comprise(s) a source of calcium, a source of carbon, a source of nitrogen, a source of phosphate or phosphorous, a source of sulfur, a source of iron, a source of vitamin, and a source of calcium, and:
   the source of carbon has a concentration in the pre-growth and/or growth medium/media that is larger than the concentrations of at least one compound in the pre-growth and/or growth medium/media selected from the group consisting of: the source of phosphate or phosphorous, the source of sulfur, the source of vitamin, and the source of calcium, and/or
   the source of nitrogen has a concentration in the pre-growth and/or growth medium/media that is larger than the concentrations of at least one compound in the pre-growth and/or growth medium/media selected from the group consisting of: the source of phosphate or phosphorous, the source of sulfur, the source of vitamin, and the source of calcium.

10. The method according to claim 1, further comprising a step of storing, amplifying, preparing, or inserting in the pre-growth and/or growth and/or fed-batch medium/media a bank of ferrimagnetic or ferromagnetic iron oxide nanoparticle-producing cells, where said bank is stored, amplified, or prepared in a bank medium that comprises at least 1% of the same compounds as those of the pre-growth and/or growth and/or fed-batch medium/media and less than 100% oxygen per volume of the pre-growth and/or growth and/or fed-batch medium/media.

11. The method according to claim 1, further comprising a purifying step for obtaining high purity iron oxide based ferrimagnetic or ferromagnetic iron oxide nanoparticle(s), the purifying step comprising removal at least one impurity from the ferrimagnetic or ferromagnetic iron oxide nanoparticle(s) produced in the growth step using at least one heating step in which the ferrimagnetic or ferromagnetic iron oxide nanoparticles produced in the growth step have a temperature that is increased to a temperature T, and is then maintained at T during a heating time that is comprised between 1 second and 20 years, where T is comprised between 50° C. and 700° C.

* * * * *